(12) United States Patent
Leonard et al.

(10) Patent No.: US 8,236,500 B2
(45) Date of Patent: *Aug. 7, 2012

(54) PROMOTER VARIANTS OF THE ALPHA-7 NICOTINIC ACETYLCHOLINE RECEPTOR

(75) Inventors: Sherry Leonard, Denver, CO (US); Robert Freedman, Englewood, CO (US)

(73) Assignee: The United States of America, as represented by the Department of Veterans Affairs, Washington, DC (US)

( * ) Notice: Subject to any disclaimer, the term of this patent is extended or adjusted under 35 U.S.C. 154(b) by 24 days.

This patent is subject to a terminal disclaimer.

(21) Appl. No.: 12/474,402

(22) Filed: May 29, 2009

(65) Prior Publication Data
US 2010/0047795 A1 Feb. 25, 2010

Related U.S. Application Data

(63) Continuation-in-part of application No. 10/723,940, filed on Nov. 26, 2003, now Pat. No. 7,572,580, which is a continuation-in-part of application No. 08/956,518, filed on Oct. 23, 1997, now Pat. No. 6,875,606.

(51) Int. Cl.
C12Q 1/68 (2006.01)
(52) U.S. Cl. ........................................ 435/6.1
(58) Field of Classification Search .................. None
See application file for complete search history.

(56) References Cited

U.S. PATENT DOCUMENTS

| | | | |
|---|---|---|---|
| 5,795,976 A | 8/1998 | Oefner et al. | 536/25.4 |
| 5,888,780 A | 3/1999 | Dahlberg et al. | 435/91.53 |
| 5,952,174 A | 9/1999 | Nikiforov et al. | 435/6.11 |
| 6,001,311 A | 12/1999 | Brennan | 506/30 |
| 6,001,567 A | 12/1999 | Brow et al. | 435/5 |
| 6,043,031 A | 3/2000 | Koster et al. | 435/5 |
| 6,045,996 A | 4/2000 | Cronin et al. | 506/4 |
| 6,068,818 A | 5/2000 | Ackley et al. | 422/50 |
| 6,125,383 A | 9/2000 | Glynias et al. | 709/202 |
| 6,875,606 B1 | 4/2005 | Leonard et al. | 435/325 |
| 2004/0185468 A1 | 9/2004 | Leonard et al. | 435/6.16 |

FOREIGN PATENT DOCUMENTS

| | | |
|---|---|---|
| WO | WO/90/13678 | 11/1990 |
| WO | WO/96/15244 | 5/1996 |
| WO | WO/99/67641 | 12/1999 |
| WO | WO/00/39587 | 7/2000 |

OTHER PUBLICATIONS

US 5,962,233, 10/1999, Livak et al. (withdrawn).
Adams, C. E. and Stevens, K. E. (2007) Evidence for a role of nicotinic acetylcholine receptors in schizophrenia, *Front. Biosci.* 12, 4755-4772.
Aramakis, V. B. and Metherate, R. (1998) Nicotine selectively enhances NMDA receptor-mediated synaptic transmission during postnatal development in sensory neocortex, *J. Neurosci.* 18(20), 8485-8495.
Ars, E. et al. (2000) Mutations affecting mRNA splicing are the most common molecular defects in patients with neurofibromatosis type 1, *Hum. Mol. Genet.* 9(2), 237-247.
Baker, N. et al. (1987) Neurophysiological assessment of sensory gating in psychiatric inpatients: Comparison between schizophrenia and other diagnoses, *Biol. Psychiatry* 22(5), 603-617.
Baron, M. (2001) Genetics of Schizophrenia and the New Millennium: Progress and Pitfalls, *The American Journal of Human Genetics* 68(2), 299-312.
Barrett, J. C. et al. (2005) Haploview: analysis and visualization of LD and haplotype maps, *Bioinformatics* 21(2), 263-265.
Berg, D. K. and Conroy, W. G. (2002) Nicotinic α7 receptors: Synaptic options and downstream signaling in neurons, *J. Neurobiol.* 53(4), 512-523.
Blouin, J.-L. et al. (1998) Schizophrenia susceptibility loci on chromosomes 13q32 and 8p21, *Nat. Genet.* 20(1), 70-73.
Breese, C. R. et al. (1997) Effect of Smoking History on [3H]Nicotine Binding in Human Postmortem Brain, *J. Pharmacol. Exp. Ther.* 282(1), 7-13.
Brophy, V. H. et al. (2001) Effects of 52 Regulatory-Region Polymorphisms on Paraoxonase-Gene (PON1) Expression, *Am. J. Hum. Genet.* 68(6), 1428-1436.
Brzustowicz, L. et al. (2000) Location of a major susceptibility locus for familial schizophrenia on chromosome 1q21-q22, *Science* 288(5466), 678-682.
Cao, Q. et al. (1997) Suggestive Evidence for a Schizophrenia Susceptibility Locus on Chromosome 6q and a Confirmation in an Independent Series of Pedigrees, *Genomics* 43(1), 1-8.
Carrasco-Serrano, C. et al. (1998) GC- and E-box Motifs as Regulatory Elements in the Proximal Promoter Region of the Neuronal Nicotinic Receptor α7 Subunit Gene, *J. Biol. Chem.* 273(32), 20021-20028.
Cartegni, L. et al. (2002) Listening to silence and understanding nonsense: exonic mutations that affect splicing, *Nat. Rev. Genet.* 3(4), 285-298.
Chen, W.-Y. et al. (2004) Case-control study and transmission disequilibrium test provide consistent evidence for association between schizophrenia and genetic variation in the 22q11 gene ZDHHC8, *Hum. Mol. Genet.* 13(23), 2991-2995.
Clementz, B. A. et al. (1998) Poor P50 Suppression Among Schizophrenia Patients and Their First-Degree Biological Relatives, *Am. J. Psychiatry* 155(12), 1691-1694.
Clementz, B. A. et al. (1998) Multiple site evaluation of P50 suppression among schizophrenia and normal comparison subjects, *Schizophr. Res.* 30(1), 71-80.
Court, J. et al. (1999) Neuronal Nicotinic Receptors in Dementia with Lewy Bodies and Schizophrenia, *J. Neurochem.* 73(4), 1590-1597.
Croft, R. J. et al. (2001) Associations of P50 suppression and desensitization with perceptual and cognitive features of "unreality" in schizotypy, *Biol. Psychiatry* 50(6), 441-446.

(Continued)

*Primary Examiner* — John Ulm
(74) *Attorney, Agent, or Firm* — Medlen & Carroll, LLP

(57) ABSTRACT

The present invention is directed to methods and compositions related to α7 acetylcholine nicotinic receptor genes, in particular, the human α7 nicotinic acetylcholine receptor gene. The human α7 nicotinic acetylcholine receptor gene is associated with the pathophysiological aspects of the disease schizophrenia. The present invention further provides methods and compositions to screen populations for abnormal α7 alleles, as well as methods and compositions for development of therapeutics.

8 Claims, 18 Drawing Sheets

OTHER PUBLICATIONS

Dajas-Bailador, F. and Wonnacott, S. (2004) Nicotinic acetylcholine receptors and the regulation of neuronal signalling, *Trends Pharmacol. Sci.* 25(6), 317-324.

Dudbridge, F. (2003) Pedigree disequilibrium tests for multilocus haplotypes, *Genet. Epidemiol.* 25(2), 115-121.

Edenberg, H. J. et al. (1997) Initial genomic scan of the NIMH genetics initiative bipolar pedigrees: Chromosomes 3, 5, 15, 16, 17, and 22, *Am. J. Med. Genet.* 74(3), 238-246.

Egan, M. F. et al. (2001) Effect of COMT Val108/158 Met genotype on frontal lobe function and risk for schizophrenia, *Proc. Natl. Acad. Sci. U. S. A.* 98(12), 6917-6922.

Elmslie, F. V. et al. (1997) Genetic Mapping of a Major Susceptibility Locus for Juvenile Myoclonic Epilepsy on Chromosome 15q, *Hum. Mol. Genet.* 6(8), 1329-1334.

Erwin, R. J. et al. (1998) P50 abnormalities in schizophrenia: relationship to clinical and neuropsychological indices of attention, *Schizophr. Res.* 33(3), 157-167.

Fallin, M. D. et al. (2003) Genomewide Linkage Scan for Schizophrenia Susceptibility Loci among Ashkenazi Jewish Families Shows Evidence of Linkage on Chromosome 10q22, *Am. J. Hum. Genet.* 73(3), 601-611.

Faraone, S. V. et al. (1998) Genome scan of European-American schizophrenia pedigrees: Results of the NIMH genetics initiative and millennium consortium, *Am. J. Med. Genet.* 81(4), 290-295.

Felgner, P. L. and Ringold, G. M. (1989) Cationic liposome-mediated transfection, *Nature* 337(6205), 387-388.

Flora, A. et al. (2000) Transcriptional regulation of the human α5 nicotinic receptor subunit gene in neuronal and non-neuronal tissues, *Eur. J. Pharmacol.* 393(1-3), 85-95.

Freedman and Leonard. (2001) *Schizophr. Res.* 49, 70.

Freedman, R. et al. (1987) Candidate for inherited neurobiological dysfunction in schizophrenia, *Somat. Cell Mol. Genet.* 13(4), 479-484.

Freedman, R. et al. (1994) Schizophrenia and Nicotinic Receptors, *Harv. Rev. Psychiatry* 2, 179-192.

Freedman, R. et al. (1999) Alternative phenotypes for the complex genetics of schizophrenia, *Biol. Psychiatry* 45(5), 551-558.

Freedman, R. et al. (1997) Linkage of a neurophysiological deficit in schizophrenia to a chromosome 15 locus, *Proc. Natl. Acad. Sci. U. S. A.* 94(2), 587-592.

Freedman, R. et al. (1995) Evidence in postmortem brain tissue for decreased numbers of hippocampal nicotinic receptors in schizophrenia, *Biol. Psychiatry* 38(1), 22-33.

Freedman, R. and Leonard, S. (2001) Genetic linkage to schizophrenia at chromosome 15q14, *Am. J. Med. Genet.* 105(8), 655-657.

Freedman, R. et al. (2001) Linkage disequilibrium for schizophrenia at the chromosome 15q13-14 locus of the α7-nicotinic acetylcholine receptor subunit gene (CHRNA7), *Am. J. Med. Genet.* 105(1), 20-22.

Freedman, R. et al. (2001) Evidence for the multigenic inheritance of schizophrenia, *Am. J. Med. Genet.* 105(8), 794-800.

Freedman, R. et al. (1991) Elementary neuronal dysfunctions in schizophrenia, *Schizophr. Res.* 4(2), 233-243.

Gabriel, S. B. et al. (2002) The Structure of Haplotype Blocks in the Human Genome, *Science* 296(5576), 2225-2229.

Ganguly, A. et al. (1993) Conformation-sensitive gel electrophoresis for rapid detection of single-base differences in double-stranded PCR products and DNA fragments: evidence for solvent-induced bends in DNA heteroduplexes, *Proc. Natl. Acad. Sci. U. S. A.* 90(21), 10325-10329.

Gauderman, W. J. (2002) Sample Size Requirements for Association Studies of Gene-Gene Interaction, *Am. J. Epidemiol.* 155(5), 478-484.

Gauderman, W. J. (2002) Sample size requirements for matched case-control studies of gene-environment interaction, *Stat. Med.* 21(1), 35-50.

Gault, J. et al. (2003) Comparison of polymorphisms in the α7 nicotinic receptor gene and its partial duplication in schizophrenic and control subjects, *American Journal of Medical Genetics Part B: Neuropsychiatric Genetics* 123B(1), 39-49.

Gejman, P. V. et al. (2001) Linkage analysis of schizophrenia to chromosome 15, *Am. J. Med. Genet.* 105(8), 789-793.

George, T. P. et al. (2006) A preliminary study of the effects of cigarette smoking on prepulse inhibition in schizophrenia: Involvement of nicotinic receptor mechanisms, *Schizophr. Res.* 87(1), 307-315.

Gershon, E. S. (2000) Bipolar illness and schizophrenia as oligogenic diseases: implications for the future, *Biol. Psychiatry* 47(3), 240-244.

Glatt, S. J. et al. (2003) Association Between a Functional Catechol O-Methyltransferase Gene Polymorphism and Schizophrenia: Meta-Analysis of Case-Control and Family-Based Studies, *Am. J. Psychiatry* 160(3), 469-476.

Gotti, C. et al. (2006) Brain nicotinic acetylcholine receptors: native subtypes and their relevance, *Trends Pharmacol. Sci.* 27(9), 482-491.

Grabowski, P. J. and Black, D. L. (2001) Alternative RNA splicing in the nervous system, *Prog. Neurobiol.* 65(3), 289-308.

Guan, Z. et al. (1999) Decreased protein level of nicotinic receptor alpha7 subunit in the frontal cortex from schizophrenic brain, *Neuroreport* 10(8), 1779-1782.

Harrison, P. J. and Weinberger, D. R. (2004) Schizophrenia genes, gene expression, and neuropathology: on the matter of their convergence, *Mol. Psychiatry* 10(1), 40-68.

Hodgkinson, C. A. et al. (2008) Addictions Biology: Haplotype-Based Analysis for 130 Candidate Genes on a Single Array, *Alcohol Alcohol.* 43(5), 505-515.

Horikawa, Y. et al. (2000) Genetic variation in the gene encoding calpain-10 is associated with type 2 diabetes mellitus, *Nat. Genet.* 26(2), 163-175.

Kaufman, J. et al. (1997) Schedule for Affective Disorders and Schizophrenia for School-Age Children—Present and Lifetime Version (K-SADS-PL): Initial Reliability and Validity Data, *J. Am. Acad. Child Adolesc. Psychiatry* 36(7), 980-988.

Kaufmann, C. A. et al. (1998) NIMH genetics initiative millennium schizophrenia consortium: Linkage analysis of African-American pedigrees, *Am. J. Med. Genet.* 81(4), 282-289.

Knight, J. C. et al. (1999) A polymorphism that affects OCT-1 binding to the TNF promoter region is associated with severe malaria, *Nat. Genet.* 22(2), 145-150.

Kumari, V. and Postma, P. (2005) Nicotine use in schizophrenia: The self medication hypotheses, *Neuroscience &Biobehavioral Reviews* 29(6), 1021-1034.

Leonard, S. (2003) Consequences of low levels of nicotinic acetylcholine receptors in schizophrenia for drug development, *Drug Dev. Res.* 60(2), 127-136.

Leonard, S. et al. (2001) Smoking and mental illness, *Pharmacol. Biochem. Behav.* 70(4), 561-570.

Leonard, S. and Bertrand, D. (2001) Neuronal nicotinic receptors: from structure to function, *Nicotine Tob. Res.* 3(3), 203-223.

Leonard, S. et al. (2000) Smoking and schizophrenia: abnormal nicotinic receptor expression, *Eur. J. Pharmacol.* 393(1-3), 237-242.

Leonard, S. et al. (1998) Nicotinic Receptors, Smoking and Schizophrenia, *Restorative Neurology and Neuroscience* 12(2), 195-201.

Leonard, S. et al. (1993) Biological stability of mRNA isolated from human postmortem brain collections, *Biol. Psychiatry* 33(6), 456-466.

Leonard, S. et al. (2007) Smoking, Genetics and Schizophrenia: Evidence for Self Medication, *Journal of Dual Diagnosis* 3(3-4), 43-59.

Levin, E. et al. (2006) Nicotinic effects on cognitive function: behavioral characterization, pharmacological specification, and anatomic localization, *Psychopharmacology* 184(3), 523-539.

Levin, E. D. et al. (1998) Transdermal nicotine effects on attention, *Psychopharmacology* 140(2), 135-141.

Lin, P.-I. et al. (2007) No Gene Is an Island:The Flip-Flop Phenomenon, *Am. J. Hum. Genet.* 80(3), 531-538.

Liu, C.-M. et al. (2001) Suggestive evidence for linkage of schizophrenia to markers at chromosome 15q13-14 in Taiwanese families, *Am. J. Med. Genet.* 105(8), 658-661.

Machy, P. et al. (1988) Gene transfer from targeted liposomes to specific lymphoid cells by electroporation, *Proc. Natl. Acad. Sci. U. S. A.* 85(21), 8027-8031.

Martin, L. F. et al. (2004) Alpha-7 nicotinic receptor agonists: potential new candidates for the treatment of schizophrenia, *Psychopharmacology* 174(1), 54-64.

Marutle, A. et al. (2001) Laminar distribution of nicotinic receptor subtypes in cortical regions in schizophrenia, *J. Chem. Neuroanat.* 22(1-2), 115-126.

McClellan, J. M. et al. (2007) Schizophrenia: a common disease caused by multiple rare alleles, *The British Journal of Psychiatry* 190(3), 194-199.

Melnikova, I. N. et al. (2000) Interactions between regulatory proteins that bind to the nicotinic receptor β4 subunit gene promoter, *Eur. J. Pharmacol.* 393(1-3), 75-83.

Mexal, S. et al. (2008) Regulation of a novel αN-catenin splice variant in schizophrenic smokers, *American Journal of Medical Genetics Part B: Neuropsychiatric Genetics* 147B(6), 759-768.

Moore, L. et al. (2001) Evaluation of buccal cell collection protocols for genetic susceptibility studies, *Biomarkers* 6(6), 448-454.

O'Connell, J. R. and Weeks, D. E. (1998) PedCheck: A Program for Identification of Genotype Incompatibilities in Linkage Analysis, *Am. J. Hum. Genet.* 63(1), 259-266.

Olincy, A. et al. (2006) Proof-of-Concept Trial of an α7 Nicotinic Agonist in Schizophrenia, *Arch. Gen. Psychiatry* 63(6), 630-638.

Olincy, A. et al. (1998) Improvement in Smooth Pursuit Eye Movements after Cigarette Smoking in Schizophrenic Patients, *Neuropsychopharmacology* 18, 175-185.

Orita, M. et al. (1989) Rapid and sensitive detection of point mutations and DNA polymorphisms using the polymerase chain reaction, *Genomics* 5(4), 874-879.

Park, T.-W. et al. (2002) Functional catechol-O-methyltransferase gene polymorphism and susceptibility to schizophrenia, *European neuropsychopharmacology : the journal of the European College of Neuropsychopharmacology* 12(4), 299-303.

Parra, E. J. et al. (1998) Estimating African American Admixture Proportions by Use of Population-Specific Alleles, *Am. J. Hum. Genet.* 63(6), 1839-1851.

Patterson, J. V. et al. (2000) Effects of Temporal Variability on P50 and the Gating Ratio in Schizophrenia: A Frequency Domain Adaptive Filter Single-Trial Analysis, *Arch. Gen. Psychiatry* 57(1), 57-64.

Pritchard, J. K. and Rosenberg, N. A. (1999) Use of Unlinked Genetic Markers to Detect Population Stratification in Association Studies, *Am. J. Hum. Genet.* 65(1), 220-228.

Pritchard, J. K. et al. (2000) Inference of Population Structure Using Multilocus Genotype Data, *Genetics* 155(2), 945-959.

Quandt, K. et al. (1995) MatInd and MatInspector: new fast and versatile tools for detection of consensus matches in nucleotide sequence data, *Nucleic Acids Res.* 23(23), 4878-4884.

Rezvani, A. H. and Levin, E. D. (2001) Cognitive effects of nicotine, *Biol. Psychiatry* 49(3), 258-267.

Riley, B. et al. (2002) A 3-Mb Map of a Large Segmental Duplication Overlapping the α7-Nicotinic Acetylcholine Receptor Gene (CHRNA7) at Human 15q13-q14, *Genomics* 79(2), 197-209.

Riley, B. P. et al. (2000) Haplotype transmission disequilibrium and evidence for linkage of the CHRNA7 gene region to schizophrenia in Southern African Bantu families, *Am. J. Med. Genet.* 96(2), 196-201.

Robinson, W. et al. (1998) The mechanisms involved in formation of deletions and duplications of 15q11-q13, *J. Med. Genet.* 35(2), 130-136.

Sanders, A. R. et al. (2004) Haplotypic association spanning the 22q11.21 genes COMT and ARVCF with schizophrenia, *Mol. Psychiatry* 10(4), 353-365.

Singleton, A. et al. (2003) alpha-Synuclein locus triplication causes Parkinson's disease, *Science* 302(5646), 841.

Stevens, K. E. et al. (1996) Genetic Correlation of Inhibitory Gating of Hippocampal Auditory Evoked Response and α-Bungarotoxin-Binding Nicotinic Cholinergic Receptors in Inbred Mouse Strains, *Neuropsychopharmacology* 15, 152-162.

Stevens, K. E. et al. (1998) Selective α7-nicotinic agonists normalize inhibition of auditory response in DBA mice, *Psychopharmacology* 136(4), 320-327.

Stöber, G. et al. (2000) Splitting Schizophrenia: Periodic Catatonia Susceptibility Locus on Chromosome 15q15, *Am. J. Hum. Genet.* 67(5), 1201-1207.

Tan, E.-K. et al. (2003) Alpha synuclein promoter and risk of Parkinson's disease: microsatellite and allelic size variability, *Neurosci. Lett.* 336(1), 70-72.

Theuns, J. et al. (2000) Genetic variability in the regulatory region of presenilin 1 associated with risk for Alzheimer's disease and variable expression, *Hum. Mol. Genet.* 9(3), 325-331.

Tsuang, D. W. et al. (2001) Examination of genetic linkage of chromosome 15 to schizophrenia in a large Veterans Affairs Cooperative Study sample, *Am. J. Med. Genet.* 105(8), 662-668.

Turecki, G. et al. (2001) Mapping susceptibility genes for bipolar disorder: a pharmacogenetic approach based on excellent response to lithium, *Mol. Psychiatry* 6(5), 570-578.

Underhill, P. A. et al. (1996) A pre-Columbian Y chromosome-specific transition and its implications for human evolutionary history, *Proc. Natl. Acad. Sci. U. S. A.* 93(1), 196-200.

Valor, L. M. et al. (2002) Role of the Large Cytoplasmic Loop of the α7 Neuronal Nicotinic Acetylcholine Receptor Subunit in Receptor Expression and Function, *Biochemistry* 41(25), 7931-7938.

Vijayaraghavan, S. et al. (1992) Nicotinic receptors that bind ±-bungarotoxin on neurons raise intracellular free ca2+, *Neuron* 8(2), 353-362.

Waldo, M. C. et al. (2000) Familial transmission of risk factors in the first-degree relatives of schizophrenic people, *Biol. Psychiatry* 47(3), 231-239.

Wonodi, I. et al. (2003) Association between Val108/158 met polymorphism of the COMT gene and schizophrenia, *American Journal of Medical Genetics Part B: Neuropsychiatric Genetics* 120B(1), 47-50.

Wu, G.Y. et al. (1992) Hepatocyte-directed gene transfer in vivo leads to transient improvement of hypercholesterolemia in low density lipoprotein receptor-deficient rabbits, *J. Biol. Chem.* 267(2), 963-967.

Xu, J. et al. (2001) Evidence for linkage disequilibrium between the alpha 7-nicotinic receptor gene (CHRNA7) locus and schizophrenia in Azorean families, *Am. J. Med. Genet.* 105(8), 669-674.

Yee, C. M. et al. (1998) P50 suppression in recent-onset schizophrenia: Clinical correlates and risperidone effects, *J. Abnorm. Psychol.* 107(4), 691-698.

Adler et al., "Normalization by Nicotine of Deficient Auditory Sensory Gating in the Relatives of Schizophrenics," *Biol. Psych.* 32: 607-616 (1992).

Adler et al., "Normalization of Auditory Physiology by Cigarette Smoking in Schizophrenic Patients," *Am. J. Psychol.* 150: 1856-1861 (1993).

Adler et al., "Neurophysiological Studies of Sensory Gating in Rats: Effects of Amphetamine, Phencyclidine, and Haloperidol," *Biol. Psychiat.* 21: 787-798 (1986).

Adler et al., "Neurophysiological Evidence for a Defect in Neuronal Mechanisms Involved in Sensory Gating in Schizophrenia," *Biol. Psychiat.* 17: 639-654 (1982).

Albertsen et al., "Construction and characterization of a yeast artificial chromosome library containing seven haploid human genome equivalents," *Proc. Natl. Acad. Sci.* 87: 4256-4260 (1990).

Alkondon and Albuquerque, "Diversity of Nicotinic Acetylcholine Receptors in Rat Hippocampal Neurons. I. Pharmacological and Functional Evidence for District Structural Subtypes," *J. Pharm. Ex. Ther.* 265: 1455-1473 (1993).

Amar et al., "Agonist pharmacology of the neuronal α7 nicotinic receptor expressed in *Xenopus* oocytes," *FEBS* 327: 284-288 (1993).

Anderson and Young, "Quantitative Filter Hybridization," in *Nucleic Acid Hybridization A Practical Approach*, Hames and Higgins (eds.), pp. 73-109, IRL Press (1985).

Beard et al., "Transcription Mapping of Mouse Adenovirus Type 1 Early Region 3," *Virology*, pp. 75-81 (1990).

Beeson et al., "The human muscle nicotinic acetylcholine receptor α-subunit exists as two isoforms: a novel exon," *EMBO J.* 9: 2101-2106 (1990).

Bender et al., "Evidence that the Packaging Signal of Moloney Murine Leukemia Virus Extends into the *gag* Region," *J. Virol.* 61: 1639-1646 (1987).

Bernstein et al., "Gene Transfer with Retrovirus Vectors," *Genet. Eng.* 7: 235-261 (1985).

Bessis et al., "Negative regulatory elements upstream of a novel exon of the neuronal nicotinic acetylcholine receptor of α2 subunit gene," *Nucl. Acids Res.* 21: 2185-2192 (1993).

Bickford-Wimer et al., "Auditory Sensory Gating in Hippocampal Neurons: A Model System in the Rat," *Biol. Psychiat.* 27: 183-192 (1990).

Bickford and Wear, "Restoration of sensory gating of auditory evoked response by nicotine in fimbria-fornix lesioned rats," *Brain Res.* 705: 235-240 (1995).

Biedler et al., "Multiple Neurotransmitter Synthesis by Human Neuroblastoma Cell Lines and Clones," *Cancer Res.* 38: 3751-3757 (1978).

Blount and Merlie, "Mutational Analysis of Muscle Nicotinic Acetylcholine Receptor Subunit Assembly," *J. Cell Biol.* 111: 2613-2622 (1990).

Boshart et al., "A Very Strong Enhancer is Located Upstream of an Immediate Early Gene of Human Cytomegalovirus," *Cell* 41: 521-530 (1985).

Boutros and Overall, "Replication and Extension of P50 Findings in Schizophrenia," *Clin. Electroencephalog.* 22: 40-45 (1991).

Braff et al., "Gating and Habituation of the Startle Reflex in Schizophrenic Patients," *Arch. Gen. Psychiat.* 49: 206-215 (1992).

Breier et al., "National Institute of Mental Health Longitudinal Study of Chronic Schizophrenia, Prognosis and Predictors of Outcome," *Arch. Gen. Psychiat.*, 48: 239-246 (1991).

Brownstein et al., "Isolation of Single-Copy Human Genes from a Library of Yeast Artificial Chromosome Clones," *Science* 244: 1348-1351 (1989).

Burke et al., "Cloning of Large Segments of Exogenous DNA into Yeast by Means of Artificial Chromosome Vectors," *Science* 236: 806-812 (1987).

Calzolari et al., "Psychiatric Disorder in a Familial 15;18 Translocation and Sublocalization of Myelin Basic Protein to 18q22.3," *Am. J. Med. Genet.* 67: 154-161 (1996).

Cameron et al., "Dendritic Cells Exposed to Human Immunodeficiency Virus Type-1 Transmit a Vigorous Cytophathic Infection to $CD4^+$ T Cells," *Science* 257: 383-387 (1992).

Casaubon et al., "The Gene Responsible for a Severe Form of Peripheral Neuropathy and Agenesis of the Corpus Callosum Maps to Chromosome 15q," *Am. J. Hum. Genet.* 58: 28-34 (1996).

Chamberlin et al., "New RNA Polymerase from *Escherichia coli* infected with Bacteriophage T7," *Nature* 228: 227-231 (1970).

Chomczynski and Sacchi, "Single-Step Method of RNA Isolation by Acid Guanidinium Thiocyanate-Phenol-Chloroform Extraction," *Anal. Biochem.* 162: 156-159 (1987).

Chumakov et al., "Continuum of overlapping clones spanning the entire human chromosome 21q," *Nature* 359: 380-386 (1992).

Clarke, "Prader-Willi Syndrome and Psychoses," *Brit. J. Psychiat.* 163: 680-684 (1993).

Cole et al., "The EBV-Hybridoma Technique and its Application to Human Lung Cancer," in *Monoclonal Antibodies and Cancer Therapy,* Reisfeld et al. (eds.), pp. 77-96, Alan R. Liss, Inc. (1985).

Conti-Tronconi et al., "Brain and muscle nicotinic acetylcholine receptors are different but homologous proteins," *Proc. Natl. Acad. Sci. U.S.A.* 82: 5208-5212 (1985).

Coon et al., "Search for Mutations in the $\beta 1$ $GABA_A$ Receptor Subunit Gene in Patients with Schizophrenia," *Am. J. Med. Genet.* 54: 12-20 (1994).

Coon et al., "Use of a Neurophysiological Trait in Linkage Analysis of Schizophrenia," *Biol. Psychiat.* 34: 277-289 (1993).

Cooper et al., "Pentameric structure and subunit stoichiometry of a neuronal nicotinic acetylcholine receptor," *Nature* 350: 235-238 (1991).

Cote et al., "Generation of human monoclonal antibodies reactive with cellular antigens," *Proc. Natl. Acad. Sci. U.S.A.* 80: 2026-2030 (1983).

Couturier et al., "A Neuronal Nicotinic Acetylcholine Receptor Subunit ($\alpha 7$) Is Developmentally Regulated and Forms a Homo-Oligomeric Channel Blocked by $\alpha$-BTX," *Neuron* 5: 847-856 (1990).

Cullum et al., "Neurophysiological and neuropsychological evidence for attentional dysfunction in schizophrenia," *Schizophrenia Res.* 10: 131-141 (1993).

Curiel et al., "High-Efficiency Gene Transfer Mediated by Adenovirus Coupled to DNA-Polylysine Complexes," *Hum. Gene Ther.* 3: 147-154 (1992).

De Amicis et al., "Reaction Time Crossover as a Marker of Schizophrenia and of Higher Functioning," *J. Nerv. Ment. Dis.* 174: 177-179 (1986).

deLeon et al., "Schizophrenia and Smoking: An Epidemiological Survey in a State Hospital," *Am. J. Psychiat.* 152: 453-455 (1995).

Den-Dunnen et al., "Topography of the Duchenne Muscular Dystrophy (DMD) Gene: FIGE and cDNA Analysis of 194 Cases Reveals 115 Deletions and 13 Duplications," *Am. J. Hum. Genet.* 45: 835-847 (1989).

Deneris et al., "Genes Encoding Neuronal Nicotinic Acetylcholine Receptors," *Clin. Chem.* 35: 731-737 (1989).

Dijkema et al., "Cloning and expression of the chromosomal immune interferon gene of the rat," *EMBO J.* 4: 761-767 (1985).

Dominguez del Toro et al., "Immunocytochemical Localization of the $\alpha 7$ Subunit of the Nicotinic Acetylcholine Receptor in the Rat Central Nervous System," *J. Comp. Neurol.* 349: 325-342 (1994).

Eaton, "Epidemiology of Schizophrenia," *Epidemiol. Rev.* 7: 105-126 (1985).

Elgoyhen et al., "$\alpha 9$: An Acetylcholine Receptor with Novel Pharmacological Properties Expressed in Rat Cochlear Hair Cells," *Cell* 79: 705-715 (1994).

Endicott and Spitzer, "A Diagnostic Interview, The Schedule for Affective Disorders and Schizophrenia," *Arch. Gen. Psychiat.* 35: 837-844 (1978).

Erwin et al., "Midlatency Auditory Evoked Responses in Schizophrenia," *Biol. Psychiat.* 30: 430-442 (1991).

Felgner and Ringold, "Cationic liposome-mediated transfection," *Nature* 337: 387-388 (1989).

Felgner et al., "Lipofection: A highly efficient, lipid-mediated DNA-transfection procedure," *Proc. Natl. Acad. Sci. U.S.A.* 84: 7413-7417 (1987).

Freedman et al., "$\alpha$-Bungarotoxin Binding to Hippocampal Interneurons: Immunocytochemical Characterization and Effects on Growth Factor Expression," *J. Neurosci.* 13: 1965-1975 (1993).

Freedman et al., "Elementary neuronal dysfunctions in schizophrenia," *Schiz. Res.* 4: 233-243 (1991).

Freedman et al., "Schizophrenia and Nicotinic Receptors," *Harvard Rev. Psychiat.* 2: 179-192 (1994).

Freedman et al., "Evidence in Postmortem Brain Tissue for Decreased Numbers in Hippocampal Nicotinic Receptors in Schizophrenia," *Biol. Psychiat.* 38: 22-33 (1995).

Galzi et al., "Functional Architecture of the Nicotinic Acetylcholine Receptor: From Electric Organ to Brain," *Ann. Rev. Pharmacol.* 31: 37-72 (1991).

Goff et al., "Cigarette Smoking in Schizophrenia: Relationship to Psychopathology and Medication Side Effects," *Am. J. Psychiat.* 149: 1189-1194 (1992).

Goff et al., "Neural Origins of Long Latency Evoked Potentials Recorded from the Depth and from the Cortical Surface of the Brain in Man," *Prog. Clin. Neurophysiol.* 7: 126-145 (1980).

Goldman et al., "Members of a Nicotinic Acetylcholine Receptor Gene Family Are Expressed in Different Regions of the Mammalian Central Nervous System," *Cell* 48: 965-973 (1987).

Gorman et al., "The Rous sarcoma virus long terminal repeat is a strong promoter when introduced into a variety of eukaryotic cells by DNA-mediated transfection," *Proc. Natl. Acad. Sci. USA* 79: 6777-6781 (1982).

Graham and van der Eb, "A New Technique for the Assay of Infectivity of Human Adenovirus 5 DNA," *Virology* 52: 456-467 (1973).

Green, "Biochemical Mechanisms of Constitutive and Regulated Pre-mRNA Splicing," *Ann. Rev. Cell. Biol.* 7: 559-599 (1991).

Griffith et al., "Effects of sound intensity on a midlatency evoked response to repeated auditory stimuli in schizophrenic and normal subjects," *Psychophysiology* 32: 460-466 (1995).

Hamera et al., "Alcohol, Cannabis, Nicotine, and Caffeine Use and Symptom Distress in Schizophrenia," *J. Nerv. Mental Dis.* 183: 559-565 (1995).

Hershman et al., "$GABA_B$ antagonists diminish the inhibitory gating of auditory response in the rat hippocampus," *Neurosci. Lett.* 190: 133-136 (1995).

Holzman et al., "A Single Dominant Gene Can Account for Eye Tracking Dysfunctions and Schizophrenia in Offspring of Discordant Twins," *Arch. Gen. Psychiat.* 45: 641-647 (1988).

Hu and Worton, "Partial Gene Duplication as a Cause of Human Disease," *Hum. Mutat.* 1: 3-12 (1992).
Huse et al., "Generation of a Large Combinatorial Library of the Immunoglobulin Repertoire in Phage Lambda," *Science* 246: 1275-1281 (1989).
Hyman, "Schizophrenia," in *Scientific American Medicine*, 13 VII: 1-5, Dale and Federman (eds.), New York, New York (1994).
Judd et al., "Sensory Gating Deficits in Schizophrenia: New Results," *Am. J. Psychiat.* 149: 488-493 (1992).
Kacian et al., "A Replicating RNA Molecule Suitable for a Detailed Analysis of Extracellular Evolution and Replication," *Proc. Natl. Acad. Sci. USA* 69: 3038-3042 (1972).
Kaplitt et al., "Expression of a Functional Foreign Gene in Adult Mammalian Brain following in Vivo Transfer via a Herpes Simplex Virus Type 1 Defective Viral Vector," *Mol. Cell. Neurosci.* 2: 320-330 (1991).
Kim et al., "Use of the human elongation factor 1α promoter as a versatile and efficient expression system," *Gene* 91:217-223 (1990).
Kohler and Milstein, "Continuous cultures of fused cells secreting antibody of predefined specificity," *Nature* 256: 495-497 (1975).
Kozbor et al., "The production of monoclonal antibodies from human lymphocytes," *Immun. Today* 4: 72-79 (1983).
Kruglyak et al., "Parametric and Nonparametric Linkage Analysis: A Unified Multipoint Approach," *Am. J. Hum. Genet.* 58: 1347-1363 (1996).
Kuo et al., "Efficient Gene Transfer Into Primary Murine Lymphocytes Obviating the Need for Drug Selection," *Blood* 82: 845-852 (1993).
Lamond, "The Spliceosome," *BioEssays* 15: 595-603 (1993).
La Salle et al., "An Adenovirus Vector for Gene Transfer into Neurons and Glia in the Brain," *Science* 259: 988-990 (1993).
Lathrop et al.,"Strategies for multilocus linkage analysis in humans," *Proc. Natl. Acad. Sci. U.S.A.* 81: 3443-3446 (1984).
Lebkowski et al., "Adeno-Associated Virus: a Vector System for Efficient Introduction and Integration of DNA into a Variety of Mammalian Cell Types," *Mol. Cell. Biol.* 8: 3988-3996 (1988).
Lehrman et al., "Duplication of Seven Exons in LDL Receptor Gene Caused by Alu-Alu Recombination in a Subject with Familial Hypercholesterolemia," *Cell* 48: 827-835 (1987).
Lindstrom et al., "Neuronal Nicotinic Receptor Subtypes," *Ann. NY Acad. Sci.* 757: 100-116 (1996).
Lukas and Bencherif, "Heterogeneity and Regulation of Nicotinic Acetylcholine Receptors," *Int. Rev. Neurobiol.* 34: 25-131 (1992).
Luntz-Leybman et al., "Cholinergic gating of response to auditory stimuli in rat hippocampus," *Brain. Res.* 587: 130-136 (1992).
Machy et al., "Gene transfer from targeted liposomes to specific lymphoid cells by electroporation," *Proc. Natl. Acad. Sci. U.S.A.* 85: 8027-8031 (1988).
Mäkelä et al., "Whole-head mapping of middle-latency auditory evoked magnetic fields," *Electroencephalogr. Clin. Neurophysiol.* 92: 414-421 (1994).
Maniatis et al., "Regulation of Inducible and Tissue-Specific Gene Expression," *Science* 236: 1237-1244 (1987).
Mann et al., "Construction of a Retrovirus Packaging Mutant and Its Use to Produce Helper-Free Defective Retrovirus," *Cell* 33: 153-159 (1983).
Markowitz et al., "A Safe Packaging Line for Gene Transfer: Separating Viral Genes on Two Different Plasmids," *J. Virol.* 62: 1120-1124 (1988).
Marks and Collins, "Characterization of Nicotine Binding in Mouse Brain and Comparison with the Binding of α-Bungarotoxin and Quinuclidinyl Benzilate," *Mol. Pharmacol.* 22: 554 (1982).
Marks et al., "Nicotinic Binding Sites in Rat and Mouse Brain: Comparison of Acetylcholine, Nicotine, and α-Bungarotoxin," *Mol. Pharmacol.* 30: 427-437 (1986).
Matter-Sadzinski et al., "Neuronal specificity of the α7 nicotinic acetylcholine receptor promoter develops during morphogenesis of the central nervous system," *EMBO J.* 11: 4529-4538 (1992).
Maue et al., "Neuron-Specific Expression of the Rat Brain Type II Sodium Channel Gene Is Directed by Upstream Regulatory Elements," *Neuron* 4: 223-231 (1990).

Melissari et al., "Mitral valve prolapse in a case of Marfan syndrome with congenital cardiac disease, chronic obstructive pulmonary disease and schizophrenia," *Pathologica* 87: 78-81 (1995).
Miller et al.,"A simple salting out procedure for extracting DNA from human nucleated cells," *Nucl. Acids Res.* 16: 1215 (1988).
Miller and Rosman, "Improved Retroviral Vectors for Gene Transfer and Expression," *BioTechniques* 7: 980-990 (1992).
Miller and Freeman, "The Activity of Hippocampal Interneurons and Pyramidal Cells During The Response of the Hippocampus to Repeated Auditory Stimuli," *Neurosci.* 69: 371-381 (1995).
Mizushima and Nagata, "pEF-BOS, a powerful mammalian expression vector," *Nucl. Acids. Res.* 18: 5322 (1990).
Nagamoto et al., "Sensory Gating in Schizophrenics and Normal Controls: Effects of Changing Stimulation Interval," *Biol. Psychiat.* 25: 549-561 (1989).
Nagamoto et al., "Gating of Auditory P50 in Schizophrenics: Unique Effects of Clozapine," *Biol. Psychiat.* 40: 181-188 (1996).
Newland et al., "Functional and non-functional isoforms of the human muscle acetylcholine receptor," *J. Physiol.* 489: 767-778 (1995).
Nielsen et al., "Peptide nucleic acids (PNAs): Potential anti-sense and anti-gene agents," *Anticancer Drug Des.* 8:53-63 (1993).
Orr-Urtreger et al., "Cloning and Mapping of the Mouse α7-Neuronal Nicotinic Acetylcholine Receptor," *Genomics* 26: 399-402 (1995).
Patrick et al., "Molecular Biology of Nicotinic Acetylcholine Receptors," *Ann. NY Acad. Sci.* 505: 194 (1987).
Pauly et al., "Glucocorticoid Regulation of Sensitivity to Nicotine," in *The Biology of Nicotine: Current Research Issues*, Lippiello et al. (eds.), pp. 121-139, Raven Press, New York (1992).
Peng et al., "Human α7 Acetylcholine Receptor: Cloning of the α7 Subunit from the SH-SY5Y Cell Line and Determination of Pharmacological Properties of Native Receptors and Functional α7 Homomers Expressed in *Xenopus* Oocytes," *Mol. Pharm.* 45: 546-554 (1994).
Pulver et al., "Follow-Up of a Report of a Potential Linkage for Schizophrenia on Chromosome 22q12-q13.1: Part 2," *Am. J. Med. Genet.* 54: 44-50 (1994).
Risch, "Genetic Linkage and Complex Diseases, With Special Reference to Psychiatric Disorders," *Genet. Epidemiol.* 7: 3-16 (1990).
Rollins et al., "Cellular Localization of α-Bungarotoxin Binding and α7 mRNA in the Hippocampus Related to Auditory Gating in the Awake, Behaving Rat," *Soc. Neurosci. Abst.* 22: 1272 (1996).
Saksela et al., "Human immunodeficiency virus type 1 mRNA expression in peripheral blood cells predicts disease progression independently of the numbers of CD4+ lymphocytes," *Proc. Natl. Acad. Sci. U.S.A.* 91: 1104-1108 (1994).
Saksela et al., "High Viral Load in Lymph Nodes and Latent Human Immunodeficiency Virus (HIV) in Peripheral Blood Cells of HIV-1 Infected Chimpanzees," *J. Virol.* 67: 7423-7427 (1993).
Sambrook et al., *Molecular Cloning: A Laboratory Manual*, 2nd ed., pp. 7.39-7.52, 9.31-9.58, 16.6-16.15, Cold Spring Laboratory Press, New York (1989).
Samulski et al., "A Recombinant Plasmid from Which an Infectious Adeno-Associated Virus Genome Can Be Excised In Vitro and Its Use To Study Viral Replication," *J. Virol.* 61: 3096-3101 (1987).
Samulski et al., "Helper-Free Stocks of Recombinant Adeno-Associated Viruses: Normal Integration Does Not Require Viral Gene Expression," *J. Virol.* 63: 3822-3828 (1989).
Sauerwald et al., "The 5'-Flanking Region of the Synapsin I Gene," *J. Biol. Chem.* 265: 14932-14937 (1990).
Schmid, "Alu: Structure, Origin, Evolution, Significance and Function of One-Tenth of Human DNA," *Prog. Nucl. Acid Res.* 53: 283-319 (1996).
Séguéla et al., "Molecular Cloning, Functional Properties, and Distribution of Rat Brain α7: A Nicotinic Cation Channel Highly Permeable to Calcium," *J. Neurosci.* 13: 596-604 (1993).
Sham et al., "Segregration analysis of complex phenotypes: an application to schizophrenia and auditory P300 latency," *Psychiat. Genet.* 4: 29-38 (1994).
Siegel et al., "Deficits in Sensory Gating in Schizophrenic Patients and Their Relatives, Evidence Obtained With Auditory Evoked Responses," *Arch. Gen. Psychiat.* 41: 607-612 (1984).

Silverman et al., "Evidence of a Locus for Schizophrenia and Related Disorders on the Short Arm of Chromosome 5 in a Large Pedigree," *Am. J. Med. Genet.* 67: 162-171 (1996).

Sirota et al., "Schizophrenia and Marfan Syndrome," *Br. J. Psychiat.* 157: 433-436 (1990).

Spitzer et al., "Research Diagnostic Criteria, Rationale and Reliability," *Arch. Gen. Psychiat.* 35: 773-782 (1978).

Stratford-Perricaudet et al., "Widespread Long-term Gene Transfer to Mouse Skeletal Muscles and Heart," *J. Clin. Invest.* 90: 626-630 (1992).

Tsuang et al., "Long-term Outcome of Major Psychoses I. Schizophrenia and Affective Disorders Compared with Psychiatrically Symptom-Free Surgical Conditions," *Arch. Gen. Psychiat.* 36: 1295-1301 (1979).

Tsuang et al., "Genotypes, Phenotypes, and the Brain, A Search for Connections in Schizophrenia," *Brit. J. Psychiat.* 163: 299-307 (1993).

Uetsuki et al., "Isolation and Characterization of the Human Chromosomal Gene for Polypeptide Chain Elongation Factor-1α," *J. Biol. Chem.* 264: 5791 (1989).

Ulmer et al., "Heterologous Protection Against Influenza by Injection of DNA Encoding a Viral Protein," *Science* 259: 1745-1748 (1993).

Vinogradova et al., "Do Semantic Priming Effects Correlate with Sensory Gating in Schizophrenia," *Biol. Psychiat.* 39: 821-824 (1996).

Vinogradova, in *The Hippocampus 2: Neurophysiology and Behavior*, Issacson and Pribram (eds.), pp. 3-69, Plenum Press, New York, New York (1975).

von Heijne, "A new method for predicting signal sequence cleavage sites," *Nuc. Acids Res.* 14: 4683-4690 (1986).

Voss et al., "The role of enhancers in the regulation of cell-type-specific transcriptional control," *Trends Biochem. Sci.* 11: 287-289 (1986).

Wada et al., "Distribution of Alpha2, Alpha3, Alpha4, and Beta2 Neuronal Nicotinic Receptor Subunit mRNAs in the Central Nervous System: A Hybridization Histochemical Study in the Rat," *J. Compar. Neurol.* 284: 314-335 (1989).

Waldo et al., "Codistribution of a Sensory Gating Deficit and Schizophrenia in Multi-affected Families," *Psychiat. Res.* 39: 257-268 (1991).

Waldo et al., "Auditory sensory gating, hipppocampal volume, and catecholamine metabolism in schizophrenics and their siblings," *Schizophr. Res.* 12: 93-106 (1991).

Wang et al., "Evidence for a susceptibility locus for schizophrenia on chromosome 6pter-p22," *Nature Genet.* 10: 41-46 (1995).

Williams et al., "Introduction of foreign genes into tissues of living mice by DNA-coated microprojectiles," *Proc. Natl. Acad. Sci. U.S.A.* 88: 2726-2730 (1991).

Wilson et al., "Habituation of Human Limbic Neuronal Response to Sensory Stimulation," *Exp. Neurol.* 84: 74-97 (1984).

Wilson et al., "Hepatocyte-directed Gene Transfer in Vivo Leads to Transient Improvement of Hypercholesterolemia in Low Density Lipoprotein Receptor-deficient Rabbits," *J. Biol. Chem.* 267: 963-967 (1992).

Wonnacott, "α-Bungarotoxin Binds to Low-Affinity Nicotine Binding Sites in Rat Brain," *J. Neurochem.* 47: 1706-1712 (1986).

Wu and Wallace, "The Ligation Amplification Reaction (LAR)—Amplification of Specific DNA Sequences Using Sequential Rounds of Template-Dependent Ligation," *Genomics* 4:560-569 (1989).

Wu and Wu, "Receptor-mediated Gene Delivery and Expression in Vivo," *J. Biol. Chem.* 263: 14621-14624 (1988).

Wu and Wu, "Receptor-mediated in Vitro Gene Transformation by a Soluble DNA Carrier System," *J. Biol. Chem.* 262: 4429-4432 (1987).

Zhang et al., "Neuronal Acetylcholine Receptors That Bind α-Bungarotoxin with High Affinity Function as Ligand-Gated Ion Channels," *Neuron* 12: 167-177 (1994).

Adler et al., "Schizophrenia, Sensory Gating, and Nicotinic Receptors," *Schizophrenia Bulletin* 24: 189-202 (1998).

Anand and Lindstrom, "Nucleotide sequence of the human nicotinic acetylcholine receptor β2 subunit gene," *Nuc. Acids Res.* 18: 4272 (1990).

Breese et al., "Abnormal Regulation of High Affinity Nicotinic Receptor Binding in Schizophrenics," *Abstracts, Society for Neuroscience*, 27th Annual Meeting, Oct. 25-30 (1997).

Breese et al., "Abnormal Regulation of the High Affinity Nicotinic Receptors in Schizophrenia," *Abstracts, Society for Neuroscience*, 28th Annual Meeting, Nov. 7-12 (1998).

Breese et al., "Comparison of the Regional Expression of Nicotinic Acetylcholine Receptor α7 mRNA and [$^{125}$I]-α-bungarotoxin binding in Human Postmortem Brain," *J. Comp. Neurol.* 387: 385-398 (1997).

Chini et al., "Molecular Cloning and Chromosomal Localization of the Human α7-Nicotinic Receptor Subunit Gene (CHRNA7)," *Genomics* 19: 379-381 (1994).

Deneris et al., "Primary Structure and Expression of β2: A Novel Subunit of Neuronal Nicotinic Acetylcholine Receptors," *Neuron* 1: 45-54 (1988).

Doucette-Stamm et al., "Cloning and Sequence of the Human α7 Nicotinic Acetylcholine Receptor," *Drug Dev. Res.* 30: 252-256 (1993).

Drebing et al., "Expression of the Human α7 Neuronal Nicotinic Acetylcholine Receptor and a Partial Gene Duplication," *Abstracts, Society for Neuroscience*, 28th Annual Meeting, Nov. 7-12 (1998).

Dudek et al., "Expression in Human Brain of Novel Exons Associated with a Partial Duplication of the α7 Neuronal Nicotinic Receptor," *Abstracts, Society for Neuroscience*, 28th Annual Meeting, Nov. 7-12 (1998).

Fornasari et al., "Molecular cloning of human neuronal nicotinic receptor α3-subunit," *Neurosci. Lett.* 111: 351-356 (1990).

Fornasari et al., "Structural and Functional Characterization of the Human α3 Nicotinic Subunit Gene Promoter," *Mol. Pharmacol.* 51: 250-261 (1997).

Freedman et al., "Linkage of a neurophysiological deficit in schizophrenia to a chromosome 15 locus," *Proc. Natl. Acad. Sci. U.S.A.* 94: 587-592 (1997).

Garcia-Guzman et al., "α-Bungarotoxin-sensitive Nicotinic Receptors on Bovine Chromaffin Cells: Molecular Cloning, Functional Expression and Alternative Splicing of the α7 Subunit," *Eur. J. Neuorosci.* 7: 647-655 (1995).

Gault et al., "Contig construction across the 15q14 schizophrenia linkage region and candidate gene characterization of the partially duplicated α7 nicotinic receptor," *Am. J. Human Genet.* 63: A249 (1998).

Gault et al., Genomic Organization and Partial Duplication of the Human α7 Neuronal Nicotinic Acetylcholine Receptor Gene (CHRNA7), *Genomics* 52: 173-185 (1998).

Gault et al., "Comparison of polymorphisms in the alpha7 nicotinic receptor gene and its partial duplication in schizophrenic and control subjects," *Am J Med Genet B Neuropsychiatr Genet*, 123: 39-49 (2003).

GenBank Accession No. X70297 (1993).

GenBank Accession No. Z58126 (1995).

Lee et al., "The Effect of Nicotine and Haloperidol on High Affinity Nicotinic Receptors and Dopamine D2 Receptors in the Rat Brain," *Abstracts, Society for Neuroscience*, 28th Annual Meeting, Nov. 7-12 (1998).

Leonard et al., "Additional evidence for a chromosome 15 locus in schizophrenia: Analysis of affected sibpairs from the NMH genetics initiative," *Am. J. Human Genet.* 63: A297 (1998).

Leonard et al., "Further Investigation of a Chromosome 15 Locus in Schizophrenia: Analysis of Affected Sibpairs From the NIMH Genetics Initiative," *Am. J. Med. Genet.* 81: 308-312 (1998).

Leonard et al., "Genomic Organization and Partial Duplication of the Human α7 Neuronal Nicotinic Acetylcholine Receptor Subunit Gene," *Abstracts, Society for Neuroscience*, 28th Annual Meeting, Nov. 7-12 (1998).

Leonard et al., "Genomic Structure of the Human α7 Neuronal Nicotinic Acetylcholine Receptor Subunit," *Abstracts, Society for Neuroscience*, 27th Annual Meeting, Oct. 25-30 (1997).

Leonard et al., "Linkage of a chromosome 15 locus to a neurophysiological deficit in schizophrenia," *Am. J. Human Genet.* 59: A225 (1996).

Leonard et al., "Association of promoter variants in the alpha7 nicotinic acetylcholine receptor subunit gene with an inhibitory deficit found in schizophrenia," *Arch Gen Psychiatry*, 59: 1085-1096 (2002).

Leonard, Consequences of low levels of nicotinic acetylcholine receptors in schizophrenia for drug development, *Drug Development Research*, 60: 127-136 (2003).

Logel et al., "Expression of High and Low Affinity Neuronal Nicotinic Receptors in Tissues of Neural Crest Origin," *Abstracts, Society for Neuroscience*, 27th Annual Meeting, Oct. 25-30 (1997).

Mexal et al., Differential modulation of gene expression in the NMDA postsynaptic density of schizophrenic and control smokers, *Mol Brain Res*, 139: 317-332 (2005).

Zetterström et al., "Polymorphisms at the Calcitonin/CGRP-α Gene Locus: Investigation of Possible Associations with Neurological or Psychiatric Disease," *Abstracts, Society for Neuroscience*, 28th Annual Meeting, Nov. 7-12 (1998).

Exon-Intron Boundary Sequences of the Human alpha-7 nAChR Subunit Gene

| Exon Number | Exon length (bp) | cDNA position | splice acceptor | flanking exon sequence | splice donor | Intron number | Intron Size approximate (Kb) |
|---|---|---|---|---|---|---|---|
| 1 | 55 | 1-55 |  | ...CTG CAC G<br>L H | GTAAAGCCAC | 1 | 0.3 |
| 2 | 140 | 56-195 | TCTCCCTTAAG | TG TCC......GAC GTG<br>V S D V | GTGAGTCCCG | 2 | Unknown |
| 3 | 45 | 196-240 | TTTTTTGAAG | GAT GAG......CAA ATG<br>D E Q M | GTAAGTTAAG | 3 | 9.0 |
| 4 | 110 | 241-350 | TGTGTGTCAG | TCT TGG......AAC AG<br>S W N S | GTAAGCATAT | 4 | Unknown |
| 5 | 80 | 351-430 | CTGTTTCTAG T | GCT GAT......CCT CCA G<br>A D P P | GTAAGTCTGCA | 5 | 4.0 |
| 6 | 168 | 431-598 | ACCCACACAG | GC ATA......CTA GTG G<br>G I L V | GTAAGCCATG | 6 | 1.0 |
| 7 | 195 | 599-793 | CCCTATGGAG | GA ATC......TCC CTG G<br>G I S L | GTAAGCGCCC | 7 | 1.0 |
| 8 | 87 | 794-880 | TATGTTTTAG | GG ATA......TTG ATA G<br>G I L I | GTAAGGCAAG | 8 | 3.5 |
| 9 | 110 | 881-990 | CTCTCCACAG | CC CAG......AAG TGG<br>A Q K W | GTACGTTCCT | 9 | 5.0 |
| 10 | 519 | 991-1509 | GTCTCCCCAG | ACC AGA...<br>T R |  |  |  |

Figure 1

Sequence Variants Identified in Full-Length and Duplicated Genomic Clones

| DNA | EXONS CONT. | EXON 6 +/- 497-498 | EXON 7 654 | EXON 7 690 | EXON 10 1269 | EXON 10 1335 | L76630 |
|---|---|---|---|---|---|---|---|
| CHR15 HYBRID | 5-10 | +TG | C/T | G/A | C/C | C/C | 6GT |
|  | 1-10 | -TG |  |  |  |  | 8GT |
| YAC |  |  |  |  |  |  |  |
| D-948a10 | 5-10 | -TG | T |  | C | C | 6GT |
| D-853b12 | 6-10 | -TG | T |  | C | C | 6GT |
| D/F |  |  |  |  |  |  |  |
| 969b11 | 5-10 | +TG | C/T | G/A | C/T | C/C | 6GT |
|  | 1-10 | -TG |  |  |  |  | 8GT |
| F-134h10 | 1-10 | +TG | C | G | C | C | 8GT |
| F-776a12 | 1-10 | +TG | C | G | C | C | 8GT |
| F-791e6 | 1-10 | +TG | C | G | C | C | 8GT |
| F-811b6 | 1-10 | +TG | C | G | C | C | 8GT |
| F-953g6 | 1-10 | +TG | C | G | C | C | 8GT |
| F-859c11 | 1-10 | +TG | C | G | C | C | 8GT |
| F-810f11 | 1-10 | +TG | C | G | C | C | 8GT |
| F-801e1 | 1-10 | +TG | C | G | C | C | 8GT |
| BAC |  |  |  |  |  |  |  |
| F-467o18 | 1-10 | +TG | C | G | C |  | 8GT |

| DNA | EXON 6 +/- 497-498 | | | EXON 7 654 | | | EXON 7 690 | | | EXON 10 1269 | | | EXON 10 1335 | | |
|---|---|---|---|---|---|---|---|---|---|---|---|---|---|---|---|
| Control # | +/+ | +/- | -/- | C/C | C/T | T/T | G/G | G/A | A/A | C/C | C/T | T/T | C/C | C/T | T/T |
| Control Genomic DNA | 43 | 10 | 33 | 0 | 5 | 38 | 0 | 0 | 43 | 0 | 6 | 36 | 1 | 24 | 19 | 0 |

Figure 2

Expression Analysis of Sequence Variants

| Subj | Bases 497-498 | | | Base 654 | | | Base 690 | | | Base 933 | | | Base 1296 | | | Base 1335 | | |
|---|---|---|---|---|---|---|---|---|---|---|---|---|---|---|---|---|---|---|
| | DNA | 1-10 cDNA | 5-10 cDNA | DNA | 1-10 cDNA | 5-10 cDNA | DNA | 1-10 cDNA | 5-10 cDNA | DNA | 1-10 cDNA | 5-10 cDNA | DNA | 1-10 cDNA | 5-10 cDNA | DNA | 1-10 cDNA | 5-10 cDNA |
| SL061 | +/- | + | +/- | CT | C | CT | GA | G | GA | G | G | G | CT | CT | CT | C | C | C |
| SL084 | + | + | + | C | C | C | GA | G | GA | G | G | G | CT | C | CT | C | C | C |
| SL111 | +/- | + | +/- | CT | C | CT | GA | G | GA | G | G | G | CT | CT | CT | CT | CT | CT |
| SL097 | + | + | + | CT | C | CT | GA | G | GA | G | G | G | CT | CT | CT | C | C | C |
| SL089 | + | + | + | C | C | C | GA | GA | GA | GA | GA | GA | CT | CT | C | C | C | C |
| SHSY | +/- | + | +/- | CT | C | CT | GA | GA | GA | GA | GA | GA | C | C | C | C | C | C |

Figure 3

```
-392  agaacgcaag ggagaggtag agcctggcct tgggcagccc ctggctggc cagaggcgcg aggccgagag
                                                       AP-2
-322  cccgctcggt ggagactggg ggtggaggtg cccggagcgt acccagcgcc gggagtacct cccgctcaca
-252  cctcgggctg cagttccctg ggtggccgcc gagacgctgg cccggctgg agggatggcg gggcggggac
-182  gggggcgggg gcggggctgg tcacgtgag aggcgcgg ggcgggggcg ggggggcg cgcgcccgc
                        CREB                                    Sp1
-112  tccttaaagg cgcgcgagcc gagcggcgag gtgcctctgt ggccgcaagc gcaggcccgg gcgacagccg
-42   agacgtggag cgcgccggct cgctgcagct ccgggactca acATGCGCTG CTCGCCGGGA GGCGTCTGGC
                                                     Met
+29   TGGCGGCTGGC CCGGTCCCTC CTGCACGgta aagccac
```

```
EXON D       1
297bp    CAGGCCGCCA  CATAGCTCCC  GCCAAGTCCT  CGGTGCCCCT  TGCCATTTTC  CAGCCGCGTC  CCACGAGGGT
         CACGGCGGCG  GGGAGAGGTG  GAGCCGCGAG  AGCTCGGCCG  GGGCCCCGC   GGGCCCCGCG  CGGCCATGAC
         AGCGGCTCGG  GACTGGCTCC  TTTTCCGCGC  CCCTCCCGCC  GGAGGTGAGG  GGAAGATGTC  CATGTCAGGG
         TTCAAGGCCA  AACCGAAGTT  ACTGGCCTCT  ATCTTCCAGG  AGAACCAGGA  GCCACAGCCG  CGGCTCACGC
         CCCACCGCAA  CATTAAGgtg  agtcgcc·····
                        297

EXON C     ····ctc    atttcagATT  ACAAGTGGAC  ACCTGAGTCA  GCAGGACCTG  GAATCCCAGA  TGAGAGAGCT
125bp    TATCTACACG  ACTCAGATCT  TGTTGTCACC  CCCATTATTG  ACAATCCAAA  GGTGCAGAAA  GCACTCTGAC
         AAgtgagttg  ta······
          422          423

EXON B   ··ttaaccac  agATAATGAA  ACAACCACCA  TCGGTTAAAT  TTGATGCAAA  AATATTGCAT  CTACCAGCAT
64bp     TTTCAGgtag  gatcat······
          486          487

EXON A   ·····ttta   ttctagTTCC  AATTGCTAAT  CCAGCATTTG  TGGATAGCTG  CAAACTCCGA  TATgtaagta
47bp     aca······
                      534         533

EXON 5   ····ctgtttc tagTGCTGAT  GAGGCTTTG   ACGCCACATT  CCACACTAAC  GTGTTGGTGA  ATTCTTCTGG
80bp                GCATTGCCAG  TACCTGCCTC  CAGgtaagctgca······
                      614         613

EXON 6   ····acccaca cagGCATATT  TGCTACATCG  CAAGAGTTCC
27bp                              640
```

Figure 6

```
  1 agaacgcaag ggagaggtag agcctggcct tgggcagccc ctggcctggc cagaggcgcg
 61 aggccgagag cccgctcggt ggagactggg ggtggaggtg cccggagcgt acccagcgcc
121 gggagtacct cccgctcaca cctgggcctg cagttccctg ggtggccgcc gagacgctgg
181 ccggggctgg agggatggcg gggcggggac ggggcgggg gggggctcg tcacgtggag
241 aggcgcgcgg gggcgggcgg ggcggggcg cgcgccggc tccttaaagg cgcgcgagcc
301 gagcggcgag gtgcctctgt ggccgcaggc gcaggcccgg gcgacagccg agacgtggag
361 cgcgccggct cgctgcagct ccgggactca ac
```

FIG. 8

```
  1 caggccgcca catagctccc gccaagtcct cggtgcccct tgccattttc cagccgcgct
 61 cccacgaggg tcacggcggc ggggagaggt ggagccgcga gagctcggcc ggggccccg
121 cctggtggcc gggccatga cagcggctcg ggactggctc cttttccgcg cccctcccgc
181 cggaggtgag gggaagatgt ccatgtcagg gttcaaggcc aaaccgaagt tactggcctc
241 tatcttccag gagaaccagg agccacagcc gcggctcacg cccaccgca acattaagat
301 tacaagtgga cacctgagtc agcaggacct ggaatcccag atgagagagc ttatctacac
361 gactcagatc ttgttgtcac cccdattatt gacaatccaa aggtgcagaa agcactctga
421 caaataatga acaaccacc atcggttaaa tttgatgcaa aaatattgca tctaccagca
481 ttttcagttc caattgctaa tccagcattt gtggatagct gcaaactgcg atattgctga
541 tgagcgcttt gacgccacat tccacactaa cgtgttggtg aattcttctg ggcattgcca
601 gtacctgcct ccaggcatat tcaagagttc ctgctacatc g
```

FIG. 9

```
  1 agccctttcc caggcggtag cggggcagt ggtgctgttg ccctttaaa ctgcggcttg
 61 acgggagccg cgcctcctgt cggtggagtc ggttataaag ggagcagccc cgcaggccgc
121 cacatagctc ccgccaagtc ctggtgcc cttgccattt tccagccgcg ctccacgag
181 ggtcacggcg ggggagag gtggagccgc gagagctcgg ccggggcc cgcctggtgg
241 ccgcggccat gacagcggct cgggactggc tccttttccg cgcccctccc gccggaggtg
301 agggaagat gtccatgtca gggttcaagg ccaaaccgaa gttactggcc tctatcttcc
361 aggagaacca ggagccacag ccgcggctca cgcccaccg caacattaag attacaagtg
421 gacacctgag tcagcaggac ctggaatccc agatgagaga gcttatctac acgactcaga
481 tcttgttgtc accccatta ttgacaatcc aaaggtgcag aaagcactct gacaattcca
541 attgctaatc cagcatttgt ggatagctgc aaactgcgat attgctgatg acgctttga
601 cgccacattc cacactaacg tgttggtgaa ttcttctggg cattgccagt acctgcctcc
661 aggcatattc aagagttcct gctacatcg
```

FIG. 10

A
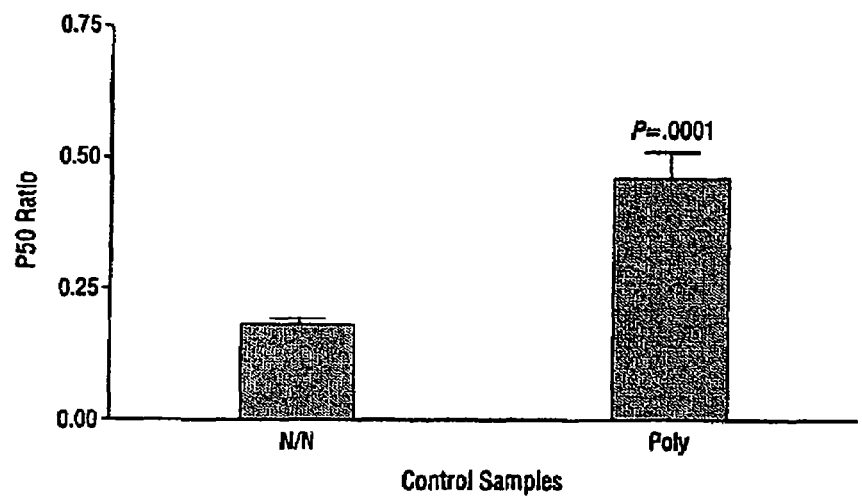
B
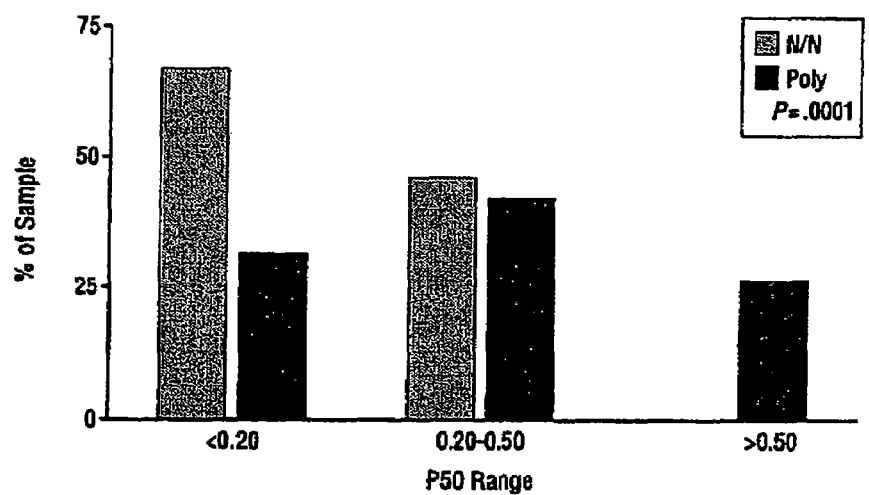
FIG. 15

SEQ ID No: 181

```
-2040 gtcctacatt gtaagctgag tgagtggact gcgcttgcag gtcctccagg tgcctagcga
-1980 gaacagagga caaataaata tttacgaatt gcttgtctca cctgaaaatg gtttatttct
-1920 aggtttctga tattatgggg tgcaatggcg gtaaagaagc agttctggtt tcaggaatgt
-1860 gatcctgata gccatactcc agaaaaatc aataaattcc cttggcccca tgggctcatg
                                 EBP/alp -1831                    USF
-1800 ctcttctaga agggaagaca gggctcttag gtactttcag cgctcgtaga agagtgttgt
-1740 tacagtccca tgaccagtgc aggggatgtg ccactgagaa tcttttcact gatgcttcat
-1680 gggctttctc tattctgcta ctgggtttta tttccsttct tctaattctc cctttaccaa
-1620 caactaatcc cctgtagata attaattcat caagtgcctg ctgtgtgatg tcgggactgc
                       HNF-1                   -1587    c-Jun/CREB
-1560 tagaagtggt aggggactc aagagccaga tgaagctaag gacacgcctg tctgctctcc
                                                   Sp1     -1512
-1500 agggacccct ggcgtccctt tctcctggca gaatgactgc tatcctttga ggtgaatcca
                                                              -1452
-1440 gttcagctgt cacctcttct attaaccact ctccaaaaac agctaatcct tcttctaccc
                                                                      -1392
-1380 tcttaccgga gttatgaaag cctatgctga cccttttgttt aaacatgtgt acattaacag
      EBP/alp-1372
-1320 taatacattt aagacactc atggcaaggg caatatactg cgttattctt ccaaatcaaa
      EBP/alp-1313
-1260 tagtbgggct cagtccccga ttcctgctac tgggbacag tcaagctcag tcacctttg
           -1252 -1248-1247 Sp1
-1200 gtgagcctt ccctagttct tggagtctta aaagaatccc gtggttttcg gcagttcaga
-1140 aaccaggca ttgcgctgc gtggtccacg ggagttgctc tggtggagct cggatgcccg
-1080 gggctgcag gaaagaaggt ggcagcgccc cctacgcgga cgcagggcgc tgctgtgctc
-1020 agcagaaggg agcaaatggg atggagcttc agccaccctg gaagccgcc cttgcgcct
-960 tcctccctcc cttctctttt ccaaatcaa gcccctctt caacatcaag aactctccgc
                                    Sp1 -929                        -905
-900 actcctgga cctctcagag cctctcctca tttactcttt ccaatgcgct ggctcaaaag
-840 agcctagata agaacaccaa cttctggctg tccttccagc aaagagttag gagttaactt
                       EBP/alp         -815
-780 ttcaatcttt ttaatctcc tttaaaaaag aatgagccat acattagggt aaccactggg
           -768 MEB-1
-720 aatcccatca cacacattgg cggcatctct cctcccgac agggtgcctc cagcacttca
                      -704  NF1
-660 gatcccagcc gagagtctgg ctgctggcgc ccagcaaacg gtgcggaaag caaaccgggg
           -653                  Ap1
-600 ctgcggaaa gcgggaggag ggggcttcc tgggtctgt tttgtctggt tggcaagact
-540 tccgaagcct ggttccctat agatgccacc cggtcgctgg cgtggaggag ggagtccggg
                        NF1 -518
-480 aagactggac ccagaattg tcccggcttt ctcccgagtg cccagcgcag cttctggctg
                     NFkB
-420 agagcgggag cgggctgagt ggggacaaag aacgcaaggg agaggtagag cctggccttg
-360 ggcagcccct ggcctggcca gaggcgcgag gccagagcc cgctgagtgg agagtagggg
                                                NF1  -322 -316  Sp1
-300 tggaggtgcc cggagcgtac ccagcgccgg gagtacctcc cgctcacacc tgggctgca
                                                             Sp1 -241
-240 gttccctggg tggccgccga gacgctggcc cgggctggag ggatccgggg cgggggacgg
                                                        -194-191-190 Sp1/Egr1
-180 gcgcggggc ggggctcgtc acgtggagag gcgcgcaggg acgggcgggg cggggcgcg
     -180-178 Egr1      -166          Sp1/Egr1-149 147-143 -140
-120 cgccggctc cttaaaggcg cgcgagcgga gcgcgaggt ggctctgtgg ccgcaggcgc
                                   -93-92       -66 Sp1 -60
-60 aggcccgggc gacagccgag acgtggagcg cgccggctcg ctgcagctcc gggactcaac
                 -46 ATF-2
+1 ATG
```

FIGURE 18

| Products | Polymorphisms detected | Size (bp) | Primers | Melting temp | Thermal profile |
|---|---|---|---|---|---|
| Amplicon 1 | -46,-86,-92,-178 -190,-191,-194,-241 | 271 | SEQ ID No: 184 5' AGTACCTCCCGCTCACACCTCG 3' SEQ ID No: 185 3' ATGTTGAGTCCCGCAGCTGCAG 5' | 70.2 °C | 95 °C 3 min, {95 °C 30 s, 56 °C 30 s, 72 °C 1 min}× 38 cycles, hold 4 °C |
| Amplicon 3 | -316,-322 | 195 | SEQ ID No: 186 5' CGCGAGCGGCCTCGAGTGCGCACAAA 3' SEQ ID No: 187 5' CGGCCGGCCACCCAGGGAACTGC 3' | 65.7 °C | 95 °C 3 min, {94 °C 30 s, 70 °C 1 min} × 5 cycles {94 °C 30 s, 65 °C 1 min}×5 cycles {94 °C 20 s, 66 °C 1 min}×25 cycles, 68 °C 3 min, hold 4 °C |
| Amplicon 4 | -322,-518 | 373 | SEQ ID No: 188 5' CAGCACTTCAGATCCCAGCCGAGAG 3' SEQ ID No: 189 5' CCACCCCCAGTCTCCACCGA 3' | 64.4 °C | 95 °C 3 min, {94 °C 30 s, 68 °C 1 min}×5 cycles {94 °C 30 s, 66 °C 1 min}×5 cycles {94 °C 20 s, 64 °C 1 min}×25 cycles, 68 °C 3 min, hold 4 °C |
| Amplicon 5 | -653,-704 | 215 | SEQ ID No: 190 5' GAATGAGCCATACATTAGGGTAACC 3' SEQ ID No: 191 5' CGGAAGTCTTGCCAACCAGACAA 3' | 61.7 °C | 95 °C 10 min, [94 °C 20 s, 58 °C {-0.5 °C to 55 °C} 1 min, 72 °C 1 min]× 14 cycles {94 °C 20 s, 51 °C 1 min, 72 °C 1 min}× 20 cycles, 72 °C 10 min, hold 4 °C |
| Amplicon 6 | -768,-813 | 178 | SEQ ID No: 192 5' TCTTTCCAATCCGCTGGCTCAAAAG 3' SEQ ID No: 193 5' AGGAGAGATGCCGCCAATGTCTG 3' | 58.1 °C | 95 °C 2 min, [95 °C 30 s, 67 °C {-0.5 °C to 60 °C} 30 s, 72 °C 30 s]× 14 cycles {95 °C 30 s, 60 °C 30 s, 72 °C 30 s}× 19 cycles, 72 °C 5 min, hold 4 °C |
| Amplicon 7 | -905,-929 | 209 | SEQ ID No: 194 5' GGAGCAAATGGCGATGGAGCTTCA 3' SEQ ID No: 195 5' CGAAGGACAGCCAGAACTTGGTGTT 3' | 61.5 °C | 95 °C 2 min, [95 °C 30 s, 67 °C {-0.5 °C to 60 °C} 30 s 72 °C 30 s]× 14 cycles {95 °C 30 s, 60 °C 30 s, 72 °C 30 s}× 19 cycles, 72 °C 5 min, hold 4 °C |
| Amplicon 9 | -1247,-1248,-1252 rs3826029(-1313) -1372,-1382,-1452 | 340 | SEQ ID No: 196 5' CTGTCTGCTCTCCAGGGACC 3' SEQ ID No: 197 3' GACTCCAAGAACTAGGCAAACGC 5' | 57.6 °C | 95 °C 10 min, [94 °C 20 s, 62 °C {-0.5 °C to 55 °C} 1 min, 72 °C 1 min]× 15 cycles {94 °C 30 s, 55 °C 1 min, 72 °C 1 min}× 20 cycles, 72 °C 10 min, hold 4 °C |
| Amplicon 10 | rs6494165(-1512) -1587 | 269 | SEQ ID No: 198 5' CTCCCTTTACCACACACTAATCCC 3' SEQ ID No: 199 3' CATAACTGCGGTAAGAGCCTAGA 5' | 61.6 °C | 95 °C 2 min, [95 °C 30 s, 64.4 °C {-0.5 °C to 55 °C} 30 s, 72 °C 30 s]× 15 cycles {95 °C 30 s, 57.4 °C 30 s, 72 °C 30 s}× 20 cycles, 72 °C 5 min, hold 4 °C |
| Amplicon 11 | rs3087454(-1831) | 162 | SEQ ID No: 200 5' AAGCAGTTCTGCTTTCAGGAATCTG 3' SEQ ID No: 201 3' ACTGGTCATGGCGACTGTAACAACAC 5' | 56.6 °C | 95 °C 10 min, [94 °C 20 s, 62 °C {-0.5 °C to 55 °C} 1 min, 72 °C 1 min]× 14 cycles {94 °C 20 s, 55 °C 1 min, 72 °C 1 min}× 20 cycles, 72 °C 10 min, hold 4 °C |

Figure 20

PROMOTER VARIANTS OF THE ALPHA-7 NICOTINIC ACETYLCHOLINE RECEPTOR

This is a Continuation-In-Part of application Ser. No. 10/723,940, filed Nov. 26, 2003 now U.S. Pat. No. 7,572,580 which is a Continuation-In-Part of application Ser. No. 08/956,518, filed on Oct. 23, 1997 now issued as U.S. Pat. No. 6,875,606.

STATEMENT OF GOVERNMENT SUPPORT

This invention was made with government support under National Institutes of Health Grants DA09457, DA12231, AG00029, MH36321, and MH44212, and the Veterans Affairs Medical Research Service. The Government has certain rights in the invention.

FIELD OF THE INVENTION

The present invention is related to the alpha-7 neuronal nicotinic acetylcholine receptor gene. In particular, the present invention provides the human alpha-7 gene. In addition, the present invention provides methods and compositions for the diagnosis and treatment of schizophrenia. Such compositions include, but are not limited to, polymorphisms within the human alpha-7 gene promoter core and/or 5' upstream regulatory regions.

BACKGROUND OF THE INVENTION

Schizophrenia is the most common chronic psychotic disorder of humans, affecting approximately one percent of the population worldwide (Eaton, Epidemiol Rev, 7:105, 1985). The mean lifetime risk of schizophrenia has been estimated at one percent (Eaton, supra, 985). As the onset of disease usually occurs early in life, and results in serious chronic impairment of cognition, behavior, and emotional state, schizophrenia is a major social problem in terms of cost, lost potential and productivity, and family stress. Furthermore, estimates indicate that the mortality of schizophrenic patients is twice that of the general population (Tsuang et al., Arch Gen Psychiat, 36:1295, 1979). The medical care of schizophrenic patients also presents a significant challenge, as the patients are often unable to provide an accurate medical history, and have difficulty complying with medical treatment.

The essential features of schizophrenia are the presence of psychotic symptoms during some phase of the illness, a chronic course, and deterioration in function. However, no combination of signs or symptoms is truly pathognomic of the disease. The DSM-IV criteria for schizophrenia (See, Hyman, "Schizophrenia," in Dale and Federman (eds.), *Scientific American Medicine*, New York, N.Y., 13 VII: 1-5, 1994), requires a duration of at least six months, and a deterioration in function. Psychotic symptoms typically exhibited by schizophrenia patients include disturbances in perception, abnormalities in thought content, and abnormalities in the form of thought. Perceptual disturbances typically consist of hallucinations and illusions. The course of schizophrenia is variable, although it is generally characterized by periods with exacerbation of psychotic symptoms, followed by periods of remission. Over a period of years, social and cognitive function usually deteriorates. Suicide attempts and depression are common. As measured by frequency and severity of relapses, continuing symptoms, and overall functioning, approximately 80% of schizophrenics have a poor outcome (Breier et al., Arch Gen Psychiat, 48:239, 1991).

Although family, twin, and adoption studies indicate that schizophrenia has a significant genetic component, these studies also show that the inheritance of schizophrenia is complex, involving an uncertain mode of transmission, incomplete penetrance, and probable genetic heterogeneity (Risch, Genet Epidemiol, 7:3, 1990; and Tsuang, Brit J Psychiat, 163:299, 1993). Linkage studies using schizophrenia and related psychiatric cases as phenotypes have found possible loci for schizophrenia at various chromosomal sites in subsets of families (Pulver et al., Am J Med Genet, 54:44, 1994; Coon et al., Am J Med Genet, 54:12, 1994; Wang et al., Nature Genet, 10:41, 1995; and Silverman et al., Am J Med Genet, 67:162, 1996). However, the findings do not account completely for the inheritance of schizophrenia, nor do they delineate which aspects of this multifactoral illness might be influenced by a specific locus.

A variety of psychiatric disorders may mimic schizophrenia and the symptoms of many disorders are similar. Thus, diagnosis has been based on the course of illness (for example, acute onset and episodic course in mania, compared with an insidious onset and chronic course in schizophrenia). In addition to schizophrenia, psychotic symptoms may also occur as a result of metabolic disturbances, structural brain lesions, other medical conditions, or drug toxicity. Thus, the differential diagnosis of schizophrenia must take into consideration such medical conditions as central nervous system neoplasm, hyperviscosity syndromes (i.e., due to hematologic malignancy), paraneoplastic syndromes, anoxia and postanoxic encephalopathy, hypertensive encephalopathy, AIDS encephalopathy, encephalitis, meningitis, brain abscess, Lyme disease, neurosyphilis, acute intermittent porphyria, Addison's disease, Cushing's disease, hepatic encephalopathy, hypocalcemia, hypercalcemia, hypoglycemia, hypothyroidism, hyperthyroidism, Alzheimer's disease, complex partial seizures, Huntington's disease, multiple sclerosis, stroke, Wilson's disease, folic acid deficiency, pellagra, vitamin $B_{12}$ deficiency, and lupus cerebritis. Some drugs, such as alcohol, high-dose cocaine, high-dose amphetamines, marijuana, phencyclidine (PCP), hallucinogens, sedative-hypnotics, meperidine, non-steroidal anti-inflammatory drugs, pentazocine and other opiate mixed agonist-antagonists, anti-tuberculosis drugs (e.g., cycloserine, isoniazid, rifampin), other antimicrobials, anticholinergic anti-parkinsonians, anti-histamines (e.g., diphenhydramine), atropine and derivatives, cyclic antidepressants, low-potency antipsychotic drugs (e.g., thioridazine and clozapine), meclizine, scopolamine, anti-arrhythmic (e.g., amiodarone, digitalis, and procainamide), captopril, amantadine, $D_2$ dopamine receptor antagonists (e.g., bromocriptine, and pergolide), levodopa, estrogens, testosterone, glucocorticoids and adrenocorticotropic hormone (ACTH), thyroid replacement overdose, cimetidine, ranitidine, dextroamphetamine, methylphenidate, and over-the-counter decongestants (e.g., pseudoephedrine), diet pills, and pep pills, are commonly associated with psychotic symptoms.

Treatment of schizophrenic patients usually involves the use of anti-psychotic drugs (e.g., haloperidol, haloperidol-like drugs, and atypical neuroleptics such as clozapine), maintenance of a safe, predictable environment, and supportive psychotherapy to improve social and coping skills of patients. Stress reduction also appears to prevent relapses. While these drugs are useful in treating the symptoms of schizophrenia, there are also problems associated with their use. For example, the use of clozapine is complicated by the idiosyncratic occurrence of agranulocytosis, necessitating weekly monitoring of the white blood cell counts of patients taking this drug (See, Hyman, supra, 1994).

Despite advances in treatment and diagnostic methods, there remains a need for methods to diagnose and treat schizophrenic patients. Indeed, methods to diagnose and screen large populations for genetic component(s) associated with schizophrenia, as well as other psychoses are needed in order to provide reliable diagnoses that are not dependent upon the multifactoral criteria presently in use. Improved methods of treatment are also needed, including drugs and other therapeutics that do not have the side effects and other undesirable properties associated with the currently used drugs.

SUMMARY OF THE INVENTION

The present invention is related to the alpha-7 neuronal nicotinic acetylcholine receptor gene. In particular, the present invention provides the human alpha-7 gene. In addition, the present invention provides methods and compositions for the diagnosis and treatment of schizophrenia. Such compositions include, but are not limited to, polymorphisms within the human alpha-7 gene promoter core and/or 5' upstream regulatory regions.

In one embodiment, the present invention contemplates a composition comprising an isolated 5' upstream regulatory nucleotide sequence of a human alpha-7 nicotinic receptor, wherein the nucleotide sequence comprises at least one polymorphism. In one embodiment, the sequence comprises a portion of SEQ ID NO:181. In one embodiment, the at least one polymorphism comprises one or more of those listed in Table 23. In one embodiment, the polymorphism is rs3087454 (−1831 bp).

In one embodiment, the present invention contemplates a composition comprising an isolated regulatory binding site sequence encoded by an isolated 5' upstream regulatory nucleotide sequence of a human alpha-7 nicotinic receptor, wherein the nucleotide sequence comprises at least one polymorphism. In one embodiment, the sequence comprises a portion of SEQ ID NO:181. In one embodiment, the at least one polymorphism comprises one or more of those listed in Table 23. In one embodiment, the polymorphism is rs3087454 (−1831 bp).

In one embodiment, the present invention contemplates a method of identifying individuals predisposed to schizophrenia comprising: providing a nucleic acid from a human subject; wherein the nucleic acid comprises an α7 regulatory allele; detecting the presence of at least one polymorphism within the α7 regulatory allele; and correlating the presence of the at least one polymorphism with a predisposition to schizophrenia. In some embodiments, the at least one polymorphism comprises one or more of those listed in Table 23. In one embodiment, the polymorphism is rs3087454 (−1831 bp). In other embodiments the allele comprises two or more polymorphisms. In one embodiment, the at least one polymorphism comprises a promoter polymorphism that contributes to reduced α7 regulatory protein transcription. In one embodiment, the detecting comprises at least one technique selected from the group including, but not limited to, polymerase chain reaction, heteroduplex analysis, single stand conformational polymorphism analysis, denaturing high performance liquid chromatography, ligase chain reaction, comparative genome hybridization, Southern blotting or nucleic acid sequencing. In some embodiments, the nucleic acid from the subject is derived from a sample selected from the group including, but not limited to, a biopsy material or blood. In one embodiment, the method further comprises step d) providing a diagnosis to the subject based on the presence or absence of the at least one polymorphism. In one embodiment, the diagnosis differentiates schizophrenia from other forms of mental illness.

In one embodiment, the present invention contemplates a method, comprising: a) providing; i) a biological sample suspected of containing a first polynucleotide encoding an α7 regulatory protein; ii) a second polynucleotide comprising at least a portion of SEQ ID NO: 181, wherein said portion is capable of hybridizing to said first polynucleotide; b) hybridizing said first polynucleotide to said second polynucleotide to produce a hybridization complex; c) detecting an α7 nicotinic acid regulatory allele within said first polynucleotide, wherein said allele comprises at least one polymorphism. In one embodiment, the at least one polymorphism is rs3087454 (−1831 bp). In one embodiment, the at least one polymorphism comprises one or more of those listed in Table 23. In one embodiment, the method further comprises step (d) detecting said hybridization complex, wherein said complex correlates with said first polynucleotide. In one embodiment, the biological sample is selected from the group consisting of brain tissue and blood. In one embodiment, the biological sample is from a human. In one embodiment, the human is suspected of suffering from a condition selected from the group including, but not limited to, schizophrenia, small cell lung carcinoma, breast cancer, or nicotine-dependent illness. In one embodiment, the method further comprises, before step (b) amplifying said first polynucleotide by polymerase chain reaction.

In one embodiment, the present invention contemplates a composition comprising a vector comprising a 5' upstream regulatory nucleotide sequence of a human alpha-7 nicotinic receptor, wherein said sequence comprises at least one polymorphism. In one embodiment, the nucleotide sequence comprises at least a portion of SEQ ID NO:181. In one embodiment, the polymorphism is rs3087454 (−1831 bp). In one embodiment, the at least one polymorphism comprises one or more of those listed in Table 23.

In one embodiment, the present invention contemplates a composition comprising a host cell transformed with a vector comprising a 5' upstream regulatory nucleotide sequence of a human alpha-7 nicotinic receptor, wherein the nucleotide sequence comprises a polymorphism. In one embodiment, the nucleotide sequence comprises at least a portion of SEQ ID NO:181. In one embodiment, the polymorphism is rs3087454 (−1831 bp). In one embodiment, the at least one polymorphism comprises one or more of those listed in Table 23. In one embodiment, the host cell is selected from the group including, but not limited to, bacteria, yeast, amphibian, or mammalian cells. In one embodiment, the host cell is a human cell. In one embodiment, the host cell is a cell line. In one embodiment, the host cell is contained within an animal.

In one embodiment, the present invention contemplates a composition comprising hybridization complex, wherein the complex comprises a first polynucleotide sequence comprising at least fifteen nucleotides, wherein said first polynucleotide is hybridized, under stringent conditions, to at least a portion of a second polynucleotide sequence, wherein the second polynucleotide sequence comprises at least a portion of SEQ ID NO:181 and at least one polymorphism. In one embodiment, the polymorphism is rs3087454 (−1831 bp). In one embodiment, the at least one polymorphism comprises one or more of those listed in Table 23.

In one embodiment, the present invention contemplates a method for amplifying a nucleic acid derived from a biological sample comprising; providing the biological sample is suspected of containing nucleic acid encoding an alpha-7 nicotinic acid gene regulatory protein and a test sample suspected of containing amplifiable nucleic acid encoding the alpha-7 regulatory protein; isolating the amplifiable nucleic acid from the test sample; combining the amplifiable nucleic acid with amplification reagents, and at least two primers selected from the group comprising SEQ ID NO:182, SEQ ID NO: 183, and primers having the nucleic acid sequence set forth in FIG. 20 to form a reaction mixture; and combining the reaction mixture with an amplification enzyme under conditions wherein the amplifiable nucleic acid is amplified to form amplification product. In one embodiment, the method further comprises the step of detecting the amplification product.

In one embodiment, the method further comprises the step of detecting the amplification product by hybridizing the amplification product with a probe having a nucleic acid sequence is selected from a group comprising SEQ ID NO: 182, SEQ ID NO: 183, or the sequences set forth in FIG. 20 SEQ ID NOS: 184-201. In one embodiment, the test sample is a sample selected from the group including, but not limited to, brain tissue or blood. In one embodiment, the test sample is from a human. In one embodiment, the human is suspected of suffering from a condition selected from the group including, but not limited to, schizophrenia, small cell lung carcinoma, breast cancer, and nicotine-dependent illness.

In one embodiment, the present invention contemplates a method for amplifying a nucleic acid from a sample suspected of containing nucleic acid encoding an alpha-7 nicotinic acid receptor gene regulatory protein comprising the steps of: providing a test sample suspected of containing amplifiable nucleic acid encoding the alpha-7 regulatory protein; isolating the amplifiable nucleic acid from the test sample; combining the amplifiable nucleic acid with amplification reagents, and a first primer set comprising at least two primers selected from the group consisting of SEQ ID NO: 182, SEQ ID NO: 183, and those set forth in FIG. 20 SEQ ID NOS: 184-201, to form a first reaction mixture; combining the reaction mixture with an amplification enzyme under conditions wherein the amplifiable nucleic acid is amplified to form a first amplification product; combining the first reaction mixture with amplification reagents, and a second primer set comprising at least two primers selected from the group consisting of the sequences set forth in Table 20 SEQ ID NOS: 184-201, to form a second reaction mixture; combining the second reaction mixture with an amplification enzyme under conditions wherein the amplifiable nucleic acid is amplified to form a second amplification product; and detecting the first or second amplification product. In one embodiment, the method further comprises the step of detecting the amplification product by hybridizing the amplification product with a probe having a nucleic acid sequence selected from the group consisting of the nucleic acid sequence set forth in FIG. 20. In one embodiment, the test sample is a sample selected from the group including, but not limited to, brain tissue or blood. In one embodiment, the test sample is derived from a human. In one embodiment, the human is suspected of suffering from a condition selected from the group including, but not limited to, schizophrenia, small cell lung carcinoma, breast cancer, and nicotine-dependent illness.

In one embodiment, the present invention contemplates a kit for determining if a subject is predisposed to schizophrenia, comprising: at least one reagent suitable for use in specifically detecting at least one polymorphism in an α7 nicotinic acid receptor regulatory allele; and instructions for determining whether a subject is predisposed to schizophrenia. In some embodiments, the at least one polymorphism comprises one or more of those listed in Table 23. In preferred embodiments, the at least one polymorphism comprises a promoter polymorphism that contributes to reduced α7 regulatory protein transcription. In one embodiment, the at least one reagent comprises a nucleic acid probe that hybridizes under stringent conditions to a nucleic acid sequence selected from the group including, but not limited to, the coding strand of the α7 regulatory allele, or the noncoding strand of the α7 regulatory allele. In one embodiment, the at least one reagent comprises a sense primer and an antisense primer flanking the at least one polymorphism in the α7 regulatory allele. In one embodiment, at least one of the primers comprises a fluorescent tag. In one embodiment, the instructions comprise instructions required by the United States Food and Drug Administration for use in in vitro diagnostic products.

In one embodiment, the present invention contemplates a method of screening compounds, comprising: providing: i) at least one cell comprising an α7 nicotinic acid receptor regulatory allele with at least one polymorphism, and ii) one or more test compounds; and contacting the at least one cell with the test compound; and detecting a change in α7 regulatory allele expression in the at least one cell in the presence of the test compound relative to the absence of the test compound. In one embodiment, the detecting comprises detecting α7 regulatory allele mRNA. In one embodiment, the detecting comprises detecting α7 regulatory protein. In one embodiment, the cell is a neuroblastoma cell. In one embodiment, the test compound comprises a drug. In one embodiment, the at least one polymorphism comprises a promoter polymorphism that contributes to reduced α7 transcription.

In one embodiment, the present invention contemplates a method of screening compounds, comprising: providing: i) at least one cell comprising an α7 nicotinic acid receptor promoter in operable combination with a reporter gene, wherein said α7 promoter comprises a regulatory allele having at least one polymorphism, and ii) one or more test compounds; and contacting the at least one cell with the test compound; and detecting a change in expression of the reporter gene in the at least one cell in the presence of the test compound relative to the absence of the test compound. In one embodiment, the detecting comprises detecting reporter gene mRNA or polypeptide. In one embodiment, the detecting comprises detecting reporter gene function. In one embodiment, the cell is a neuroblastoma cell. In one embodiment, the test compound comprises a drug. In one embodiment, the reporter gene is the firefly luciferase gene.

In one embodiment, the present invention contemplates a method of identifying individuals predisposed to schizophrenia, comprising: providing a nucleic acid sample from a subject, the sample containing an α7 nicotinic acid receptor regulatory allele; correlating the identity of the α7 regulatory allele with a predisposition to schizophrenia. In one embodiment, the identity of the α7 regulatory allele is determined using at least one technique selected from the group including, but not limited to, polymerase chain reaction, heteroduplex analysis, single strand conformational polymorphism analysis, denaturing high performance liquid chromatography, ligase chain reaction, comparative genome hybridisation, Southern blotting or nucleic acid sequencing. In one embodiment, the nucleic acid sample from the subject is selected from the group including, but not limited to, a biopsy material or blood. In one embodiment, the method further comprises a step providing a diagnosis to the subject based on the identity of the α7 regulatory allele.

In one embodiment, the present invention contemplates a method for producing anti-α7 nicotinic acid receptor regulatory protein antibodies, comprising, exposing an animal having immunocompetent cells to an immunogen comprising at least an antigenic portion of α7 regulatory protein, under conditions such that immunocompetent cells produce antibodies directed against the portion of α7 regulatory protein. In one embodiment, the α7 regulatory binding site has affinity for a α7 regulatory peptide or protein. In one embodiment, the method further comprises the step of harvesting the antibodies. In one embodiment, the method further comprises the step of fusing the immunocompetent cells with an immortal cell line under conditions such that a hybridoma is produced. In one embodiment, the immunogen comprises a fusion protein.

In one embodiment, the present invention contemplates a method for detecting abnormal α7 nicotinic acid receptor regulatory gene expression comprising the steps of: a) providing a biological sample suspected of containing a test α7 regulatory gene; and a control containing a quantitated α7 regulatory gene; and b) comparing the test α7 regulatory gene in the sample with the quantitated α7 regulatory gene in the control to determine the relative concentration of the test α7 regulatory gene in the sample. In one embodiment, the control contains a higher concentration of quantitated α7 regulatory gene than the concentration of the test α7 regulatory gene in the sample. In one embodiment, the biological sample comprises a patient sample, wherein said patient sample comprises reduced α7 regulatory protein. In one embodiment, the sample contains a normal amount of the α7 regulatory protein. In one embodiment, the comparing comprises a detection method selected from the group including, but not limited to, Western blot analysis, Northern blot analysis, Southern blot analysis, denaturing polyacrylamide gel electrophoresis, reverse transcriptase-coupled polymerase chain reaction, enzyme-linked immunosorbent assay, radioimmunoassay, or fluorescent immunoassay. In one embodiment, the method detects α7 regulatory gene or mRNA in the genome of the animal source of the biological sample. In one embodiment, the method detects the expression of α7 regulatory protein in the genome of the animal source of the biological sample. In one embodiment, the method detects the presence of abnormal or mutated α7 regulatory proteins or gene sequences in the biological sample.

In one embodiment, the present invention provides an isolated nucleotide sequence encoding at least a portion of the human alpha-7 nicotinic receptor, wherein the sequence is selected from the group consisting of SEQ ID NOS:84-103. In an alternative embodiment, the present invention provides an isolated regulatory peptide sequence that binds to the isolated nucleotide sequence, wherein the nucleotide sequence is selected from the group consisting of SEQ ID NOS:84-103. In another embodiment, the nucleotide sequence further comprises 5' and 3' flanking regions. In yet another embodiment, the nucleotide sequence further comprises intervening regions. In a further embodiment, the present invention provides an isolated polynucleotide sequence comprising a combination of two or more nucleotide sequences, wherein the nucleotide sequences are selected from the group consisting of SEQ ID NOS:84-103. It is not intended that the combination comprise any particular number or order of these nucleotide sequences, nor is it intended that the combination be limited to the inclusion of any particular nucleotide sequence.

In another embodiment, the present invention provides vectors comprising a nucleotide sequence, wherein the nucleotide sequence comprises at least one nucleotide sequence selected from the group consisting of SEQ ID NOS:84-103. In another embodiment, the present invention provides a host cell transformed with a vector comprising a nucleotide sequence, wherein the nucleotide sequence comprises at least one nucleotide sequence selected from the group consisting of SEQ ID NOS:84-103. In one embodiment, the host cell is selected from the group consisting of bacteria, yeast, amphibian, and mammalian cells. In one preferred embodiment, the host cell is a human cell. In an alternative preferred embodiment, the host cell is a cell line, while in another preferred embodiment, the host cell is contained within an animal.

The present invention also provides a first polynucleotide sequence comprising at least fifteen nucleotides, which hybridizes under stringent conditions to at least a portion of a second polynucleotide sequence, wherein the second polynucleotide sequence is selected from the polynucleotide sequences selected from the group consisting of SEQ ID NOS:84-103.

The present invention also provides methods for detection of a polynucleotide encoding alpha-7 protein in a biological sample suspected of containing the polynucleotide encoding alpha-7, comprising the step of hybridizing at least a portion of a polynucleotide sequence selected from the group consisting of SEQ ID NOS:9-11, and 84-103, to nucleic acid of the biological sample to produce an hybridization complex. In one embodiment, the method further comprises the step of detecting the hybridization complex, wherein the presence of the complex correlates with the presence of a polynucleotide encoding alpha-7 in the biological sample. In another embodiment, the biological sample is a sample selected from the group consisting of brain tissue and blood. In one preferred embodiment, the biological sample is from a human. In yet another embodiment, the human is suspected of suffering from a condition selected from the group consisting of schizophrenia, small cell lung carcinoma, breast cancer, and nicotine-dependent illness. In yet another preferred embodiment of the method, the nucleic acid of the biological sample is amplified by the polymerase chain reaction prior to hybridization.

The present invention also provides methods for amplification of nucleic acid from a sample suspected of containing nucleic acid encoding alpha-7, comprising the steps of: providing a test sample suspected of containing amplifiable nucleic acid encoding alpha-7; isolating the amplifiable nucleic acid from the test sample; combining the amplifiable nucleic acid with amplification reagents, and at least two primers selected from the group consisting of primers having the nucleic acid sequence set forth in SEQ ID NOS:1-8, and 12-83 to form a reaction mixture; and combining the reaction mixture with an amplification enzyme under conditions wherein the amplifiable nucleic acid is amplified to form amplification product. In one embodiment, the method further comprises the step of detecting the amplification product. In an alternative embodiment, the detecting is accomplished by hybridization of the amplification product with a probe having the nucleic acid sequence is selected from group of the sequences set forth in SEQ ID NO:9-11. In one preferred embodiment, the test sample is a sample selected from the group consisting of brain tissue and blood. In an alternative preferred embodiment, the test sample is from a human. In yet another embodiment, the human is suspected of suffering from a condition selected from the group consisting of schizophrenia, small cell lung carcinoma, breast cancer, and nicotine-dependent illness.

The present invention also provides methods for amplification of nucleic acid from a sample suspected of containing nucleic acid encoding alpha-7 comprising the steps of: providing a test sample suspected of containing amplifiable nucleic acid encoding alpha-7; isolating the amplifiable nucleic acid from the test sample; combining the amplifiable nucleic acid with amplification reagents, and a first primer set comprising at least two primers selected from the group consisting of the sequences set forth in SEQ ID NOS:65-70, to form a first reaction mixture; combining the reaction mixture with an amplification enzyme under conditions wherein the amplifiable nucleic acid is amplified to form a first amplification product; combining the first reaction mixture with amplification reagents, and a second primer set comprising at least two primers selected from the group consisting of the sequences set forth in SEQ ID NOS:57-59, 61, 63, 67, and 73-75, to form a second reaction mixture; combining the second reaction mixture with an amplification enzyme under conditions wherein the amplifiable nucleic acid is amplified to form a second amplification product; and detecting the first or second amplification product.

In one preferred embodiment of the method, the detecting comprises hybridizing the amplification product with a probe having a nucleic acid sequence selected from the group consisting of the nucleic acid sequence set forth in SEQ ID NOS:9-11. In yet another embodiment, the test sample is a sample selected from the group consisting of brain tissue and blood. In another preferred embodiment of the method, the test sample is from a human. In a further embodiment, the human is suspected of suffering from a condition selected from the group consisting of schizophrenia, small cell lung carcinoma, breast cancer, and nicotine-dependent illness.

Additionally, the present invention provides methods of identifying individuals predisposed schizophrenia comprising: providing a nucleic acid from a human subject; wherein the nucleic acid comprises an α7 allele; detecting the presence of at least one polymorphism within the α7 allele; and correlating the presence of the at least one polymorphism with a predisposition to schizophrenia. In some embodiments the at least one polymorphism comprises one or more of a −241 A to G substitution, a −194 G to C substitution, a −191 G to A substitution, a −190 G insertion, a −180 G to C substitution, a −178 CGGGGG insertion, a −178 G deletion, a −166 C to T substitution, a −143 G to A substitution, a −140 CGGG insertion, a −93 C to G substitution, a −92 G to A substitution, a −86 C to T substitution, and a 46 G to T substitution. In other embodiments the at least one polymorphism comprises two or more polymorphisms. In some preferred embodiments, the at least one polymorphism comprises a promoter polymorphism that contributes to reduced α7 transcription. The present invention provides methods wherein the detecting step is accomplished using at least one technique selected from the group consisting of polymerase chain reaction, heteroduplex analysis, single stand conformational polymorphism analysis, denaturing high performance liquid chromatography, ligase chain reaction, comparative genome hybridisation, Southern blotting and sequencing. In some embodiments, the nucleic acid from the subject is derived from a sample selected from the group consisting of a biopsy material and blood. Moreover embodiments are provided which further comprise step d) providing a diagnosis to the subject based on the presence or absence of the at least one polymorphism. In preferred embodiments, the diagnosis differentiates schizophrenia from other forms of mental illness.

The present invention also provides kits for determining if a subject is predisposed to schizophrenia, comprising: at least one reagent suitable for use in specifically detecting at least one polymorphism in an α7 allele; and instructions for determining whether a subject is predisposed to schizophrenia. In some embodiments, the at least one polymorphism comprises one or more of a −241 A to G substitution, a −194 G to C substitution, a −191 G to A substitution, a −190 G insertion, a −180 G to C substitution, a −178 CGGGGG insertion, a −178 G deletion, a −166 C to T substitution, a −143 G to A substitution, a −140 CGGG insertion, a −93 C to G substitution, a −92 G to A substitution, a −86 C to T substitution, and a −46 G to T substitution. In preferred embodiments, the at least one polymorphism comprises a promoter polymorphism that contributes to reduced α7 transcription. The present invention further provides embodiments in which the at least one reagent comprises a nucleic acid probe that hybridizes under stringent conditions to a nucleic acid sequence selected from the group consisting of the coding strand of the α7 gene, and the noncoding strand of the α7 gene. In some preferred embodiments, the at least one reagent comprises a sense primer and an antisense primer flanking the at least one polymorphism in the α7 allele. In a subset of these, at least one of the primers comprises a fluorescent tag. Moreover, in some embodiments, the instructions comprise instructions required by the United States Food and Drug Administration for use in in vitro diagnostic products.

Also provided by the present invention are methods of screening compounds, comprising: providing: i) at least one cell comprising an α7 allele with at least one polymorphism, and ii) one or more test compounds; and contacting the at least one cell with the test compound; and detecting a change in α7 expression in the at least one cell in the presence of the test compound relative to the absence of the test compound. In some embodiments the detecting comprises detecting α7 mRNA, while in others the detecting comprises detecting α7 polypeptide. In preferred embodiments, the cell is a neuroblastoma cell. In other preferred embodiments, the test compound comprises a drug. Moreover, in particularly preferred embodiments, the at least one polymorphism comprises a promoter polymorphism that contributes to reduced α7 transcription.

In alternative embodiments, the present invention provides methods of screening compounds, comprising: providing: i) at least one cell comprising an α7 promoter in operable combination with a reporter gene, wherein said α7 promoter comprises at least one polymorphism, and ii) one or more test compounds; and contacting the at least one cell with the test compound; and detecting a change in expression of the reporter gene in the at least one cell in the presence of the test compound relative to the absence of the test compound. In some embodiments the detecting comprises detecting reporter gene mRNA or polypeptide, while in others the detecting comprises detecting reporter gene function. In preferred embodiments, the cell is a neuroblastoma cell. In other preferred embodiments, the test compound comprises a drug. In an exemplary embodiment, the reporter gene is the firefly luciferase gene.

Furthermore, the present invention provides methods of identifying individuals predisposed to schizophrenia, comprising: providing a nucleic acid sample from a subject, the sample containing an α7 allele; correlating the identity of the α7 allele with a predisposition to schizophrenia. In some embodiments, the identity of the α7 allele is determined using at least one technique selected from the group consisting of polymerase chain reaction, heteroduplex analysis, single stand conformational polymorphism analysis, denaturing high performance liquid chromatography, ligase chain reaction, comparative genome hybridisation, Southern blotting and sequencing. In preferred embodiments, the nucleic acid sample from the subject is selected from the group consisting of a biopsy material and blood. Moreover embodiments are provided which further comprise step c) providing a diagnosis to the subject based on the identity of the α7 allele.

The present invention also provides methods for producing anti-α7 antibodies (including, but not limited to antibodies directed against peptides comprising α7), comprising, exposing an animal having immunocompetent cells to an immunogen comprising at least an antigenic portion of α7 protein, under conditions such that immunocompetent cells produce antibodies directed against the portion of α7. In preferred embodiments, the α7 peptide or protein is human α7. In one embodiment, the method further comprises the step of harvesting the antibodies. In an alternative embodiment, the method comprises the step of fusing the immunocompetent cells with an immortal cell line under conditions such that a hybridoma is produced. In other embodiments, the immunogen comprises a fusion protein.

The present invention also provides methods for detecting abnormal α7 expression comprising the steps of: a) providing a sample suspected of containing test α7; and a control containing a quantitated α7; and b) comparing the test α7 in the sample with the quantitated α7 in the control to determine the relative concentration of the test α7 in the sample. In one embodiment of the method, the control contains a higher concentration of quantitated α7 than the concentration of the test α7 in the sample. Thus, the methods are capable of identifying samples (e.g., patient samples) with reduced α7 protein. The methods also provide means to detect samples that contain a normal amount of the α7 protein. In addition, the methods may be conducted using any suitable means to determine the relative concentration of α7 in the test and control samples, including but not limited to the means selected from the group consisting of Western blot analysis, Northern blot analysis, Southern blot analysis, denaturing polyacrylamide gel electrophoresis, reverse transcriptase-coupled polymerase chain reaction, enzyme-linked immunosorbent assay, radioimmunoassay, and fluorescent immunoassay. Thus, the methods may be conducted to determine the presence of α7 in the genome of the animal source of the test sample, or the expression of α7 (mRNA or protein), as well as detect the presence of abnormal or mutated α7 proteins or gene sequences in the test samples.

In one preferred embodiment, the presence of α7 is detected by immunochemical analysis. For example, the immunochemical analysis can comprise detecting binding of an antibody specific for an epitope of α7. In another preferred embodiment of the method, the antibody comprises polyclonal antibodies, while in another preferred embodiment, the antibody is comprises monoclonal antibodies.

The antibodies used in the methods invention may be prepared using various immunogens. In one embodiment, the immunogen is a human α7 peptide to generate antibodies that recognize human α7. Such antibodies include, but are not limited to polyclonal, monoclonal, chimeric, single chain, Fab fragments, and a Fab expression library.

Various procedures known in the art may be used for the production of polyclonal antibodies to α7 (e.g., human α7). For the production of antibody, various host animals can be immunized by injection with the peptide corresponding to the human α7 epitope including but not limited to rabbits, mice, rats, sheep, goats, etc. In a preferred embodiment, the peptide is conjugated to an immunogenic carrier (e.g., diphtheria toxoid; bovine serum albumin, BSA; or keyhole limpet hemocyanin, KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

For preparation of monoclonal antibodies directed against α7, any technique that provides for the production of antibody molecules by continuous cell lines in culture may be used (See, e.g., Harlow and Lane, *Antibodies: A Laboratory Manual*, Cold Spring Harbor Laboratory Press, Cold Spring Harbor, N.Y.). These include but are not limited to: the hybridoma technique originally developed by Köhler and Milstein (Köhler and Milstein, Nature 256:495-497, 1975); the trioma technique; the human B-cell hybridoma technique (See e.g., Kozbor et al., Immunol Today, 4:72, 1983); and the EBV-hybridoma technique (Cole et al., in *Monoclonal Antibodies and Cancer Therapy*, Alan R. Liss, Inc., pp. 77-96, 1985).

In an additional embodiment of the invention, monoclonal antibodies can be produced in germ-free animals utilizing recent technology (See e.g., PCT/US90/02545). According to the invention, human antibodies may be used and can be obtained by using human hybridomas (Cote et al., Proc Natl Acad Sci USA, 80:2026-2030, 1983), or by transforming human B cells with EBV virus in vitro (Cole et al., supra, 1985).

According to the invention, techniques described for the production of single chain antibodies (U.S. Pat. No. 4,946, 778; herein incorporated by reference) can be adapted to produce α7 single chain antibodies. An additional embodiment of the invention utilizes the techniques described for the construction of Fab expression libraries (Huse et al., Science, 246:1275-1281, 1989) to allow rapid and easy identification of monoclonal Fab fragments with the desired specificity for α7.

Antibody fragments that contain the idiotype (antigen binding region) of the antibody molecule can be generated by known techniques. For example, such fragments include but are not limited to: the F(ab')2 fragment which can be produced by pepsin digestion of the antibody molecule; the Fab' fragments which can be generated by reducing the disulfide bridges of the F(ab')2 fragment, and the Fab fragments which can be generated by treating the antibody molecule with papain and a reducing agent.

In the production of antibodies, screening for the desired antibody can be accomplished by techniques known in the art including but not limited to radioimmunoassay, enzyme-linked immunosorbent assay, "sandwich" immunoassay, gel diffusion precipitin reactions, immunodiffusion assays, in situ immunoassays (using colloidal gold, enzyme or radioisotope labels, for example), Western Blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. (As is well known in the art, the immunogenic peptide should be provided free of the carrier molecule used in any immunization protocol. For example, if the peptide was conjugated to KLH, it may be conjugated to BSA, or used directly, in a screening assay.)

The foregoing antibodies can be used in methods known in the art relating to the localization and structure of α7 (e.g., for Western blotting), measuring levels thereof in appropriate biological samples, etc. The antibodies can be used to detect α7 in a biological sample from an individual. The biological sample can be a biological fluid, such as but not limited to, blood, serum, plasma, cerebrospinal fluid (CSF), and the like, containing cells. In particular, α7 can be detected from cellular sources, such as, but not limited to, brain tissue.

The biological samples can then be tested directly for the presence of α7 using an appropriate strategy (e.g., ELISA or radioimmunoassay) and format (e.g., microwells, dipstick for instance as described in International Patent Publication WO 93/03367, etc.). Alternatively, proteins in the sample can be size separated (e.g., by polyacrylamide gel electrophoresis, PAGE, in the presence or absence of sodium dodecyl sulfate, SDS), and the presence of α7 detected by immunoblotting (Western blotting). Immunoblotting techniques are generally more effective with antibodies generated against a peptide corresponding to an epitope of a protein, and hence, are particularly suited to the present invention.

The foregoing explanations of particular assay systems are presented herein for purposes of illustration only, in fulfillment of the duty to present an enabling disclosure of the invention. It is to be understood that the present invention contemplates a variety of immunochemical assay protocols within its spirit and scope.

In some preferred aspects, genomic DNA or mRNA is amplified by PCR, and the amplified DNA is tested for the presence of mutation(s). PCR amplification is well known in the art (Cameron et al., Science, 257:383-387, 1992; Saksela et al., Proc Natl Acad Sci USA, 91:1104-1108, 1994). For example, mRNA can be detected by reverse transcriptase-initiated PCR (See, e.g., Saksela et al., J Virol, 67:7423-27, 1993). PCR can be carried out (e.g., by use of a Perkin-Elmer Cetus thermal cycler and Taq polymerase, e.g., Gene Amp®, Boehringer Mannheim). The amplified PCR products can be analyzed by immobilization on membranes and hybridization with specific oligonucleotide probes, or by treatment with specific endonucleases and analysis of the products by gel electrophoresis. Labeling of the cleaved PCR products can be accomplished by incorporation of radiolabeled nucleotides, endlabeling (e.g., with $^{32}$P-ATP), or by staining with ethidium bromide.

The present invention also provides methods and compositions suitable for gene therapy for individuals deficient in α7 expression, production, or function. Viral vectors commonly used for in vivo or ex vivo targeting and therapy procedures are DNA-based vectors and retroviral vectors. Methods for constructing and using viral vectors are known in the art (See, e.g., Miller and Rosman, BioTechn, 7:980-990, 1992). Preferably, the viral vectors are replication defective, that is, they are unable to replicate autonomously in the target cell. In general, the genome of the replication defective viral vectors which are used within the scope of the present invention lack at least one region which is necessary for the replication of the virus in the infected cell. These regions can either be eliminated (in whole or in part), be rendered nonfunctional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (i.e., on the isolated DNA) or in situ, using the techniques of genetic manipulation or by treatment with mutagenic agents.

Preferably, the replication defective virus retains the sequences of its genome, which are necessary for encapsidating the viral particles. DNA viral vectors include an attenuated or defective DNA virus, including, but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred, as defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Mol. Cell. Neurosci., 2:320-330, 1991), defective herpes virus vector lacking a glycoprotein L gene (See e.g., Patent Publication RD 371005 A), or other defective herpes virus vectors (See e.g., International Patent Publication No. WO 94/21807; and International Patent Publication No. WO 92/05263); an attenuated adenovirus vector, such as the vector described (Stratford-Perricaudet et al., J Clin Invest, 90:626-630, 1992; and La Salle et al., Science, 259:988-990, 1993); and a defective adeno-associated virus vector (Samulski et al., J Virol, 61:3096-3101, 1987; Samulski et al., J Virol, 63:3822-3828, 1989; and Lebkowski et al., Mol Cell Biol, 8:3988-3996, 1988).

Preferably, for in vivo administration, an appropriate immunosuppressive treatment is employed in conjunction with the viral vector (e.g., adenovirus vector), to avoid immuno-deactivation of the viral vector and transfected cells. For example, immunosuppressive cytokines, such as interleukin-12 (IL-12), interferon-gamma (IFN-γ), or anti-CD4 antibody, can be administered to block humoral or cellular immune responses to the viral vectors. In addition, it is advantageous to employ a viral vector that is engineered to express a minimal number of antigens.

In a preferred embodiment, the vector is an adenovirus vector. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to type 2 or type 5 human adenoviruses (Ad 2 or Ad 5), or adenoviruses of animal origin (See, WO94/26914). Those adenoviruses of animal origin, which can be used within the scope of the present invention, include adenoviruses of canine, bovine, murine (e.g., Mav1, described by Beard et al., Virol, 75-81, 1990), ovine, porcine, avian, and simian (e.g., SAV) origin. Preferably, the adenovirus of animal origin is a canine adenovirus, more preferably a CAV2 adenovirus (e.g., Manhattan or A26/61 strain ATCC VR-800, for example).

In another embodiment the gene can be introduced in a retroviral vector (e.g., as described in U.S. Pat. Nos. 5,399, 346, 4,650,764, 4,980,289 and 5,124,263; all of which are herein incorporated by reference; Mann et al., Cell, 33:153, 1983; Markowitz et al., J Virol, 62:1120, 1988; PCT/US95/ 14575; EP 453242; EP178220; Bernstein et al., Genet Eng, 7:235, 1985; McCormick, BioTechnol, 3:689, 1985; International Patent Publication No. WO95/07358; and Kuo et al., Blood, 82:845, 1993). The retroviruses are integrating viruses that infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are disclosed in WO95/ 02697.

In general, in order to construct recombinant retroviruses containing a nucleic acid sequence, a plasmid containing the LTRs, the encapsidation sequence and the coding sequence is constructed. This construct is used to transfect a packaging cell line, which cell line is able to supply in trans the retroviral functions that are deficient in the plasmid. In general, the packaging cell lines are thus able to express the gag, pol and env genes. Such packaging cell lines have been described in the prior art, in particular the cell line PA317 (U.S. Pat. No. 4,861,719, herein incorporated by reference); the PsiCRIP cell line (See, WO90/02806), and the GP+envAm-12 cell line (See, WO89/07150). In addition, the recombinant retroviral vectors can contain modifications within the LTRs for suppressing transcriptional activity as well as extensive encapsidation sequences which may include a part of the gag gene (Bender et al., J Virol, 61:1639, 1987). Recombinant retroviral vectors are purified by standard techniques known to those having ordinary skill in the art.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome-mediated transfection can be used to prepare liposomes for in vivo transfection of a gene encoding a marker (Felgner et al., Proc Natl Acad Sci USA, 84:7413-7417, 1987; Mackey, et al., Proc Natl Acad Sci USA, 85:8027-8031, 1988; and Ulmer et al., Science, 259:1745-1748, 1993). The use of cationic lipids may promote encapsulation of negatively charged nucleic acids, and also promote fusion with negatively charged cell membranes (Felgner and Ringold, Science, 337:387-388, 1989). Particularly useful lipid compounds and compositions for transfer of nucleic acids are described in International Patent Publications WO95/18863 and WO96/17823, and in U.S. Pat. No. 5,459,127, herein incorporated by reference.

Other molecules are also useful for facilitating transfection of a nucleic acid in vivo, such as a cationic oligopeptide (e.g., International Patent Publication WO95/21931), peptides derived from DNA binding proteins (e.g., International Patent Publication WO96/25508), or a cationic polymer (e.g., International Patent Publication WO95/21931).

It is also possible to introduce the vector in vivo as a naked DNA plasmid. Methods for formulating and administering naked DNA to mammalian muscle tissue are disclosed in U.S. Pat. Nos. 5,580,859 and 5,589,466, both of which are herein incorporated by reference.

DNA vectors for gene therapy can be introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g., Wu et al., J Biol Chem, 267:963-967, 1992; Wu and Wu, J Biol Chem, 263:14621-14624, 1988; and Williams et al., Proc Natl Acad Sci USA, 88:2726-2730, 1991). Receptor-mediated DNA delivery approaches can also be used (Curiel et al., Hum Gene Ther, 3:147-154, 1992; Wu and Wu, J Biol Chem, 262:4429-4432, 1987).

The present invention also provides methods and compositions for the production of in vitro cell cultures that express wild-type or mutated human $\alpha 7$, as well as transgenic animals capable of expressing wild-type or mutated human $\alpha 7$. For example, the genomic $\alpha 7$ clone can be expressed in mammalian cells (e.g., cell lines, including but not limited to mammalian kidney cells, such as HEK). It is also contemplated that in some embodiments, the cells and animals also express other foreign genes in conjunction with the introduced $\alpha 7$.

The present invention also provides methods for producing non-human transgenic animals, comprising the steps of: a) introducing into an embryonal cell of a non-human animal a polynucleotide sequence encoding an $\alpha 7$ protein; b) transplanting the transgenic embryonal target cell formed thereby into a recipient female parent; and c) identifying at least one offspring containing the transgene wherein the $\alpha 7$ mRNA is overexpressed in the tissue of the offspring. In one preferred embodiment, the $\alpha 7$ mRNA is human $\alpha 7$ mRNA. In an alternative embodiment, the polynucleotide sequence encoding an $\alpha 7$ protein comprises a yeast artificial chromosome, while in another embodiment, the polynucleotide sequence encoding an $\alpha 7$ is a bacterial artificial chromosome, and in yet another embodiment, the polynucleotide sequence encoding an $\alpha 7$ protein is a P1 artificial chromosome. In a further embodiment, the non-human animal is a member of the Order Rodentia. In a preferred embodiment, the non-human animal is a mouse.

DEFINITIONS

To facilitate understanding of the invention, a number of terms are defined below.

The term "$\alpha 7$ gene" (or Alpha-7, or "Alpha-7 gene") refers to the full-length $\alpha 7$ nucleotide sequence. However, it is also intended that the term encompass fragments of the $\alpha 7$ sequence, such as those set forth as SEQ ID NOS:94, 101, 122, and 125, as well as other domains within the full-length $\alpha 7$ nucleotide sequence. Furthermore, the terms "Alpha-7 nucleotide sequence" or "Alpha-7 polynucleotide sequence" (or "$\alpha 7$ nucleotide sequence" or "$\alpha 7$ polynucleotide sequence") encompasses DNA, cDNA, and RNA (e.g., mRNA) sequences. In preferred embodiments, the $\alpha 7$ is human $\alpha 7$.

A "variant" of human $\alpha 7$ as used herein, refers to an amino acid sequence that is altered by one or more amino acids. The variant may have "conservative" changes, wherein a substituted amino acid has similar structural or chemical properties, (e.g., replacement of leucine with isoleucine). More rarely, a variant may have "nonconservative" changes (e.g., replacement of a glycine with a tryptophan). Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

The term "biologically active," as used herein, refers to a protein or other biologically active molecules (e.g., catalytic RNA) having structural, regulatory, or biochemical functions of a naturally occurring molecule. Likewise, "immunologically active" refers to the capability of the natural, recombinant, or synthetic $\alpha 7$, or any oligopeptide or polynucleotide thereof, to induce a specific immune response in appropriate animals or cells and to bind with specific antibodies.

The term "agonist," as used herein, refers to a molecule which, when bound to $\alpha 7$, causes a change in $\alpha 7$, which modulates the activity of $\alpha 7$. Agonists may include proteins, nucleic acids, carbohydrates, or any other molecules that bind to or interact with $\alpha 7$.

The terms "antagonist" or "inhibitor," as used herein, refer to a molecule which, when bound to $\alpha 7$, blocks or modulates the biological or immunological activity of $\alpha 7$. Antagonists and inhibitors may include proteins, nucleic acids, carbohydrates, or any other molecules, which bind or interact with $\alpha 7$.

The term "modulate," as used herein, refers to a change or an alteration in the biological activity of $\alpha 7$. Modulation may be an increase or a decrease in protein activity, a change in binding characteristics, or any other change in the biological, functional, or immunological properties of $\alpha 7$.

The term "derivative," as used herein, refers to the chemical modification of a nucleic acid encoding α7, or the encoded α7. Illustrative of such modifications would be replacement of hydrogen by an alkyl, acyl, or amino group. A nucleic acid derivative would encode a polypeptide that retains essential biological characteristics of the natural molecule.

The term "gene" refers to a nucleic acid (e.g., DNA) sequence that comprises coding sequences necessary for the production of a polypeptide or precursor (e.g., human α7). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene.

A genomic form or clone of a gene contains the coding region interrupted with non-coding sequences termed "introns" or "intervening regions" or "intervening sequences." Introns are segments of a gene that are transcribed into nuclear RNA (hnRNA). Introns may contain regulatory elements such as enhancers. Introns are removed or "spliced out" from the nuclear or primary transcript, and thus introns are absent in the messenger RNA (mRNA) transcript. The mRNA functions during translation to specify the sequence or order of amino acids in a nascent polypeptide.

Where "amino acid sequence" is recited herein to refer to an amino acid sequence of a naturally occurring protein molecule, "amino acid sequence" and like terms, such as "polypeptide" or "protein," are not meant to limit the amino acid sequence to the complete, native amino acid sequence associated with the recited protein molecule.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation. The present invention provides DNA sequence of the α7 promoter (SEQ ID NO:101; See, FIG. 8). The present invention also provides DNA sequence for the region located 5' to the human α7 gene (SEQ ID NO:94; See, FIG. 4).

"Peptide nucleic acid," as used herein, refers to a molecule that comprises an oligomer to which an amino acid residue, such as lysine, and an amino group have been added. These small molecules, also designated anti-gene agents, stop transcript elongation by binding to their complementary strand of nucleic acid (Nielsen et al., Anticancer Drug Des, 8:53-63, 1993).

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics when compared to the wild-type gene or gene product.

As used herein, the term "polymorphism" refers to the regular and simultaneous occurrence in a single interbreeding population of two or more alleles of a gene, where the frequency of the rarer allele(s) is greater than can be explained by recurrent mutation alone (typically greater than 1%). In preferred embodiments, the term "polymorphism" refers to at least one substitution, insertion and/or deletion in the 5' untranslated region of α7. In particularly preferred embodiments, the polymorphism is in the α7 promoter and contributes to a reduction in α7 transcription. In other preferred embodiments, the polymorphism is associated with a predisposition to schizophrenia.

The term "allele" refers to one of at least two mutually exclusive forms of the same gene, occupying the same locus on homologous chromosomes, and governing the same biochemical and developmental process.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotide or a polynucleotide, referred to as the "5'end" if its 5' phosphate is not linked to the 3' oxygen of a mononucleotide pentose ring and as the "3'end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in either a cDNA, a genomic DNA or an RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements are splicing signals, polyadenylation signals, termination signals, etcetera.

Transcriptional control signals in eukaryotes comprise "promoter" and "enhancer" elements, and in some cases further comprise operator sequences. Promoters and enhancers consist of short arrays of DNA sequences that interact specifically with cellular proteins involved in transcription (Maniatis et al., Science, 236:1237, 1987). Promoter and enhancer elements have been isolated from a variety of eukaryotic sources including genes in yeast, insect and mammalian cells and viruses (analogous control elements, i.e., promoters, are also found in prokaryote). The selection of a particular promoter and enhancer depends on what cell type is to be used to express the protein of interest. Some eukaryotic promoters and enhancers have a broad host range while others are functional in a limited subset of cell types (Voss et al., Trends Biochem Sci, 11:287, 1986; and Maniatis et al., supra, 1987). For example, the SV40 early gene enhancer is very active in a wide variety of cell types from many mammalian species and has been widely used for the expression of proteins in mammalian cells (Dijkema et al., EMBO J, 4:761, 1985). Two other examples of promoter/enhancer elements active in a broad range of mammalian cell types are those from the human elongation factor 1α gene (Uetsuki et al., J Biol Chem, 264:5791, 1989; Kim et al., Gene 91:217, 1990; and Mizushima and Nagata, Nuc Acids Res, 18:5322, 1990) and the long terminal repeats of the Rous sarcoma virus (Gorman et al., Proc Natl Acad Sci USA, 79:6777, 1982) and the human cytomegalovirus (Boshart et al., Cell, 41:521, 1985).

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one that is naturally linked with a given gene in the genome. An "exogenous" or "heterologous" enhancer/promoter is one that is placed in juxtaposition to a gene by means of genetic manipulation (i.e., molecular biological techniques) such that transcription of that gene is directed by the linked enhancer/promoter.

The term "repressor" as used herein refers to a regulatory protein that binds to an operator of a gene to prevent transcription of the gene. The binding affinity of repressors for the operator may be affected by other molecules. Inducers bind to repressors and decrease their binding to the operator, while corepressors increase the binding. As used herein, the terms "operator" and "repressor sequence" refer to the site on DNA to which a specific repressor protein binds thereby preventing the initiation of transcription at the adjacent promoter.

The presence of "splicing signals" on an expression vector often results in higher levels of expression of the recombinant transcript. Splicing signals mediate the removal of introns from the primary RNA transcript and consist of a splice donor and acceptor site (Sambrook et al., *Molecular Cloning: A Laboratory Manual,* 2nd ed., Cold Spring Harbor Laboratory Press, New York, pp. 16.6-16.8, 1989). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "polyA site" or "polyA sequence" as used herein denotes a DNA sequence, which directs both the termination and polyadenylation of the nascent RNA transcript. Efficient polyadenylation of the recombinant transcript is desirable as transcripts lacking a polyA tail are unstable and are rapidly degraded. The polyA signal utilized in an expression vector may be "heterologous" or "endogenous." An endogenous polyA signal is one that is found naturally at the 3' end of the coding region of a given gene in the genome. A heterologous polyA signal is one that is isolated from one gene and placed 3' of another gene. A commonly used heterologous polyA signal is the SV40 polyA signal. The SV40 polyA signal is contained on a 237 bp BamHI/BclI restriction fragment and directs both termination and polyadenylation (Sambrook, supra, 1989).

Eukaryotic expression vectors may also contain "viral replicons" or "viral origins of replication." Viral replicons are viral DNA sequences that allow for the extrachromosomal replication of a vector in a host cell expressing the appropriate replication factors. Vectors that contain either the SV40 or polyoma virus origin of replication replicate to high copy number (up to 104 copies/cell) in cells that express the appropriate viral T antigen. Vectors that contain the replicons from bovine papillomavirus or Epstein-Barr virus replicate extrachromosomally at low copy number (~100 copies/cell).

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described above.

A gene may produce multiple RNA species, which are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe which can hybridize (i.e., it is the complement of) the single-stranded nucleic acid sequence under conditions of low stringency as described above.

The term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in Nucleic Acid Hybridization, 1985). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under 'medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition above for "stringency").

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (Kacian et al., Proc Natl Acad Sci USA, 69:3038, 1972). This amplification enzyme does not replicate other nucleic acids. Similarly, in the case of T7 RNA polymerase, this amplification enzyme has a stringent specificity for its own promoters (Chamberlin et al., Nature, 228:227, 1970). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics, 4:560, 1989). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (Erlich (ed.), *PCR Technology*, Stockton Press, 1989).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample, which is analyzed for the presence of "target" (defined below). In contrast, "background template" is used in reference to nucleic acid other than sample template, which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method. The present invention provides sequences for numerous primers (i.e., SEQ ID NOS:1-8, and 12-83).

The term "sense primer" refers to an oligonucleotide capable of hybridizing to the noncoding strand of gene. The term "antisense primer" refers to an oligonucleotide capable of hybridizing to the coding strand of a gene.

As used herein, the term "fluorescent tag" refers to a molecule having the ability to emit light of a certain wavelength when activated by light of another wavelength. "Fluorescent tags" suitable for use with the present invention include but are not limited to fluorescein, rhodamine, Texas red, 6-FAM, TET, HEX, Cy5, Cy3, and Oregon Green.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label. The present invention provides sequences for suitable for use as probes (e.g., SEQ ID NO:9-11, as well as the primer sequences described above).

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the method of Mullis (See e.g., U.S. Pat. Nos. 4,683,195 4,683,202, and 4,965,188, hereby incorporated by reference), which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the term "RT-PCR" refers to the replication and amplification of RNA sequences. In this method, reverse transcription is coupled to PCR, most often using a single enzyme procedure in which a thermostable polymerase is employed, as described in U.S. Pat. No. 5,322,770, herein incorporated by reference. In RT-PCR, the RNA template is converted to cDNA due to the reverse transcriptase activity of the polymerase, and then amplified using the polymerizing activity of the polymerase (i.e., as in other PCR methods).

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule comprising segments of DNA joined together by means of molecular biological techniques.

As used herein, the term "antisense" is used in reference to RNA sequences that are complementary to a specific RNA sequence (e.g., mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter, permitting the synthesis of a coding strand. Once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

As used herein, the term "polyA$^+$ RNA" refers to RNA molecules having a stretch of adenine nucleotides at the 3' end. This polyadenine stretch is also referred to as a "poly-A tail." Eukaryotic mRNA molecules contain poly-A tails and are referred to as polyA$^+$ RNA.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs, which encode a multitude of proteins. However, isolated nucleic acid encoding a mammalian α7 protein includes, by way of example, such nucleic acid in cells ordinarily expressing an α7 protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

As used herein, a "portion of a chromosome" refers to a discrete section of the chromosome. Chromosomes are divided into sites or sections by cytogeneticists as follows: the short (relative to the centromere) arm of a chromosome is termed the "p" arm; the long arm is termed the "q" arm. Each arm is then divided into 2 regions termed region 1 and region 2 (region 1 is closest to the centromere). Each region is further divided into bands. The bands may be further divided into sub-bands. For example, the 11p15.5 portion of human chromosome 11 is the portion located on chromosome 11 (11) on the short arm (p) in the first region (1) in the 5th band (5) in sub-band 5 (0.5). A portion of a chromosome may be "altered;" for instance the entire portion may be absent due to a deletion or may be rearranged (e.g., inversions, translocations, expanded or contracted due to changes in repeat regions). In the case of a deletion, an attempt to hybridize (i.e., specifically bind) a probe homologous to a particular portion of a chromosome could result in a negative result (i.e., the probe could not bind to the sample containing genetic material suspected of containing the missing portion of the chromosome). Thus, hybridization of a probe homologous to a particular portion of a chromosome may be used to detect alterations in a portion of a chromosome.

The term "sequences associated with a chromosome" means preparations of chromosomes (e.g., spreads of metaphase chromosomes), nucleic acid extracted from a sample containing chromosomal DNA (e.g., preparations of genomic DNA); the RNA which is produced by transcription of genes located on a chromosome (e.g., hnRNA and mRNA) and cDNA copies of the RNA transcribed from the DNA located on a chromosome. Sequences associated with a chromosome may be detected by numerous techniques including probing of Southern and Northern blots and in situ hybridization to RNA, DNA or metaphase chromosomes with probes containing sequences homologous to the nucleic acids in the above listed preparations.

As used herein the term "coding region" when used in reference to structural gene refers to the nucleotide sequences which encode the amino acids found in the nascent polypeptide as a result of translation of a mRNA molecule. The coding region is bounded, in eukaryotes, on the 5' side by the nucleotide triplet "ATG" which encodes the initiator methionine and on the 3' side by one of the three triplets that specify stop codons (i.e., TAA, TAG, TGA).

As used herein, the term "structural gene" refers to a DNA sequence coding for RNA or a protein. In contrast, "regulatory genes" are structural genes that encode products that control the expression of other genes (e.g., transcription factors).

As used herein, the term "purified" or "to purify" refers to the removal of contaminants from a sample. For example, anti-α7 antibodies are purified by removal of contaminating non-immunoglobulin proteins; they are also purified by the removal of immunoglobulin that does not bind α7. The removal of non-immunoglobulin proteins and/or the removal of immunoglobulins that do not bind α7, results in an increase in the percent of α7-reactive immunoglobulins in the sample. In another example, recombinant α7 polypeptides are expressed in bacterial host cells and the polypeptides are purified by the removal of host cell proteins; the percent of recombinant α7 polypeptides is thereby increased in the sample.

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "portion" when used in reference to a nucleotide sequence refers to fragments of that nucleotide sequence. The fragments may range in size from 5 nucleotide residues to the entire nucleotide sequence minus one nucleic acid residue.

As used herein, the term "fusion protein" refers to a chimeric protein containing the protein of interest (i.e., mouse or human α7 and fragments thereof) joined to an exogenous protein fragment (the fusion partner which consists of a non-α7 protein). The fusion partner may enhance solubility of the α7 protein as expressed in a host cell, may provide an affinity tag to allow purification of the recombinant fusion protein from the host cell or culture supernatant, or both. If desired, the fusion protein may be removed from the protein of interest (i.e., α7 protein or fragments thereof) by a variety of enzymatic or chemical means known to the art.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (Sambrook et al., *Molecular Cloning: A Laboratory Manual*, Cold Spring Harbor Press, NY, pp 9.31-9.58, 1989).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (Sambrook et al., supra, pp 7.39-7.52, 1989).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The terms "specific binding" or specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

The present invention also contemplates "non-human animals" comprising any non-human animal capable of overexpressing α7 mRNA and/or proteins. Such non-human animals include vertebrates such as rodents, non-human primates, ovines, bovines, ruminants, lagomorphs, porcines, caprines, equines, canines, felines, aves, etc. Preferred non-human animals are selected from the order Rodentia, most preferably mice. The term "order Rodentia" refers to rodents (i.e., placental mammals [Class Euthria] which include the family Muridae (rats and mice).

The "non-human animals having a genetically engineered genotype" of the invention are preferably produced by experimental manipulation of the genome of the germline of the non-human animal. These genetically engineered non-human animals may be produced by several methods including the introduction of a "transgene" comprising nucleic acid (usually DNA) into an embryonal target cell or integration into a chromosome of the somatic and/or germ line cells of a non-human animal by way of human intervention, such as by the methods described herein. Non-human animals that contain a transgene are referred to as "transgenic non-human animals."

A transgenic animal is an animal whose genome has been altered by the introduction of a transgene.

The term "transgene" as used herein refers to a foreign gene that is placed into an organism by introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally occurring gene.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome-binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the $\alpha 7$ mRNA-specific signal observed on Northern blots). The amount of mRNA present in the band corresponding in size to the correctly spliced $\alpha 7$ transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell, which has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol, 52:456, 1973), has been modified by several groups to optimize conditions for particular types of cells. The art is well aware of these numerous modifications.

As used herein, the term "selectable marker" refers to the use of a gene which encodes an enzymatic activity that confers the ability to grow in medium lacking what would otherwise be an essential nutrient (e.g., the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity, which can be detected in any eukaryotic cell line. Examples of dominant selectable markers include the bacterial aminoglycoside 3' phosphotransferase gene (also referred to as the neo gene) which confers resistance to the drug G418 in mammalian cells, the bacterial hygromycin G phosphotransferase (hyg) gene which confers resistance to the antibiotic hygromycin and the bacterial xanthine-guanine phosphoribosyl transferase gene (also referred to as the gpt gene) which confers the ability to grow in the presence of mycophenolic acid. Other selectable markers are not dominant in that there use must be in conjunction with a cell line that lacks the relevant enzyme activity. Examples of non-dominant selectable markers include the thymidine kinase (tk) gene, which is used in conjunction with tk$^-$ cell lines, the CAD gene, which is used in conjunction with CAD-deficient cells and the mammalian hypoxanthine-guanine phosphoribosyl transferase (hprt) gene, which is used in conjunction with hprt$^-$ cell lines. A review of the use of selectable markers in mammalian cell lines is provided in Sambrook et al., *Molecular Cloning: A Laboratory Manual,* 2nd ed., Cold Spring Harbor Laboratory Press, New York, pp. 16.9-16.15, 1989.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro.

The term "compound" refers to any chemical entity, pharmaceutical, drug, and the like that can be used to treat or prevent a disease, illness, sickness, or disorder of bodily function. Compounds comprise both known and potential therapeutic compounds. A compound can be determined to be therapeutic by screening using the screening methods of the present invention. A "known therapeutic compound" refers to a therapeutic compound that has been shown (e.g., through animal trials or prior experience with administration to humans) to be effective in such treatment. In other words, a known therapeutic compound is not limited to a compound efficacious in the treatment of cancer.

The term "test compound" refers to any chemical entity, pharmaceutical, drug, and the like that can be used to treat or prevent a disease, illness, sickness, or disorder of bodily function. Test compounds comprise both known and potential therapeutic compounds. A test compound can be determined to be therapeutic by screening using the methods of the present invention. A "known therapeutic compound" refers to a therapeutic compound that has been shown (e.g., through animal trials or prior experience with administration to humans) to be effective in such treatment or prevention. In other words, a known therapeutic compound is not limited to a compound efficacious in the treatment of $\alpha 7$ instability or inactivity in animals.

A "composition comprising a given polynucleotide sequence" as used herein refers broadly to any composition containing the given polynucleotide sequence. The composition may comprise an aqueous solution. Compositions comprising polynucleotide sequences encoding human α7 (e.g., SEQ ID NO:123), or fragments thereof, may be employed as hybridization probes. In other embodiments, compositions comprising the promoter and upstream untranslated sequence of human α7 (e.g., SEQ ID NO:122) or fragments thereof (e.g., SEQ ID NO:94, 101, 125, etc) may be employed as hybridization probes. In these cases, the human α7-encoding polynucleotide sequences are typically employed in an aqueous solution containing salts (e.g., NaCl), detergents (e.g., SDS) and other components (e.g., Denhardt's solution, dry milk, salmon sperm DNA, etc.).

The term "sample" as used herein is used in its broadest sense. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

The term "test α7" refers to a sample suspected of containing α7. The concentration of α7 in the test sample is determined by various means, and may be compared with a "quantitated amount of α7" (i.e., a positive control sample containing a known amount of α7), in order to determine whether the concentration of test α7 in the sample is within the range usually found within samples from wild-type organisms. Thus, comparison of the positive control with the test sample allows the determination to be made whether a particular individual produces a "normal" amount of α7, is deficient in production of α7, or produces a concentration of α7 that is greater than normal. It is intended that such test methods also contain "negative" controls (i.e., samples that are known to contain no α7). Furthermore, it is intended that the testing be conducted using the α7 gene, α7 mRNA, and/or α7 protein (or polypeptides), or fragments of any of these.

The term "heteroduplex analysis" as used herein refers to a method of detecting mutations based on the retardation of the heteroduplex compared with the corresponding homoduplex on a non-denaturing polyacrylamide gel. Heteroduplexes migrate more slowly than their corresponding homoduplexes due to a more open double-stranded configuration surrounding the mismatched bases.

As used herein, the terms "DHPLC" and "denaturing high performance liquid chromatography" refer to a scanning method for mutation detection based on the capability of ion-pair reverse phase liquid chromatography on alkylated nonporous particles to resolve homo from heteroduplex molecules under conditions of partial denaturation (Underhill et al., Proc Natl Acad Sci USA, 93:196-2000, 1996 and U.S. Pat. No. 5,795,976, herein incorporated by reference in their entirety).

The terms "single-strand conformation polymorphism" and "SSCP," as used herein, refer to the ability of single strands of nucleic acid to take on characteristic conformations under non-denaturing conditions, which in turn can influence the electrophoretic mobility of the single-stranded nucleic acids. Changes in the sequence of a given fragment (i.e., mutations) will also change the conformation, consequently altering the mobility and allowing this to be used as an assay for sequence variations (Orita et al., *Genomics* 5:874-879, 1989).

As used herein, the terms "conformation-sensitive gel electrophoresis" or "CSGE" refer to methods for detecting mutations involving distinguishing DNA heteroduplexes from homoduplexes via mildly denaturing gel electrophoresis. CSGE protocols are well known in the art (Ganguly et al., *Proc Natl Acad Sci USA* 90:10325-10329, 1993).

As used herein, the terms "ligase chain reaction" and "ligase amplification reaction" refer to methods for detecting small quantities of a target DNA, with utility similar to PCR. Ligase chain reaction relies on DNA ligase to join adjacent synthetic oligonucleotides after they have bound the target DNA. Their small size means that they are destabilized by single base mismatches and so form a sensitive test for the presence of mutations in the target sequence.

The term "DNA sequencing" refers to methods used to determine the order of nucleotide bases in a DNA molecule or fragment. The term "DNA sequencing" includes for example, dideoxy sequencing and Maxam-Gilbert sequencing.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness (e.g., major depressive disorder), sickness, or disorder of bodily function. Test compounds comprise both known and potential therapeutic compounds. A test compound can be determined to be therapeutic by screening using the screening methods of the present invention.

The term "change" as used herein refers to a difference or a result of a modification or alteration. In preferred embodiments, the term "change" refers to a measurable difference between states (e.g., higher or lower α7 mRNA or protein expression in a cell in the presence and absence of a test compound). In some embodiments, the change is at least 10%, preferably at least 25%, more preferably at least 50%, and most preferably at least 90% more or less than that of a control condition.

As used herein, the term "sample" is meant to include a specimen obtained from subject. The term "sample" encompasses fluids, solids, and tissues. In preferred embodiments, the term "sample" refers to blood or biopsy material obtained from a living body for the purpose of examination via any appropriate technique (e.g., needle, sponge, scalpel, swab, etc.). In particularly preferred embodiments, the term "sample" refers to buccal cells (e.g., cells of the inner lining of the mouth or cheek). Buccal cell samples are obtained using any suitable method, including but not limited to collection via tongue depressor, cytobrush or mouthwash (See, Moore et al., Biomarkers, 6:448-454, 2001).

The terms "subject" as used herein, refers to a human. It is intended that the term encompass healthy individuals, as well as, individuals predisposed to, or suspected of having schizophrenia. Typically, the terms "subject" and "patient" are used interchangeably. In some preferred embodiments of the present invention, the term subject refers to specific subgroups of patients.

The term "schizophrenia" as used herein refers to a major mental disorder featuring psychotic symptoms during some phase of the illness, a long term course and a deterioration in function. Schizophrenic symptoms can be classified as positive, negative, cognitive and mood symptoms, which together or separately may result in behavioral disturbances (e.g., bizarre, apparently purposeless and stereotyped activity or inactivity). Various embodiments of the present invention are contemplated to effectively treat all subtypes of schizophrenia, including but not limited to catatonic, disorganized, paranoid and undifferentiated subtypes. In addition, the compositions and methods of the present invention are also contemplated to benefit patients with schizoid personality disorder (socially distant, detached) and patients with schizotypal personality disorder (odd, eccentric).

As used herein, the term "positive symptoms" refers to symptoms including but not limited to hallucinations (e.g., hearing voices), delusions (e.g., of persecution or grandiosity), disorganized speech and thought, altered sense of self and bizarre behavior. They are called positive symptoms because they are added on to the individuals experience and behavior.

The term "negative symptoms" as used herein, refers to deficit symptoms, including experience and behavior that should be there and is not. Negative symptoms include but are not limited to loss of motivation, flattened emotions, withdrawal from an active social life, poverty of thought and speech, and loss of former interests and pleasures.

As used herein, the term "cognitive symptoms," refers to symptoms associated with a loss of cognitive ability including but not limited to attention deficits, memory loss, inability to plan for the future and poor capacity for abstract thought.

The term "mood symptoms" as used herein, refers to symptoms associated with a disturbed state of mind or predominant emotion such as dysphoria.

As used herein, the term "risk of developing schizophrenia" refers to a subject's relative risk (e.g., the percent chance or a relative score) of developing schizophrenia during their lifetime.

The term "subject suspected of having schizophrenia" refers to a subject that presents one or more symptoms indicative of schizophrenia (e.g., delusions, hallucinations, disorganized speech, catatonic behavior, negative symptoms such as effective flattening, alogia or avolition, etc.) or is being screened for schizophrenia (e.g., during a routine physical).

As used herein, the term "diagnosis" refers to the determination of the nature of a case of disease. In some preferred embodiments of the present invention, methods for making a diagnosis are provided which permit schizophrenia to be distinguished from other forms of mental illness including but not limited to psychosis due to a general medical condition; delirium, or dementia; substance-induced or related disorders; depressive disorder; and bipolar disorder (e.g., manic depression).

The term "reagent(s) suitable for use in specifically detecting at least one polymorphism in an α7 allele" refers to reagent(s) used to detect a polymorphism of interest in an α7 gene, cDNA, or RNA. Examples of suitable reagents include but are not limited to, nucleic acid probes and primers capable of specifically hybridizing to α7 mRNA or cDNA. In some preferred embodiments, the term suitable reagents refers to primers for amplifying an α7 fragment suspected of containing a polymorphism of interest.

As used herein, the term "instructions for determining whether a subject is predisposed to schizophrenia" refers to instructions for using the reagents contained in the kit for the detection and characterization of an α7 allele in a sample from a subject. In some embodiments, the instructions further comprise the statement of intended use required by the U.S. Food and Drug Administration (FDA) in labeling in vitro diagnostic products. The FDA classifies in vitro diagnostics as medical devices and required that they be approved through the 510(k) procedure. Information required in an application under 510(k) includes: 1) The in vitro diagnostic product name, including the trade or proprietary name, the common or usual name, and the classification name of the device; 2) The intended use of the product; 3) The establishment registration number, if applicable, of the owner or operator submitting the 510(k) submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labeling and advertisements sufficient to describe the in vitro diagnostic product, its intended use, and directions for use, including photographs or engineering drawings, where applicable; 5) A statement indicating that the device is similar to and/or different from other in vitro diagnostic products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; and 8) Any additional information regarding the in vitro diagnostic product requested that is necessary for the FDA to make a substantial equivalency determination. Additional information is available at the Internet web page of the U.S. FDA.

DESCRIPTION OF THE FIGURES

The file of this patent contains at least one drawing executed in color. Copies of this patent with color drawings will be provided by the Patent and Trademark Office upon request and payment of the necessary fee.

FIG. 1 shows the exon-intron boundary sequences of the human α7 nAChR subunit gene. The 3' portion of exon 1 is disclosed as SEQ ID NO:84. Also shown are the splice acceptor sequences of: intron 1 (SEQ ID NO:85), intron 2 (SEQ ID NO:86), intron 3 (SEQ ID NO:87), intron 4 (SEQ ID NO:88), intron 5 (SEQ ID NO:89), intron 6 (SEQ ID NO:90), intron 7 (SEQ ID NO:91), intron 8 (SEQ ID NO:92) and intron 9 (SEQ ID NO:93), as well as the splice donor sequences of: intron 1 (SEQ ID NO:104), intron 2 (SEQ ID NO:106), intron 3 (SEQ ID NO:108), intron 4 (SEQ ID NO:110), intron 5 (SEQ ID NO:112), intron 6 (SEQ ID NO:114), intron 7 (SEQ ID NO:116), intron 8 (SEQ ID NO:118), and intron 9 (SEQ ID NO:120). Additionally, flanking exon sequences are shown: exon 2 (SEQ ID NO:105), exon 3 (SEQ ID NO:107), exon 4 (SEQ ID NO:109), exon 5 (SEQ ID NO:111), exon 6 (SEQ ID NO:113), exon 7 (SEQ ID NO:115), exon 8 (SEQ ID NO:117), exon 9 (SEQ ID NO:119), and exon 10 (SEQ ID NO:121).

FIG. 2 shows the sequence variants identified in full-length and duplicated genomic clones.

FIG. 3 provides an expression analysis of sequence variants.

FIG. 4 provides the nucleotide sequence of the region 5' of the human α7 nAChR subunit gene (SEQ ID NO:94).

Figure 5:
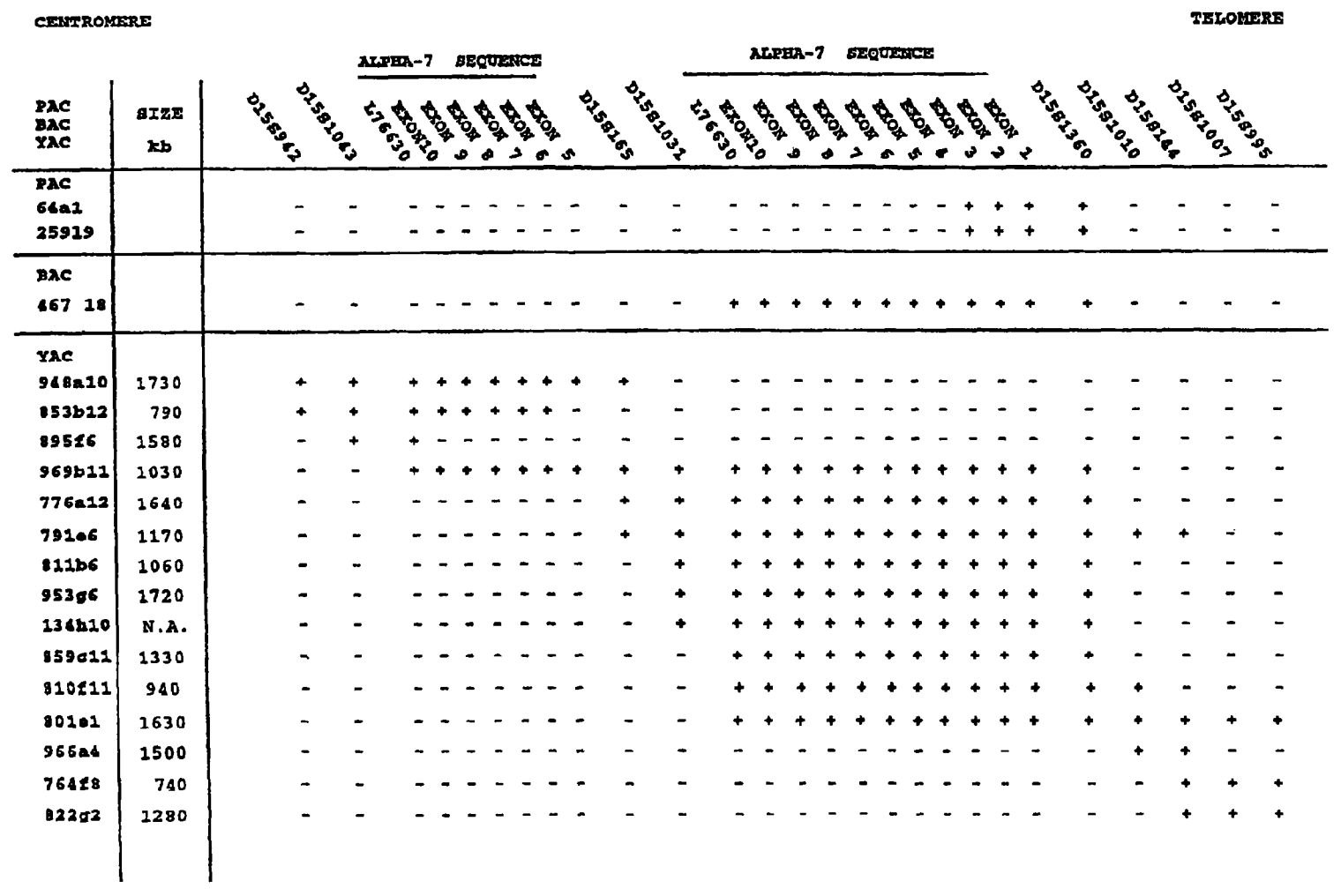

FIG. 5 shows the genomic contig of clones positive for α7 nAChR gene sequences and surrounding loci.

FIG. 6 provides a partial sequence of a RACE clone, with exon sequences shown in upper case and intron sequences shown in lower case: exon D (SEQ ID NO:95), exon C (SEQ ID NO:96), exon B (SEQ ID NO:97), exon A (SEQ ID NO:98), exon 5 (SEQ ID NO:99), and exon 6 (SEQ ID NO:100).

FIG. 8 provides the DNA sequence of the human α7 neuronal nicotinic receptor promoter (SEQ ID NO:101).

FIG. 9 provides the DNA sequence of the alternatively spliced human α7 neuronal nicotinic receptor RACE product A/C/D (SEQ ID NO:102).

FIG. 10 provides the DNA sequence of the alternatively spliced human α7 neuronal nicotinic receptor RACE product A/B/C/D (SEQ ID NO:103).

FIG. 15 depicts the association between promoter variants and P50 gating in control subjects. In Panel A, mean P50 ratios are shown for control subjections without (N/N) and with one or more polymorphisms (Poly) in the α7 core promoter. In Panel B, promoter variants in control subjects are shown to fit into three P50 gating ranges.

FIG. 18 presents several embodiments of polymorphisms identified in the CHRNA7 proximal promoter and 5'-upstream regulatory region (SEQ ID NO: 181). Polymorphisms identified are in red. The polymorphism associated with schizophrenia in the current study is highlighted in yellow. Transcription factor binding sites are indicated by blue bars.

FIG. 20 presents illustrative amplicon embodiments useful for the detection and identification of polymorphisms. Primers used to detect these amplicons include SEQ ID NOS: 184-201.

DESCRIPTION OF THE INVENTION

Figure 7:
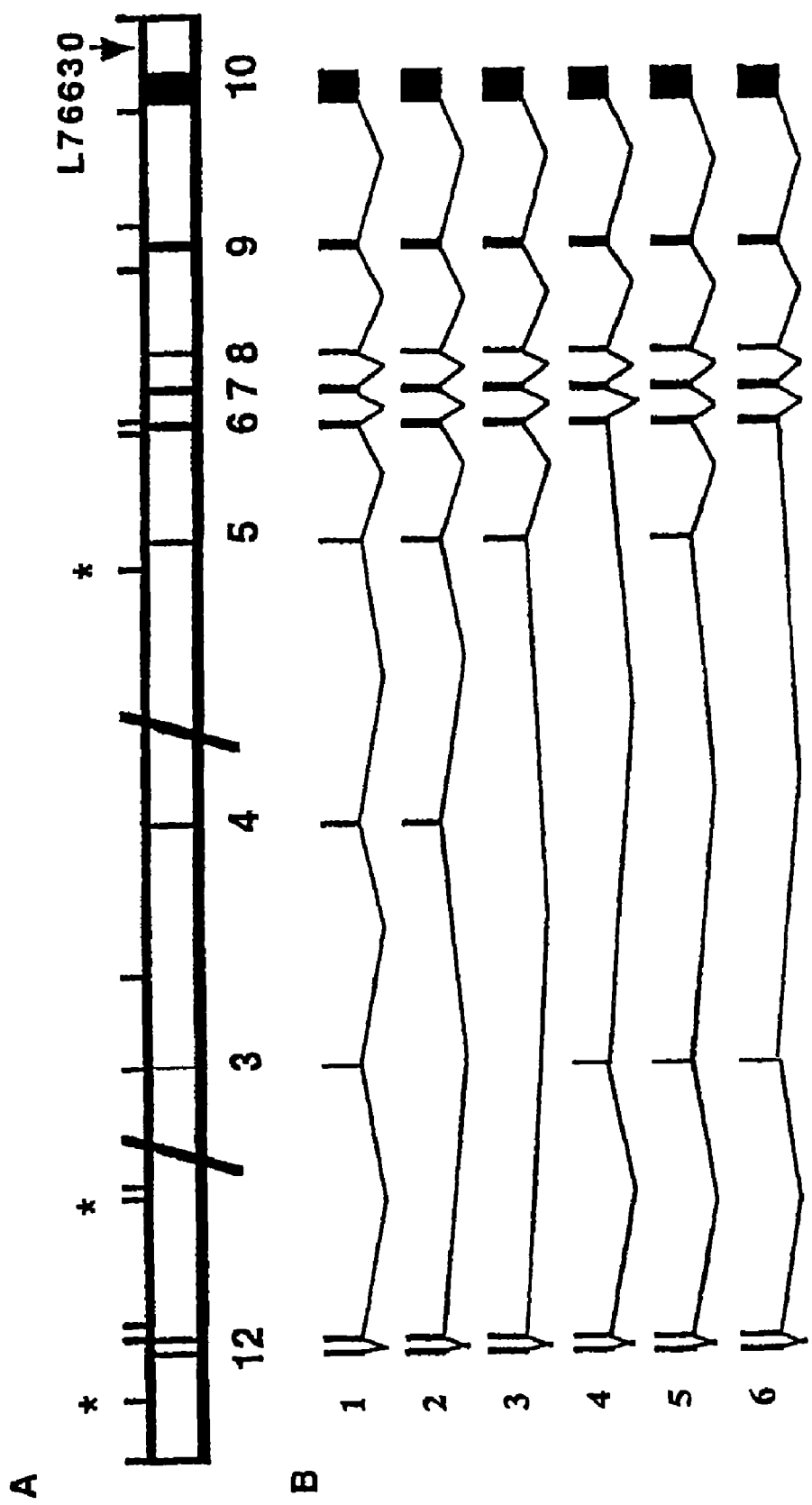
FIG. 7 provides a map of the full-length α7 nAChrR gene. Panel A shows a physical map of the region and the structure of the full-length α7 nAChR gene. Panel B shows the structure of alternatively spliced transcripts.

The present invention is related to the alpha-7 neuronal nicotinic acetylcholine receptor gene. In particular, the present invention provides the human alpha-7 gene. In addition, the present invention provides methods and compositions for the diagnosis and treatment of schizophrenia. Such compositions include, but are not limited to, polymorphisms within the human alpha-7 gene promoter core and/or 5' upstream regulatory regions.

As the methods of the prior art have been unsuccessful in providing needed information regarding the genetics of schizophrenia, an alternative strategy for genetic studies of complex diseases involving the use of a specific neurobiological characteristic of the illness (e.g., as an additional phenotype more closely reflecting the effect of a single genetic alteration), was used during the development of the present invention. Such information is needed in order to provide diagnostic and treatment methods, as well as animal models for schizophrenia, as well as other psychoses. It is contemplated that such a trait is part of the inherited diathesis of the illness, which produces schizophrenia in combination with other pathogenic elements.

The present invention provides genetic information (i.e., sequences, including sequence location and information on intron/exon boundaries) for the α7 nicotinic receptor, as well as methods to assess the function of this receptor in normal, as well as schizophrenic individuals. The present invention also provides methods and compositions for analyzing samples from patients suspected of suffering from diverse conditions, including epilepsy (e.g., juvenile myoclonic epilepsy), small cell lung carcinoma and other nicotine-dependent diseases, Prader-Willi, Angelman's syndrome, and other genetic disorders, etc. Indeed, it is not intended that the present invention be limited to schizophrenia.

I. Schizophrenia and Smoking

Schizophrenia is a complex neuropsychiatric disorder partially characterized by sensory processing and cognitive deficits. Leonard et al., "Smoking and mental illness" *Pharmacol. Biochem. Behav.* 70:561-570 (2001); Light et al., "Sensory gating deficits in schizophrenia: can we parse the effects of medication, nicotine use, and changes in clinical status?" *Clin. Neurosci. Res.* 3:47-54 (2003); George et al., "A preliminary study of the effects of cigarette smoking on prepulse inhibition in schizophrenia: involvement of nicotinic receptor mechanisms" *Schizophr. Res.* 87:307-315 (2006); Adams et al., "Evidence for a role of nicotinic acetylcholine receptors in schizophrenia" *Front. Biosci.* 12:4755-4772 (2007); and Martin et al., "Schizophrenia and the alpha7 nicotinic acetylcholine receptor" *Int. Rev. Neurobiol.* 78:225-246 (2007). Sensory processing deficits may be normalized in schizophrenic patients and first-degree relatives by smoking. Adler et al., "Normalization of auditory physiology by cigarette smoking in schizophrenic patients"

Am. J. Psych. 150:1856-1861 (1993); Adler et al., "Schizophrenia, sensory gating, and nicotinic receptors" Schizofr. Bull. 24:189-202 (1998); Olincy et al., "Improvement in smooth pursuit eye movements after cigarette smoking in schizophrenic patients" Neuropsychopharmacology 18:175-185 (1998); and Leonard et al., "Genetics of smoking and schizophrenia" J. Dual Diag. 3:43-59 (2007). Further, it has been reported that cognitive deficits may be improved by nicotine administration. Levin et al., "Transdermal nicotine effects on attention" Psychopharmacology 140:135-141 (1998); Levin et al., "Nicotinic effects on cognitive function: behavioral characterization, pharmacological specification, and anatomic localization" Psychopharmacology 184:523-539 (2006); and Rezvani et al., "Cognitive effects of nicotine" Biol. Psychiatry 49:258-267 (2001).

Consequently, it has been suggested that schizophrenics may smoke to 'self-medicate', thereby correcting an underlying biological deficit. Leonard et al., "Consequences of low levels of nicotinic acetylcholine receptors in schizophrenia for drug development" Drug Dev. Res. 60:127-136 (2003); Leonard et al., "Smoking and schizophrenia: evidence for self medication" Schizophr. Bull. 33:262-263 (2007); and Kumari et al., "Nicotine use in schizophrenia: the self-medication hypotheses" Neurosci. Biobehav. Rev. 29:1021 (2005). This hypothesis has been investigated in studies demonstrating that smoking alters gene expression in normal individuals and differentially regulates gene expression in schizophrenics. Mexal et al., "Differential modulation of gene expression in the NMDA postsynaptic density of schizophrenic and control smokers" Mol Brain Res. 139:317-332 (2005); Mexal et al., "Regulation of a novel alphaN-catenin splice variant in schizophrenic smokers" Am. J. Med. Genet. B Neuropsychiatr. Genet. 147B:759-768 (2008); 2008; and Kuehn, "Link between smoking and mental illness may lead to treatments" J. Am. Med. Assoc. 295:483-484 (2006).

Nicotine is believed to exert its effect through neuronal nicotinic acetylcholine receptors expressed in the brain and periphery. Leonard et al., "Neuronal nicotinic receptors: from structure to function" Nicotine Tob. Res. 3:203-223 (2001); and Gotti et al., "Brain nicotinic acetylcholine receptors: native subtypes and their relevance" Trends Pharmacol. Sci. 27:482-491 (2006). The α7 neuronal nicotinic receptor subunit gene (CHRNA7), localized at 15q14, was first genetically linked to the P50 auditory sensory processing deficit in schizophrenia (infra). Freedman et al., "Linkage of a neurophysiological deficit in schizophrenia to a chromosome 15 locus" Proc. Natl. Acad. Sci. USA 94:587-592 (1997). Subsequently, the gene was linked to the development and expression of schizophrenia. For example, patient cohorts of European American, African American, South African Bantu, Azorean, and Han Chinese ancestry, indicated that the linkage may be observed across ethnicities. Coon et al., "Genomic scan for genes predisposing to schizophrenia" Am. J. Med. Genet. 54:59-71 (1994); Kaufmann et al., "NIMH Genetics Initiative Millenium Schizophrenia Consortium: linkage analysis of African-American pedigrees" Am. J. Med. Genet. 81:282-289 (1998); Leonard et al., "Further investigation of a chromosome 15 locus in schizophrenia: analysis of affected sibpairs from the NIMH Genetics Initiative" Am. J. Med. Genet. 81:308-312 (1998); Riley et al., "Haplotype transmission disequilibrium and evidence for linkage of the CHRNA7 gene region to schizophrenia in Southern African Bantu families" Am. J. Med. Genet. 96: 196-201 (2000); Freedman et al., "Linkage disequilibrium for schizophrenia at the chromosome 15 q13-14 locus of the alpha 7-nicotinic acetylcholine receptor subunit gene (CHRNA7)" Am. J. Med. Genet. 105:20-22 (2001); Gejman et al., "Linkage analysis of schizophrenia to chromosome 15" Am. J. Med. Genet. 105: 789-793 (2001); Liu et al., "Suggestive evidence for linkage of schizophrenia to markers at chromosome 15q13-14 in Taiwanese families" Am. J. Med. Genet. 105:658-661 (2001); Tsuang et al., "Examination of genetic linkage of chromosome 15 to schizophrenia in a large veterans affairs cooperative study sample" Am. J. Med. Genet. 105:662-668 (2001); Xu et al., "Evidence for linkage disequilibrium between the alpha 7-nicotinic receptor gene (CHRNA7) locus and schizophrenia in Azorean families" Am. J. Med. Genet. 105:669-674 (2001); and Fallin et al., "Genome-wide linkage scan for schizophrenia susceptibility loci among Ashkenazi Jewish families shows evidence of linkage on chromosome 10q22" Am. J. Hum. Genet. 73:601-611 (2003).

Activation of the homopentameric α7* receptor has been reported to result in the influx of $Ca^{2+}$ and concomitant neurotransmitter release. Vijayaraghavan et al., "Nicotinic receptors that bind α-bungarotoxin on neurons raise intracellular free $Ca^{++}$" Neuron 8: 353-362 (1992); Aramakis et al., "Nicotine selectively enhances NMDA receptor-mediated synaptic transmission during postnatal development in sensory neocortex" J. Neurosci. 18: 8485-8495 (1998); Berg et al., "Nicotinic alpha 7 receptors: synaptic options and downstream signaling in neurons" J. Neurobiol. 53:512-523 (2002); Dajas-Bailador et al., "Nicotinic acetylcholine receptors and the regulation of neuronal signalling" Trends Pharmacol. Sci. 25:317-324 (2004). Binding studies with an α7* receptor antagonist (i.e., for example, α-bungarotoxin) show there are 50% fewer receptors in post-mortem hippocampus of individuals with schizophrenia compared to control subjects. Freedman et al., "Evidence in postmortem brain tissue for decreased numbers of hippocampal nicotinic receptors in schizophrenia" Biol. Psychiatry 38:22-33 (1995). Decreased α7* receptor expression was also found in cortex and in the reticular thalamic nucleus. Guan et al., "Decreased protein level of nicotinic receptor alpha7 subunit in the frontal cortex from schizophrenic brain" Neuroreport 10:1779-1782 (1999); Marutle et al., "Laminar distribution of nicotinic receptor subtypes in cortical regions in schizophrenia" J. Chem. Neuroanat. 22:115-126 (2001); and Court et al., Neuronal nicotinic receptors in dementia with Lewy bodies and schizophrenia: alpha-bungarotoxin and nicotine binding in the thalamus" J. Neurochem. 73:1590-1597 (1999), respectively. Although it is not necessary to understand the mechanism of an invention, it is believed that low levels of the α7* receptor may have downstream consequences for multiple neurotransmitter systems, thereby altering the balance of neurotransmitter release and activation. Leonard S., "Consequences of low levels of nicotinic acetylcholine receptors in schizophrenia for drug development" Drug Dev. Res. 60:728: 127-136 (2003).

The CHRNA7 gene has been suggested as a candidate gene for schizophrenia. Harrison et al., "Schizophrenia genes, gene expression, and neuropathology: on the matter of their convergence" Mol. Psychiatry 10:40-68 (2005). Further, α7* receptor agonists have been identified as putative targets for drug development to treat schizophrenic cognitive impairments. Psychiatric News, Molecular Targets Ranked. Psych. News 41:16-1a (2006). Recent Phase I and Phase II studies of an α7* receptor partial agonist, DMXB-A, resulted in improvements of both sensory processing and attention in non-smoking schizophrenics. Martin et al., "Alpha-7 nicotinic receptor agonists: potential new candidates for the treatment of schizophrenia" Psychopharmacology 174:54-64 (2004); Olincy et al., "Proof-of-concept trial of an alpha 7 nicotinic agonist in schizophrenia" Arch. Gen. Psychiatry 63:

630-638 (2006); Freedman et al., "Initial phase 2 trial of a nicotinic agonist in schizophrenia" *Am. J. Psychiatry* (submitted, 2008).

The α7 nicotinic receptor subunit gene, CHRNA7, was found to be partially duplicated, with both loci mapping to the 15q14 region. Gault et al., "Genomic organization and partial duplication of the human α7 neuronal nicotinic acetylcholine receptor gene" *Genomics* 52:173-185 (1998); Riley et al., "A 3 Mb map of a large segmental duplication overlapping the alpha 7-nicotinic acetylcholine receptor gene (CHRNA7) at human 15q13-q14" *Genomics* 79:197-209 (2002). The partially duplicated gene (CHRFAM7A) is believed located 1.6 Mb centromeric to the full-length gene, however, its function remains unknown. Mutation screening of the coding region and intron/exon borders of CHRNA7 and of CHRFAM7A has identified thirty-three (33) putative polymorphisms. Three (3) of the polymorphisms were non-synonymous and mapped to the full length CHRNA7 coding region. These polymorphisms, however, were very rare and were not associated with either schizophrenia or the P50 112340123456789 gating deficit. Gault et al., "Comparison of polymorphisms in the α7 nicotinic receptor gene and its partial duplication in schizophrenic and control subjects" *Am. J. Med. Genet.* 123B:39-49 (2003).

In contrast, mutation screening of the core promoter in the CHRNA7 gene identified a large number of polymorphisms predictive of schizophrenia. For example, a functional analysis of polymorphisms in the two hundred and thirty-one (231) base pairs upstream of the α7* translation initiation site (i.e., for example, the core promoter region) demonstrated that many of the identified polymorphisms decrease α7* receptor transcription. These polymorphisms were also found to be statistically more prevalent in schizophrenics than in control subjects (P=0.007). Further, the presence of a promoter polymorphism in non-schizophrenic controls was associated with a P50 gating deficit (P<0.0001). Reporter gene assays with fragments 1.0 kb and 2.6 kb proximal to the translation initiation site exhibit less activity than the core promoter, suggesting that repressor elements may lie upstream of the core promoter. Leonard et al., "Association of promoter variants in the alpha 7 nicotinic acetylcholine receptor subunit gene with an inhibitory deficit found in schizophrenia" *Arch. Gen. Psychiatry* 59:1085-1096 (2002).

I. Inhibition of the P50 Auditory Response

Various psychophysiological paradigms demonstrate altered brain functions in schizophrenic patients and their relatives that might reflect inherited traits (See e.g., Sham et al., Psychiat Genet, 4:29, 1994; De Amicis et al., J Nerv Ment Dis, 174:177, 1986; Holzman et al., Arch Gen Psychiat, 45:641, 1988; and Braff et al., Arch Gen Psychiat, 49:206, 1992). Basic deficits in the regulation of response to sensory stimuli may underlie patients' more apparent symptoms such as hallucinations and delusions. In addition to hearing voices, patients often attend to apparently extraneous stimuli in their surroundings that normal individuals generally ignore. Such symptoms suggested that neuronal mechanisms responsible for the filtering or gating of sensory input to higher brain centers are deficient. One method developed for examining such neuronal mechanisms compares the responses to first and second of paired stimuli. The first stimulus elicits an excitatory response that also activates inhibitory mechanisms, which then diminish the excitatory response to the second stimulus. The ratio of the amplitude of the second response to the first is inversely related to the strength of inhibition.

During the development of the present invention, this method was used to study the response to auditory stimuli in schizophrenia, using an electrically positive evoked potential occurring 50 ms after an auditory stimulus (P50). Inhibition of the P50 response to a second identical stimulus (presented 500 ms after the first) has been reported to be diminished in schizophrenics (Adler et al., Biol Psychiat, 17:639, 1982; Boutros and Overall, Clin Electroencephalog, 22:20, 1991; Erwin et al., Biol Psychiat, 30, 430, 1991; and Judd et al., Am J Psychiat, 149:488, 1992). This diminished inhibition, measured as an elevation in the ratio of P50 amplitudes, has been correlated with schizophrenics' decreased performance in a neuropsychological measure of sustained attention, as well as diminished performance in a word recognition task (Cullum et al., Schizophrenia Res, 10:131, 1993; and Vinogradova et al., Biol Psychiat, 39: 821, 1996).

In the development of the present invention, inhibition of the P50 response was measured in animal and related clinical investigations, to identify neurobiological mechanisms related to genes of interest, as well as a phenotype for linkage analysis to identify chromosomal areas containing genes responsible for the abnormality in schizophrenics.

The neurobiological inhibition of human P50 to repeated auditory stimuli was initially investigated using an auditory evoked potential recorded from the rat as a model. Both the human and rat potentials show similar decreased responses to repeated auditory stimuli (Adler et al., Biol Psychiat, 21:787, 1986). Neuronal recordings identified the pyramidal neurons of the hippocampus as a major source of the rat evoked potential. These pyramidal neurons have a decremented response to repeated auditory stimuli that parallels the decrement in the evoked potential (Bickford-Wimer et al., Biol Psychiat, 27:183, 1990). The decrement is lost after transfection of the fimbria-fornix, a fiber tract that includes afferents to the hippocampus from cholinergic neurons in the basal forebrain (Vinogradova, in *The Hippocampus* 2: *Neurophysiology and Behavior*, Issacson and Pribram (eds), Plenum Press, New York, N.Y., pp 3-69, 1975).

However, nicotine has been found to normalize inhibition of response in the fimbria-fornix lesioned animals (See e.g., Bickford and Wear, Brain Res, 705:235, 1995). Studies with pharmacological antagonists in unlesioned animals indicate that a specific subset of nicotinic cholinergic receptors is involved in the inhibitory mechanism. The inhibition is selectively blocked by the snake toxin α-bungarotoxin (Luntz-Leybman et al., Brain Res, 587:130, 1992), suggesting that the receptor contains the α7 nicotinic cholinergic receptor subunit, as it is the only known nicotinic receptor subunit in the mammalian brain sensitive to this toxin (Couturier et al., Neuron, 5:847-856, 1990; and Schoepfer et al., Neuron, 5:35, 1990). Neither scopolamine, nor mecamylamine, nor α-bungarotoxin (i.e., antagonists of other types of cholinergic receptors), blocked the inhibition. Receptor autoradiography using [125I]-α-bungarotoxin showed the most intense binding to non-pyramidal hippocampal neurons containing the inhibitory neurotransmitter γ-aminobutyric acid (Freedman et al., J Neurosci, 13:1965, 1993). This labeling was consistent with physiological evidence that cholinergic synapses activate interneurons, which inhibit the pyramidal neuron response to the second stimulus (See e.g., Miller and Freedman, Neurosci, 69:371-381, 1995; and Hershman et al., Neurosci Lett, 190:133, 1995).

There are several areas of apparent concordance between these findings in rats and P50 inhibition in humans. First, P50 has been recorded from the human hippocampus (Goff et al., Prog Clin Neurophysiol, 7:126, 1980; and Makela et al., Electroencephalogr Clin Neurophysiol, 92:414, 1994), and human hippocampal neurons have rapidly decreasing responses to auditory stimuli, similar to those observed with rat hippocampal neurons (Wilson et al., Exp Neurol, 84:74, 1984). Second, nicotine in high doses transiently normalizes the abnormality in P50 inhibition in schizophrenics and in their relatives, much as it normalizes inhibition in rats after fimbria-fornix lesions (Bickford and Wear, supra, 1995; Adler et al., Biol Psychiatry, 32:607, 1992; and Adler et al., Am J Psychiat, 150:1856, 1993). However, the effect of nicotine on P50 inhibition in relatives of schizophrenics is not blocked by mecamylamine, which blocks all known nicotinic receptors in human brain, except the α7 nicotinic receptor (Freedman et al, Harvard Rev Psychiat, 2:179, 1994). In situ hybridization has shown that α7 nicotinic receptor mRNA is expressed in human hippocampal neurons (Freedman et al., Harvard Rev Psychiat, 2:179, 1994). Some of the non-pyramidal neurons of the human hippocampus were intensely labeled by α-bungarotoxin, as was also observed with rats.

A preliminary study showed that α-bungarotoxin labeling was decreased in post mortem hippocampus from eight schizophrenics (Freedman et al., Biol Psychiat, 38:22, 1995). In addition, schizophrenic patients are particularly heavy tobacco smokers, even when compared to other psychiatric patients (deLeon et al., Am J Psychiat, 152:453, 1995; and Hamera et al., J Nerv Mental Dis, 183:559, 1995). This heavy nicotine use may reflect an attempt at self-medication of an endogenous neuronal deficit (Goff et al., Am J Psychiat, 149: 1189, 1992). However, nicotine's efficacy as an anti-psychotic is limited, due to rapid desensitization and cardiovascular toxicity.

In parallel with these biological studies in human and animals, the P50 evoked potential abnormality was also investigated as a phenotype for genetic linkage analysis. A genome-wide scan was initiated, independent of any candidate gene hypothesis, in nine multiplex schizophrenic pedigrees, which were also phenotyped with P50 recordings. The deficit in inhibition of the P50 response in these and other schizophrenic families is generally found in one of the parents and half the siblings, including the schizophrenic probands (Siegel et al., Arch Gen Psychiat, 41:607-612, 1984). Although elevated P50 ratios are significantly associated with the apparent genetic risk for schizophrenia, many individuals in the pedigrees who have the deficit are clinically unaffected (Waldo et al., Psychiat Res, 39:257, 1991). In this respect, the distribution of the trait resembles several other neurobiological abnormalities in schizophrenics and their relatives, such as deficits in smooth pursuit eye movements and reaction time (De Amicis et al., J Nerv Ment Dis, 174:177, 1986; and Holzman et al. Arch Gen Psychiat, 45:641, 1988). These traits may represent alternative expressions of a latent trait or endophenotype, which, in combination with other pathogenic elements, gives rise to schizophrenia.

During the development of the present invention, preliminary linkage analyses between the P50 ratio abnormality and 318 restriction fragment length polymorphism and tandem repeat DNA markers in the nine kindreds were conducted. DNA markers mapping to four chromosomal regions, one of which was 15q14, revealed small positive lod scores (maximum logarithm of the odds) assuming autosomal dominant transmission. Subsequently, the α7 nicotinic receptor gene was localized to the 15q14 region (Orr-Urtreger et al., Genomics, 26:399, 1995; and Spitzer et al., Arch Gen Psychiat, 35:773, 1978). As converging evidence from neurobiological investigations implicated α7 receptor function in abnormal P50 inhibition, and the preliminary linkage study provided suggestive evidence for heritability of the trait near the chromosomal location of the α7 receptor gene, additional experiments, using informative markers at the α7 receptor gene locus were undertaken. Two new DNA polymorphic loci were isolated, namely D15S1360 from a yeast artificial chromosome (YAC) containing the α7 nicotinic receptor gene, and L76630 from an α7-containing clone in a genomic phage library. These markers were used with over 500 highly polymorphic markers in a 10 centiMorgan resolution genome-wide scan of the nine pedigrees. The results demonstrate a highly significant linkage between D15S1360 and the abnormality in P50 suppression.

Indeed, the data obtained during the development of the present invention strongly suggest that the P50 auditory sensory deficit in schizophrenia is genetically linked to the locus of the α7 nicotinic receptor gene on chromosome 15q14. Thus, the present invention provides a heretofore unknown linkage between nicotinic receptors and schizophrenia. The significant linkage obtained with the P50 ratio phenotype supports the value of this strategy. This provides methods for assessing the effects of therapy to correct abnormalities in α7 structure and/or function, as well as providing methods for developing and identifying drugs suitable for use in treating such abnormalities.

Although an understanding of the mechanism is not necessary in order to use the present invention, it has been suggested that the clinical illness may be less penetrant, because multiple genetic and non-genetic factors are required to produce clinical illness, whereas a specific biological defect may occur as the result of a single gene effect. Thus, some gene carriers would be expected to have abnormal P50 ratio, the more penetrant phenotype, but not schizophrenia, which is less penetrant. The lower lod scores observed during the development of the present invention with schizophrenia as a phenotype support that position; several kindreds had higher lod scores for P50 ratio than for schizophrenia because there were many family members with abnormal P50 ratios who did not have schizophrenia.

The possibility that the chromosome 15q13-14 region is involved in psychotic illness has also been investigated in relationship to other diseases. For example, psychoses resembling schizophrenia have been observed in Prader-Willi syndrome, a mental retardation linked to deletions and abnormal DNA imprinting in the 15 q11-13 region (Clarke, Brit J Psychiat, 163:680, 1993). The imprinting abnormality affects the expression of many genes in this region. Several families in Sephardic and other populations have co-existent schizophrenia and Marfan's syndrome (i.e., a disease linked to dominant mutations in the fibrillin gene at 15q21; Sirota et al., Br J Psychiat, 157: 433, 1990; and Melissari et al., Pathologica, 87:78, 1995). The co-segregation of the two illnesses may be based on their chromosomal proximity. Psychosis was also observed in a large French-Canadian kindred that has a recessive demyelination disease, linked to markers at 15q14 (Casaubon et al., Am J Hum Genet, 58:28, 1996). In addition, an Italian kindred contains two cousins with psychotic illness and a partial trisomy of chromosome 15, derived independently from abnormal meioses involving a balanced familial translocation with a 15q13 breakpoint, that was present in each of their mothers. It was suggested that the new trisomies may have caused the de novo appearance of illness (Calzolari et al., Am J Med Genet, 67:154, 1996). The present invention provides the means to determine to what extent the appearance of psychoses in these families with other genetic abnormalities at 15q13-14 involves the α7 gene.

In addition to providing means to assess the risk for development of schizophrenia, the present invention also provides new data about the identity of neuronal abnormalities involved in its pathophysiology, as well as the means to develop treatment methods and compounds, diagnostic methods and reagents, and models (e.g., cell lines and transgenic animals) of these neuronal abnormalities. These results are consistent with clinical and neurobiological evidence for the involvement of the α7 nicotinic receptor gene in sensory gating deficits in schizophrenia.

The present invention also provides the means to determine the role the α7 receptor in the sensory processing defects and other abnormalities in schizophrenia. The finding of a significant linkage supporting the role of the α7 nicotinic receptor in the pathophysiology of sensory and attentional disturbance in schizophrenia, is unique. Many neurotransmitter systems have been hypothesized to be at least partly responsible for schizophrenia, but direct biological assessment of a specific neuronal receptor function in human subjects is generally not feasible because of the brain's complexity and inaccessibility. The present invention provides compositions and methods to overcome these drawbacks. Genetic investigations, including linkage studies, have represented the critical test of the involvement of a particular mechanism in schizophrenia. The present invention provides methods and compositions to complement and/or replace such tests for schizophrenia. Indeed, linkage at the α7 nicotinic receptor locus thus supports the neurobiological evidence that this gene plays a role in a pathophysiological aspect of schizophrenia, a role that prior to the present invention, had not been previously considered nor described, despite schizophrenics' well-known heavy dependence on nicotine.

II. Neuronal Nicotinic Receptor Subunit Family

As discussed above, during the development of the present invention, the α7 nicotinic receptor was associated with pathophysiological aspect(s) of schizophrenia. This receptor is a member of the neuronal nicotinic receptor subunit gene family, which is expressed in mammalian brain as pentameric, ligand-gated ion channels (Patrick et al., Ann NY Acad Sci, 505:194, 1987; Cooper et al., Nature, 350:235, 1991; and Lindstrom et al., Ann NY Acad Sci, 757:100, 1996). In the muscle, five different types of subunits constitute the holoreceptor, but in brain only two types of subunits, designated as "α" and "β," have been found (Galzi et al., Ann Rev Pharmacol, 31:37, 1991; and Lukas and Bencherif, Int Rev Neurobiol, 34:25, 1992).

Neuronal receptors can be functionally differentiated into two principal classes, which differ in their affinity for nicotine and the snake toxin, α-bungarotoxin (Marks and Collins, Mol Pharmacol, 22:554, 1982; Wonnacott, J Neurochem, 47:1706, 1986; Marks et al., Mol Pharmacol, 30:427, 1986; and Amar et al., FEBS, 327:284, 1993). Receptors that bind nicotine with high affinity contain α2-α6 as ligand binding subunits and require an association with β subunits for functional expression (Goldman et al., Cell, 48:965, 1987; Deneris et al., Clin Chem, 35:731, 1989; and Wada et al., J Compar Neurol, 284:314, 1989). A second class of receptors (α7-α9) bind nicotine with low affinity, have a high affinity for α-bungarotoxin, and function as homomeric ion channels in in vitro expression systems (Marks et al., supra, 1986; Wonnacott, supra, 1986; Alkondon and Albuquerque, J Pharm Ex Ther, 265:1455, 1993; Amar et al., FEBS, 327:284, 1993; and Zhang et al., Neuron, 12:167, 1994). The α7 receptor is the only α-bungarotoxin-binding receptor identified in mammalian brain. The α8 receptor appears to be only expressed in chick (Schoepfer et al., Neuron, 5:35, 1990), and the α9 receptor has limited expression in cochlear hair cells and pituitary (Elgoyhen et al., Cell, 79:705, 1994). In addition, a cDNA clone of the human α7 was isolated from a human brain library (GenBank Accession No. U40583).

Expression and function of a specific subset of the nicotinic receptor family, the α7 receptor, has recently been implicated in a neuronal pathway controlling the filtering or gating of auditory stimuli in both human and rat brain (Adler et al., Biol Psych, 32:607, 1992; Adler et al., Am J Psychol, 150:1856, 1993; Freedman et al., Harvard Rev Psychiat, 2:179, 1994; and Leonard et al., supra 1996). This sensory processing mechanism is aberrant in a majority of subjects with schizophrenia (Freedman et al., Schiz Res, 4:233-243, 1991). Pharmacological studies in both humans and rats suggest that the deficit in humans can be normalized by nicotine (Adler et al., supra, 1992; and Adler et al., supra 1993) and reproduced in a rodent model by antagonists of the low affinity α7 nicotinic receptor but not by high affinity antagonists (Luntz-Leybman et al., Brain Res, 587:130, 1992; and Rollins et al., Soc Neurosci Abst, 22:1272, 1996). Expression of α-bungarotoxin binding receptors is decreased in schizophrenic hippocampi by approximately 40% (Freedman et al., Biol. Psychiat, 38:22, 1995).

During the development of the present invention, the locus D15S1360, a polymorphic marker <120 kb from the full-length α7 nicotinic receptor gene at 15q14, was genetically linked to this auditory gating deficit in schizophrenic pedigrees. However, it is contemplated that other genes mapping to the 15q14 region are potential alternative or additional genetic candidates to α7 for pathogenic features of schizophrenia.

Also during the development of the present invention, expression of the α7 nicotinic receptor was examined in human postmortem brain. This gene was widely expressed in most nuclei, albeit at low levels. Regions of highest expression included those involved in processing of sensory information, such as the hippocampus, lateral and medial geniculates, and the reticular nucleus of the thalamus.

The present invention further provides the physical mapping of a full-length human genomic clone for the α7 receptor subunit and sequencing of a putative promoter region. The gene and promoter structure are similar to that of the chick α7. Additionally, a partial α7 gene duplication including exons 5-10 and intervening intronic sequence, which lies <1 Mb from the full-length gene has been identified. In addition, four novel exons at the 5' end of the duplicated α7 sequences were sequenced and intron/exon junctions identified. The duplicated α7 sequences were found to be expressed as alternatively spliced transcripts containing some or all of these novel exons.

The present invention also provides the structural organization of the human α7 neuronal nicotinic acetylcholine receptor gene, and presents data indicating a partial gene duplication. Large insert genomic clones were isolated from YAC, BAC and PAC libraries. There are 10 exons in the gene; the splice junctions are consistent with consensus splice sites (Green, Ann Rev Cell Biol, 7:559, 1991; Lamond, Bioessays, 15:595, 1993) and have an identical location to those in the chick α7 gene (Matter-Sadzinski et al., EMBO J, 11:4529, 1992), the only species for which genomic α7 gene sequence has been previously published.

The promoter region of the gene was found to be 77% G/C, and contains no TATA box. It thus fits a growing group of eukaryotic promoters, which demonstrate multiple transcription start sites (Maue et al., Neuron, 4:223, 1990; and Sauerwald et al., J Biol Chem, 265:14932, 1990). The nucleotide sequence, between the human and chick promoter regions, was poorly conserved. However, there are consensus transcription factor binding sites located in similar positions in the two promoters (Matter-Sadzinski et al., supra, 1992). These include SP-1 and AP-2 binding sites. SP-1 and AP-2 consensus motifs are frequently found in other ligand-gated ion channel genes (See e.g., Bessis et al., Nucl Acids Res, 21:2185, 1993), and may contribute to neuronal specificity.

A cyclic AMP response element (CREB) binding site motif was also identified in the human promoter, but is not found in the chick gene. The presence of this CREB site in the human promoter is interesting since the mammalian α7 gene is known to be down-regulated by corticosterone (Pauly et al., "Glucocorticoid Regulation of Sensitivity to Nicotine," in *The Biology of Nicotine: Current Research Issues*, Raven Press, New York, N.Y., pp. 121-139, 1992), which affects expression of the CREB-binding protein. Thus, it is contemplated that corticosterone and other glucocorticoids affect the α7 gene in some embodiments of the present invention.

In addition, alternative splicing of the full-length α7 gene was detected during the development of the present invention. Six different splice variants were identified through sequencing full-length transcripts. However, only one, missing exon 3, did not interrupt the frame of translation.

Several important motifs, which affect correct splicing of heterogeneous RNA, were identified during the development of the present invention. For example, there are two Chi(X) sequences (consensus: CCTGGTGG) known to enhance splicing, present in the human α7 gene of the present invention; there is one in intron 4 and one in the 3'-UT of the cDNA. Another group of splice enhancers with sequence (T)GCATG (A), have been localized as well. There are seven motifs of this enhancer class in sequence identified for intron 2 (approximately >25 kb in size). An additional enhancer of this type has been found in the large intron 4. It is contemplated that additional splicing motifs are localized in the human α7 sequence.

Exons 5-10 of the α7 nicotinic receptor gene were found to be duplicated in the human genome. The duplicated sequences lie within 1 Mb and are centromeric to the full-length α7 gene on chromosome 15. The evidence for the duplication includes mapping of the duplicated sequences to a different site on a YAC contig of the region. Additionally, heterozygous polymorphic sequences at exonic sites and at the L76630 locus, located 1.4 kb beyond the 3' end of the coding region, were detected in both a somatic cell chromosome 15 hybrid and in a single YAC (969b11) containing both the full-length gene and duplicated α7 exons. The apparent arrangement of the duplication is head to tail in relation to the full-length gene.

Further complexity for the α7 gene structure was introduced when it was determined that some of the RACE clones isolated during cloning of a human α7 cDNA contained only exons 5-10, and additional non-α7 sequences 5' of exon 5. These sequences were identical to sequences found in several EST clones that were located by homology screening with α7 cDNA sequence. The EST clones also contained only exons 5-10 of the α7 gene, with the previously unreported sequences again 5' of exon 5. PCR products from genomic DNA and from YACs 948a10 and 953g6 revealed that these non-α7 sequences were present in genomic clones containing either the full-length gene or the duplicated α7 sequences, and four novel exons were defined. It is contemplated that these sequences are arranged as alternatively spliced exons, as the positions of the consensus splice junctions between them correspond to the spliced products seen in the RACE and EST clones. These new exons were designated as "3'-α7A," "α7B," "α7C" and "α7D-5'." The RACE products were variable in their inclusion of exon B, similar to the EST clones.

Partial gene duplication has been implicated in human disease (See e.g., Hu and Worton, Hum Mutat, 1:3, 1992; Lehrman et al., Cell, 48:827, 1987; and Den-Dunnen, et al., Am J Hum Genet, 45:835, 1989). Thus, it is contemplated that although transcription of mRNAs containing the novel exons was found to occur at levels similar to those of the full-length coding region, the novel exons may be expressed only from the duplicated α7 sequences. There is also evidence for novel exons in another gene on chromosome 15, the small nuclear riboprotein-N(SNRPN); these exons at both the 5'- and 3'-ends of the SNRPN gene are also transcribed as alternative mRNAs. In fact, dupCHRNA7 is missing in some people, and the deletion of the duplicated gene is more commonly observed in schizophrenics than in control subjects.

It is contemplated that the human alternative transcripts containing the novel exons α7D, α7C, α7B, and α7A, might be translated. These alternatives lack the α7 signal peptide and disulfide bridge, which have been shown to be necessary for assembly of the homologous alpha subunit in muscle (Blount and Merlie, J Cell Biol, 111:2613, 1990). However, an alternatively spliced transcript of the muscle alpha, containing an additional exon, is expressed at equal levels to the correctly spliced isoform. It is also translated, but not assembled and is localized to the endoplasmic reticulum (Beeson et al., EMBO J, 9:2101, 1990; and Newland et al., J Physiol, 489:767, 1995). It is contemplated that a similar localization occurs for the human α7 alternative transcripts, containing the novel exons, if translated. However, it is not intended that the present invention be limited to any particular localization of these alternative transcripts.

Antibodies to the cytoplasmic loop of the chick α7, between membrane spanning regions III and IV, have been shown to detect α7 protein in pyramidal cells of rat hippocampus (Dominguez del Toro et al., J Comp Neurol, 349:325, 1994). However, during the development of the present invention, no α-bungarotoxin binding (i.e., indicative of a functional receptor), was observed on the plasma membranes of these cells. Since protein, translated from alternative α7 mRNAs containing D-C-B-A-5-10, would have the epitope used as antigen for cytoplasmic loop antibodies, it is possible that sequestered, but dysfunctional α7 protein internally localized would be detected as well as cell surface protein. The abundance of the D-C-B-A-5-10 alternative transcripts, thus, raises the possibility that they are regulatory for functional expression of α7 nicotinic receptors.

Although the mechanism responsible for the gene duplication is unclear, and an understanding of the mechanism is not necessary in order to use the present invention, two alu repeats were found in the genomic clones. One is located in intron 4, 500 bp upstream of exon 5. The second is located in the 3'-end of the gene outside of the poly-adenylation site. Alu repeats are known to have several possible functions, including as either positive or negative enhancers of transcription. In addition, they have also been shown to mediate duplication or deletion of DNA sequences (Schmid, Prog Nucl Acid Res, 53:283, 1996; and Lehrman et al., Cell, 48:827, 1987).

It is clear that the duplicated and expressed sequences involving the human α7 nicotinic receptor gene of the present invention provide the methods and compositions needed for mutation screening in disease. The present invention also provides methods and compositions for treatment (including, but not limited to gene therapy) of deficits in α7 expression and/or function.

The present invention provides methods and compositions needed to determine the control of α7 expression, through the use of the DNA sequences in its promoter region, as well as DNA sequences located at its intron/exon boundaries, and DNA sequences present elsewhere in its introns. In addition, the present invention provides the locations and sequences of newly identified duplicated and additional exons. It is contemplated that these sequences may be involved in pathogenic mutational events. Although the coding sequence of α7 shares some similarities between various animals (e.g., chickens, rodents, and humans), the genomic structure provided in the present invention in the promoter and introns is unique to humans, and could not have been predicted based on the knowledge of the genome structure of any other species.

Furthermore, the coding region alone cannot be used for genetic screening of individuals to identify mutations, because the appropriate primers (e.g., for PCR) are needed from introns positioned outside of the coding region. In addition, the genomic sequence is necessary for the production of cell lines and transgenic animals (i.e., for models useful for the development of therapeutic targets in drug discovery). The present invention provides the needed genomic sequences and primers for genetic screening methods and drug discovery.

III. Association of CHRNA7 Promoter Variants with P50 Inhibitory Deficits

Schizophrenia is a complex disorder, in which heterogeneity, reduced penetrance, and environmental factors have made identification of genetic defects difficult. The work of many investigators has resulted in the discovery and replication of eight principal linkage regions in the human genome. These include linkages at chromosome 1q21-q22 (Brzustowicz et al., Science, 288:678-682, 2000), chromosome 6p22-p24 (Straub et al., Mol Psychiatry, 1:89-92, 1996), chromosome 6q21-q22 (Cao et al., Genomics, 43:1-8, 1997), chromosome 8p21-p22 (Blouin et al., Nat Genet, 20:70-73, 1998), chromosome 10p11-p15 (Faraone et al., Am J Med Genet, 81:290-295, 1998), chromosome 13q14-q32 (Blouin et al., supra, 1998), chromosome 15q13-q15 (Riley et al., Am J Med Genet, 96:196-201, 2000; Stober et al., Am J Med Genet, 67:1201-1207, 2000, Stassen et al., Am J Med Genet, 96:173-177, 2000; Freedman et al., Am J Med Genet, 105:20-22, 2001; Liu et al., Am J Med Genet, 105:658-661, 2001; Xu et al., Am J Med Genet, 105:669-674, 2001; Tsuang et al., Am J Med Genet, 105:662-668, 2001; and Gejman et al., Am Med Genet, 105:789-793, 2001), and chromosome 22q11-q13 (Pulver et al., Am J Med Genet, 54:36-43, 1994). Additional linkages on six other chromosomes may be contributory in some populations (Baron, Am J Med Genet, 68:299-312, 2001). In general, linkage in any given cohort is found in only a subset of the total number of families examined, indicating that abnormalities in different gene sets may result in the same illness. Identification of pathogenic mutations in candidate genes that lie in the major linkage regions is necessary for a rigorous understanding of how several genes interact in the development of schizophrenia. As is described in more detail in Examples 11-16, the inventors provide evidence that functional polymorphisms in the promoter region of the α7 neuronal nicotinic acetylcholine receptor subunit gene (CHRNA7 or α7), a candidate gene in the 15q13-q14 linkage region, were more frequently found in schizophrenic patients and were associated with a sensory deficit found in this common mental illness.

Figure 11:
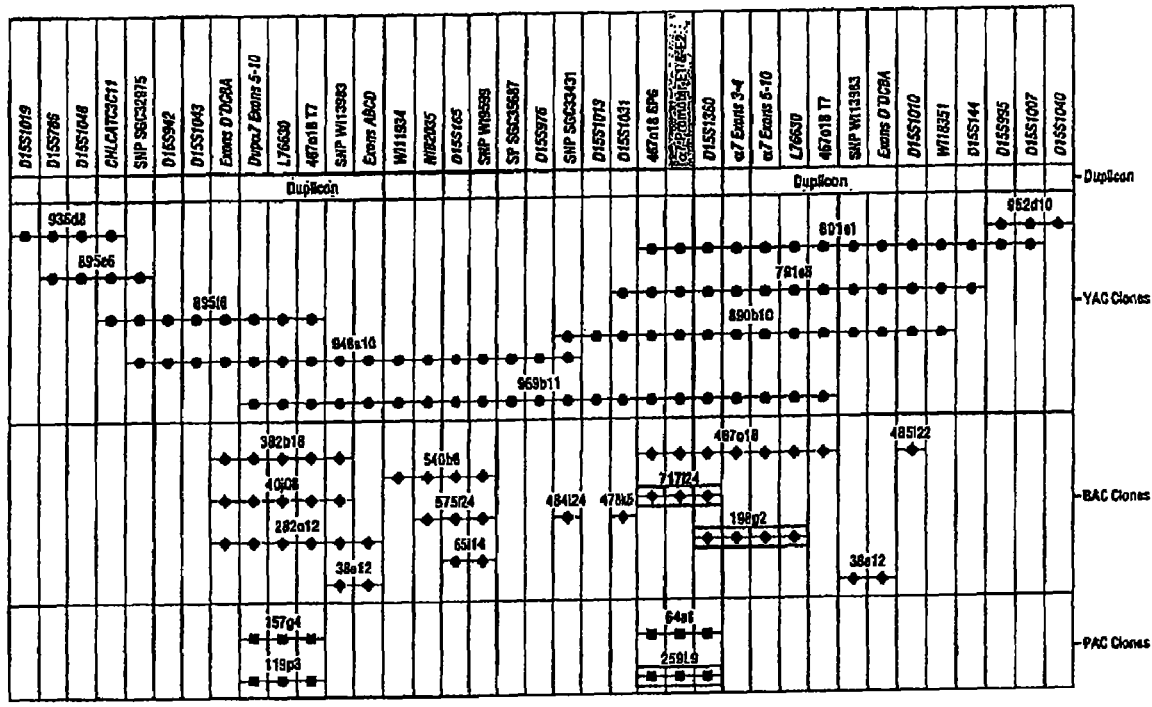
FIG. 11 provides a physical map of the linkage region to schizophrenia on chromosome 15q13-q14. The estimated size of the region is 4 cm.

The CHRNA7 gene cluster maps to a region of replicated linkage in schizophrenia on chromosome 15q13-q14 (See, FIG. 11). D15S1360, a polymorphic marker in intron 2 of the CHRNA7 gene, is genetically linked to a sensory deficit trait in the disease, namely a failure to inhibit the response to repeated auditory stimuli in the immediate environment (lod=5.3, θ=0.0, P<0.001 as described Freedman et al., Proc Natl Acad Sci USA, 94:587-592, 1997). Linkage to schizophrenia was also positive in this study of nine families, although not as significant (lod=1.33). Additional evidence for linkage of this locus to schizophrenia as the phenotype was found in pedigrees from the National Institute of Mental Health (NIMH) Schizophrenia Genetics Initiative (Freedman et al., Am J Med Genet, 105:20-22, 2001; and Leonard et al., Am J Med Genet, 81:308-312, 1998). A sibpair analysis showed that a significant proportion of D15S1360 alleles were shared identical-by-descent in the schizophrenics (0.58; P<0.0024). In a transmission disequilibrium study of schizophrenia, significant genotype-wise disequilibrium (P<007) was found at D15S165, a polymorphic simple sequence marker localized within one megabase of the α7 nicotinic receptor gene at 15q13-q14 (Freedmen et al., Am J Med Genet, 105:20-22, 2001). Recently a full genomic linkage analysis was completed of the NIMH Schizophrenia Initiative pedigrees, for which the genotyping was available from Millenium Pharmaceuticals (Cambridge, Mass.). A parametric genetic analysis and an autosomal codominant model was used, with a diagnosis of schizophrenia and schizoaffective disorder, depressed type, as the affected phenotype. One genetic linkage was found significant by genome-wide criteria (multipoint lod score, 3.94; P=0.00005), to the locus on 15q13-q14, within one cM of the previous finding for linkage to the locus of the α7 nicotinic receptor gene (Freedman and Leonard, Schizophr Res, 49:70, 2001; and Freedman et al., Am J Med Genet, 105:794-800, 2001. Several different groups have independently replicated this finding by using nonparametric methods in the NIMH sample (Kaufmann et al., Am J Med Genet, 81:282-289, 1998), and in other samples. The same region has been linked to juvenile myoclonic epilepsy (Elmslie et al., Hum Mol Genet, 6:1329-1334, 1997) and more recently to bipolar disorder (Edenberg et al., Am J Med Gen, 74:238-246, 1997; and Turecki et al., Mol Psychiatry, 6:570-578, 2001), indicating that the locus may contain defects in a gene or genes common to several neuronal disorders.

Biological and pharmacologic evidence also supports the CHRNA7 gene as a candidate gene for schizophrenia (Adler et al., Schizophr Bull, 24:189-202, 1998; and Leonard et al., "The role of nicotine and nicotinic receptors in psychopathology," in Arneric and Brioni (eds.) *Neuronal Nicotinic Receptors: Pharmacology and Therapeutic Opportunities*. New York, N.Y.: Wiley-Liss Inc., pp 305-320, 1999). Nicotine normalizes a sensory gating abnormality, the P50 inhibitory deficit, found in most patients with schizophrenia and in 50% of their first-degree relatives (Adler et al., Biol Psychiatry, 32:607-616, 1992; Adler et al., Am J Psychiatry, 150:1856-1861, 1993; and Freedman et al., Schizophr Res, 4:233-243, 1991). This trait, which involves inhibition of the response to repeated stimuli presented through the auditory system to the brain, can be measured by means of auditory evoked potentials in a paired pulse paradigm. Electrodes on the scalp record waves with a 50 millisecond latency (P50) following paired auditory stimuli delivered 0.5 second apart (Freedman et al., Schizophr Res, 4:233-243, 1991; and Baker et al., Biol Psychiatry, 22:603-617, 1987). In a normal response, the subject decreases the amplitude of the second response (test response), compared with the response to the first stimulus (conditioning response), through the action of an inhibitory neuronal pathway. The results are reported as the P50 test-conditioning (T/C) ratio. More than 85% of schizophrenic patients have abnormally increased P50 ratios, where the test response is greater than expected in the normal population (Adler et al., Biol Psychiatry, 17:639-654, 1982; Clementz et al., Schizophr Res, 30:71-80, 1998; Yee et al., J Abnorm Psychol, 107:691-698, 1998; Erwin et al., Schizophr Res, 33:157-167, 1998; and Patterson et al., Arch Gen Psychiatry, 57:57-64, 2000). This P50 inhibitory deficit is inherited in families of schizophrenic patients in an apparently autosomal dominant pattern (Freedman et al., Proc Natl Acad Sci USA, 94:587-592, 1997; Freedman et al., Somat Cell Mol Genet, 13:479-484, 1987; and Clementz et al., Am J Psychiatry, 155:1691-1694, 1998). Thus, half of family members have aberrant gating of the P50 auditory evoked potential, whether or not they have the disease. The increased incidence in schizophrenic patients and their families indicates that the P50 deficit represents a trait that predisposes to schizophrenia. The deficit is also present, but at much lower levels, in the general population, in subjects with no familial history of schizophrenia (Waldo et al., Biol Psychiatry, 47:231-239, 2000). The P50 inhibitory deficit, as previously discussed, is also genetically linked to 15q13-q14 (Freedman et al., Proc Natl Acad Sci USA, 94:587-592, 1997; and Coon et al., Biol Psychiatry, 34:277-289, 1993).

It is contemplated that the deficit in P50 inhibition, reflects decreased activity or expression of the CHRNA7 receptor. Pharmacologic antagonists of the CHRNA7 receptor reproduce the inhibitory deficit in several animal models (Luntz-Leybman et al., Brain Res, 587:130-136, 1992; and Rollins et al., Soc Neurosci Abstr, 19:837, 1993). The DBA/2j mouse strain has 50% lower levels of CHRNA7 than most other inbred strains, it does not show inhibition of its auditory evoked response to repeated stimuli, and the inhibition is normalized by both nicotine and a specific agonist of the α7 receptor, 2,4-dimethoxybenzylidene anabaseine (Stevens et al., Neuropsychopharm, 15:152-162, 1996; and Stevens et al., Psychopharmacology, 136:320-327, 1998). The inventors have previously found that the expression of the CHRNA7 gene was also decreased by approximately 50% in human postmortem hippocampus isolated from schizophrenic subjects, compared with matched control subjects (Freedman et al., Biol Psychiatry, 38:22-33, 1995). Expression of the CHRNA7 gene was also decreased in different brain regions, including the reticular thalamic nucleus and frontal cortex, in schizophrenic subjects (Court et al., J Neurochem, 73:15980-1597, 1999; and Guan et al., Neuroreport, 10:1779-1782, 1999).

As described in more detail in Examples 1-10, a genomic clone for the human CHRNA7 subunit was isolated from a yeast artificial chromosome (YAC) library. Mapping of the gene showed that exons 5 to 10 of the CHRNA7 gene were duplicated as part of a large DNA cassette. The duplication was inserted approximately one Mb proximal to the full-length α7 gene and directly 3' of five novel exons (D'-D-C-B-A). The duplicated exons 5 to 10 are expressed with the novel exons D'-A (dupCHRNA7) as messenger RNA in both human brain and peripheral tissues. Interestingly, dupCHRNA7 was homozygotically missing in five (4.2%) of 118 schizophrenic patients, but not in 59 control subjects. Mutation screening of the amino acid coding region for the full-length CHRNA7 and dupCHRNA7 genes, and a core promoter region for the full-length gene, has been completed during development of the present invention. Although multiple polymorphisms were found in the coding region, almost all were synonymous.

In addition, a core promoter region for the full-length CHRNA7 gene was isolated that supports efficient transcription of the reporter gene, luciferase. This 231 base pair fragment contains consensus binding sites for a number of transcription factors, including stimulating protein Sp1, activator protein AP-4, and a corticosteroid-responsive element, SRE as determined by using MatInspector (Quandt et al., Nucleic Acids Res, 23:4878-4884, 1995). The regions near the Sp1 binding sites contain several G/C-rich areas, which are contemplated to be binding sites for other transcription factors, such as Egr1. The location and spacing of these sites with respect to the start of exon 1 are conserved in the bovine α7 gene, where they have been shown to regulate transcription (Carrasco-Serrano et al., J Biol Chem, 273:20021-20028, 1998). During development of the present invention, mutation screening of this fragment in human DNA samples from control and schizophrenic subjects, showed a large cluster of polymorphisms, many lying in these putative transcription factor binding sites.

Although schizophrenia has a large genetic component, it is thought to be oligogenic (Freedman et al., Am J Med Genet, 105:794-800, 2001; and Gershon, Biol Psychiatry, 47:240-244, 2000). Heterogeneity in the inheritance of predisposing traits further complicates the orderly process of gene identification. At present, there are 14 chromosomes on which genetic linkage to schizophrenia has been identified or is suggested (Baron, Am J Hum Genet, 68:299-312, 2001). Many of these regions are contemplated to contain a gene variant contributing to the disease in the linked populations, indicating that many genes may interact in the disorder, but that not all the gene variants at these loci may be present in a single individual. Furthermore, the actual polymorphism present in any given gene is contemplated to result in differences in gene expression between subjects, which can also be affected by other genes and environmental factors. Some variants are contemplated to manifest in early development and some during puberty or postpuberty, when schizophrenia is usually first diagnosed. Additionally, some gene variants are contemplated to compensate for others, or to actually have a beneficial effect.

Three principal issues contribute to a discussion of the present invention. First, the study of a candidate gene for an endophenotype in schizophrenia, rather than the multigenic disease itself, has permitted the identification herein of a single gene defect. Endophenotypic traits found in complex disorders have been examined in attempts to simplify the biology and genetics of schizophrenia (Venables, "Input dysfunction in schizophrenia," in Maher (ed.) *Progress in Experimental Personality Research*, New York, N.Y.: Academic Press, pp. 1-47, 1964; and Freedman et al., Biol Psychiatry, 45:551-558, 1999). Examples of such traits are inhibitory gating of the P50 auditory evoked response (Freedman et al., Biol Psychiatry, 45:551-558, 1999; and Freedman et al., Somat Cell Mol Genet, 13:479-484, 1987), and smooth-pursuit eye tracking (Holzman, Int Rev Neurobiol, 27:179-205, 1985; and Holzman et al., Arch Gen Psychiatry, 45:641-647, 1988), both of which are found in the general population at lower levels than in the disease. In control subjects with no history of psychosis, variants in only one or a few different genes may be required to produce a specific abnormal phenotype or trait. In a disease such as schizophrenia, interdependence of multiple neurotransmitters in a single brain pathway and the presence of multiple gene defects may worsen performance in a given quantitative trait. However, even in schizophrenia, only a subset of the genes involved in the full clinical diagnosis is contemplated to be associated with a specific endophenotype.

Second, the nicotinic acetylcholine receptor subunit gene, CHRNA7, was implicated as a candidate gene in the 15q13-q15 linkage region for schizophrenia by genetic and biological data, supporting its role in sensory processing deficits in the disease (Leonard et al., Eur J Pharmacol, 393:237-242, 2000; and Leonard et al., Restor Neurol Neurosci, 12:195-201, 1998). Expression of the CHRNA7 gene is decreased in postmortem brain isolated from schizophrenic subjects compared with that of controls (Freedman et al., Biol Psychiatry, 38:22-33, 1995; Court et al., J Neurochem, 73:1590-1597, 1999; and Guan et al., J Neuroreport, 10:1779-1782, 1999). However, the present invention is the first description of CHRNA7 alleles associated with decreased α7 expression.

Specifically, the promoter variants in CHRNA7 identified herein are expected to contribute to the decreased expression of this gene in vivo. As described in Example 15 below, several of the polymorphisms have been tested in an in vitro reporter gene assay, where 6 of 8 variants were found to have decreased transcriptional activity. In fact, the most common variant at −86 bp, associated with schizophrenia (P=0.04), decreased transcription of the luciferase reporter gene by 20% (P=0.0001). Comparable transcriptional effects have been seen for other gene promoters (e.g., presenilin 1, tumor necrosis factor, and paraoxonase) with single-base pair mutations (Theuns et al., Hum Mol Genet, 9:325-331, 2000; Knight et al., Nat Genet, 22:145-150, 1999; and Brophy et al., Am J Hum Genet, 68:1428-1436, 2001). Many of the single and double promoter variants identified herein, were found principally in schizophrenic patients. Indeed, the functional variants isolated thus far are statistically more prevalent in schizophrenic subjects (P=0.007) than in controls. Additionally, the double variants examined thus far, where more than one variant was present, were combinations of the known single variants, and were found on separate alleles. This indicates inheritance of one mutation from each parent.

It is possible that some variants in the core promoter region have been missed because of ascertainment bias. The sample studied herein included more schizophrenic subjects than controls, and had fewer African Americans and Hispanic subjects than whites. Polymorphisms at −92 bp, −143 bp, −180 bp, and −241 bp were found more often in schizophrenic patients, but were rare in the study sample. Thus, when additional African Americans, Hispanics, and other ethnic cohorts are screened, more subjects with these rare variants (and possibly even new variants) are expected to be identified. Furthermore, during development of the present invention, an additional 2302 bp of sequence upstream of the CHRNA7 core promoter was isolated. Preliminary analysis of two subclones indicated the presence of upstream repressor elements. Upstream regulatory elements have been found in several other nicotinic receptor subunit genes indicative of complex developmental and tissue-specific regulation of expression (Flora et al., Eur J Pharmacol, 393:85-95, 2000; and Melnikova et al., Eur J Pharmacol, 393:75-83, 2000). Other functional or more complex variants in schizophrenic subjects are contemplated to lie in these regulatory regions of the human α7 nicotinic receptor subunit gene, perhaps in disequilibrium with some of the polymorphisms in the core promoter. Although the frequency of core promoter polymorphisms in multiply affected families was small, the polymorphisms associated with decreased α7 expression are expected to contribute to the transmission of sensory processing deficits in schizophrenia.

Third, because the CHRNA7 gene was targeted as a candidate gene as having a biological role in a sensory processing endophenotype seen in most schizophrenic patients and in one half of their first degree relatives (Leonard et al., "The role of nicotine and nicotinic receptors in psychopathology," in Arneric and Brioni (eds.), *Neuronal Nicotinic Receptors: Pharmacology and Therapeutic Opportunities*, New York, N.Y.: Wiley-Liss Inc., pp. 305-320, 1998; and Leonard et al., Restro Neurol Neurosci, 12:195-201, 1988), it is significant that a measure of auditory evoked inhibition in humans (the P50 gating phenotype), is correlated with the presence or absence of variants in the CHRNA7 core promoter. Inhibition of the P50 response is abnormal in most schizophrenic patients, where the test response is often larger than the conditioning response, resulting in T/C ratios much greater than 0.50. In control subjects with no history of schizophrenia, a T/C ratio range lower than in schizophrenic patients was found ($t_{205}$=8.49, P<0.0001). However, the ratios were significantly higher in controls with promoter variants than in controls with no polymorphisms (P=0.0001). The relationship between the presence of a promoter polymorphism and the P50 T/C ratio appeared to place the control subjects into three groups. The grouping is contemplated to indicate either a gene dosage effect or the presence of additional gene interactions. Inhibitory pathways in schizophrenic subjects are contemplated to be much more complex than in individuals with no history of mental illness. Measurement of the P50 phenotype in control subjects is, thus, contemplated to be less complicated and more representative of the effect of a few genes or possibly even a single gene defect. The present results indicate that the α7 promoter variants are associated with a measurable phenotype found in the general population, but present more frequently in schizophrenia. Coincidentally, other investigators have noted correlations between higher P50 ratios and schizotypy (Croft et al., Biol Psychiatry, 50:441-446, 2001), particularly in individuals with a family history of schizophrenia (Cadenhead et al., Am J Psychiatry, 157:1660-1668, 2000). However, none of these investigators had identified or suggested a correlation between CHRNA7 promoter variants, elevated P50 ratios, and predisposition to schizophrenia.

Last, the design and interpretation of candidate gene association studies, such as the present report, are not obvious. In the human lipoprotein lipase gene, for example, it has been found that the average individual is heterozygous at 17 sites, probably because of a combination of historical population founding, stratification of polymorphic changes, and recombination (Clark et al., Am J Hum Genet, 63:595-612, 1998). Not all of these polymorphisms will be functional, although they may be in disequilibrium with other variants and/or with the disease. This emphasizes the importance of a thorough functional analysis of any polymorphisms associated with schizophrenia. Furthermore, the complexity and dependence on the interactions of functional variants contributing to a complex major mental illness is consistent with the hypothesis that many of these functional polymorphisms are likely to be common in the general population (Lander and Schork, Science, 265:2037-2048, 1990; and Gershon, Biol Psychiatry, 47:240-244, 2000). In that regard, a variant in the catechol O-methyltransferase gene (COMT), found in 50% of non-mentally ill subjects, has recently been associated with prefrontal cortical deficits in schizophrenia, but estimated to contribute only a small percentage of the risk for the disease (Egan et al., Proc Natl Acad Sci USA, 98:6917-6922, 2001). Likewise, functional variants in the CHRNA7 gene promoter were found in 28% of the control subjects with no family history of schizophrenia, but were strongly associated (P=0.0001) with having a deficit in auditory sensory processing. The genotype relative risk for schizophrenia at one of the polymorphisms, −86 bp, was 2.39 (95% confidence interval, 1.07-5.32), indicating a small but real contribution to the disorder. This sort of inheritance of gene variants is contemplated to be the case for many complex disorders. Indeed, a role for calpain 10 in type-2 diabetes has been recently reported, where the aberrant allele was found in 75% of the control population but in 80% of those with diabetes (Horikawa et al., Nat Genet, 26:163-175, 2000). Thus, the assemblage of a group of functional variants in one individual is contemplated to be required for the development of a complex disease such as schizophrenia.

IV. Polymorphisms in CHRNA7 and dupCHRNA7

Evidence for genetic linkage to schizophrenia in the 15q13-q14 region has grown as marker density on the human genomic map has improved as described herein and as subsequently published (Stober et al., Am J Hum Gen, 67:1201-1207, 2000; Riley et al., Am J Med Gen, 96:196-201, 2000; Liu et al., Am J Med Gen, 105:658-661, 2001; Tsuang et al., Am J Med Gen, 105:662-668, 2001; and Xu et al., Am J Med Gen, 105:6698-674, 2001). The region has also been linked to bipolar disorder (Turecki et al., Mol. Psych, 6:570-578, 2001).

A candidate gene in this region, the α7 nicotinic acetylcholine receptor subunit gene CHRNA7, has been identified pharmacologically, as playing a role in an aberrant inhibitory pathway found in schizophrenia, the P50 auditory evoked potential deficit as described herein and elsewhere (Luntz-Lebman et al., Brain Res, 587:130-136, 1992; Stevens et al., Psychopharm, 136:320-327, 1998; Leonard et al., Pharmacol Biochem Behav, 70:561-570, 2001; and Leonard et al., Eur J Pharmacol, 393:237-242, 2000). The P50 deficit, an endophenotype of schizophrenia, is genetically linked to D15S1360, a dinucleotide marker in intron 2 of CHRNA7 (Freedman et al., Proc Natl Acad Sci USA, 94:587-592, 1997).

A. Proximal Promoter Polymorphisms

Functional gene variants have been isolated in the proximal promoter region of CHRNA7 that appear to be associated with both schizophrenia and with the P50 deficit as described in Section III herein. Now polymorphisms in the coding region and intron/exon borders of the CHRNA7 gene cluster in schizophrenic and control subjects are presented.

The mutation screening was complex, due to the partial duplication of the α7 gene. Exons 5-10, and intervening introns, were duplicated and inserted with a large cassette of DNA into a position proximal to the full-length CHRNA7. The duplicated exons are expressed as mRNA with five non-α7 exons in several tissue types, including postmortem brain (dupCHRNA7, See, GenBank Accession No. AF029838). Thus, mapping was required, for polymorphisms found in exons 5-10 in genomic DNA, to either the full-length CHRNA7 gene or the dupCHRNA7 gene. Transcripts were isolated, specific for each gene, from either postmortem brain tissue or lymphoblasts.

Variants in both coding region and introns were identified. As shown in Table 17, 21 polymorphisms were found the exons, nine of which changed an amino acid. Three of these amino acid changes, although rare, mapped to the full-length gene. These three amino acids are conserved between human, mouse (GenBank accession #A57175) and rat (GenBank accession #T01378) genes. One amino acid change in exon 4 (1112V) lies in part of the putative agonist-binding site (Galzi et al., Annu Rev Pharmacol, 31:37-72, 1991). In the three families, in which these amino acid changes occurred, cosegregation with neither the P50 deficit nor with schizophrenia was observed. In such a complex disorder, bilineal inheritance or reduced penetrance is contemplated to explain this result. However, functional promoter variants were found in all three of these families as described herein and as published (Leonard et al., Arch Gen Psychiatry, 59:1085-1096, 2002).

Ten intronic variants and two variants in the 3'-untranslated region were identified. Two polymorphisms in introns 2 and 3 were in the full-length gene, but the seven variants in introns 7 and 9 and those in the 3'untranslated region (3'UTR) could not be easily mapped because of the gene duplication. One variant in intron 9 at +37 was associated with schizophrenia in African Americans ($X^2$=9.986, 1; P=0.0016) and was in linkage disequilibrium with a synonymous variant mapped to CHRNA7. A number of the intronic polymorphisms either introduce a cryptic splice site or alter a splice site. The 2 bp deletion at 497/8, present in the duplicated gene in more than 50% of subjects examined, disrupts an exonic splice enhancer site (EXE). Thus, if exon 6 were aberrantly spliced out in this gene variant, the translation of a putative protein would remain in frame, indicating that this splice variant has regulatory effects. Interestingly, multiple alternatively spliced transcripts were identified in initial studies of the α7 gene cluster as described in herein. Splice variants have been found to be a common causal element in disease (Ars et al., Hum Mol Gen, 9:237-247, 2000; Grabowski and Black, Prog Neurobiol, 65:289-308, 2001; and Cartegni et al., Nat Rev Gen, 3:285-298, 2002). Since the CHRNA7 receptor assembles as a pentamer, the presence of splice variants represents a possible mechanism for dominant-negative decreased expression (Garcia-Guzman et al., Eur J Neurosci, 7:647-655, 1995).

The partial duplication of exons 5-10 and flanking regions not only introduced complexity into the mutation screen, but suggests yet another mechanism of mutation. The duplicon containing α7 exons 5-10 was inserted 3' of five exons, duplicated from another gene, and the chimera is transcribed in both lymphocytes and brain. This fusion gene or gene product is contemplated to interfere with expression, assembly or function of the CHRNA7 gene product in a manner similar to a splice variant. Variants in transcribed regions, common to both the CHRNA7 and dupCHRNA7 genes were mapped in mRNA from only a limited number of individuals. Thus, it is also contemplated that gene conversion plays a role in disruption of full-length CHRNA7 in some individuals.

Further, presence of the partial duplication is contemplated to lead to deletion or additional duplication events. For instance, the duplicated sequence is contemplated to prime misalignment, then recombination and subsequent deletion of the intervening sequences including part of the full-length gene. Deletions primed by duplications have been extensively characterized in Prader Willi and Angelman syndromes, which map nearby at 15q11-q13 (Robinson et al., J Med Gen, 35:130-136, 1998). In this regard, five schizophrenic subjects with homozygotic deletions of the duplicated gene have been identified, although none of these subjects appears to be missing any part of the full-length gene. Deletion of both copies of dupCHRNA7 has not yet been observed in controls.

Although a large number of polymorphisms were found in both the full-length CHRNA7 gene and its partial duplication, no nucleotide changes that either cosegregate with the P50 gating deficit or schizophrenia, or that obviously disrupt the function of the full-length CHRNA7 gene were isolated. In addition, none of the coding region variants were found to be in linkage disequilibrium with a functional promoter mutation. Previously, a decreased expression of CHRNA7 receptors in several regions of postmortem brain in individuals with schizophrenia compared to control subjects has been observed. Since no prominent coding region mutations were found, the promoter polymorphisms described herein in Section III are contemplated to be particularly important, as are intronic variants in the gene. These results also indicate that α7 nicotinic receptors in schizophrenic subjects, though reduced in number, are functionally normal and thus are contemplated to respond to therapies that modulate α7 activity or response.

B. Distal Promoter Polymorphisms

The data presented herein utilize overlapping genomic fragments to identify at least thirty-five (35) SNPs in the 2 kb 5' upstream regulatory region of the CHRNA7 gene. SNPs were genotyped utilizing a combination of heteroduplex analysis by denaturing high-performance liquid chromatography and sequencing, and were analyzed for association with schizophrenia in Caucasian-Non Hispanic and African-American subjects. Smoking history was considered as a secondary outcome. The results show significant association of a specific SNP, rs3087454 (−1831 bp), in the 5' upstream regulatory region of the CHRNA7 gene with schizophrenia.

In one embodiment, the present invention contemplates detecting distal α7 promoter polymorphisms using Hardy Weinberg Equilibrium (HWE) Conformance And Linkage Disequilibrium Estimations calculated in accordance with Example 21.

Thirty-five polymorphisms (i.e., for example, a single nucleotide polymorphism, SNP) were identified in the 2 kb of a CHRNA7 5'-upstream regulatory sequence (SEQ ID NO: 181). Many of these SNPs reside in transcription factor binding sites. See, FIG. 18. The minor allele frequency (MAF) of twenty-six (26) SNPs occurring in Caucasian-Non Hispanic subjects and/or in African-American subjects are presented. See, Table 23.

casian-Non Hispanic samples. The frequency of the rs3087454 (−1831 bp) "C" allele was 0.360 in the Caucasian-Non Hispanic samples, and 0.350 for the "A" allele in the African-American samples.

Figure 19:
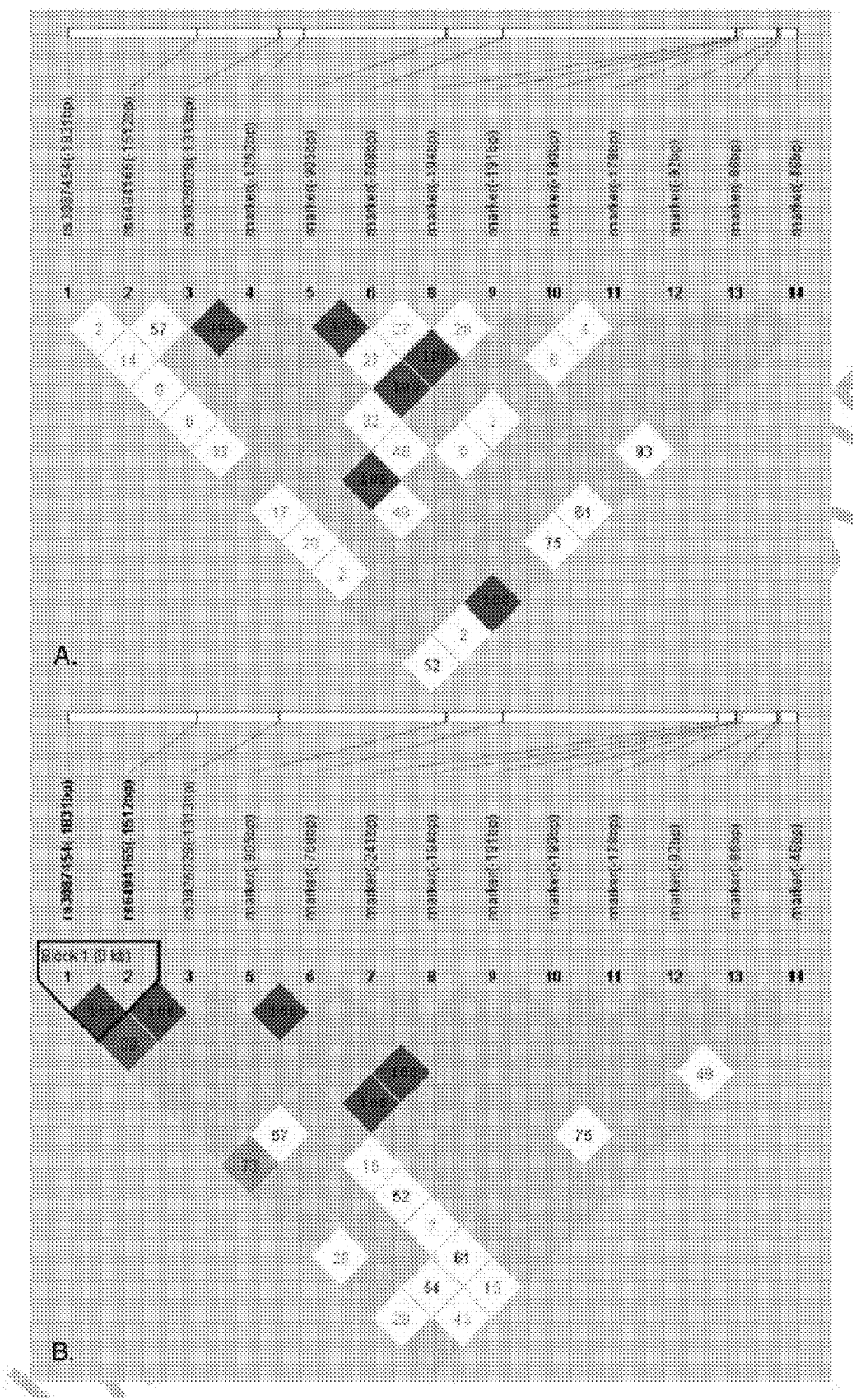
FIG. 19 presents exemplary data using a Haploview graph of the pairwise linkage disequilibrium (LD) between SNPs in the proximal promoter of CHRNA7, and SNPs in the upstream regulatory region of the gene. A) African-American sample population and B) Caucasian sample population. Numbers inside the squares are D'×100.

A linkage disequilibrium (LD) plot for the disclosed SNPs in the core promoter of CHRNA7 and in the 5' upstream regulatory region of the α7 gene was constructed. See, FIG. 19. LD parameter estimates were generated using the case-control data. Many of the found twenty-six (26) polymorphisms are rare and were not included in the LD plots. In the Caucasian sample, markers rs3087454 (−1831 bp) and rs6494165 (−1512 bp) were designated as a haplotype block using the Gabriel definition. Gabriel et al., "The structure of haplotype blocks in the human genome" *Science* 296:2225-2229 (2002). Two SNP marker pairs, rs3087454 (−1831 bp)/rs3826029 (−1313 bp) (D'=0.89), and rs6494165 (−1512 bp)/rs3826029 (−1313 bp) (D'=1.0) were in particularly strong LD as they are all contained within a 500 bp region. See, Table 23. In the African-American sample, SNP marker rs3826029 (−1313 bp) was in strong LD with marker −1252 bp (D'=1.0), as well as two core promoter polymorphisms (−190 bp (D'=1.0) and −46 bp (D'=1.0)). Additionally, in both sample populations, SNP markers at −905 bp/−768 bp were in LD with one another (D'=1.0) and with a core promoter polymorphism at −191 bp (D'=1.0).

b. Association of rs3087454 (−1831 bp) with Schizophrenia

1. Case-Control Results

Eight regulatory region SNPs, −46 bp, −86 bp, −178 bp, −190 bp, −1252 bp, rs3826029 (−1313 bp), rs6494165

TABLE 23

Chromosomal location and minor allele frequencies for SNPs in the regulatory region of CHRNA7

| SNP marker | rs # | Chromosomal location (bp) | Minor allele frequency (Caucasian-Non Hispanic) | Minor allele frequency (African-American) |
|---|---|---|---|---|
| −46 G/T | | 30110044 | 0.003 | 0.097 |
| −80 G/A | | 30110010 | 0.003 | 0.0 |
| −86 C/T | | 30110004 | 0.064 | 0.004 |
| −92 G/A | | 30109998 | 0.006 | 0.004 |
| −93 C/G | | 30109997 | 0.003 | 0.0 |
| −178 −G | | 30109912 | 0.004 | 0.076 |
| −190 +G | | 30109900 | 0.001 | 0.05 |
| −191 G/A | | 30109899 | 0.001 | 0.0 |
| −194 G/C | | 30109896 | 0.042 | 0.02 |
| −241 A/G | | 30109849 | 0.001 | 0.0 |
| −316 C/A | | 30109778 | 0.004 | 0.0 |
| −518 C/T | | 30109306 | 0.0 | 0.017 |
| −653 G/A | | 30109441 | 0.001 | 0.0 |
| −704 C/A | | 30109390 | 0.007 | 0.0 |
| −768 T/A | | 30109326 | 0.003 | 0.003 |
| −813 C/A | | 30109281 | 0.0 | 0.001 |
| −905 T/C | | 30109189 | 0.001 | 0.003 |
| −929 C/G | | 30109165 | 0.0 | 0.002 |
| −1247 T/A | | 30108843 | 0.001 | 0.0 |
| −1248 G/C | | 30108842 | 0.001 | 0.0 |
| −1252 C/A | | 30108838 | 0.0 | 0.053 |
| −1313 C/T | rs3826029 | 30108777 | 0.205 | 0.436 |
| −1382 G/A | | 30108708 | 0.001 | 0.0 |
| −1452 G/C | | 30108638 | 0.001 | 0.0 |
| −1512 T/G | rs6494165 | 30108578 | 0.059 | 0.081 |
| −1831 C/A[a] | rs3087454 | 30108259 | 0.360 | 0.350 |

[a]The minor alleles are different in African-Americans and Caucasians at −1831 bp C/A (rs3087454). In African-Americans, C is the most common allele and A is the minor allele. In Caucasians, A is the most common allele and C is the minor allele.

Genotype frequencies of all SNPs were consistent with HWE (all P>0.05; data not shown). Only SNPs with MAFs ≧ 0.05 in at least one ethnic population were considered for statistical analyses. Of note, the minor alleles for rs3087454 (−1831 bp) were different in the African-American and Cau- (−1512 bp), and rs3087454 (−1831 bp), were analyzed for association with schizophrenia and smoking in schizophrenia. P-values were adjusted by generating empirical P-values via permutation that were corrected for the number of SNPs tested and are indicated by an (*) See, Table 24.

TABLE 24

Case-control analyses under a genotypic model of association

| SNP | Schizophrenia vs No Diagnosis | | Smokers vs Non-Smokers | | SZ smokers vs SZ non-smokers | |
|---|---|---|---|---|---|---|
| | AA | Cauc | AA | Cauc | AA | Cauc |
| −46 bp | 0.309 | 0.325 | 0.501 | 0.098 | 0.096 | 0.134 |
| −86 bp | 0.397 | 0.521 | 1 | 0.167 | 1 | 0.302 |
| −178 bp | 0.319 | 0.633 | 0.50 | 0.575 | 0.618 | 0.372 |
| −190 bp | 0.699 | 0.325 | 0.482 | 0.099 | 0.619 | 0.134 |
| −1252 bp | 0.639 | 1 | 0.564 | 1 | 0.601 | 1 |
| rs3826029 (−1313 bp) | 0.864 | 0.733 | 0.288 | 0.209 | 0.653 | 0.265 |
| rs6494165 (−1512 bp) | 0.134 | 0.638 | 0.228 | 0.505 | 0.937 | 0.229 |
| rs3087454 (−1831 bp) | 0.000017, 0.0009* | 0.0005, 0.013* | 0.349 | 0.204 | 0.06 | 0.734 |

AA = African American,
Cauc = Caucasian non-Hispanic.
Adjusted P-values are indicated with an (*).

A significant difference was found in the genotype distribution of the rs3087454 (−1831 bp C/A) polymorphism between control and schizophrenic subjects. In the Caucasian-Non Hispanic sample, the "C/C" genotype was associated with schizophrenia (P=0.0009*)(OR=1.57; 95% CI=1.31-2.19) and in the African-American sample, the "A/A" genotype was associated with schizophrenia (P=0.013*)(OR=2.0; 95% CI=1.19-3.35).

Under an allelic model, the "C" allele was only nominally associated with schizophrenia (P=0.005) in the Caucasian-Non Hispanic sample, and the "A" allele was nominally associated with schizophrenia in the African-American sample (P=0.005). See, Table 25.

TABLE 25

Case-Control Analysis Under An Allelic Model Of Association

| SNP | Schizophrenia vs No Diagnosis | | Smokers vs Non-Smokers | | SZ smokers vs SZ non-smokers | |
|---|---|---|---|---|---|---|
| | AA | Cauc | AA | Cauc | AA | Cauc |
| −46 bp | 0.331 | 0.326 | 0.519 | 0.099 | 0.104 | 0.135 |
| −86 bp | 0.398 | 0.411 | 1 | 0.798 | 1 | 0.389 |
| −178 bp | 0.139 | 0.634 | 0.521 | 0.576 | 0.595 | 0.373 |
| −190 bp | 0.695 | 0.326 | 0.342 | 0.69 | 0.610 | 0.135 |
| −1252 bp | 0.648 | 1 | 0.573 | 1 | 0.610 | 1 |
| rs3826029 (−1313 bp) | 0.592 | 0.652 | 0.120 | 0.992 | 0.410 | 0.724 |
| rs6494165 (−1512 bp) | 0.149 | 0.445 | 0.247 | 0.817 | 0.940 | 0.824 |
| rs3087454 (−1831 bp) | 0.005, 0.198* | 0.005, 0.135* | 0.952 | 0.649 | 0.083 | 0.958 |

AA = African American,
Cauc = Caucasian non-Hispanic.
Adjusted P-values are indicated with an (*).

Polymorphism rs3087454 (−1831 bp C/A) was not significantly associated with the outcome of smoking status in either ethnic population despite its high correlation with schizophrenia. P-values were combined for the ethnic groups to determine the overall significance. Fisher, R. A., "Combining independent tests of significance" *Am. Stat.* 2:30 (1948), See, Table 26.

TABLE 26

Combined P-values at SNP rs3087454 for case-control analyses using Fisher's method with the outcome of schizophrenia versus controls

| Polymorphism | Model of association | Sample | P$^a$ |
|---|---|---|---|
| rs3087454 C/A (−1831 bp) | Genotypic | Controls | — |
| | | SZ | 0.0001 |
| | Allelic | Controls | — |
| | | SZ | 0.124 |

$^a$P-values were combined with the formula:

$$X_{2k}^2 = -2\sum_{i=1}^{k} \log_e(pi).$$

Where k = degrees of freedom, and $p_i$ = P-value.

As expected, this meta-analysis of the rs3087454 (−1831 bp) SNP indicated a significant association with schizophrenia (P=0.0001) under a genotypic model, but not under an allelic model (P=0.124).

The 58 childhood-onset subjects included in this study were analyzed separately for association with rs3087454 (−1831 bp), but there was no evidence for association (P=0.560*). When childhood-onset subjects were excluded from the Caucasian-Non Hispanic case-control sample (a majority of childhood-onset subjects were Caucasian), the P-value for an allelic model of association decreased from P=0.135* to P=0.033*. Similarly, the P– value for a genotypic model of association decreased from P=0.0009* to P=0.0002*.

In an attempt to further refine the schizophrenia phenotype, additional analyses were performed that included the assumption that schizophrenic smokers may be biologically distinct from schizophrenic non-smokers. These analyses included the following dependent variables; schizophrenic smokers versus control smokers, schizophrenic non-smokers versus control non-smokers, and schizophrenic smokers versus all controls. In the African-American sample, nominally significant P-values at rs3087454 (−1831 bp) were found with the outcomes of schizophrenic smokers versus control smokers (P=0.018, genotype; P=0.508, allele), schizophrenic non-smokers versus control non-smokers (P=0.0025, genotype; P=0.008, allele), and schizophrenic smokers versus all controls (P=0.001, genotype; P=0.606 allele). In the Caucasian-Non Hispanic sample, a nominally significant P-value at rs3087454 (−1831 bp) was found with the outcome of schizophrenic smokers versus all controls (P=0.041 genotype; P=0.179 allele).

c. Relationship of the Schizophrenia "Risk" Allele rs3087454 to Rare CHRNA7 5' Regulatory Region Polymorphisms The frequency of a polymorphism is an important factor in determining the power to detect the risk allele(s) in a given association study. Many of the CHRNA7 5' regulatory region polymorphisms are very rare with minor allele frequencies (MAF)<0.001. For example, the data was fitted to the 'common disease-rare alleles' model that has been suggested to explain some cases of schizophrenia. McClellan et al., "Schizophrenia: a common disease caused by multiple rare alleles. *Br. J. Psychiatry* 190:194-199 (2007). The relationship between the rs3087454 (−450 1831 bp) "risk" genotype and rare proximal promoter polymorphisms was examined. The number of individuals positive for both a proximal promoter polymorphism and the schizophrenia "risk" genotype at rs3087454 (−1831 bp) were compared against those with only proximal promoter polymorphisms. See, Table 27.

TABLE 27

Comparison of the number of individuals positive for both 5'
polymorphisms AND the schizophrenia "risk" genotype
at rs3087454 against those with only 5' polymorphisms and
without the "risk" genotype in the case-control sample

| | Ethnicity | | | | | |
| --- | --- | --- | --- | --- | --- | --- |
| | Caucasian | | | African-American | | |
| Genotype at rs3087454 (−1831) | C/C (N = 43) | A/C (N = 193) | A/A (N = 153) | A/A (N = 7) | C/A (N = 55) | C/C (N = 41) |
| CHRNA7 5' Polymorphisms | | | | | | |
| −46 G/T | 1 | 1 | 0 | 0 | 8 | 11 |
| −86 C/T | 2 | 20 | 24 | 0 | 0 | 0 |
| −92 G/A | 0 | 2 | 2 | 0 | 0 | 0 |
| −178 −G | 1 | 1 | 1 | 2 | 6 | 6 |
| −190 +G | 0 | 1 | 0 | 1 | 8 | 0 |
| −191 G/A | 0 | 1 | 0 | 0 | 1 | 5 |
| −194 G/C | 10 | 22 | 0 | 0 | 2 | 1 |
| −241 A/G | 0 | 2 | 0 | 0 | 0 | 0 |
| −316 G/A | 0 | 1 | 3 | 0 | 0 | 0 |
| −518 C/T | 0 | 0 | 0 | 0 | 2 | 0 |
| −653 G/A | 0 | 1 | 0 | 0 | 0 | 0 |
| −704 C/A | 0 | 3 | 0 | 0 | 0 | 0 |
| −768 T/A | 0 | 1 | 0 | 0 | 1 | 2 |
| −813 C/T | 0 | 0 | 0 | 0 | 1 | 0 |
| −905 T/C | 0 | 1 | 0 | 0 | 1 | 3 |
| −929 C/G | 0 | 0 | 0 | 0 | 1 | 3 |
| −1247 T/A | 0 | 1 | 0 | 0 | 0 | 0 |
| −1252 C/A | 0 | 0 | 0 | 0 | 3 | 5 |
| rs3826029 C/T (−1313) | 29 | 118 | 0 | 2 | 24 | 36 |
| −1382 G/A | 0 | 1 | 0 | 0 | 0 | 0 |
| −1452 G/C | 0 | 0 | 1 | 0 | 0 | 0 |
| rs6494165 T/G (−1512) | 11 | 30 | 0 | 0 | 3 | 9 |

The CC genotype is associated with schizophrenia in the Caucasian sample population and the AA genotype is associated with schizophrenia in the African-American sample population.

Of the rare promoter SNPs in the Caucasian-Non-Hispanic sample population, the SNP at −194 bp occurs more often in individuals with the "C" risk allele and the "CC" risk genotype. The D' value for −194 bp and rs3087454 is 0.73, however, the confidence bounds are large (0.40-0.89). Of the rare SNPs in the African-American sample population, the SNP at −190 bp occurs more often in individuals with the "A" risk allele and the "AA" risk genotype. The D' value is 0.20 for −190 bp and rs3087454, with confidence bounds of 0.02-0.75. With many rare SNPs and relatively low D' values, haplotype analyses may have limited power to detect a risk haplotype due to the presence of many rare haplotypes and the error associated with haplotype frequency estimation. However, observations provided by Table 27 suggest rare CHRNA7 proximal promoter polymorphisms may be relevant to schizophrenia as a haplotype with rs3087454 (−1831 bp) or as single markers.

d. Family-Based Results

Results of the family-based PDT analysis in a second cohort supported the majority of results obtained in case-control studies (data not shown). At rs3087454 (−1831 bp) in the Caucasian-Non Hispanic sample, the "C" allele was found to be linked/associated with schizophrenia (nominal P=0.048). The rs3087454 SNP was not associated with schizophrenia in the African-American sample. The rs6494165 (−1512 bp) SNP was nominally associated with smoking (P=0.045) when Caucasian-Non Hispanic schizophrenic non-smokers and smokers were compared, as was the proximal promoter SNP −86 bp (P=0.026). These results were not replicated in the African-American sample.

e. Association Studies with P50 Ratios in Control Subjects

Linear regression models were estimated separately for the two ethnic groups for the SNP at rs3087454 (−1831 bp) because different alleles were associated with schizophrenia in African-Americans ("A" allele) and Caucasian-Non-Hispanics ("C" allele) at this biallelic marker. For all other SNPs, ethnic groups were combined in order to gain statistical power and ethnicity was included as a covariate. Two proximal promoter SNPs were nominally associated with higher P50 ratios in control subjects (SNP −86 bp, P=0.03; SNP −191 bp, P<0.01). This study did not identify significant association with the P50 deficit at rs3087454 (−1831 bp)

f. Functional Analysis of rs3087454 (−1831 bp)

SNP rs3087454 (−1831 bp) was examined for effects on α7 nicotinic receptor gene expression in a luciferase reporter gene assay. Results of functional studies in two cell lines (SH-SY5Y and SK-N-BE) found no significant difference in the functional expression of either the "A" or "C" alleles for this SNP (data not shown).

5. Discussion

The data presented herein demonstrates that polymorphisms relating to schizophrenia susceptibility is not limited to the α7 nicotinic acetylcholine receptor gene (CHRNA7) core promoter, but are also located in the 5' upstream regulatory region. For example, an rs3087454 (−1831 bp) polymorphism, located in a putative repressor region upstream of CHRNA7, was significantly associated with schizophrenia in both the Caucasian-Non Hispanic and African-American case-control samples.

Nominal P-values for family-based analyses supported results in the case-control sample. Notably, different "risk" alleles were associated with schizophrenia in African-Americans ("A" allele) and Caucasian-Non Hispanics ("C" allele) at this biallelic marker. Associations of different alleles at the same locus with the same disease have been reported both: i) across different ethnic groups (Singleton et al., "alpha-Synuclein locus triplication causes Parkinson's disease" *Science* 302:841. (2003); and Tan et al., "Alpha synuclein promoter and risk of Parkinson's disease: microsatellite and allelic size variability" *Neurosci. Lett.* 336:70-72 (2003)); and ii) within the same ethnic group. Park et al., "Functional catechol-O-methyltransferase gene polymorphism and susceptibility to schizophrenia" *Eur. Neuropsychopharmacol.* 12:299-303 (2002); Glatt et al., "Association between a functional catechol O— methyltransferase gene polymorphism and schizophrenia: meta-analysis of case-control and family-based studies. Am. J. Psychiatry 160, 469-476 (2003); Wonodi et al., "Association between Val108/158 Met polymorphism of the COMT gene and schizophrenia" *Am. J. Med. Genet. B Neuropsychiatr. Genet.* 120:47-50. (2003); Chen et al., "Case-control study and transmission disequilibrium test provide consistent evidence for association between schizophrenia and genetic variation in the 22q11 gene ZDHHC8" *Hum. Mol. Genet.* 13:2991-2995 (2004); and Sanders et al., "Haplotypic association spanning the 22q11.21 genes COMT and ARVCF with schizophrenia" *Mol. Psychiatry* 10:353-365 (2005).

This observation could be explained by population differences where heterogeneous effects of the same polymorphism are caused by differences in genetic background. Alternatively, in complex diseases such as schizophrenia, in which multiple loci act jointly to confer susceptibility for disease, associations of different alleles at the same locus could be attributed to a correlation with a causal polymorphism at another locus. Lin et al., "No gene is an island: the flip-flop phenomenon" *Am. J. Hum. Genet.* 80:531-538 (2007). The correlation can be due to either an interaction between the loci or to linkage disequilibrium. Although it is not necessary to understand the mechanism of an invention, it is believed that the finding that transcription levels were not changed in an in vitro reporter gene analysis of the rs3087454 (−1831 bp) polymorphism suggests that the results of the presently disclosed genetic association studies are likely due to linkage disequilibrium. Attempts to refine the schizophrenia phenotype utilizing smoking history did not improve evidence for such an association, although nominal significance was noted in several comparisons.

Exploratory examination of CHRNA7 proximal promoter polymorphisms and their relationship with rs3087454 (−1831 bp) suggests that rare CHRNA7 promoter polymorphisms may occur more frequently in individuals with the rs3087454 (−1831 bp) risk genotype and could be relevant to schizophrenia as a haplotype with rs3087454 (−1831 bp) or as single markers in some individuals. Exclusion of the child-onset subjects in the Caucasian case-control sample resulted in a more significant P-value for both allelic and genotypic models of association with schizophrenia. It is, therefore, likely that the rs3087454 "risk" allele is more relevant to the etiology of adult onset schizophrenia.

These data show that polymorphisms in the 5' upstream regulatory region of the $\alpha 7$ nicotinic receptor gene (CHRNA7) have predictive value for the onset and development of schizophrenia. Such data suggests that investigation of the CHRNA7 gene to identify the complete genetic variance in the linkage peak region by fine mapping with a combination of SNPs and microsatellite markers is warranted. Such studies could uncover a causal SNP, correlated with rs3087454, and reveal whether variance in the candidate gene CHRNA7, its upstream regulatory regions, or a relevant SNP in the partial duplication (CHRFAM7A) is associated with schizophrenia.

V. Detection of CHRNA7 and dupCHRNA7 Alleles

In some embodiments, the present invention includes alleles of CHRNA7 and dupCHRNA7 that increase a subject's susceptibility to schizophrenia (e.g., including but not limited to alleles containing the promoter variants described herein such as −86C/T, −92G/A, −143G/A, −178−G, −180G/C, −191G/A, −194G/C, and −241A/G). Analysis of naturally occurring human CHRNA7 and dupCHRNA7 alleles revealed that patients with increased susceptibility to schizophrenia have a mutant $\alpha 7$ allele that results in reduced gene transcription and decreased inhibition in sensory gating (higher P50 T/C ratio). However, the present invention is not limited to CHRNA7 and dupCHRNA7 alleles with promoter polymorphisms. In fact, any $\alpha 7$ polymorphism associated with schizophrenia is within the scope of the present invention. For example, in some embodiments, the present invention provides single-nucleotide polymorphisms in other regions of CHRNA7 and dupCHRNA7 (including but not limited to those shown herein in Tables 17-19).

Accordingly, the present invention provides methods for determining whether a patient has an increased susceptibility to schizophrenia by determining whether the individual has an $\alpha 7$ allele containing a polymorphism contributing to reduced $\alpha 7$ expression. In other embodiments, the present invention provides methods for providing a prognosis of increased risk for schizophrenia to an individual based on the presence or absence of one or more mutations in the CHRNA7 and dupCHRNA7 genes. In preferred embodiments, the mutation contributes to schizophrenia.

A number of methods are available for analysis of polymorphisms. Assays for detection of polymorphisms or mutations fall into several categories, including, but not limited to direct sequencing assays, fragment polymorphism assays, hybridization assays, and computer based data analysis. Protocols and commercially available kits or services for performing multiple variations of these assays are available. In some embodiments, assays are performed in combination or in hybrid (e.g., different reagents or technologies from several assays are combined to yield one assay). The following assays are useful in the present invention.

A. Direct Sequencing Assays

In some embodiments of the present invention, polymorphisms are detected using a direct sequencing technique. In these assays, DNA samples are first isolated from a subject using any suitable method. In some embodiments, the region of interest is cloned into a suitable vector and amplified by growth in a host cell (e.g., a bacteria). In other embodiments, DNA in the region of interest is amplified using PCR.

Following amplification, DNA in the region of interest (e.g., the region containing the polymorphism of interest) is sequenced using any suitable method, including but not limited to manual sequencing using radioactive marker nucleotides, or automated sequencing. The results of the sequencing are displayed using any suitable method. The sequence is examined and the presence or absence of a given polymorphism is determined.

B. PCR Assay

In some embodiments of the present invention, polymorphisms are detected using a PCR-based assay. In some embodiments, the PCR assay comprises the use of oligonucleotide primers to amplify CHRNA7 and/or dupCHRNA7 fragment(s) containing the polymorphism of interest. The presence of an $\alpha 7$ allele containing nucleotide additions or deletions results in the generation of a longer or shorter PCR fragments respectively, which can be detected by gel electrophoresis.

In other embodiments, the PCR assay comprises the use of oligonucleotide primers that hybridize only to the mutant or wild type allele of α7 (e.g., to the region of polymorphism). Both sets of primers are used to amplify a sample of DNA. If only the mutant primers result in a PCR product, then the patient has the mutant α7 allele. If only the wild-type primers result in a PCR product, then the patient has the wild type allele of α7.

C. Fragment Length Polymorphism Assays

In some embodiments of the present invention, polymorphisms are detected using a fragment length polymorphism assay. In a fragment length polymorphism assay, a unique DNA banding pattern based on cleaving the DNA at a series of positions is generated using an enzyme (e.g., a restriction endonuclease). DNA fragments from a sample containing a polymorphism will have a different banding pattern than wild type.

1. RFLP Assay

In some embodiments of the present invention, polymorphisms are detected using a restriction fragment length polymorphism assay (RFLP). The region of interest is first isolated using PCR. The PCR products are then cleaved with restriction enzymes known to give a unique length fragment for a given polymorphism. The restriction-enzyme digested PCR products are separated by agarose gel electrophoresis and visualized by ethidium bromide staining. The length of the fragments is compared to molecular weight markers and fragments generated from wild-type and mutant controls.

2. CFLP Assay

In other embodiments, polymorphisms are detected using a CLEAVASE fragment length polymorphism assay (CFLP; Third Wave Technologies, Madison, Wis.; See e.g., U.S. Pat. No. 5,888,780). This assay is based on the observation that when single strands of DNA fold on themselves, they assume higher order structures that are highly individual to the precise sequence of the DNA molecule. These secondary structures involve partially duplexed regions of DNA such that single stranded regions are juxtaposed with double stranded DNA hairpins. The CLEAVASE I enzyme, is a structure-specific, thermostable nuclease that recognizes and cleaves the junctions between these single-stranded and double-stranded regions.

The region of interest is first isolated, for example, using PCR. Then, the DNA strands are separated by heating. Next, the reactions are cooled to allow intrastrand secondary structure to form. The PCR products are then treated with the CLEAVASE I enzyme to generate a series of fragments that are unique to a given SNP or mutation. The CLEAVASE enzyme treated PCR products are separated and detected (e.g., by agarose gel electrophoresis) and visualized (e.g., by ethidium bromide staining). The length of the fragments is compared to molecular weight markers and fragments generated from wild-type and mutant controls.

D. Hybridization Assays

In preferred embodiments of the present invention, polymorphisms are detected by hybridization assay. In a hybridization assay, the presence of absence of a given polymorphism or mutation is determined based on the ability of the DNA from the sample to hybridize to a complementary DNA molecule (e.g., a oligonucleotide probe). A variety of hybridization assays using a variety of technologies for hybridization and detection are available. A description of a selection of assays is provided below.

1. Direct Detection of Hybridization

In some embodiments, hybridization of a probe to the sequence of interest (e.g., polymorphism) is detected directly by visualizing a bound probe (e.g., a Northern or Southern assay; See e.g., Ausabel et al. (eds.), *Current Protocols in Molecular Biology*, John Wiley & Sons, NY, 1991). In these assays, genomic DNA (Southern) or RNA (Northern) is isolated from a subject. The DNA or RNA is then cleaved with a series of restriction enzymes that cleave infrequently in the genome and not near any of the markers being assayed. The DNA or RNA is then separated (e.g., agarose gel electrophoresis) and transferred to a membrane. A labeled (e.g., by incorporating a radionucleotide) probe or probes specific for the mutation being detected is allowed to contact the membrane under a condition of low, medium, or high stringency conditions. Unbound probe is removed and the presence of binding is detected by visualizing the labeled probe.

2. Detection of Hybridization Using "DNA Chip" Assays

In some embodiments of the present invention, polymorphisms are detected using a DNA chip hybridization assay. In this assay, a series of oligonucleotide probes are affixed to a solid support. The oligonucleotide probes are designed to be unique to a given polymorphism. The DNA sample of interest is contacted with the DNA "chip" and hybridization is detected.

In some embodiments, the DNA chip assay is a GeneChip (Affymetrix, Santa Clara, Calif.; See e.g., U.S. Pat. No. 6,045, 996) assay. The GeneChip technology uses miniaturized, high-density arrays of oligonucleotide probes affixed to a "chip." Probe arrays are manufactured by Affymetrix's light-directed chemical synthesis process, which combines solid-phase chemical synthesis with photolithographic fabrication techniques employed in the semiconductor industry. Using a series of photolithographic masks to define chip exposure sites, followed by specific chemical synthesis steps, the process constructs high-density arrays of oligonucleotides, with each probe in a predefined position in the array. Multiple probe arrays are synthesized simultaneously on a large glass wafer. The wafers are then diced, and individual probe arrays are packaged in injection-molded plastic cartridges, which protect them from the environment and serve as chambers for hybridization.

The nucleic acid to be analyzed is isolated, amplified by PCR, and labeled with a fluorescent reporter group. The labeled DNA is then incubated with the array using a fluidics station. The array is then inserted into the scanner, where patterns of hybridization are detected. The hybridization data are collected as light emitted from the fluorescent reporter groups already incorporated into the target, which is bound to the probe array. Probes that perfectly match the target generally produce stronger signals than those that have mismatches. Since the sequence and position of each probe on the array are known, by complementarity, the identity of the target nucleic acid applied to the probe array can be determined.

In other embodiments, a DNA microchip containing electronically captured probes (Nanogen, San Diego, Calif.) is utilized (See e.g., U.S. Pat. No. 6,068,818). Through the use of microelectronics, Nanogen's technology enables the active movement and concentration of charged molecules to and from designated test sites on its semiconductor microchip. DNA capture probes unique to a given SNP or mutation are electronically placed at, or "addressed" to, specific sites on the microchip. Since DNA has a strong negative charge, it can be electronically moved to an area of positive charge.

First, a test site or a row of test sites on the microchip is electronically activated with a positive charge. Next, a solution containing the DNA probes is introduced onto the microchip. The negatively charged probes rapidly move to the positively charged sites, where they concentrate and are chemically bound to a site on the microchip. The microchip is then washed and another solution of distinct DNA probes is added until the array of specifically bound DNA probes is complete.

A test sample is then analyzed for the presence of target DNA molecules by determining which of the DNA capture probes hybridize, with complementary DNA in the test sample (e.g., a PCR amplified gene of interest). An electronic charge is also used to move and concentrate target molecules to one or more test sites on the microchip. The electronic concentration of sample DNA at each test site promotes rapid hybridization of sample DNA with complementary capture probes (hybridization may occur in minutes). To remove any unbound or nonspecifically bound DNA from each site, the polarity or charge of the site is reversed to negative, thereby forcing any unbound or nonspecifically bound DNA back into solution away from the capture probes. A laser-based fluorescence scanner is used to detect binding, In still further embodiments, an array technology based upon the segregation of fluids on a flat surface (chip) by differences in surface tension (ProtoGene, Palo Alto, Calif.) is utilized (See e.g., U.S. Pat. No. 6,001,311). Protogene's technology is based on the fact that fluids can be segregated on a flat surface by differences in surface tension that have been imparted by chemical coatings. Once so segregated, oligonucleotide probes are synthesized directly on the chip by ink-jet printing of reagents. The array with its reaction sites defined by surface tension is mounted on a X/Y translation stage under a set of four piezoelectric nozzles, one for each of the four standard DNA bases. The translation stage moves along each of the rows of the array and the appropriate reagent is delivered to each of the reaction site. For example, the A amidite is delivered only to the sites where amidite A is to be coupled during that synthesis step and so on. Common reagents and washes are delivered by flooding the entire surface, and are then removed by spinning.

DNA probes unique for the polymorphism of interest are affixed to the chip using Protogene's technology. The chip is then contacted with the PCR-amplified genes of interest. Following hybridization, unbound DNA is removed and hybridization is detected using any suitable method (e.g., by fluorescence de-quenching of an incorporated fluorescent group).

In yet other embodiments, a "bead array" is used for the detection of polymorphisms (Illumina, San Diego, Calif.; See e.g., PCT Publications WO 99/67641 and WO 00/39587, each of which is herein incorporated by reference). Illumina uses a BEAD ARRAY technology that combines fiber optic bundles and beads that self-assemble into an array. Each fiber optic bundle contains thousands to millions of individual fibers depending on the diameter of the bundle. The beads are coated with an oligonucleotide specific for the detection of a given SNP or mutation. Batches of beads are combined to form a pool specific to the array. To perform an assay, the BEAD ARRAY is contacted with a prepared subject sample (e.g., DNA). Hybridization is detected using any suitable method.

3. Enzymatic Detection of Hybridization

In some embodiments of the present invention, genomic profiles are generated using a assay that detects hybridization by enzymatic cleavage of specific structures (INVADER assay, Third Wave Technologies; See e.g., U.S. Pat. No. 6,001,567). The INVADER assay detects specific DNA and RNA sequences by using structure-specific enzymes to cleave a complex formed by the hybridization of overlapping oligonucleotide probes. Elevated temperature and an excess of one of the probes enable multiple probes to be cleaved for each target sequence present without temperature cycling. These cleaved probes then direct cleavage of a second labeled probe. The secondary probe oligonucleotide can be 5'-end labeled with fluorescein that is quenched by an internal dye. Upon cleavage, the de-quenched fluorescein labeled product may be detected using a standard fluorescence plate reader.

The INVADER assay detects specific mutations and SNPs in unamplified genomic DNA. The isolated DNA sample is contacted with the first probe specific either for a SNP/mutation or wild type sequence and allowed to hybridize. Then a secondary probe, specific to the first probe, and containing the fluorescein label, is hybridized and the enzyme is added. Binding is detected by using a fluorescent plate reader to compare the signal of the test sample to known positive and negative controls.

In some embodiments, hybridization of a bound probe is detected using a TaqMan assay (PE Biosystems, Foster City, Calif.; See e.g., U.S. Pat. No. 5,962,233). The assay is performed during a PCR reaction. The TaqMan assay exploits the 5'-3' exonuclease activity of the AMPLITAQ GOLD DNA polymerase. A probe, specific for a given allele or mutation, is included in the PCR reaction. The probe consists of an oligonucleotide with a 5'-reporter dye (e.g., a fluorescent dye) and a 3'-quencher dye. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In still further embodiments, polymorphisms are detected using the SNP-IT primer extension assay (Orchid Biosciences, Princeton, N.J.; See e.g., U.S. Pat. No. 5,952,174). SNPs are identified in this assay, by using a specially synthesized DNA primer and a DNA polymerase, to selectively extend the DNA chain by one base at the suspected SNP location. DNA in the region of interest is amplified and denatured. Polymerase reactions are then performed using miniaturized systems called microfluidics. Detection is accomplished by adding a label to the nucleotide suspected of being at the SNP or mutation location. Incorporation of the label into the DNA can be detected by any suitable method (e.g., if the nucleotide contains a biotin label, detection is via a fluorescently labeled antibody specific for biotin).

E. Mass Spectroscopy Assay

In some embodiments, a MassARRAY system (Sequenom, San Diego, Calif.) is used to detect polymorphisms (See e.g., U.S. Pat. No. 6,043,031). DNA is isolated from blood samples using standard procedures. Next, specific DNA regions containing the polymorphism of interest, about 200 base pairs in length, are amplified by PCR. The amplified fragments are then attached by one strand to a solid surface and the non-immobilized strands are removed by standard denaturation and washing. The remaining immobilized single strand then serves as a template for automated enzymatic reactions that produce genotype specific diagnostic products.

Very small quantities of the enzymatic products, typically five to ten nanoliters, are then transferred to a SpectroCHIP array for subsequent automated analysis with the SpectroREADER mass spectrometer. Each spot is preloaded with light absorbing crystals that form a matrix with the dispensed diagnostic product. The MassARRAY system uses MALDI-TOF (Matrix Assisted Laser Desorption Ionization-Time of Flight) mass spectrometry. In a process known as desorption, the matrix is hit with a pulse from a laser beam. Energy from the laser beam is transferred to the matrix and it is vaporized resulting in a small amount of the diagnostic product being expelled into a flight tube. As the diagnostic product is charged when an electrical field pulse is subsequently applied to the tube they are launched down the flight tube towards a detector. The time between application of the electrical field pulse and collision of the diagnostic product with the detector is referred to as the time of flight. This is a very precise measure of the product's molecular weight, as a molecule's mass correlates directly with time of flight with smaller molecules flying faster than larger molecules. The entire assay is completed in less than one thousandth of a second, enabling samples to be analyzed in a total of 3-5 second including repetitive data collection. The SpectroTYPER software then calculates, records, compares and reports the genotypes at the rate of three seconds per sample.

F. Kits for Analyzing Risk of Schizophrenia

The present invention also provides kits for determining whether an individual possesses an α7 allele with a specific polymorphism. In some embodiments, the kits are useful in determining whether the subject is at risk of developing schizophrenia. The diagnostic kits are produced in a variety of ways. In some embodiments, the kits contain at least one reagent for specifically detecting a mutant α7 allele. In preferred embodiments, the kits contain reagents for detecting polymorphisms in the α7 gene promoter. In preferred embodiments, the reagents are primers for amplifying the region of DNA containing the promoter. In other preferred embodiments, the reagent is a probe that binds to the polymorphic region. In some embodiments, the kit contains instructions for determining whether the subject is at risk for developing schizophrenia. In preferred embodiments, the instructions specify that risk for developing schizophrenia is determined by detecting the presence or absence of a mutant α7 allele in the subject, wherein subjects having an allele containing a promoter polymorphism associated with decreased α7 transcription, have an increased risk of developing schizophrenia. In some embodiments, the kits include ancillary reagents such as buffering agents, nucleic acid stabilizing reagents, protein stabilizing reagents, and signal producing systems (e.g., fluorescence generating systems). The test kit may be packaged in any suitable manner, typically with the elements in a single container or various containers as necessary along with a sheet of instructions for carrying out the test. In some embodiments, the kits also preferably include a positive control sample.

G. Bioinformatics

In some embodiments, the present invention provides methods of determining an individual's risk of developing schizophrenia based on the presence of one or more mutant alleles of α7. In some embodiments, the analysis of polymorphism data is automated. For example, in some embodiments, the present invention provides a bioinformatics research system comprising a plurality of computers running a mullet-platform object oriented programming language (See e.g., U.S. Pat. No. 6,125,383). In some embodiments, one of the computers stores genetics data (e.g., the risk of contracting schizophrenia associated with a given polymorphism). In some embodiments, one of the computers stores application programs (e.g., for analyzing transmission disequilibrium data or determining genotype relative risks and population attributable risks). Results are then delivered to the user (e.g., via one of the computers or via the internet).

VI. Treatment and Diagnosis of Schizophrenia and Other Psychoses

The present invention provides methods and compositions for the development and identification of alternative means to diagnose and treat schizophrenia. The methods and compositions of the present invention will find use in the functional assessment of α7 nicotinic receptors in schizophrenic patients, as well as for screening populations for deficits in receptor function. The present invention finds use in genetic screening methods for genetic and parentage counseling, as well as for identification of individuals at risk for developing schizophrenia.

The present invention also provides methods and compositions for modifying α7 nicotinic receptor function. For example, the present invention contemplates the development of genetic therapy methods to correct deficiencies in the receptor structure and/or function, as well as other therapeutic methods to enhance or decrease the function of the receptor, as appropriate for the treatment of any given individual.

It is also contemplated that the present invention will find use in relation to other psychosis. For example, the present invention will find use in the diagnosis and treatment of genetic disorders, in particular those genetic disorders known to have a genetic component associated with chromosome 15, such as Prader-Willi syndrome, Angelman's syndrome, etc., as well as other diseases, such as epilepsy (e.g., juvenile myoclonic epilepsy), breast, and other types of cancers. The present invention also finds use in the diagnosis and treatment of nicotine-dependent illnesses, including, but not limited to, small cell lung carcinoma.

Indeed, it is contemplated that the present invention will find use in the development of antipsychotic drugs targeted to the α7 nicotinic receptor and/or the α7 nicotinic receptor subunit gene. For example, dimethylbenzylidene anabaseine (DMXB-A; [(2-4) Dimethoxy-benzylidene anabaseine hydrochloride]) and its congeners are selectively agonistic at the α7 receptor. During the development of the present invention, an animal model of the deficit observed in schizophrenics was used to show that DMXB-A is effective in repeated doses, whereas the effect of nicotine itself is completely inactivated after one dose. DMXB-A also has significantly less cardiovascular effects than nicotine, consistent with its antagonist effects at α4-α2 nicotinic receptors. Thus, it is contemplated that DMXB-A will find use as an anti-psychotic drug.

In addition to the physiological deficit found in schizophrenics and some of their relatives, similar deficits are also found as state-related changes in other psychotic disorders, including Parkinson's, Alzheimer's, mania and cocaine dependence. In stimulant dependence, neuroleptic anti-psychotic drugs have poor patient compliance, possibly due to their anhedonic, catecholamine-blocking effects. Thus, it is contemplated that nicotinic cholinergic therapeutic strategies, such as those developed using the methods and/or compositions of the present invention will be effective against a broad spectrum of clinical indications.

It is further contemplated that the present invention will be used to develop antibodies and other diagnostic reagents. For example, the present invention finds use in the production of peptide antibodies using sequences identified using the present invention.

VII. Transgenic Animals

The present invention provides methods and compositions for production of transgenic animal models of schizophrenia, nicotine-dependent illnesses, and cancer. It is also contemplated that such systems as *Xenopus* oocytes will be used to express human α7 receptors and gene sequences of the present invention.

In preferred embodiments, transgenic mice are generated using microinjection of DNA containing α7 gene sequences into mammalian oocytes. However, equivalent transgenic mice can also be produced by homologous recombination in embryonic stem (ES) cells. Techniques for the isolation, culture, microinjection and implantation of a variety of mammalian oocytes (e.g., murine, porcine, ovine, bovine, etc.) are known to the art.

Two mouse models are provided in the present invention. The first model involves introduction of an intact human α7 gene into the mouse genome by microinjection of a fertilized egg with DNA from the clone containing the full-length nAChR gene described in Example 8. The integrity of the clone in the transgenic mice is examined by PCR amplification, using all of the identified STSs on the clone map. Large flanking DNA sequences are included in this transgene, in order to ensure proper expression of the human α7 gene in the mice. The expression of the human α7 gene in mice is examined by an RNase protection assay designed to specifically detect the human α7 mRNA. This expression pattern coincides with the expression pattern of α7 in human tissues, as analyzed by Northern hybridization. The transgenic mouse model provides animals for determinations of α7 function in nicotine-dependence, nicotine-dependent illnesses, cancers associated with chromosome 15, schizophrenia, and other psychoses. These animals also facilitate the development of drugs and other therapeutics that affect the function of human α7 in vivo.

The second model is exemplified using transgenic mice that contain targeted disruptions of the α7 gene. These animals, termed "knockout" animals, lack the ability to express α7 ("α7 knockouts"). In this model, mice are generated with a deletion specifically in the α7 gene, in order to allow assessment of phenotypic changes. In order to produce the transgenic knockout mice of the present invention, cloned human α7 gene sequences are used to disrupt the α7 gene in such a manner that α7 cannot be produced. In this model, two types of deletions are designed. The first removes the α7 gene entirely from the germline cells. The second type of deletion is engineered so as to provide control over the specific tissue and developmental stage in which α7 expression is interrupted. In the second model, the viability of the mutated animals is maintained, permitting analysis of the animals' phenotypes (including expression in specific tissues).

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: nAChR (nicotinic acetylcholine receptor); ° C. (degrees Centigrade); rpm (revolutions per minute); BSA (bovine serum albumin); $H_2O$ (water); HCl (hydrochloric acid); aa (amino acid); bp (base pair); kb or kbp (kilobase pair); Mb (megabase pair); kD (kilodaltons); gm or g (grams); μg (micrograms); mg (milligrams); ng (nanograms); μl (microliters); ml (milliliters); mm (millimeters); nm (nanometers); μm (micrometer); M (molar); mM (millimolar); M (micromolar); nM (nanomolar); pM (picomolar); U or u (units); V (volts); MW (molecular weight); sec (seconds); min(s) (minute/minutes); hr(s) (hour/hours); dNTP (deoxynucleotide); $MgCl_2$ (magnesium chloride); NaCl (sodium chloride); KCl (potassium chloride); DTT (dithiothreitol); DMSO (dimethyl sulfoxide); NaOH (sodium hydroxide); 3'UT (3'-untranslated region); $OD_{280}$ (optical density at 280 nm); $OD_{600}$ (optical density at 600 nm); EST (expressed sequence tag); PAGE (polyacrylamide gel electrophoresis); PBS (phosphate buffered saline [150 mM NaCl, 10 mM sodium phosphate buffer, pH 7.2]); PCR (polymerase chain reaction); DMEM (Dulbecco's Modified Eagle Medium); PEG (polyethylene glycol); PMSF (phenylmethylsulfonyl fluoride); RT-PCR (reverse transcription PCR); SDS (sodium dodecyl sulfate); SSC (saline-sodium citrate buffer); Tris (tris (hydroxymethyl)aminomethane); w/v (weight to volume); v/v (volume to volume); YAC (yeast artificial chromosome); BAC (bacterial artificial chromosome); PAC (P1 artificial chromosome); RACE (Rapid Amplification of cDNA Ends); TAFE (Transverse Alternating Field Electrophoresis); lod (maximum logarithm of the odds); STS (sequence-tagged site); Beckman (Beckman Instruments, Inc., Fullerton, Calif.); Amersham (Amersham Life Science, Inc. Arlington Heights, Ill.); Qiagen (Qiagen Inc., Santa Clarita, Calif.); Genome Systems (Genome Systems, St. Louis, Mo., USA); ICN (ICN Pharmaceuticals, Inc., Costa Mesa, Calif.); Amicon (Amicon, Inc., Beverly, Mass.); NCBI (National Center for Biotechnology Information, Bethesda, Md.); ATCC (American Type Culture Collection, Rockville, Md.); Research Genetics (Research Genetics, Huntsville, Ala.); Pharmacia (Pharmacia and Upjohn Diagnostics, Kalamazoo, Mich.); Boehringer-Mannheim (Boehringer-Mannheim, Indianapolis, Ind.); National Biosciences (National Biosciences, Inc., Plymouth Minn.); MJ Research (MJ Research, Watertown, Mass.); Perkin-Elmer (Perkin-Elmer, Foster City, Calif.); BioRad (BioRad, Richmond, Calif.); Clontech (CLONTECH Laboratories, Palo Alto, Calif.); Gibco, GIBCO BRL, or Gibco BRL (Life Technologies, Inc., Gaithersburg, Md.); Gene Codes (Gene Codes Corporation, Ann Arbor, Mich.); Invitrogen (Invitrogen Corp., San Diego, Calif.); Kodak (Eastman Kodak Co., New Haven, Conn.); Promega (Promega, Corp., Madison, Wis.); New England Biolabs (New England Biolabs, Inc., Beverly, Mass.); Novagen (Novagen, Inc., Madison, Wis.); Pharmacia (Pharmacia, Inc., Piscataway, N.J.); Schleicher & Schuell (Schleicher and Schuell, Inc., Keene, N.H.); Sigma (Sigma Chemical Co., St. Louis, Mo.); Sorvall (Sorvall Instruments, a subsidiary of DuPont Co., Biotechnology Systems, Wilmington, Del.); Stratagene (Stratagene Cloning Systems, La Jolla, Calif.); Whatman (Whatman LabSales, Hillsboro, Oreg.); Bethyl Laboratories (Bethyl Laboratories, Montgomery, Tex.); Ambion (Ambion, Inc., Austin, Tex.); and Zeiss (Carl Zeiss, Inc., Thornwood, N.Y.).

Unless otherwise indicated, all restriction enzymes were obtained from New England BioLabs and were used according to the manufacturer's instructions.

Example 1

Samples

Samples were obtained from various normal individuals for use as controls in the Examples described below. To prepare these samples, blood was drawn from normal subjects, seen in the Denver Schizophrenia Center. Of the 43 subjects used for the polymorphism analysis, 22 were female and 21 were male. There were 38 Caucasians, 2 Blacks, 1 Asian and 2 Hispanics. None of the subjects had a history of mental illness or a family history of mental illness.

In addition to the "normal" samples, pedigrees were selected for presence of at least two cases of schizophrenia in a nuclear family. Two psychiatrists made clinical diagnoses of schizophrenia, chronic type, blind to pedigree and genetic information, using Research Diagnostic Criteria (Spitzer et al., Arch Gen Psychiat, 35:773, 1978; and Endicott and Spitzer, Arch Gen Psychiat, 35:837, 1978). Nine families with 104 members were studied (i.e., nine pedigrees containing individuals diagnosed with schizophrenia were analyzed). All subjects gave written informed consent. Blood was also drawn from these individuals for DNA analysis.

DNA was extracted from blood samples as described by Miller et al. (Miller et al., Nuc Acids Res, 16:1215, 1988), with one additional step. Briefly, red blood cells were lysed by incubating 10-15 ml of anticoagulated blood at 4 C for 10 minutes in 40 ml blood cell lysis solution (BCL) (BCL contains 0.3 M sucrose, 0.01 M Tris HCl pH 7.5, 0.005 M MgCl$_2$ and 1% Triton X-100) with occasional rocking to mix. The cells were then centrifuged at 850×g at 4 C for 15 minutes. The pellet was resuspended by repeated pipetting with a 1 ml wide bore glass pipet in 30 ml BCL (4° C.) and centrifuged as before.

DNA was then extracted from the pellet as described (Miller et al., Nucl Acids Res, 16:1215, 1988). Briefly, the pellet was resuspended as before in 3 ml Nuclei Lysis buffer (NL) (NL contains 0.075 M NaCl, and 0.024 M EDTA pH 8.0). Then, 200 µl of 10% SDS, 440 µl of digest diluent (1% SDS, 2 mM Na$_2$EDTA), and 60 µl of Proteinase K (20 mg/ml stock) were then added to the suspension. The suspension was then incubated at 37° C. for 16-20 hours with gentle mixing by inversion. Following this digestion, 1 ml of saturated (approx. 6 M) NaCl was added and then the suspension briefly (15 seconds) was vigorously shaken. The suspension was then centrifuged at 1340×g at room temperature for 15 minutes. The supernatant was transferred to a new tube, leaving the pellet at the bottom of the previous tube undisturbed. Exactly 2 volumes of absolute ethanol were added. The tube was then inverted several times until the DNA pellet was visible and floated to the top. The pellet was then transferred to a new tube. The pellet was resuspended in 0.67 ml TE pH 8 (10 mM Tris, 1 mM EDTA) by gently mixing on a roller drum for 3-5 days at 37° C.

In addition to the samples described above, a chromosome 15 somatic cell hybrid line, R379-2B2 generously provided by Dr. Carol Jones (The Eleanor Roosevelt Institute for Cancer Research, Denver, Colo.), was also used. This cell line was cultured in Ham's F12, supplemented with 5% fetal bovine serum and 10 µg/ml gentamicin.

Another cell line, the human neuroblastoma cell line, SH-SY5Y (Biedler et al., Cancer Res, 38:3751, 1978), was obtained from Dr. June Biedler (Memorial Sloan-Kettering Cancer Center, New York, N.Y.), and grown in DMEM/Ham's F12 (1:1 ratio, supplemented with 15% fetal bovine serum, 4 mM glutamine, and 10 µg/ml gentamicin).

Example 2

Genomic Clone Isolation

In this Example, YAC clones were identified by PCR screening of two genomic libraries, namely the St. Louis YAC library (Burke et al., Science, 236:806, 1987) and the CEPH YAC Library 3 (Albertsen et al., Proc Natl Acad Sci, USA, 87:4256, 1990), using α7 cDNA specific primers and methods known in the art (See e.g., Brownstein et al., Science, 244:1348, 1989; Chumakov et al., Nature, 359:380, 1992; and Dracopoli et al., Current Protocols in Human Genetics, John Wiley & Sons, Inc., New York, N.Y., 1994).

Additional YACs, positive for loci in the α7 nAChR region were identified initially by using Infoclone on the CEPH/Genethon Integrated Map courtesy of the Fondation Jean Dausset—CEPH world wide web server. Loci on the YAC contig were verified by PCR screening with either α7 primer sets or primer sets for the specific polymorphic markers listed in the YAC contig (See, FIG. 6), which are available from either the CEPH database or GenBank. The PCR conditions were 94° C. for 2 minutes, 1 cycle; followed by 35 cycles of 94° C. for 30 seconds, 55° C. for 30 seconds, and then 72° C. for 30 seconds, followed by 72° C. for 7 minutes-1 cycle. These PCR conditions were used for all PCR amplifications, unless otherwise indicated.

In addition, α7-specific primer sets were used to identify the two PAC clones 64a1 and 25919. A Research Genetics BAC library was screened with α7 coding region primers by PCR to identify the BAC clone 467o18. The BAC library purchased from Research Genetics was a "pooled DNA" library, with each hit-positive PCR product of correct size being indicative of a location on a subsequent plate of pools. A hit on this plate gave an address to yet another plate, where the clone of interest was found. These "BAC clone" plates are maintained by Research Genetics. When the positive PCR reactions produced a final plate address in the clone library, that clone was ordered from Research Genetics. The PCR conditions and primers were as described herein (the primers used are shown in Tables 1 and 2). The two PAC clones (64a1 and 25919) were identified using the following PCR primers.

The primers used in these experiments were:

| | |
|---|---|
| TCCTGATGTCGGCTCCCAACT | (SEQ ID NO: 1) |
| GGTACGGATGTGCCAAGGATA | (SEQ ID NO: 2) |
| TTTGGGGGTGCTAATCCAGGA | (SEQ ID NO: 3) |
| TTGTTTTCCTTCCACCAGTCA | (SEQ ID NO: 4) |
| CTCGCTGCAGCTCCGGGACTCA | (SEQ ID NO: 5) |
| GGAGGCTCAGGGAGAAGTAG | (SEQ ID NO: 6) |

The first two sets of primers were used to amplify the 3' untranslated region of the gene and the third primer set was used to amplify the first and second exons of the gene with the intervening intron 1 sequence. All PCR reactions were optimized in a Perkin Elmer 480 PCR using normal human DNA and cDNA. Conditions were as follows for the control reactions in the 3' sets: 96° C. for two min, then 35 cycles of 96° C. for 30 sec, 56° C. for 30 sec, 72° C. for 1 min, and cool to 4° C., using 4 mM MgCl$_2$ and 10% DMSO. The 5' PCR set was used in 1.5 mM MgCl$_2$ and 10% DMSO with the following conditions: 96° C. for 3 min, then cycles 1-6 were 94° C. for 1 min, 68° C.-58° C. for 1 min (dropping from 68° C. to 58° C., by 2° C. increments each cycle), 72° C. for 1 min, followed by 30 cycles of 94° C. for 1 min, 58° C. for 1 min, 72° C. for 1 min, then a 4 min extension at 4° C., followed by chilling at 4° C.

In these experiments, a genomic clone of the human α7 nicotinic receptor was identified. A YAC designated as b134h10 of approximately 250 kb, was isolated from the St. Louis YAC library. A Southern blot comparison of YAC b134h10 with human genomic DNA indicated that it contained the full-length α7 nAChR gene. This YAC was used to isolate a polymorphic marker, D15S1360, as described in greater detail below.

The polymorphic marker D15S1360, a complex microsatellite with four alleles, was isolated from a YAC containing the α7 nicotinic receptor gene. The GenBank sequence for rat α7 (GenBank Accession No. M85273) was used to design primers to the conserved regions of the α7 coding sequence. These primers were then used to PCR amplify normal human hippocampal cDNA obtained from a normal brain postmortem. The products were sequenced by Automated dye-terminator chemistry (as described in Example 5). The human sequence in transmembrane regions III and IV was then used to design PCR primers. These primers were: 5'-CTCCAG-GATC TTGGCCAAGT C-3' (sense strand; SEQ ID NO:7), and 5'-AGATGCCCAA GTGGACCAGA G-3' (antisense strand; SEQ ID NO:8).

The PCR reactions were conducted with 2 mM $MgCl_2$ and 10% DMSO, in a Perkin-Elmer 4800 using the following cycles: 94° C. for 2 min, then 5 cycles of 94° C. for 1 min, 56° C. for 30 sec, 72° C. for 1 min then 35 cycles 94° C. for 1 min, 54° C. for 30 sec, 72° C. for 1 min, and cooling at 4° C. The product was reamplified with primers extended to contain a sense Xba and antisense Bam site. The products were cut and ligated into a BlueScript SK-vector. Sequence of the probe was confirmed by automated dye-primer sequencing. Subsequent PCR based screening of the original YAC clones were based on the above primers and conditions, substituting YAC DNA for hippocampal cDNA as the template.

The PCR fragment (i.e., the probe) was sequenced and human primers were designed to generate a 338 bp product, which was cloned into pBluescript SK(-). The sequence of the 338 bp probe was:

```
                                              (SEQ ID NO: 9)
AGATGCCCAAGTGGACCAGAGTCATCCTTCTGAACTGGTGCGCGTGGTTC

CTGCGAATGAAGAGGCCCGGGGAGGACAAGGTGCGCCCGGCCTGCCAGCA

CAAGCAGCGGCGCTGCAGCCTGGCCAGTGTGGAGATGAGCGCCGTGGGCC

CGCCGCCCGCCAGCAACGGGAACCTGCTGTACATCGGCTTCCGCGGCCTG

GACGGCGTGCACTGTGTCCCGACCCCCGACTCTGGGGTAGTGTGTGGCCG

CATGGCCTGCTCCCCCACGCACGATGAGCACCTCCTGCACGGCGGGCAAC

CCCCCGAGGGGGACCCGGACTTGGCCAAGATCCTGGA.
```

This probe was used to isolate a human α7 cDNA (GenBank Accession No. U40583). The Washington University human YAC library was screened with the same primers. Two clones were isolated, B132H10 (150 kbp) and B134H10 (300 kbp), on the TAFE (Beckman) gel system, using the procedures recommended by the manufacturer.

A sub-library of B134H10 was prepared in the λZAP phagemid vector by complete MboI digestion of the intact YAC DNA in a low-melt agarose plug. The DNA was extracted and ligated into BamH1 digested and phosphatased vector, transformed into XL1Blue-(MRF'), and screened with a $(CA)_{16}$ (SEQ ID NO:10) oligonucleotide. One clone contained a microsatellite $[(CA)_5T(CA)_{12}TA(CA)_5C(CA)_3]$ (SEQ ID NO:11), which mapped to chromosome 15 (Human/Rodent Hybrid Mapping Panel #1, Coriell, Camden N.J.). Flanking primers amplified seven additional alleles (97, 107, 109, 111, 113, 115, and 117 bp). The primers used were 5'-GATCTTTGGT AGAAGC-3' (SEQ ID NO:12), and 5'-ACCACCACTA CCATACAGAC-3' (SEQ ID NO:13). Allele frequencies (0.006, 0.006, 0.006, 0.516, 0.370, 0.090, and 0.006; heterozygosity 0.57) were estimated from individuals marrying into the pedigrees described in Example 1. Primer sets used for mapping α7 exons to YAC clones are listed in Table 1, below. Primers used for mapping STS/dinucleotide repeat markers to YAC clones were obtained from GenBank, and are listed in Table 2. In these Tables, and unless otherwise indicated, all DNA sequences are shown in 5' to 3' orientation.

TABLE 1

Primer Sets Used to Amplify Exon and Flanking Intron Sequence from Human Alpha-7 Nicotinic Acetylcholine Receptor

| Sequence Amplified Primer Number | Sequence | SEQ ID NO: |
|---|---|---|
| Promoter #1234 | CAAAGAACGCAAGGGAGAGGT | SEQ ID NO: 14 |
| Promoter #1235 | CGGCTCGCGCGCCTTTAAGGA | SEQ ID NO: 15 |
| Exon 1 #1331 or #1236 | GGGCTCGTCACGTGGAAAAGC | SEQ ID NO: 16 |
| Exon 1 #1233 | GGATCCCACGGAGGAGTGGAG | SEQ ID NO: 17 |
| Exon 2 #1198 | CCTGCCCGGGTCTTCTCTCCT | SEQ ID NO: 18 |
| Exon 2 #1138 | AACTAGAGTGCCCCAGCCGAGCT | SEQ ID NO: 19 |
| Exon 3 #1475 | AACAACGCTCTCGACAGTCAGATC | SEQ ID NO: 20 |
| Exon 3 #1476 | AAGATCTTGCAGCCCATGGGAG | SEQ ID NO: 21 |
| Exon 4 #1368 | GGAATTCTCTTTGGTTTTGCAC | SEQ ID NO: 22 |
| Exon 4 #1369 | ACATATCCAGCATCTCTGTGA | SEQ ID NO: 23 |
| Exon 5 #1218 | TCATGCAGTCCTTTTCCTGTTTC | SEQ ID NO: 24 |
| Exon 5 #1142 | CTCGCTTCAGTTTTCTAACATGG | SEQ ID NO: 25 |
| Exon 6 #1124 | GGAACTGCTGTGTATTTTCAGC | SEQ ID NO: 26 |
| Exon 6 #1144 | TTAAAGCTTGCCCAGGAATAGG | SEQ ID NO: 27 |
| Exon 7 #1143 | GCTTGTGTGTGGTATACACATTG | SEQ ID NO: 28 |
| Exon 7 #1126 | TCCAGAGCTGATCTCAGCAGAAG | SEQ ID NO: 29 |
| Exon 8 #1125 | GCCCCTCGTTAGACAGAATTGAG | SEQ ID NO: 30 |
| Exon 8 #1145 | CTGGGCACACTCTAACCCTAACC | SEQ ID NO: 31 |
| Exon 9 #1146 | TGTGACGTGCAGTGCCACAGGA | SEQ ID NO: 32 |
| Exon 9 #1127 | AAAACCCTAGGAGGAGCCTCCTT | SEQ ID NO: 33 |
| Exon 10 #1128 | GATCAGCCCGTTTCCGCCTCA | SEQ ID NO: 34 |
| Exon 10 #589 | GGTACGGATGTGCCAAGGATA | SEQ ID NO: 35 |
| Exon A #1516 | GGACTCTGCTTTTGATAAATATGTATG | SEQ ID NO: 36 |
| Exon A #1517 | TTGCTGTCACTTTCTGTGTTTCAT | SEQ ID NO: 37 |
| Exon B #1283 | GACAATCCAAAGGTGCAGAAAGC | SEQ ID NO: 38 |
| Exon B #1538 | TTCGTATCTGTATACAGACAGTC | SEQ ID NO: 39 |
| Exon C #1567 | CCTCAGCATCATATTAGTTCAGTG | SEQ ID NO: 40 |
| Exon C #1572 | GCGGACAAGAGAAACAGGAAAG | SEQ ID NO: 41 |
| Exon D #1534 | GGCAGTGGTGCTGTTGCCCTT | SEQ ID NO: 42 |
| Exon D #1568 | TTTCTCCTGGGACTCTGGGCAC | SEQ ID NO: 43 |

TABLE 2

STS/Dinucleotide Repeat Markers

| Marker | GenBank Accession # |
|---|---|
| D15S942 | G04933 |
| D15S1043 | Z51622 |
| D15S165 | Z17271 |
| D15S1031 | Z51346 |
| D15S1010 | Z53401 |
| D15S144 | Z23286 |
| D15S1007 | Z53384 |
| D15S995 | Z53051 |
| D15S1040 | Z51533 |

Additionally, genomic P1 artificial chromosome (PAC) clones for α7 were obtained from Genome Systems. PAC-64-A1 is 120 kbp long and contains both D15S1360 and the 5' end of the coding region. L76630 was localized in a genomic fragment containing the α7 nicotinic receptor gene (CHRNA7), isolated from a human genomic library (Stratagene), by screening with a human α7 cDNA clone (HP411).

A 6 kbp EcoRI genomic fragment was identified, partially sequenced, and found to include a CA dinucleotide repeat 3' of the last exon (GenBank Accession No. L76630). Flanking primers amplified 3 alleles (180, 178, 176 bp); allele frequencies were 0.06, 0.62, 0.32, with heterozygosity 0.51.

PCR was performed with 1.5 mM MgCl$_2$: 94° C. for 5 min, 20 cycles of 94° C. for 1 min, 56° C. for 2 min, 72° C. for 1 min and 72° C. for 5 min. The two polymorphisms were genetically mapped in 96 individuals from 6 reference families (Centre d'Etude du Polymorphisme Humain). These reference families were selected because they have three generations of individuals available for genotyping. Their DNA is available for genetic localization of markers, but their identities are confidential.

Example 3

Generation of Templates for Sequence Analysis of the Intron/Exon Borders

In this Example, extra-long PCR (XLPCR), originally described by Barnes (Barnes, Proc Natl Acad Sci USA, 91:2216, 1994), was conducted using rTth polymerase with the Perkin Elmer XL/PCR kit (Perkin-Elmer), on a PTC 200 (MJ Research) thermal cycler with the following conditions: 94° C., 1 min, 1 cycle; 94° C., 15 sec/68° C., 10 min, 16 cycles; 94° C., 15 sec/68° C., 10 min 15 sec, 12 cycles; 72° C., 10 min, 1 cycle. Enzyme, primer concentration, and dNTP concentrations were as recommended by the manufacturer. A sublibrary of YAC b134H10 was constructed by EcoRI digestion and subcloning into Bluescript (SK−), (Stratagene), for splice junction determination on the larger introns.

To characterize the promoter and borders around exon 1 and 2, an EcoRI and KpnI sublibrary of PAC 25919 was constructed in Bluescript (SK−). A 2.9 kb clone containing exon 1, and a 5 kb clone containing exon 2 were identified by screening the PAC sublibrary by hybridization with an α7 cDNA subclone containing 90 bp of 5' untranslated sequence, exon 1 and exon 2.

Tentative exon borders were deduced based upon the organization of the α7 nAChR gene in the chick (Couturier et al., Neuron, 5:847, 1990). Oligonucleotide primers, as shown in the table below, were designed from within the predicted exons that would amplify across the putative introns using extra-long PCR (XLPCR) with both genomic DNA and YAC b134h10 DNA. The exon primers used were as follows. For exon 5 to exon 10, the primers used were Primer #661 (TGACGCCACA TTCCACACTA A, SEQ ID NO:44); and Primer #591 (TTGTTTTCCT TCCACCAGTC A, SEQ ID NO:45). These primers amplify introns 5, 6, 7, 8, and 9, with an approximate size of 14 kb. For exon 3 to exon 4, the primers used were Primer #1019 (CCAAGTTTTA ACCAC-CAACA TTTGG, SEQ ID NO:46); and Primer #1020 (TC-CCCGCGGA AGAATGTCTG GTTTCCAAAT CTG, SEQ ID NO:47). These primers amplify intron 3, with an approximate size of 8 kb.

The majority of intron-exon borders were determined from sequencing the XLPCR products. XLPCR products were not generated between exons 2 and 3 and between exons 4 and 5, suggesting that these introns are large. Preliminary Southern blot data suggested that both are >25 kb. The intron 2 acceptor border, and the intron 4 donor and acceptor borders were determined after sequencing EcoRI subclones derived from YAC b134h10. The intron 2 donor was determined from sequencing a KpnI/EcoRI fragment, subcloned from PAC 25919. Exon/intron border sequence and approximate lengths for introns and exons are summarized in FIG. 1. All of the identified intron-exon borders are consistent with 5' donor and 3' acceptor RNA splice site consensus sequences.

The organization of the human α7 nAChR gene was found to be identical to that found in chick with respect to number and size of exons. A signal peptide sequence predicted by homology with the rat α7 and muscle α7 coding sequences (See e.g., Séguéla et al., J Neurosci, 13:596, 1993; Conti-Tronconi et al., Proc Natl Acad Sci USA, 82:5208, 1985; and von Heijne, Nuc Acids Res, 14:4683, 1986), was found to be encoded by exon 1. Putative glycosylation sites (See e.g., Séguéla et al., supra, 1993; Schoepfer et al., Neuron, 5:35, 1990) were found in exons 2, 4 and 5. The cysteine residues that form a putative disulfide bridge (Galzi et al., Ann Rev Pharmacol, 31:37, 1991), were found to be encoded by exon 6. The vicinal cysteines at the acetylcholine (ACh) binding site, the α-bungarotoxin binding site, and membrane spanning region I, are all coded by exon 7. Membrane spanning regions II and III (as in the rat) were found to be encoded by exons 8 and 9, respectively, while membrane-spanning region IV was found to be encoded by exon 10.

The putative promoter, and the borders for exons 1 and 2 were determined from sequencing KpnI and EcoRI subclones derived from PAC 25919, which contains exons 1-3 and sequences 5' of the coding region. A 2.9 kb EcoRI-KpnI fragment contained 2.6 kb of the region 5' of exon 1, exon 1 and 200 bp of intron 1. Sequence analysis indicated that 392 bp of the 5' region (GenBank Accession No. AF029837), shown in FIG. 4, is 77% GC rich and lacks a consensus TATA box sequence. In this Figure, the nucleotides are numbered relative to the ATG translation initiation site (indicated with Met); the coding sequence is indicated in bold. Consensus AP-2, Sp1, and CREB sequences are shown in boxes. Alignment of the chick (Matter-Sadzinski et al., EMBO J, 11:4529, 1992) and human promoter sequences indicate they share only 52.9% homology. However, consensus Sp1, and AP-2 transcription factor binding sites are present in both human and chick α7 promoters at approximately the same location, relative to the start of translation (Matter-Sadzinski et al., supra, 1992). A CREB consensus binding sequence is present in the human promoter, but is not found in the chick.

The primers listed in Table 1 provide a means to obtain sequence information from genomic DNA. Using sequencing techniques standard in the art (e.g., including, but not limited to standard dideoxy sequencing, chain termination sequencing using Taq DNA polymerase or other thermostable polymerases, and automated processes that use these and other technologies), the sequences near the intron and exon junctions can be obtained. Such primers have been successfully used to obtain sequence information from blood samples obtained from schizophrenic patients (i.e., samples obtained as described in Example 1). Sequence obtained from this portion of the chromosome also finds use in providing linkage signal for other nicotine-dependent illnesses including, but not limited to, small cell lung cancer and juvenile myoclonic epilepsy. These sequences are then analyzed to determine if they contain pathogenic mutations that alter gene function by changing the amino acid coding, or by altering gene expression or response to promoter molecules, or by introducing variations in gene splicing. These mutant sequences are also expressed in transgenic cells in culture or in transgenic mice or in frog oocytes, to determine if they indeed cause altered gene function that produces heritable human illnesses such as schizophrenia.

Example 4

Identification of Expressed Sequence Tagged cDNAs

In this Example, expressed sequence tagged (EST) cDNA clones were identified in the EST Database at the National Center for Biotechnology Information (NCBI), Bethesda, Md., by BLAST homology searches using α7 cDNA specific sequences. Two clones (EST 3952 and EST 52861) were purchased from Research Genetics and sequenced bi-directionally as described in Example 5. Contigs were constructed using Sequencher software (Gene Codes).

Example 5

Sequence Analyses and Restriction Mapping

In this Example, sequences were determined using standard sequencing kits and automated sequencing. In addition, genomic DNA probed with portions of α7 cDNA was used to order HindIII restriction fragments.
Manual Sequencing
PCR product for hand sequencing was prepared using the Exonuclease I-Shrimp Alkaline Phosphatase reagent pack (Amersham), per the manufacturer's directions. Sequencing was done using Thermo Sequenase Radiolabeled Terminator Cycle Sequencing Kit from Amersham. The manufacturer's recommended component concentrations were used with 10 ng of template per 250 bp product per reaction. Reactions were run on a BioRad Sequi-Gene GT sequencing system (BioRad), using a 6% acrylamide/bisacrylamide (19:1) gel.
Automated Sequencing
Plasmids to be sequenced were colony purified, using a Qiagen kit (Qiagen). PCR products from PACS, BACs, and YACs were gel purified using a Qiagen PCR product gel extraction protocol. Automated sequencing (ABI 373 or 377, Perkin Elmer) was conducted using Perkin Elmer ABI Dye Terminator or M13 Dye Primer kits, following manufacturer's protocols. Sequencing was organized into contigs using the Sequencher program (Gene Codes). All sequencing was bi-directional.
Restriction Endonuclease Mapping
Southern analysis of genomic DNA probed with portions of α7 cDNA was used to order HindIII restriction fragments (Dracopoli et al., supra). DNA was transferred to Hybond N+, and hybridized at 40° C. in 5×Denharts (0.5% SDS, 6×SSC and 50% formamide), then washed twice in 0.1% SDS and 0.1×SSC at 65° C. for 10 minutes.

Example 6

Large Insert Clone Contig

Total yeast DNA was isolated from YAC-bearing yeast using a spheroplast method (Dracopoli et al., supra). Loci in and around the α7 region were PCR amplified with loci specific primers (i.e., primers shown in Table 2, as well as primers for D15S1360 described in Example 2). PCR was performed with 1.5 mM $MgCl_2$: 94° C. for 5 min, 20 cycles of 94° C. for 1 min, 56° C. for 2 min, 72° C. for 1 min and 72° C. for 5 min.
Mapping of specific exons was performed using the primers listed in Table 1 and the PCR conditions were 94° C. for 2 minutes, 1 cycle; followed by 35 cycles of 94° C. for 30 seconds, 55° C. for 30 seconds, and then 72° C. for 30 seconds, followed by 72° C. for 7 minutes-1 cycle.
Specific amplification was confirmed by sizing the products on agarose gel. PCR products from α7 exons were excised from the gel, Qiagen extracted (Qiagen), and sequenced as described in Example 5.
Additional large insert genomic clones were isolated by PCR screening with α7-specific primers (Chumakov et al., supra). YACs 953g6, 948a10, 853b12, and 969b11 were isolated from the CEPH YAC Library 3. PAC clones 64a1 and 25919 were identified by Genome Systems and BAC 467o18 was identified in a BAC library purchased from Research Genetics.
A tentative YAC contig was designed from markers in the YACs and information in the CEPH/Genathon Database. YACs providing linkage between the full-length and duplicated α7 gene sequences, YACs 895f6, 776a12, 791e6, 811b6, 859c11, 801e1, 810f11, 966a4, 764f8, and 822g2, were obtained from Research Genetics. The contig, shown in FIG. 5, was verified by PCR and sequencing of either α7 sequence or published marker sequence. Loci from the 15q13-14 region were assigned to YACs, BACs, and PACs. The results confirmed the presence of markers previously assigned by Genethon (Human Genome Research Center; a publicly accessible database that maintains human genome linkage information). As indicated in FIG. 5, two allele sizes for the L76630 loci were identified, suggesting that YAC 969B11 spans both α7 nAChr loci.
Exons 5-10 of the α7 nAChR gene and the polymorphic marker L76630 map to two distinct regions of the contig, suggesting a partial gene duplication. The distal, and full-length, α7 nAChR gene maps close to D15S1360, as indicated by two PAC clones (64a1 and 25919) and one BAC clone (467018). Both of these PACs, approximately 120 kb in size, contain the marker D15S1360 which was used to demonstrate linkage of this region at 15q14 to a schizophrenic trait. Physical mapping of the α7 gene <120 kb from the linkage marker suggested that the α7 nicotinic receptor gene is an excellent candidate gene for this trait. The proximal duplicated exon sequences 5-10 of the α7 nAChR gene map between D15S1043 and D15S165. The order of loci was determined to be D15S942, D15S1043, followed by the duplicated sequences L76630, exon 10, exon 9, exon 8, exon 7, exon 6, and exon 5, and then D15S165 and D15S1031. The closest marker flanking the 3' end of the α7 nAChR gene could not be established and is either D15S1031 or D15S1010. Thus, the full-length gene with the 3'-end closest to D15S1031 has been tentatively oriented, based on the confirmed orientation of the duplicated sequences.
In order to determine if sequence differences were present that might distinguish duplicated exons 5-10 from the full-length gene, PCR products were generated and sequenced from 11 of the genomic YAC clones in the contig. Of these 11 clones, two (948a10 and 853b12) clearly mapped to the duplicated region between D15S1043 and D15S165, and eight mapped to the full-length α7 nAChR gene region near D15S1360. All of the α7 exons were found to be present in YACs 776a12, 791e6, 811b6, 953g6, b134h10, 859c11, 810f11 and 801e1. YAC 948a10 contained only exons 5-10, and 853b12, 6-10, while YAC 969b11 appeared to contain both loci. This YAC is 1.03 Mb in size (FIG. 5), suggesting that the full-length α7 gene and duplicated sequences are not more than 1 Mb apart.

Sequence variants found in DNA from duplicated and full-length genomic α7 sequences are shown in FIG. 2. In exon 6, a 2 bp deletion was identified at bases 497-498 (TG) in clones from the duplicated region, which results in a frame shift in the coding sequence and the insertion of a stop codon within the exon.

Additional sequence variants were found at bases 654, 793, 1269 and 1335 of the coding region. These are conservative base changes that do not change an amino acid. The polymorphic marker, L76630 is also duplicated as evidenced by the presence of a different number of CG repeats in the 3'UT of the full length α7 gene and the 3' sequences following exon 10 in the duplicated sequences. YAC 969b11, which contains both full length and duplicated sequences also has two copies of L76630 as does a chromosome 15 hybrid, R379-2B2 (See, FIG. 2).

Example 7

RACE Analysis

In this Example, amino terminal clones for the human α7 subunit were obtained by 5' RACE (i.e., Rapid Amplification of cDNA Ends; See, Frohman, Amplifications 5:11, 1990), using a kit from Gibco-BRL, with some modifications. Although some of these products had the amino terminus nucleic acid sequences that were expected by homology with chicken and rat sequences, some had novel sequences that revealed the presence of unsuspected alternative exons. The present invention provides, for the first time, the sequences of these exons and their location in the genomic structure of α7.

Total RNA was isolated from normal human hippocampus by the method of Chomczynski and Sacchi (Chomczynski and Sacchi, Anal Biochem, 162:156, 1987). Briefly, brain tissue from the human hippocampus was disrupted in the presence of Solution D (4 M guanidium thiocyanate, 25 mM sodium citrate pH 7.0, 5% sarcosyl, 0.1 M 2-mercaptoethanol) in a tissue homogenizer. The homogenized tissue was acidified with 0.1× volume of 2 M sodium acetate, pH 4.0, with "X" referring to the initial volume of Solution D. The acidified tissue homogenate was extracted with 1× volume of water-saturated phenol and 0.2 volume of chloroform: isoamyl alcohol (49:1). The phases were separated by centrifugation (the supernatant contains RNA whereas the DNA and proteins remain in the interphase and the phenol). The RNA was precipitated by addition of an equal volume of isopropanol (20° C.), followed by centrifugation. The RNA pellet was subsequently resuspended in 1 mM EDTA, pH 8.0. The concentration of the RNA was determined by measuring the absorbance at 260 and 280 nm.

The first strand cDNA synthesis for 5'-RACE was performed as indicated in the manufacturer's instructions, with the addition of methylmercuric hydroxide (7 mM) to reduce secondary structure. The cDNA was synthesized using a human gene-specific antisense oligonucleotide: 5'-AGGAC-CCAAA CTTCAG-3' (SEQ ID NO:48), complementary to 5'-sequence in the longest human clone from the primary cDNA screen. Following cDNA synthesis, terminal deoxynucleotide transferase was used to attach homopolymeric (dCTP) tails to the 3' ends of the cDNA. A nested gene specific antisense primer and an anchor primer from the 5'-RACE kit, both containing triplet repeat sequences for annealing to the pAMP1 vector, were used for PCR amplification of a homopolymeric, tailed cDNA product. The sequences of the primers were: for the antisense primer, 5'-CAUCAUCAUC AUCCAGCGTA CATCGATGTA GCAGGAACTC TTGAATAT-3' (SEQ ID NO:49), and the anchor primer 5'-CUACUACUAC UAGGCCACGC GTC-GACTAGT ACGGGIIGGI IGGGIIG-3' (SEQ ID NO:50). In this anchor primer sequence, the "I" is inosine.

Briefly, the final composition of the PCR reaction for amplification of dC-tailed cDNA was as follows: 20 mM Tris-HCl (pH 8.4), 50 mM KCl, 1.5 mM MgCl₂, 400 nM for both primers, 200 µM each dNTP, 8% DMSO and 0.2 unit/µl Taq DNA polymerase. The PCR program was as follows: 94° C., 1 min; 57° C., 30 sec; 72° C., 2 min for 35 cycles; final extension at 72° C. for 10 min, then soak at 4° C.

PCR products were Glassmax (Gibco-BRL) purified and reamplified with the same reaction conditions using the following program: 94° C., 1 min; 50° C., 30 sec; 72° C., 2 min for 5 cycles; 94° C., 1 min; 55° C., 30 sec; 72° C., 2 min for 35 cycles; extension at 72° C. for 7 min, and soak at 4° C. Products from this PCR reaction were then gel purified and cloned into the pAMP1 vector (Gibco-BRL) with uracil DNA glycosylase according to manufacturer's directions, for subsequent automated sequencing, as described in Example 5.

A group of novel exons located in YAC, PAC and BAC clones containing the full-length gene and/or the duplicated α7 sequences was also evidenced. These novel exons were discovered in the process of comparing RACE clones, isolated during cloning of the α7 human cDNA, with EST cDNA clones (EST 3952 and EST 52861) found in the EST Database (NCBI) by homology screening. During cloning of the 5' end of the α7 coding region, the RACE technique was used to amplify the 5' end of the α7 cDNA (Frohman, supra, 1990). Although cDNA clones which matched sequence for published human α7 from a neuroblastoma cell line SH-SY5Y (Peng et al., Mol. Pharm., 45:546, 1994), were obtained, clones with 5' sequence that could not be identified were also obtained.

When EST cDNA clones were subsequently found in the EST database by homology screening, several were identified that had exons 5-10 and unknown sequence 5' of exon 5. Comparison of the 5' ends of the RACE and EST products showed that the novel sequences are partially homologous. PCR primers were designed to these novel sequences for amplification from genomic DNA. Intronic sequence and consensus splice junctions that identified these sequences as four alternatively spliced and previously unreported exons were then identified. The sizes and splice junctions for these novel exons, designated as α7D, α7C, α7B, and α7A are shown in FIG. 6. In this Figure, the sequence of the RACE clone (GenBank Accession No. AF029838) is shown in uppercase, while intron boundaries are shown in lowercase, and are not included in the nucleotide numbering. The sizes of the exons are indicated below the exon designations. RACE clones, containing these novel exons were previously deposited with GenBank (RACE D-C-B-A-5-6; AF029838; RACE D-C-A-5-6, GenBank Accession No. AF029839).

Example 8

RT-PCR Analysis

Total RNA was isolated from normal human hippocampus, human cingulate gyrus, the SH-SY5Y neuroblastoma cell line, and human immortalized lymphocytes with TRIzol reagent (Gibco-BRL) following manufacturer's instructions. The mutations seen in the PAC, BAC, YAC and published α7 sequences were screened in seven normal subjects and SH-SY5Y cells. DNA was evaluated for all subjects, while cDNA was evaluated in exons 1-10 and exons 5-10 for all subjects, and exons D-10 were evaluated in one normal subject and SH-SY5Y cells. The DNA and RNA were obtained as detailed above. The cDNA was generated as previously detailed.

Total RNA was isolated from normal human hippocampus, human cingulate gyrus and SH-SY5Y neuroblastoma cell line by the TRIzol reagent (Gibco-BRL) following manufacturer's directions. RNA was stored as an ethanol precipitate until centrifugation and resuspended in 1 mM EDTA, pH 8.0 prior to cDNA preparation.

Total RNA was reverse transcribed at 42° C. for 60 min in a 40 μl volume with Superscript II reverse transcriptase (Gibco-BRL) and random hexamer primers (Pharmacia). The final concentration of the components of the reaction were as follows: 1× first strand buffer (50 mM Tris-HCl, pH 8.3, 75 mM KCl, 3 mM $MgCl_2$), 1 mM dATP, 1 mM dGTP, 1 mM dCTP, 1 mM dTTP, 8 μM random hexamers, 10 mM DTT, 0.5 U/μl placental Rnase inhibitor (Boehringer-Mannheim), 2.5 U/μl Superscript II reverse transcriptase and 500 ng of total RNA.

Primary PCR of the exon 1-10, exon 5-10 and exon D-10 products was performed using the Advantage-GC cDNA PCR kit (Clontech). Briefly, 5 μl of RT products were diluted to 50 μl with 40 mM Tricine-KOH, pH 9.2 at 25° C., 15 mM KOAc, 3.5 mM $Mg(OAc)_2$, 5% DMSO, 3.75 μg/ml BSA, 0.2 mM of each dNTP, 0.2 μM of each primer, 1 M GC-Melt and 1× Klentaq-1 DNA polymerase mix. Samples were incubated in a Perkin-Elmer 480 DNA Thermocycler.

For Exon 1-10, the sense primer was 5'-CGCTGCAGCT CCGGGACTCA ACATG-3' (SEQ ID NO:51), and the antisense primer was 5'-TGCCCATCTG TGAGTTTTCC ACATG-3' (SEQ ID NO:52). The PCR conditions were 94° C., 1 min; 5 cycles at 94° C., 30 sec, 72° C., 3 min; 5 cycles at 94° C., 30 sec, 70° C., 3 min; 25 cycles at 94° C., 20 sec, 68° C., 3 min; final extension at 68° C., 3 min and soak at 4° C.

For Exon 5 to 3'UT α7 transcript, the sense primer was 5'-TGACGCCACA TTCCACACTA A-3' (SEQ ID NO:53), and the antisense primer was 5'-CCCCAAATCT CGC-CAAGC-3' (SEQ ID NO:54). The PCR conditions were 5 cycles at 96° C., 1 min, 50° C., 30 sec, 72° C., 1 min; 30 cycles at 95° C., 30 sec, 62° C., 20 sec, 72° C., 30 sec; final extension at 68° C., 3 min and soak at 4° C.

For Exons D-10, the sense primer was 5'-CTCGGTGCCC CTTGCCATTT-3' (SEQ ID NO:55), and the antisense primer was 5'-CCTTGCCCAT CTGTGAGTTT TCCAC-3' (SEQ ID NO:56). The PCR conditions were 94° C. 1 min, 5 cycles 94° C., 30 sec, 70° C., 3 min 5 cycles 94° C. 30 sec, 68° C., 3 min, 25 cycles 94° C. 20 sec, 66° C. 3 min 1 cycle 68° C. 3 min, cool to 4° C.

The products generated from exons 1-10, 5-10 and D-10 were further amplified to incorporate M13 primer sequences into products small enough to sequence in both directions. PCR conditions were as follows for all secondary, nested PCR amplifications. Perkin-Elmer Core reagents were used in standard concentrations using 2 mM $MgCl_2$, 0.1 mM each dNTP, 1.5 U Taq Gold, 10% DMSO and 25 pM of each primer in a 50 μL reaction. PCR reactions were heated at 96° for 5 min, then 5 cycles were performed at 96° C. for 1 min, 60° C. for 30 sec, 72° C. for 1 min; then 30 cycles for 95° C. for 30 sec, 68° C. for 20 sec, and 72° C. for 30 sec, followed by a 7 min 72° C. extension and cooling at 4° C.

All cDNA reactions were performed in duplicate using 50 ng RNA equivalents in a primary reaction, encompassing the full cDNA length of interest, then reamplified in nested, secondary PCR reactions to incorporate M13 primers into shorter products. DNA amplifications were performed in duplicate from 100 ng of needle-sheared template, within exon boundaries. The duplicates were then pooled, purified with a Centricon 100 (Amicon) column, and sequenced using standard M13 Dye Primer chemistry on an ABI 373 Automated sequencer. All templates were sequenced bi-directionally, except where sequence length did not allow a nested primer. Alternate splice products were hand called from the electropherograms. Clean sequences were aligned and checked with Sequencher Software (Gene Codes Corporation).

DNA products were generated with primer pairs 1552/1553, 1101/1102, 1097/1098 and 1099/1100 to check the 497-498 deletion, 654/690, and 1269/1335 mutations, respectively. These primers are shown in Table 3, below. In this Table, "1ry" and "2ry" refer to the first and second primer sets in nested PCR. The cDNA amplifications required three sets of primary amplifications, exons 1-10, exons 5-10 and exons D-10. Primer pair 1381/1382 was used to amplify exons 1-10; primers 1482/1483, 1101/1098 and 1099/1481 were then used as nested primers from this primary PCR to check 497-498, 654/693 and 1269/1335 respectively. The exon 5-10 product was amplified with primer pair 1502/1503, nested primers 1502/1483, 1101/1098 and 1099/1481 were used to check 497/498/654/693, 654/690 and 1269/1335 respectively. Exons D-10 were amplified with primers 1569/1562, and the nested primers 1553/1098 and 1097/1481 were used to check 497-498/654/690 and 1269/1335, respectively. Redundancy in the overlap of the secondary PCR products was used to double check some mutations, necessary when alternate splicing or base pair deletions occurred, making some base calls difficult.

Exon 3 codes for 15 amino acids near the amino terminal, in the extracellular domain. An alternate transcript without this exon appears in most PCR amplifications of this region, at a somewhat diminished concentration in comparison to the full-length transcript.

To determine if the exon 5-10 copy of α7 was expressed, a second RT-PCR product was generated, encompassing only exons 5-10. The bases which appeared to be heterozygous in the DNA, but which are not heterozygous in the exon 1-10 transcript, are now fully accounted for in the 5-10 exon product, showing the exon 5-10 gene to be expressing as cDNA. The base changes fall into three categories, those seen only in the full-length 1-10 transcript, those changes present only in the 5-10 transcript and bases changes seen in both transcripts.

The TG deletion at 497-498 is only present in the 5-10 transcript; the C at 654 can be assigned to the 1-10 transcript, the T to the 5-10 transcript; the G at 933 can be assigned to both transcripts with an A in some subjects' 1-10 transcript and at 1335 the T can be assigned to the 1-10 transcript. The base changes seen at 690 and at 1269 appear to be present in both copies of the gene. These data are consistent with the base changes seen in the YAC, PAC and BAC clones, and the assignment of each clone to the duplicated or original gene.

TABLE 3

Primer Sequences

| Primer # Description | Sequence | SEQ ID NO: |
|---|---|---|
| 1097 sense/m13fwd+ | CCCAGTACTTCGCCAGCACCATGAT | SEQ ID NO: 57 |
| 1098 antisense/m13rev+ | CCCCGTCGGGGTCGTGGTGGTGGTA | SEQ ID NO: 58 |
| 1101 sense/m13fwd+ | TCCCCGGCAAGAGGAGTGAAAGGTT | SEQ ID NO: 59 |
| 1102 antisense/m13rev+ | ACACCAGCAGGGCGAGGGCGGAGAT | SEQ ID NO: 60 |
| 1099 sense/m13fwd+ | GACCAGAGTCATCCTTCTGAACTGG | SEQ ID NO: 61 |
| 1100 antisense/m13rev+ | TTTCAGGTAGACCTTCATGCAGACA | SEQ ID NO: 62 |
| 1553 sense/m13fwd+ | CGATGTACGCTGGTTTCCCTTTGAT | SEQ ID NO: 63 |
| 1552 antisense/m13rev+ | TTCCCACTAGGTCCCATTCTCCATT | SEQ ID NO: 64 |
| 1382 sense/1ry cDNA | CGCTGCAGCTCCGGGACTCAACATG | SEQ ID NO: 65 |
| 1381 antisense | TGCCCATCTGTGAGTTTTCCACATG | SEQ ID NO: 66 |
| 1502 sense/1ry cDNA | TGACGCCACATTCCACACTAA | SEQ ID NO: 67 |
| 1503 antisense | CCCCAAATCTCGCCAAGC | SEQ ID NO: 68 |
| 1569 sense/1ry cDNA | CTCGGTGCCCCTTGCCATTT | SEQ ID NO: 69 |
| 1562 antisense | CCTTGCCCATCTGTGAGTTTTCCAC | SEQ ID NO: 70 |
| m13 sense/extension | TGTAAAACGACGGCCAGT | SEQ ID NO: 71 |
| m13 antisense/extension | CAGGAAACAGCTATGACC | SEQ ID NO: 72 |
| 1482 sense/m13fwd+/2ry | AAGGAGCTGGTCAAGAACTACAATC | SEQ ID NO: 73 |
| 1483 antisense/m13rev+ | CCGGAATCTGCAGGAAGCAGGAACA | SEQ ID NO: 74 |
| 1101 sense/m13fwd+/2ry | TCCCCGGCAAGAGGAGTGAAAGGTT | SEQ ID NO: 59 |
| 1098 antisense/m13rev+ | CCCCGTCGGGGTCGTGGTGGTGGTA | SEQ ID NO: 58 |
| 1502 sense/2ry cDNA | TGACGCCACATTCCACACTAA | SEQ ID NO: 67 |
| 1483 antisense/m13rev+ | CCGGAATCTGCAGGAAGCAGGAACA | SEQ ID NO: 74 |
| 1553 sense/m13fwd+/2ry | CGATGTACGCTGGTTTCCCTTTGAT | SEQ ID NO: 63 |
| 1098 antisense/m13rev+ | CCCCGTCGGGGTCGTGGTGGTGGTA | SEQ ID NO: 58 |
| 1097 sense/m13fwd/2ry | CCCAGTACTTCGCCAGCACCATGAT | SEQ ID NO: 57 |
| 1481 antisense/m13rev | CCAGGCGTGGTTACGCAAAGTCTTTG | SEQ ID NO: 75 |
| 1099 sense m13fwd+/2ry | GACCAGAGTCATCCTTCTGAACTGG | SEQ ID NO: 61 |
| 1481 antisense/m13rev+ | CCAGGCGTGGTTACGCAAAGTCTTTG | SEQ ID NO: 75 |

An RT-PCR product was generated from exon α7D to exon 10 from one normal brain and from SH-SY5Y cells. The resulting cDNA product contained alternate splice products with exons shown in FIG. 2. The 2 base pair deletion seen at bases 497-498 in the DNA that is not present in the exon 1-10 transcript was seen in the D-10 transcript, while all of the D-10 product in SH-SY5Y was deleted at 497-498, and subject SL061 was heterozygous for the deletion in the D-10 product. The presence of the T at base 757 connects this base change to the TG deletion. The G at 690 was not expressed in either cDNA. The A at 933 was not present in the minus TG strand of SH-SY5Y. The T at 1296 was expressed in subject SL061. These products, in subject SL061 cannot differentiate between the exon 5-10 product splicing to exon D versus exon 1, however the product in D-10 from SH-SY5Y can, since only the minus TG strand was expressed, negating the possibility that exons 5-10 from the 1-10 gene are splicing to exon D.

These new exons have been designated as 3'α7A, α7B, α7C, α7D 5'. The RACE products were variable in their inclusion of Exon B, similar to the EST clones. However, PCR products including exons D-10 gave many alternate splice products between exons D, C, B, 5 and 6. This same phenomenon was seen in the exon 1-10 transcripts between exons 2 and 6. Based on these results, it was not possible to fully evaluate whether any of the D-10 transcript contain only exons 5-10 from the duplicated region or if this transcript contains some splicing of 5-10 from the 1-10 full gene sequence, since the cell line and the brain gave differing results. Subcloning is used to fully evaluate the base changes to separate the various splice products.

These results indicate that the primer sequences described herein can be successfully used to screen both genomic DNA and mRNA for the presence in DNA and the expression in mRNA of sequences which are polymorphic (i.e., different) between individuals. Standard automated and manual sequencing methodologies are used to locate differences in samples obtained from individuals. It is contemplated that some of these polymorphisms, as well as others, have pathogenic roles. These polymorphisms are also used to relate the inheritance of specific alleles of α7 genes through families to the presence of illness or physiological dysfunction, using standard methods known in the art for linkage analysis.

Example 9

Single Strand Conformation Polymorphism (SSCP) Analysis

PCR products, <200 bp, containing a single sequence variant were amplified with $^{33}$Pγ-ATP kinased primer sets using Promega T4 kinase as known in the art (See e.g., Dracopoli et al., supra). The primers used in this Example were:

TABLE 4

Primers Used for SSCP Analysis

| Exon and Primer # | Sequence | SEQ ID NO: |
|---|---|---|
| Exon 6b/ #1243 | GATGTGCAGCACTGCAAACAA | SEQ ID NO: 76 |
| Exon 6b/ #1144 | TTAAAGCTTGCCCAGGAATAGG | SEQ ID NO: 77 |
| Exon 6d/ #1124 | GGAACTGCTGTGTATTTTCAGC | SEQ ID NO: 78 |
| Exon 6d/ #1245 | AAGACCAGGACCCAAACTTGT | SEQ ID NO: 79 |
| Exon 7d/ #1143: | GCTTGTGTGTGGTATACACATTG | SEQ ID NO: 80 |
| Exon 7/ #675 | GTAGAGTGTCCTGCGGC | SEQ ID NO: 81 |
| Exon 10(1438)/ #672 | GGTCCGCTACATTGCCAA | SEQ ID NO: 82 |
| Exon 10/ #593 | TGATGGTGAAGACCGAGAAGG | SEQ ID NO: 83 |

Products, denatured with loading dye (7.26 M urea, 60% formamide, 22 mM EDTA, 32 mM NaOH, 0.25% bromophenol blue, 0.25% xylene cynol), were analyzed on GeneAmp detection gels (Perkin Elmer) run at both 6° C. and 25° C., using Bio Rad PowerPac 3000 with a temperature probe, as described by the manufacturer.

Thus, the frequency of these sequence variants was examined, using SSCP in a group of 43 normal control subjects with no history of mental illness. Primer sets derived from the exon and intron-exon boundary sequences are used to amplify 200 bp portions of the gene from individuals with schizophrenia and their relatives, in order to identify sequence changes that affect gene function. Sequence changes that are not known to affect gene function, but can serve as markers to trace heritability of particular gene regions through families, are also identified in this process. The −2 bp deletion and the heterozygosities at 654, 690, 1269, at 1335 were found in this Example.

Almost all subjects were heterozygotic at positions 654 and 690. Nucleotide positions 1269 and 1335 were also found to be polymorphic, suggesting that the duplicated sequences have diverged since the duplication event.

These results indicate that the primer sequences described herein can be successfully used to screen genomic DNA in SSCP, a standard genome screening technique, for polymorphic differences in DNA sequences between individuals. It is contemplated that these polymorphisms, as well as others, have pathogenic roles. These polymorphisms are also used to relate the inheritance of specific alleles of α7 genes through families to the presence of illness or physiological dysfunction, using standard methods known in the art for linkage analysis.

Example 10

Electrophysiological Recording, Linkage Analysis, and Nonparametric Methods

Electroencephalographic activity was recorded at the vertex and electrooculographic activity was recorded from the superior orbital-lateral canthus. Five averages of sixteen responses each to paired clicks were obtained, using standard methods (See, Griffith et al., Psychophysiology, 32:460, 1995). The P50 responses were distinguished from pre-stimulus activity for both normals and schizophrenics at a high level of significance (P<0.001). The averages were reviewed by two investigators, blind to genetic information, who rejected any average containing excessive electrooculographic activity, drowsiness, startle, or other artifacts; the remainder were combined into a grand average, from which the P50 amplitudes were measured and their ratio (second response/first response) was calculated automatically by a computer algorithm (Nagamoto et al., Biol Psychiat, 25:549, 1989). Seven subjects were not used, because artifact-free averages could not be selected from their recordings. Recordings were initially performed, then repeated approximately three years later. The earlier recordings were reanalyzed for 2 subjects who were later deceased, for 10 subjects who refused repeat recording, and for 2 patients who were later on atypical neuroleptics, which can normalize the P50 ratio; other neuroleptic medication do not affect the phenotype (Nagamoto et al., Biol Psychiat, 40:181, 1996).

Parameters for lod score analyses of P50 ratios were determined from the distribution of values in 43 unrelated normal individuals and 36 unrelated schizophrenic patients (Waldo et al., Schizophr Res, 12:93, 1991) and from observations of the segregation of P50 ratios in the nine multiplex schizophrenic families (i.e., the families described in Example 1). Elevated P50 ratios were defined as values greater than or equal to 0.50, which were found in 91% of the unrelated schizophrenics and 6% of the normals. Of the remaining unrelated schizophrenics, most had values between 0.41 and 0.49, a range therefore coded unknown for the linkage analysis. If this unknown range was extended to include values between 0.40 and 0.60, the results were changed substantially (e.g., lod scores were decreased by an average of 0.54 across the markers in the 15q13-14 region due to the loss in information). For lod score analyses, frequency of a gene for abnormal P50 ratio was fixed at 0.05, penetrance for the normal genotype was fixed at 0.01, and penetrance for the abnormal genotypes was fixed at 0.8 (Coon et al., Biol. Psychiat., 34:277, 1993). These parameters result in a morbidity for abnormal P50 ratio of 8.7% and a phenocopy rate among abnormal subjects of 10.4%. The FASTLINK version of the LINKAGE program was used to compute lod scores at various recombination fractions, Θ (Lathrop et al., Proc Natl Acad Sci USA, 81:3443, 1984). No significant heterogeneity was found using the HOMOG program (Ott, *Analysis of Human Genetic Linkage*, Johns Hopkins Univ. Press, Baltimore, 1991). The chance of false positive lod score results was determined using SLINK (Ott, Proc Natl Acad Sci USA, 86:4175, 1989); 1000 replicates of the pedigrees were simulated, assuming no linkage to the marker under analysis. Lod score analysis was performed for each replicate under the dominant model; the highest score observed for D15S1360 and P50 under the assumption of no linkage was 1.87.

Sibling pair analysis was performed using the SIBPAL program (Elston, *SIBPAL, Statistical Analysis for Genetic Epidemiology*, Louisiana State Univ. Medical Center, New Orleans, La., version 2.2, 1995). Marker data were used to estimate the proportion of alleles shared through a common ancestor (i.e., identical by descent) for each possible sibling pairing within the linkage families. A test was performed to determine if the proportion of alleles shared was >0.50 for abnormal/abnormal pairs. To calculate P values, 1000 replicates of the 9 families were simulated for each marker to determine empirical distributions. Degrees of freedom were adjusted downward for non-independence when multiple pairings were used from the same sibship within a family.

A newly developed method, Nonparametric Linkage, uses information from all genotyped members of a pedigree to assess the extent of alleles shared identical by descent among all affected individuals. The resulting statistic was normalized, first by subtracting the expected sharing score under the null hypothesis (no linkage from the observed score), and then dividing by the score variance under the null hypothesis. Thus the statistic is asymptotically distributed as a standard normal variable (Z score) under the null hypothesis. Calculations of Nonparametric Linkage statistics were carried out using the GENEHUNTER computer programs (Elston, supra). GENEHUNTER also uses an improvement to a previously described algorithm to perform complete multipoint linkage analysis with a large number of highly polymorphic markers in pedigrees of moderate size (Kruglyak et al., Am J Hum Genet, 58:1347, 1996). Due to computational constraints, the three largest pedigrees were each split into two parts.

Only one marker, D15S1360, yielded a lod score >3.0 (lod score maximum=5.3, theta=0.0, P<0.001). DNA markers flanking D15S1360 also gave positive lod scores. Multipoint analysis showed a maximum lod score at D15S1360 of 5.29. Both the sibpair analysis and nonparametric linkage analysis gave confirming positive results of similar statistical significance. The sibpair analysis showed 0.70 proportion of D15S1360 alleles among siblings with abnormal P50 ratios (T=4.07, P<0.0005). Two point results from the non-parametric analysis were most significant for D15S1360 (Z=3.95, P<0.0002). A complete multipoint analysis using nine chromosome 15q markers gave a maximum value at D15S1360 (Z=5.04, P<0.000016).

From the above it should be clear that the present invention provides gene sequences encoding mammalian α7 genes and proteins. The present invention further provides compositions and methods for targeted therapy directed to α7 abnormalities.

Example 11

Refinement of the Physical Map of the P50-Schizophrenia Linkage Region

This example provides details of further physical mapping of the region of chromosome 15q13-q14 that is inherited in subjects with the P50 deficit and with schizophrenia. The contig depicted in FIG. 11 includes multiple bacterial artificial chromosomes, and map locations for additional expressed sequence tags and markers. The region is defined by 30 markers and is estimated to be about 4 Mb in length. The full-length CHRNA7 gene, implicated in the P50 deficit in schizophrenia, is localized at this site between unique markers D15S1013 and D15S1010. Mapping of α7 exons showed that exons 5 to 10 of CHRNA7 had been duplicated, along with a large cassette of DNA containing several other genes, and inserted proximal to the full-length gene. The insertion occurred next to novel exons D-C-B-A, with which the duplicated α7 exons are expressed as messenger RNA (dupCHRNA7; GenBank Accession No. AF029838). The novel dupCHRNA7 transcript was detected in multiple tissues, including human brain and blood leukocytes.

During development of the present invention, exons D-C-B-A were found to be both duplicated and expressed with downstream sequences that are not of α7 origin (GenBank Accession No. AA861176). These novel exons were also found to map on chromosome 3 by hybrid clone panel analysis. It is contemplated that exons D-C-B-A, contained in clone AA861176, were duplicated at least once on chromosome 15, with one insertion site near the dinucleotide repeat (D15S1043), before the partial duplication of the CHRNA7 gene. Ultimately, the large cassette containing α7 exons 5 to 10, dinucleotide repeat L76630, and expressed sequence tag WI13983 was duplicated and inserted proximally, interrupting the duplication of AA861176. Additional analysis of exons D-C-B-A indicated that exon D actually contains 2 exons and an intervening sequence. The two newly defined exons are designated as D' (proximal) and D (distal). The unique DNA sequence between the full-length CHRNA7 gene and dupCHRNA7 is approximately 1 Mb, and contains a large number of mapped expressed sequence tags and markers. The site of the marker D15S1360, isolated from a YAC containing CHRNA7, has been more precisely mapped to intron 2, by examining the sequence available from the National Human Genome Research Institute (bacterial artificial chromosomes 717i24 and 198g2). The D15S1360 repeat has been used extensively for genotyping of both schizophrenic patients and controls in the studies disclosed herein. Only two alleles were ever observed in any one individual. Furthermore, the promoter and exons 1 to 4 of the full-length α7 gene were found only in bacterial artificial chromosomes and P1 artificial chromosomes containing D15S1360, all of which map between D15S1031 and D15S1040. Thus, during development of the present invention, the region 5' of exon 4, containing the promoter region of the full-length α7 gene, was determined not to be duplicated.

Example 12

Subject Selection and Sample Collection for CHRNA7 Promoter Analysis

Subjects were analyzed in a modified case-control study for polymorphisms in the core promoter of the full length CHRNA7 gene. A total of 298 schizophrenic subjects were available for screening (See, Table 5). The sample contained 188 subjects from the NIMH Schizophrenia Genetics Initiative, including DNA samples from 20 families used in a sib-pair analysis positive for schizophrenia (Leonard et al., Am J Med Genet, 81:308-312, 1998). These DNA samples were derived from lymphoblast cultures in the NIMH collection. Three schizophrenic lymphoblast cultures were obtained from Israel, while the remaining DNA samples were isolated from either postmortem brain or lymphoblasts collected in the Denver Schizophrenic Center (Denver, Colo.). The samples collected in Denver included 25 specimens from patients with childhood onset schizophrenia.

TABLE 5

Subjects Used For Screening of the CHRNA7 Promoter*

| Source | Subjects | Number | DNA Source | P50 Ratio |
|---|---|---|---|---|
| NIMH | SZ | 188 | lymphoblasts | 0 |
| Denver | SZ | 49 | lymphoblasts | 34 |
| Denver | SZ | 33 | brain | 0 |
| Denver | COSZ | 25 | lymphoblasts | 18 |
| Israel | SZ | 3 | lymphoblasts | 0 |
| Total | SZ | 298 | both | 52 |
| Denver | Control | 152 | lymphoblasts | 151 |
| Denver | Control | 13 | brain | 0 |
| Total | Control | 165 | both | 151 |

*Abbreviations: NIMH, National Institute of Mental Health Genetics Initative for Schizophrenia; SZ, schizophrenia; and COSZ, childhood-onset schizophrenia.

Postmortem brain was donated by the family of the deceased through the Colorado Uniform Anatomical Gift Act (1968) and collected at autopsy. Hospital and autopsy records were reviewed, and family members and physicians were interviewed to determine age, sex, cause of death, and mental illness status. Brains were weighed, examined for gross pathological features, and divided sagittally. One hemisphere was preserved in formalin for neuropathological analysis. The other hemisphere was sliced coronally into 1-cm slices, from which multiple regions were dissected in blocks, frozen in dry-ice snow, and packaged for storage at −80° C. (Leonard et al., Biol Psychiatry, 33:456-466, 1993). DNA was isolated from cortex, by means of standard methods (Sambrook et al., eds., *Molecular Cloning: A Laboratory Manual* 3$^{rd}$ edition, Cold Spring Harbor, N.Y.: Cold Spring Harbor Press, 2001). Of the 165 control DNA samples used in the study, 152 were isolated from blood collected in the Denver Schizophrenia Center and had no evidence of current or past psychosis as determined with a Structured Clinical Interview for Axis I DSM-IV Disorders-Non-Patient Edition (SCID-I/NP), Version 2.0 (First et al., Biometrics Research Department, New York State Psychiatric Institute, 1996). In addition, these controls had a Family History Research Diagnostic Criteria, 3$^{rd}$ edition, interview that showed no evidence of family history of psychosis (Endicott et al., Research Assessment and Training Unit, New York State Psychiatric Institute, 1978). All local subjects included in this study provided written informed consent by means of forms approved by the University of Colorado Health Sciences Center Internal Review Board.

Auditory evoked potentials were recorded on 151 of the living controls, by published methods (Freedman et al., Schizophr Res, 4:233-243, 1991). Briefly, auditory sensory gating is measured by means of the P50 wave of the electroencephalogram response to paired auditory stimuli delivered in the form of clicks. After the second stimulus, delivered 0.5 second after the first, the P50 response is decreased in normal individuals. In most schizophrenic subjects, the response to the second stimulus is not as greatly diminished as in controls; in some subjects the second response is larger than the conditioning response. Control subjects with no history of mental illness, generally have P50 ratios of the T/C response amplitudes that are less than 0.50. Although some P50 ratios in controls are higher, before the development of the present invention, it was not known what causes this variation.

Ethnicities of all subjects were recorded from self-report or family interview and represented three major groups. White subjects accounted for approximately 65% of the samples from schizophrenic patients and 61% of the controls, and African Americans approximately 31% of the schizophrenic sample and 34% of the control subjects. Hispanics accounted for 4% of samples from schizophrenic patients and 5% of the controls. All schizophrenic subjects in each family were screened for polymorphisms to detect the possible presence of different variants in related individuals.

Example 13

Mutation Screening of the CHRNA7 Promoter

The α7 gene cluster in the 15q13-q14 linkage region was selected as the most likely candidate gene group for mutation studies, based on inclusion of the linkage marker D15S1360 within intron 2 of the full-length nAChRα7 gene and the neurobiological evidence described herein that is consistent with diminished α7 expression or function. Because nonsynonymous changes in the coding region were found to be rare and not associated with schizophrenia, the promoter region of the gene was first examined.

Genomic DNA was isolated from individuals as previously described (Gault et al., Genomics, 52:173-185, 1998), and 231 bases proximal to the α7 ATG translation start site were screened. Single-stranded conformational polymorphism (SSCP) analysis and sequence analysis were used to identify polymorphisms in this core promoter region (Gault et al., supra, 1998). Briefly, two primers sets for overlapping fragments covered the region from bases −14 to −268 (primer sets 4 and 5 of Table 6). The primer sets were phosphorylated with [γ-$^{33}$P]-adenosine triphosphate and T4 kinase (Promega), then used separately to amplify the promoter region by PCR. PCR was done with Taq Gold and a GeneAmp PCR System 9600 kit (Perkin-Elmer) using the following program: 95° C., 3 min; 95° C., 30 sec; 60° C., 30 sec; 72° C., 30 sec; for 35 cycles; then 72° C., 3 min. The products were denatured with loading dye (7.26M urea, 60% formamide, 22 mM EDTA, 32 mM sodium hydroxide, 0.25% bromophenol blue, and 0.25% xylene cyanol) and were separated on GeneAmp detection gels (Perkin-Elmer) run at 4° C. and 25° C. by means of a Bio-Rad Power Pac 3000 Power Supply with a temperature probe. The results were similar at both temperatures. SSCP analysis of DNA samples, from both schizophrenic and control subjects, was completed in the same experiment.

TABLE 6

Primer Sets Used For PCR, DNA Sequencing and SSCP Analysis

| Sets | Sequence | Size (bp) | Base | Use | SEQ ID NO |
|---|---|---|---|---|---|
| 1 S | 5'-GGTTGGCAAGACTTCCGAAGCC-3' | 618 | −553 to −531 | PCR, SEQ | 126 |
| 1 AS | 5'-GTGGCTTTACCGTGCAGGAGCG-3' | | +44 to +65 | PCR, SEQ | 127 |

TABLE 6-continued

Primer Sets Used For PCR, DNA Sequencing and SSCP Analysis

| Sets | Sequence | Size (bp) | Base | Use | SEQ ID NO |
|---|---|---|---|---|---|
| 2 S | 5'-AGTACCTCCCGCTCACACCTCG-3' | 271 | -269 to -248 | PCR, SEQ | 128 |
| 2 AS | 5'-ATGTTGAGTCCCGGAGCTGCAG-3' |  | -20 to +2 | PCR, SEQ | 129 |
| 3 S | 5'-CTGGCCAGAGGCGCGAGGCCG-3' | N/A | -347 to -327 | SEQ | 130 |
| 4 S | 5'-GGGGCTCGTCACGTGGAGAGGC-3' | 180 | -170 to -149 | SSCP | 131 |
| 4 AS | 5'-AGCAGCGCATGTTGAGTCCCGGAGC-3' |  | -14 to +10 | SSCP | 132 |
| 5 S | 5'-GTACCTCCCGCTCACACCTC-3' | 176 | -268 to -249 | SSCP | 133 |
| 5 AS | 5'-CGGCTCGCGCGCCTTTAAGGA-3' |  | -112 to -92 | SSCP | 134 |
| 6 S | 5'-AGTACCTCCCGCTCACACCTCG-3' | 696 | -269 to -248 | PCR, SEQ | 135 |
| 6 AS | 5'-GGAGGCTCAGGGAGAAGTAG-3' |  | +407 to +427 | PCR, SEQ | 136 |

*Abbreviations: S, sense; AS, antisense; and bp, base pairs.

Automated DNA sequencing on an Applied Biosystems 377 DNA Sequencer was used for verification of polymorphisms and determination of the specific bases changes, as previously described (Gault et al., supra, 1998). Generally, a large fragment of 618 bp was generated with the use of primer set 1. A final concentration of 1.25M betaine (Sigma-Aldrich), added to Master Mix 2 in the Expand Long Template PCR System kit (Roche) was used to amplify the fragment, with the following PCR program: 93° C., 2 min; 38 cycles at 93° C., 30 sec; 62° C., 30 sec; 72° C., 1 min; followed by 72° C., 7 min. Briefly, 200 ng of genomic DNA was diluted in a volume of 25 µl to the following final concentrations: 1× Expand Long Template PCR Buffer 3 (Roche), containing 0.75 mM magnesium chloride, 1.67 U of Expand Long Template enzyme mixture (Taq and Pwo thermostable DNA polymerases), 0.25 mM of each deoxynucleotide triphosphate, 0.4 µM of each primer, and 1.25M betaine. An additional primer set 2 was often used for sequencing of a shorter fragment in the proximal promoter region (271 bp). The PCR conditions for the shorter fragment were the same as for the longer fragment.

The G/C(-194) and G/A(-191) variants had indistinguishable SSCP patterns. Samples with these polymorphisms were analyzed with WAVE technology (Transgenomics). WAVE detects sequence changes in PCR products based on differential separation through temperature-modulated liquid chromatography and a high-resolution matrix with detection by absorbance at 254 nm. During development of the present invention, the PCR products generated with primer set 2 were used. An aliquot of the PCR fragment generated from control or patient DNA was then used for heteroduplex formation in the thermal cycler as follows: 95° C. for 5 min, ramp slowly from 95° C. down to 25° C. for 45 min, then hold at 4° C. The melting profile of a normal 271 bp promoter sequence was determined with the Wavemaker Program (Transgenomics). A temperature curve was generated for the heterozygous samples containing either G/C(-194) or G/A(-191) at temperature ranging from 69° C. to 73° C. The resulting chromatograms showed the presence of heteroduplex peaks that were resolved optimally at 71° C. A triethylammonium acetate and acetonitrile gradient specified by the manufacturer was used for elution. All subsequent samples were run under identical conditions.

Figure 12:
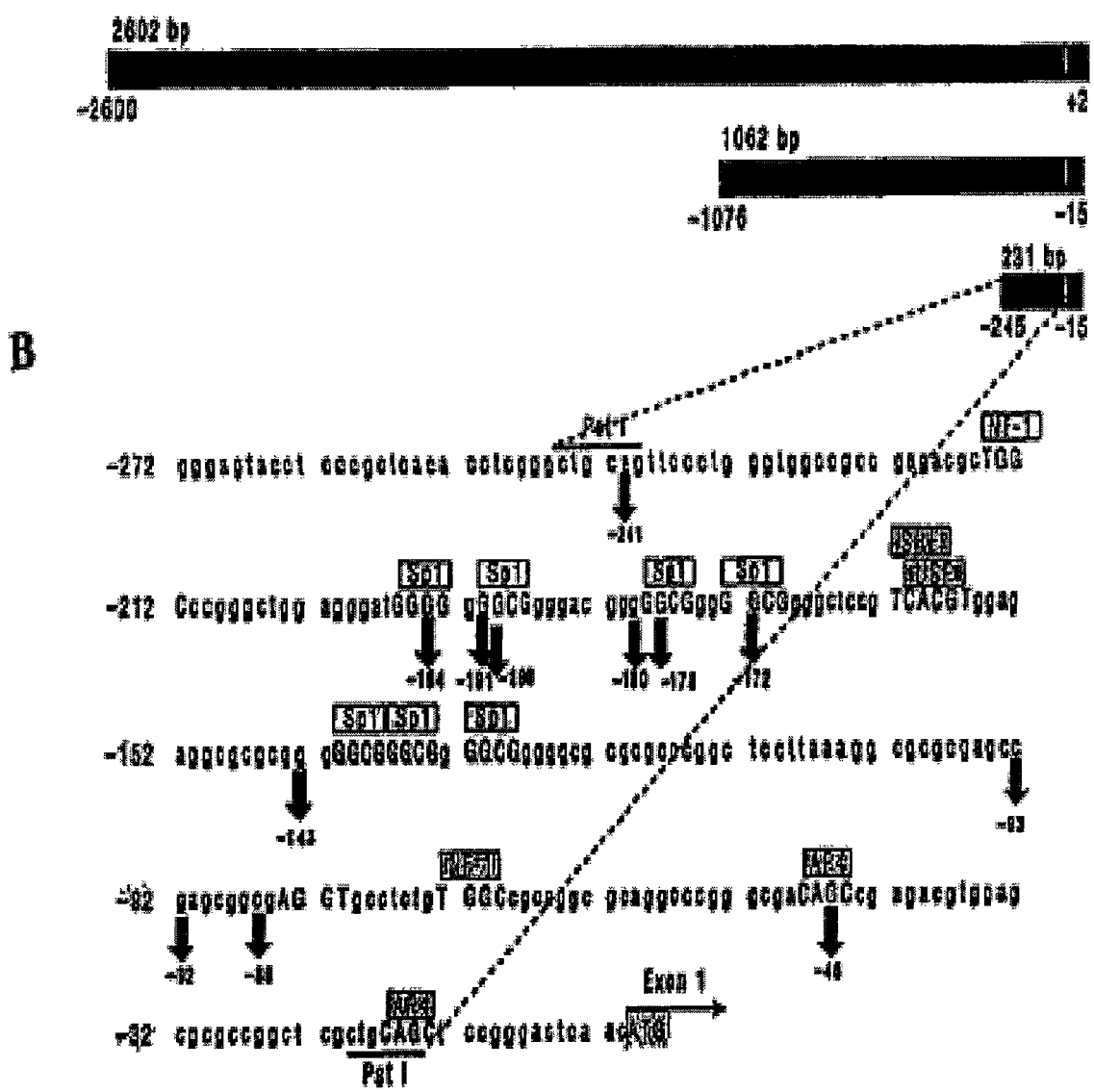
FIG. 12 depicts the promoter region of the α7 nicotinic acetylcholine receptor gene (CHRNA7). Panel A shows the fragments used to identify the core promoter region. Panel B shows the core promoter region for the CHRNA7 gene set forth as SEQ ID NO:125. Arrows depict the locations of polymorphisms identified with the mutation screen.

Approximately 2.6 kb (SEQ ID NO:122) of DNA sequence 5' of exon 1 in the full-length CHRNA7 gene was cloned from P1 artificial chromosome 24919 that contains CHRNA7 exons 1 to 3 (Incyte). Subclones of this region were constructed for determination of functional domains for gene transcription (See, FIG. 12, panel A). Base pair numbering begins with -1 at the position preceding the translation start in exon 1. The three fragments indicated were cloned into the pGL3 Basic Vector (Promega) for analysis of promoter sequence effects on the reporter gene luciferase. A fragment of 231 bp, immediately 5' of exon 1, was identified as the core promoter sequence and is sufficient to drive high levels of transcription in vitro. Sequences further upstream, included in fragments of 1.0 kb and 2.6 kb, were identified as containing putative repressor elements.

The 231-bp core promoter region is homologous to the bovine α7 core promoter region, including conservation of some transcription factor consensus sequences (Carrasco-Serrano et al., J Biol Chem, 273:20021-20028, 1998). Thus, the human α7 promoter region is contemplated to be regulated in part by SpI and AP-4 transcription factors, for which there are 2 clusters of consensus sites (See, FIG. 2, panel B). The regions including the Sp1 sites were also identified as G/C boxes, which are contemplated to bind other transcription factors. There is a consensus serum responsive element (SRE), also found in the bovine gene, but not in chick gene (Couturier et al., Neuron, 5:847-856, 1990).

Mutation screening was completed for the 231-bp core promoter in 195 schizophrenic individuals and 165 controls, demonstrating a complex cluster of variants (See, Table 7). There were 12 different single nucleotide changes, including two insertions and a deletion. Many of the variants lie in putative transcription factor consensus binding sequences (See, FIG. 2, panel B). For instance, the G/C variant at -194 introduces a new SpI site. In addition, some subjects were found to carry double variants that were combinations of the single variants (8 different combinations). The total numbers of single and double variants found in control and schizophrenic subjects are shown in Table 7 and Table 8, respectively, stratified by ethnicity. One polymorphism, an insertion of +CGGG at -140 bp, was found in a single subject with a diagnosis of psychosis, not otherwise specified (DSM-IV, 298.9). As this diagnosis was not included in either the control or schizophrenic sample diagnoses, this individual was not included in Table 7 or in the statistical analysis, but is disclosed to indicate that additional and perhaps more complex polymorphic patterns may remain to be discovered with the methods and compositions disclosed herein. Forty-seven of 165 control individuals and 71 of 195 schizophrenic patients had one of the single polymorphisms. Although one single variant (-93 bp) and two double variants (-93 bp/-194 bp and −191 bp/−194 bp) were found only in control subjects, a larger number of both single and double variants were found in schizophrenic patients than in controls. The difference was not, however, statistically significant. Eight of the 12 variants (−86 bp, −92 bp, −143 bp, −178 bp, 480 bp, −191 bp, −194 bp, and −241 bp), marked with asterisks in Table 7, were found to be more prevalent in schizophrenic subjects. Twenty-seven of 165 control subjects had one of these 8 variants, but 59 were found in the 195 schizophrenic patients. Association of the single variant −86 bp C/T with schizophrenia in the combined ethnic groups reached significance (P=0.04). This polymorphism was examined alone because −86 bp C/T was found to be the most common variant in the region, and because it was found to have the highest prevalence in schizophrenic patients. It is found more frequently in whites than in African Americans. The genotype relative risk for this variant was 2.39 (95% confidence interval, 1.07-5.32). The principal polymorphisms found in African American schizophrenic patients were the G deletion at −178 bp and the G/A substitution at −191 bp. Although more variants at these sites were found in schizophrenic subjects than in controls, fewer subjects were carrying each of the polymorphisms and the differences were not significant.

Thirty-four affected full sib pairs were examined in 30 families that had one or more of the promoter polymorphisms. Fourteen of the 34, or 0.41 sib pairs, shared at least one of these variants. For the common −86 bp C/T variant, 6 of 12 sib pairs shared the polymorphism.

TABLE 7

Single Promoter Variants in Control and Schizophrenic Subjects

| Variant | Control Subjects | | | | Schizophrenic Subjects | | | |
| --- | --- | --- | --- | --- | --- | --- | --- | --- |
| | White | African | Hispanic | Total | White | African | Hispanic | Total |
| −46 G/T | 0 | 11 | 0 | 11 | 0 | 9 | 0 | 9 |
| −86 C/T | 9 | 0 | 0 | 9 | 20 | 1 | 2 | 23*† |
| −92 G/A | 1 | 0 | 0 | 1 | 1 | 1 | 0 | 2* |
| −93 C/G | 1 | 0 | 0 | 1 | 0 | 0 | 0 | 0 |
| −143 G/A | 0 | 0 | 0 | 0 | 0 | 1 | 0 | 1* |
| −172 +CGGGGG | 1 | 0 | 0 | 1 | 0 | 0 | 0 | 0 |
| −178 −G | 0 | 3 | 0 | 3 | 0 | 9 | 0 | 9* |
| −180 G/C | 0 | 0 | 0 | 0 | 0 | 0 | 1 | 1* |
| −190 +G | 0 | 5 | 2 | 7 | 1 | 2 | 0 | 3 |
| −191 G/A | 0 | 3 | 0 | 3 | 1 | 6 | 0 | 7* |
| −194 G/C | 9 | 2 | 0 | 11 | 12 | 1 | 1 | 14* |
| −241 A/G | 0 | 0 | 0 | 0 | 2 | 0 | 0 | 2* |
| Total Variants | 21 | 24 | 12 | 47 | 37 | 30 | 4 | 71 |
| Total Subjects | 103 | 54 | 8 | 165 | 129 | 56 | 10 | 195 |

*Found more frequently in schizophrenic subjects.
†P = 0.04.

TABLE 8

Double Variants in Control and Schizophrenic Subjects

| Combination | Control Subjects | | | | Schizophrenic Subjects | | | |
| --- | --- | --- | --- | --- | --- | --- | --- | --- |
| | White | African | Hispanic | Total | White | African | Hispanic | Total |
| −46/−178 | 0 | 0 | 0 | 0 | 0 | 3 | 0 | 3* |
| −46/−190 | 0 | 0 | 0 | 0 | 0 | 1 | 0 | 1* |
| −46/−191 | 0 | 0 | 0 | 0 | 0 | 1 | 0 | 1* |
| −86/−194 | 2 | 0 | 0 | 2 | 1 | 0 | 0 | 1 |
| −86/−241 | 0 | 0 | 0 | 0 | 1 | 0 | 0 | 1* |
| −93/−194 | 1 | 0 | 0 | 1 | 0 | 0 | 0 | 0 |
| −178/−191 | 0 | 0 | 0 | 0 | 0 | 1 | 0 | 1* |
| −191/−194 | 0 | 1 | 0 | 1 | 0 | 0 | 0 | 0 |
| Total Variant | 3 | 1 | 0 | 4 | 2 | 6 | 0 | 8† |
| Total Subjects | 103 | 54 | 8 | 165 | 129 | 56 | 10 | 195 |

*Found only in schizophrenic individuals.
†P = 0.38 (not significant).

Figure 17:
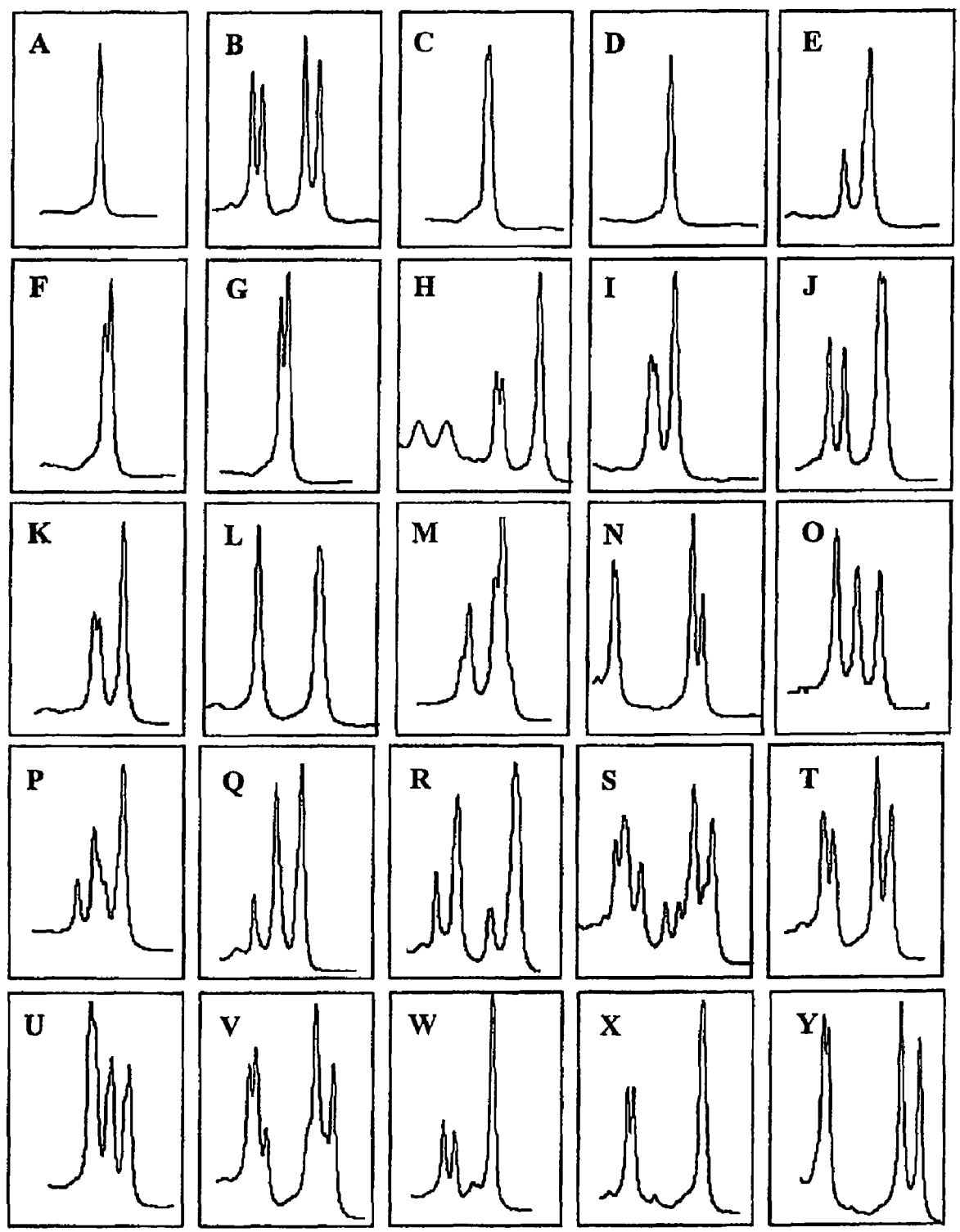
FIG. 17 depicts predictive patterns for 24 different mutations in the CHRNA7 proximal promoter determined through use of a Transgenomics WAVE™ denaturing high performance liquid chromatography (DHPLC) system. The patterns are as follows: (A) wild type; (B) −194 G/C; (C) −86 C/T; (D) −46 T; (E) −46 G/T; (F) −92 G/A; (G) −143 G/A; (H) −166 C/T; (I) −178−G; (J) −180 G/C; (K) −190+G; (L) −191 G/A; (M) −140+CGGG; (N) −178+CGGGGG; (O) −241 A/G; (P) −46 G/T and −178−G; (Q) −46 G/T and −190+G; (R) −46 G/T and −191 G/A; (S) −46 G/T and −194 G/C; (T) −86 C/T and −194 G/C; (U) −86 C/T and −241 A/G; (V) −93 C/G and −194 C/G; (W) −178−G and −190+G; (X)−178−G and −191 G/A; and (Y) −191 G/A and −194 G/C.

In other embodiments, mutation screening of the 2.6 kb upstream regulatory region is done with a Transgenomics WAVE™ denaturing high performance liquid chromatography system (DFPLC). This system detects pattern differences in PCR fragments bearing mutations. Primers are designed for overlapping fragments of approximately 300-500 bp from −2600 bp to the proximal promoter. The size of the fragment ranges from 100 bp to 300 bp and depends upon the melting profile for the sequence, as determined by utilization of the Transgenomics software. At least 10 fragments are screened. The fragments generated from each subject are then run on the DFPLC system. Fragments showing a pattern different from the wild-type are sequenced for identification of the specific mutation. Patterns similar to wild type are mixed with a wild type sample to ensure that homozygotic mutations are not missed. These have been rare in the proximal promoter region, but they do exist and this mixing protocol is used successfully for their detection. As an example of the pattern complexity, representative DFPLC patterns are shown for the proximal promoter mutations in FIG. 17.

Example 14

Analysis of Double Variants

Some subjects were found to have more than one polymorphism in the CHRNA7 core promoter. To determine whether these were on the same chromosome, the two alleles were examined individually by cloning. The PCR products were generated with the GC-RICH PCR system (Roche), with final concentrations of 1× buffer, 2.0 mM magnesium chloride, 0.25 mM deoxynucleotide triphosphates, and 0.5 µl of enzyme mix in a 25 µl volume. Three primer sets were used (See, Table 6): primer set 1, core promoter to intron 1; primer set 2, core promoter only; and primer set 6, core promoter to intron 2. The reaction for the smaller product, generated with primer set 2 (0.8 µM concentration of each primer), also included 1.0M GC-RICH resolution solution, while for the larger products generated with primer set 1 (0.4 µM concentration of each primer) or primer set 6 (0.4 µM concentration of each primer), 0.8M GC-RICH resolution solution was included. All PCR products were amplified in a Perkin-Elmer 480 PCR thermocycler by means of the following program: 96° C., 3 min; 33 cycles at 96° C., 30 sec; 56° C., 30 sec; 72° C., 7 minutes. The appropriate PCR bands were gel-purified with the cONCERT Rapid Gel Extraction System (Life Technologies), and cloned into the PCR 4-TOPO vector with the TOPO TA Cloning Kit (Invitrogen). Plasmid DNA was isolated with the S.N.A.P. Miniprep kit (Invitrogen) and analyzed by DNA sequencing. Approximately 20 clones were sequenced for each double variant cloned.

In the individuals included in this study, 8 doubly polymorphic patterns were found (subjects had more than 1 polymorphism in the core α7 promoter. Five of these double variants were found only in schizophrenic patients (marked with asterisks in Table 8). DNA fragments were cloned and sequenced from individuals with most of the double variant patterns isolated thus far. Three primer sets of Table 6 were used: 1 that amplified the core promoter of 271 bp (primer set 2); another set that amplified the core promoter, exon 1, and part of intron 1 (primer set 1); and a primer set that amplified the core promoter, exon 1, intron 1, exon 2, and part of intron 2 (primer set 6). Two variants were never found on the same chromosome, and only 2 alleles were present in all cases examined, indicating that the core promoter region is not duplicated in these individuals and, further, that each variant is a separate allele. Thus, polymorphisms in the core promoter of the full-length α7 nicotinic receptor gene are found more frequently in schizophrenic individuals than in subjects with no family history of schizophrenia, and double variants are likely to result from inheritance of one mutant allele from each parent.

Example 15

Analysis of Promoter Function

Promoter function was determined by means of a luciferase reporter gene assay. To identify a core promoter sequence in the 5' sequence upstream of the ATG translation start site in the α7 nicotinic receptor gene, fragments of this region were subcloned into the pGL3-Basic Vector (Promega), using PCR and the pGEM-T Easy Vector System II kit (Promega). Initially, a 2602 bp fragment was inserted into the pGL3 vector (See, FIG. 12 panel A, −2600 to +2). A 1064 bp clone was generated by partial PstI digestion of the original fragment and cloned into the pGL3-Basic Vector. PstI was then used to subclone a fragment of 231 bp, containing the proximal promoter region, which is conserved in the bovine α7 gene (Carrasco-Serrano et al., J Biol Chem, 273: 20021-20028, 1998). Transcription factor consensus sequences in the 5' upstream region were identified with the TRANSFAC program available on the internet, courtesy of the Research Group Bioinformatics/AG Bioinformatik. Variants discovered in the mutation screen were introduced into the normal PstI core promoter clone by using the QuikChange Site-Directed Mutagenesis Kit (Stratagene). Transient transfections were done with ProFection Mammalian Transfection Calcium Phosphate System (Promega), with the human neuroblastoma cell line SHSY-5Y (Flora et al., Eur J Pharmacol, 393:85-95, 2000). The SHSY-FY cell line was grown in 1:1 Ham F12:DMEM, and 10% fetal calf serum, plated at $2\times10^5$ cells/35 mm plate. Five µg plasmid DNA prepared with EndoFree Plasmid Kits (Qiagen) was cotransfected with 1 µg of pRL-TK Vector (Promega). Cells were harvested after 48 hours and luciferase activity was measured with the Dual-Luciferase Reporter Assay System (Promega) and a Turner Designs Luminometer Model TD 20/20.

Figure 13:
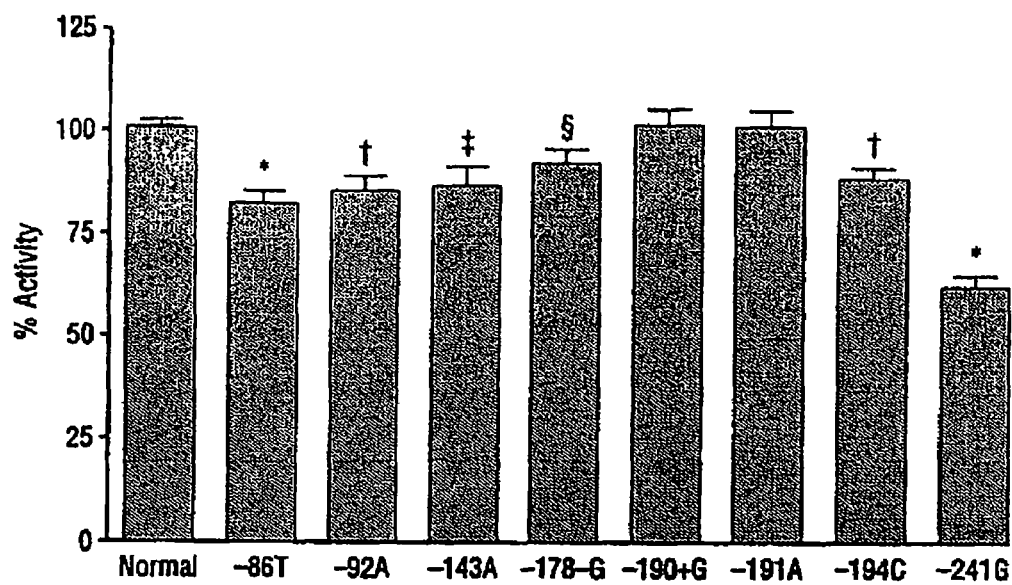
FIG. 13 provides the results of a functional assay of the α7 core promoter variants. The activity of the normal promoter sequence was set at 100%. Symbols are indicative of the following P values: asterisk, P<0.0001; dagger, P=0.005; double dagger, P=0.05; and section mark, P=0.03.

In vitro functional analysis was performed for several of the polymorphisms found more frequently in schizophrenic subjects. A luciferase reporter gene assay was used to compare the normal core promoter sequence with a fragment containing one of these variants. As shown in FIG. 13, variants at −86 bp, −92 bp, −143 bp, −178 bp, −194 bp, and −241 bp decreased transcription of the luciferase reporter gene in this in vitro assay, indicating that presence of one of these polymorphisms in the core promoter region decreases transcription from the gene. The −86 bp C/T variant resulted in a decrease in luciferase transcription of 20% (P<0.0001). The functional promoter mutations examined thus far were statistically more prevalent (chi-squared$_1$=7.302, P=0.007) in schizophrenic patients than in the control subjects.

Example 16

Statistical Analysis

For the statistical analysis, total counts from schizophrenic individuals included polymorphisms detected in only one schizophrenic individual per family, unless a second mutation was also present in another affected individual. In this case, the second variant was also counted. Subjects homozygous for the common allele were also counted. This strategy was chosen to report the full range of polymorphisms in schizophrenic patients without biasing the results by including multiple individuals who have the same polymorphism based on common ancestry. t tests were used to compare means. A Satterthwaite t test was used for comparison of means with difference variances; chi-squared tests and logistic regression were used to compare prevalence rates. For the double variants in the promoter region, cloning experiments indicated that each polymorphism is a separate allele.

Although promoter variants were found in control subjects, they were fewer in number than in schizophrenic patients. In complex disorders where multiple gene variants may be interacting with environmental factors to produce the disease, it has been suggested that functional polymorphisms are likely to be common in the general population, where each may have a more elementary phenotype, such as a biochemical or electrophysiologic abnormality that is part of the pathophysiology of the illness (Lander and Schork, Science, 265:2037-2048, 2000; and Gershon, Biol Psychiatry, 45:551-558, 1999). The association of CHRNA7 promoter polymorphisms was examined, in the living control subjects, with a functional electrophysiologic assay (e.g., inhibition of the P50 response to paired auditory stimuli). The P50 auditory sensory gating was measured in 151 of the 152 live control subjects examined in this study. The range of P50 ratios (T/C) for controls was 0.00 to 1.91. Overall mean P50 ratio was 0.22±0.27. There were 38 adult schizophrenic subjects examined locally where P50 recording was done. The mean P50 ratio for these patients was 0.92±1.02, with a range of 0.00 to 4.96. Eighteen patients with childhood-onset schizophrenia, included in the mutation screen, also had their P50 recorded. Their mean was 1.05±0.91, similar to that of the adult patients with schizophrenia. The mean ratio for the schizophrenic patients was significantly greater than that of the control subjects ($t_{205}$=8.49, P<0.0001).

Figure 14:
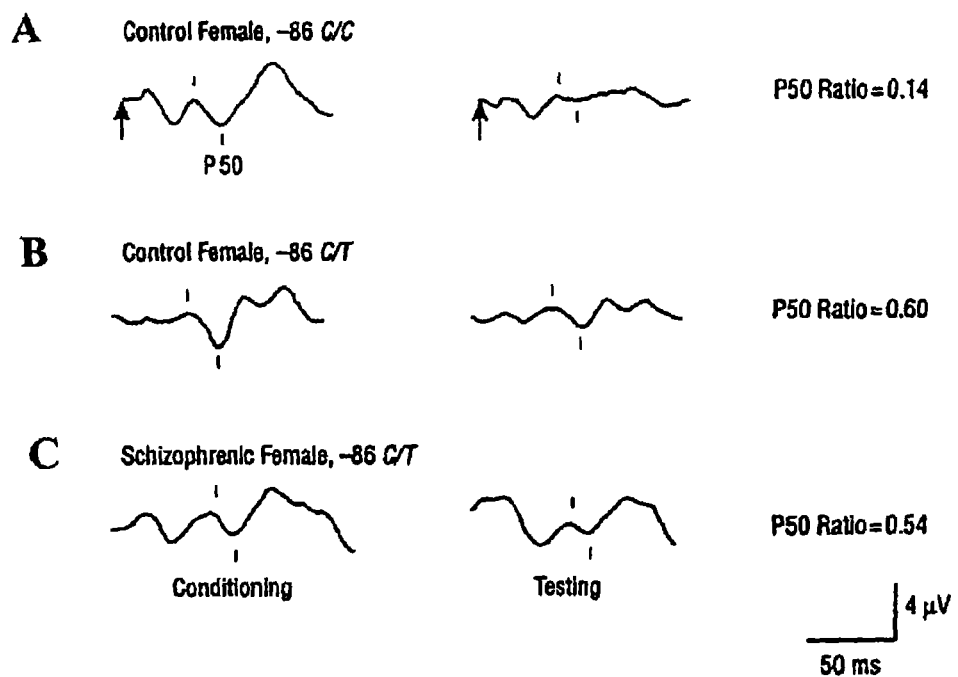
FIG. 14 shows the gating of the P50 auditory evoked potential in control subjects (Panels A and B), and in a schizophrenic subject (Panel C). Tracings are shown for both the conditioning and test responses. Arrows indicate the paired auditory stimuli.

Tracings for subjects with and without the −86 bp C/T polymorphism are shown in FIG. 14. A control subject with the normal C/C genotype had a T/C ratio (P50 ratio) of 0.14, indicating that the test response to the second auditory stimulus was being inhibited. However, a control subject carrying a −86 bp C/T heterozygotic genotype had a T/C ratio of 0.60, demonstrating a much lower level of inhibition. A schizophrenic patient with the −86 bp C/T genotype also had a higher T/C ratio of 0.54. These results indicate that the presence of a promoter variant is associated with decreased inhibition in the sensory gating paradigm and, hence, a higher T/C(P50) ratio.

The relationship between the means for the P50 T/C ratios and the presence of CHRNA7 promoter variants was then examined in the 151 control subjects. As shown in FIG. 15 panel A, the mean P50 ratio for controls with no CHRNA7 promoter variant was 0.179±0.014. However, the mean for control subjects with one of the single or double variants was 0.458±0.055. The results were analyzed, using a Satterthwaite t test for samples with different variances. The control subjects with no polymorphisms had a significantly lower mean P50 ratio than control subjects in whom a promoter variant was found (P<0.0001), demonstrating a strong relationship between the presence of a promoter variant and decreased sensory processing.

In the patients with adult-onset disease, where P50 had been recorded, 7 of 8 polymorphisms in the core promoter were found in schizophrenic patients with P50 ratios greater than 0.50. In the 18 patients with childhood-onset disease, wherein P50 had been recorded there were 7 polymorphisms, 5 of which were found in subjects with P50 ratios greater than 0.50. These results indicate that a similar relationship between the CHRNA7 promoter polymorphisms and the recorded P50 ratio exist in both adult-onset and childhood-onset schizophrenia. Logistic regression analysis of the control data indicated, that the presence of promoter variants is better described by three groups, than by a regression line on the P50 range (See, FIG. 15, panel B). One group with individual average P50 ratios less than 0.20 was found to have stable auditory gating. A second group with P50 ratios between 0.20 and 0.50 was found to have a less stable filtering mechanism. A third group with P50 ratios consistently greater than 0.50 was found to exhibit very little auditory gating, similar to what has been described herein in the schizophrenic population. Control subjects with no polymorphism in the core α7 promoter were found to have P50 ratios in the first 2 groups, with most in the less than 0.20 group. In contrast, controls with polymorphisms were more evenly distributed among the three P50 groups, while only subjects with a promoter variant were found to have P50 ratios greater than 0.50.

Example 17

Subject Selection and Sample Collection for CHRNA7 and dupCHRNA7 Analysis

Samples from 171 families with schizophrenic members and 185 samples from controls were available for screening. The sample population included 86 families from the NIMH Schizophrenia Genetics Initiative. Sixteen of these families had been used in a sib pair analysis showing greater than 50% inheritance-by-descent to a dinucleotide marker D15S1360 in the CHRNA7 gene (0.58; P<0.0024) as described (Leonard et al., Am J Med Genet, 81:308-312, 1998). Nine probands from the P50 linkage analysis (Freedman et al., Proc Natl Acad Sci USA, 94:587-592, 1997) were also included and the remaining samples were collected in the Denver Schizophrenia Center. When postmortem brain samples were used, diagnosis was based upon review of medical records and family and physician interviews. Of the controls, 166 were interviewed and found to have no evidence for current or past psychosis, using two different interviews (See, First et al., Structured Clinical Interview for DSM-IV Axis I Disorders-Non-Patient Edition, SCID-I/NP, version 2.0, NY: Biometrics Research Department, New York State Psychiatric Institute, 1996; and Endicott et al., Family History—Research Diagnostic Criteria interview, FH-RDC, 3rd edition, NY: Research Assessment and Training Unit, New York State Psychiatric Institute, 1978). In addition, auditory evoked potentials were recorded on controls, using published methods (Freedman et al., Schiz Res, 4:233-243, 1991).

The 84 samples used for cDNA mapping of the eight common variants were collected in the Denver Schizophrenic Center, and were primarily obtained from Caucasian subjects. As shown in Table 15, 28 samples from Caucasian individuals with schizophrenia (18 male and 10 female) and 49 samples from Caucasian controls (35 male and 14 female) were analyzed.

TABLE 15

Subjects Used For Screening the CHRNA7 and dupCHRNA7 Genes

| | Subjects | | | | | |
|---|---|---|---|---|---|---|
| | Schizophrenics | | | Controls | | |
| | Ethnicity | | | | | |
| tissue | Total | white | Black | Total | white | Black |
| brain | 28 | 25 | 3 | 20 | 19 | 1 |
| lymphocytes | 4 | 3 | 1 | 32 | 30 | 2 |
| totals | 32 | 28 | 4 | 52 | 49 | 3 |

TABLE 16

PCR Primers for Amplification of the CHRNA 7 Gene

| Product | Variants | SEQ ID NO | Strand | Primers | $T_A$ | SSCP |
|---|---|---|---|---|---|---|
| Exon 1 | 45, +82 | 137 | S | GCGGCGAGGTGCCTCTGT | 60° C. | 25° C. |
| | | 138 | AS | GGATCCCACGGAGGAGTGGAG | | |
| Exon 2 | | 139 | S | CCTGCCCGGGTCTTCTCTCCT | 58° C. | 25° C. |
| | | 140 | AS | AACTAGAGTGCCCCAGCCGAGCT | | |
| Exon 3 | | 141 | S | AACAACGCTCTCGACAGTCAGATC | 58° C. | 25° C. |
| | | 142 | AS | AAGATCTTGCAGCCCATGGGAG | | |
| Exon 4 | 334 | 143 | S | GGAATTCTCTTTGGTTTTGCAC | 58° C. | 6° C. |
| | | 144 | AS | ACATATCCAGCATCTCTGTGA | | |
| Exon 5 | 370 | 145 | S | TCATGCAGTCCTTTTCCTGTTTC | 60° C. | 6° C. |
| | | 146 | AS | CTCGCTTCAGTTTTCTAACATGG | | |
| Exon 6 | | 147 | S | GGAACTGCTGTGTATTTTCAGC | 58° C. | both |
| | | 148 | AS | TTAAAGCTTGCCCAGGAATAGG | | |
| Exon 7 | | 149 | S | GCTTGTGTGTGGTATACACATTG | 58° C. | both |
| | | 150 | AS | TCCAGAGCTGATCTCAGCAGAAG | | |
| Exon 8 | 861 | 151 | S | GAGGAACGGCTGTGTGTTTAT | 58° C. | 25° C. |
| | | 152 | AS | CTGGGCACACTCTAACCCTAACC | | |
| Exon 9 | | 153 | S | TGTGACGTGCAGTGCCACAGGA | 60° C. | 25° C. |
| | | 154 | AS | AAACCCTAGGAGGAGCCTCCTT | | |
| Exon 10 | | 155 | S | GATCAGCCCGTTTCCGCCTCAG | 58° C. | both |
| | | 156 | AS | CCGATGTACAGCAGGTTGCCGTTGC | | |
| Exon 6* | 497-8 | 157 | S | CAGTACCTGCCTCCAGG | 58° C. | 25° C. |
| | | 158 | AS | TCCAAGGACGAGCCTCCGTAAGA | | |
| Exon 7* | 654/690 | 159 | S | CTATGAGTGCTGCAAAGA | 58° C. | 25° C. |
| | | 160 | AS | CAGGGGATCAGCAGGTT | | |
| Exon 7* | 698/+21 | 161 | S | GCCGCAGGACACTCTAC | 58° C. | 25° C. |
| | | 162 | AS | TCCAGAGCTGATCTCAGCAGAAG | | |
| Intron 7* | −11, −20, −29 | 163 | S | GCCCCTCGTTAGACAGAATTGAG | 58° C. | 25° C. |
| | | 164 | AS | CTGGGCACACTCTAACCCTAACC | | |
| Exon 10* | 1044, 1116 | 165 | S | GATCAGCCCGTTTCCGCCTCAG | 58° C. | 25° C. |
| | | 166 | AS | CCGATGTACAGCAGGTTCCCGTTGC | | |
| Exon 10* | 1335 | 167 | S | TCCCGACCCCCGACTCT | 58° C. | 6° C. |
| | | 168 | AS | TGATGGTGAAGACCGAGAAGG | | |
| Exon 10* | 1269, 1354, 1456 | 169 | S | TCCCGACCCCCGACTCT | 58° C. | 25° C. |
| | | 170 | AS | TGATGGTGAAGACCGAGAAGG | | |
| Exon 10* | 1466 | 171 | S | CCTTCTGGGTCTTCACCATC | 58° C. | 25° C. |
| | | 172 | AS | GCCTCCACGAAGTTGGGAGC | | |
| Exon 10* | 1487 | 173 | S | GGTCCGCTACATTGCCAA | 58° C. | 25° C. |
| | | 174 | AS | CCTTGCCCATCTGTGAGTT | | |
| 3'UT* | 1737, 1837 | 175 | S | GTGTTGCTTACGGTTTCTT | 58° C. | 25° C. |
| | | 176 | AS | TTTCAGGTAGACCTTCATGCAGACA | | |
| cDNA# 1-10 | | 177 | S | TGCCCATGTGTGAGTTTTCCACATG | 72-68° C. | |
| | | 178 | AS | CGCTGCAGCTCCGGGACTCAACATG | | |
| cDNA# D-10 | | 179 | S | CTCGGTGCCCCTTGCCATTT | 72-68° C. | |
| | | 180 | AS | CCTTGCCCATCTGTGAGTTTTGCAC | | |

Example 18

Mutation Screening of the CHRNA7 and dupCHRNA7 Genes

All schizophrenic subjects in each family were screened for polymorphisms to detect the presence of different variants in related individuals. Initially, a strategy was used to screen genomic DNA from 96 samples from individuals where postmortem brain tissue or lymphoblasts were available. This was done because mRNA would be needed for the mapping of variants to either the full-length CHRNA7 or its duplication (dupCHRNA7). In the initial gene mutation screen, all the exons, intron/exon boundaries, and the 3'untranslated region (UT) were examined by means of single-strand conformation polymorphism (SSCP) analysis using the primers shown for exons 1-10 in Table 16. Exon 10 and the 3' UTR were divided into an additional eight overlapping PCR fragments of approximately 200 bp, designed from the CHRNA7 sequence (GenBank Accession No. U40583). For SSCP analysis the primer sets were kinased using [$\gamma$-$^{33}$P] ATP with Promega T4 kinase, then used to amplify regions of the CHRNA7 gene by PCR. Briefly, PCR was done using Taq Gold™ and GeneAmp® PCR System 9600 (Perkin-Elmer, Foster City, Calif.) with the following program: 95° C. for 3 min; then 35 cycles of 95° C. for 30 sec, 58° C. for 30 sec, and 72° C. for 30 se; followed by 72° C. for 3 min. Specific annealing temperatures ($T_A$) are provided in Table 16). The products, amplified and analyzed separately, were denatured with loading dye (7.26 M urea, 60% formamide, 22 mM EDTA, 32 mM NaOH, 0.25% bromophenol blue, 0.25% xylene cyanol), and separated on GeneAmp detection gels (Perkin-Elmer) run at 25° C. and 6° C. using a BioRad Power Pac 3000 with a temperature probe. Samples with unique SSCP patterns were sequenced and polymorphisms were correlated with the SSCP patterns. Identified variants were subsequently screened in additional genomic samples from controls, individuals with schizophrenia, and family members, using the appropriate primers and gel conditions. In Table 16, additional primer sets used to detect specific variants are indicated with an asterisk, while primers used in primary RT-PCR for mapping are indicated with a pound sign.

Figure 16:
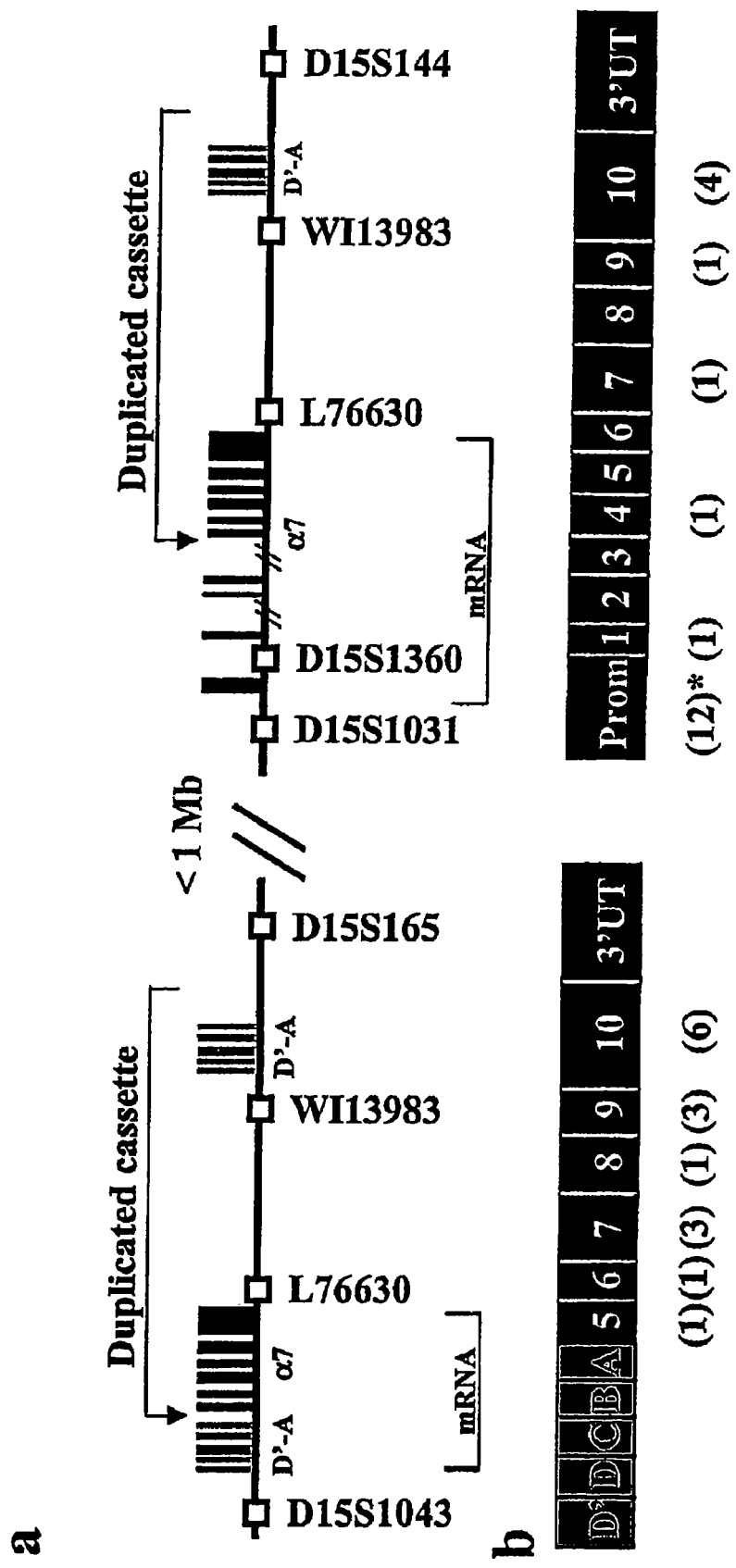
FIG. 16 provides a schematic of the 15q13-q14 region containing the CHRNA7 and dupCHRNA7 genes in Panel A. The transcripts from both the α7 containing genes are shown with their unique 5' ends in Panel B. The number of variants mapped to each exon is shown in parentheses.

Mutation analysis of the $\alpha$7 nicotinic receptor gene CHRNA7 and its partial duplication dupCHRNA7 was carried out using SSCP, and sequence analyses. FIG. 16 panel A depicts the 15q13-q14 region containing CHRNA7 and dupCHRNA7. The unique dinucleotide marker D15S1360, used in several linkage studies (Freedman et al., Am J Med Gen, 105:794-800, 2001; Freedman et al., Proc Natl Acad Sci USA, 94:587-592, 1997; Leonard et al., Am J Med Genet, 81:308-312, 1998; and Freedman et al., Am J Med Gen, 205:20-22, 2001), lies in intron two of CHRNA7 (Leonard et al., Arch Gen Psychiatry, 59:1085-1096, 2002). D15S1031 and D15S144, (also single copy) flank the full-length CHRNA7 gene and duplicated cassette (duplicon). Unique loci D15S1043 and D15S165 flank the proximal duplicon. The duplicon contains exons 5-10 of the CHRNA7 gene, the dinucleotide repeat L76630, exons D'-D-C-B-A, and the Expressed Sequence Tag (EST) WI13983. The transcripts from both $\alpha$7 containing genes are shown in FIG. 16 panel B, with their unique 5' ends and the number of variants mapped to each exon. The orientation of the duplicon is shown as head to tail, determined from yeast artificial chromosome (YAC) mapping from two separate YAC libraries (Gault et al., Genomics, 79:197-209, 2002). A head to head orientation has been reported based on BAC clone mapping from a single library (Riley et al., Genomics, 79:197-209, 2002), suggesting that the orientation of this duplicon may be polymorphic.

Thirty-three variants in the CHRNA7 gene cluster were identified in genomic DNA from individuals with schizophrenia and controls of Caucasian, African American and Hispanic descent (Tables 17, 18 and 19). Twenty-one different variants were found in the coding region of the $\alpha$7 genes, including 10 non-synonymous variants. Base pair numbering is from the first base pair in exon 1. Allele frequencies for 14 of the rare variants were calculated and are shown in Table 20. Allele frequencies for the more common variants were not determined because they could be homozygous in either dupCHRNA7 or full-length CHRNA7 genes. Six variants were found more frequently in the African Americans than the Caucasians (Table 21). Three variants at: 497-8 bp (2 bp deletion), 654 bp, and 1466 bp, were found more frequently in Caucasians than in African Americans. Two rare, but non-synonymous variants in Exon 5 at 370 bp, and in Exon 7 at 698 bp, were found only in Hispanics (See, Table 17).

In Tables 17-21, the following nomenclature and abbreviations apply: E, exon; I, intron; V, number of individuals with the variant; T, total number of individuals; $\alpha$7, full length gene; and d$\alpha$7, duplicate gene. Numbering for exons and 3'UT is from the ATG start, while numbering for introns is from the 5' donor splice site (+) or 3' acceptor splice site (-). Variants: [a]exon 4, I112V; [b]exon 5, A124T; [c]exon 6, 2 bp deletion at L166>in Caucasian subjects $X^2$=48.66, 1, P<0.0001; [d]exon 7, Y233C; [e]exon 9, G324R; [f]exon 10, S372R; [g]exon 10, E452K; [h]exon 10, 1486V; [i]exon 10, S489L; [j]exon 10, A496D; [k]intron 9, $X^2$=9.986, 1, P=0.0016; and [l]provisional mapping.

TABLE 17

Non-synonomous Variants Identified in CHRNA7 and dupCHRNA7

| | | | Schizophrenics | | | | | Controls | | | | | Map | |
|---|---|---|---|---|---|---|---|---|---|---|---|---|---|---|
| | | | Cauc. | | Afr. Am. | | Hisp. | | Cauc. | | Afr. Am. | | Hisp. | | |
| Site | bp | change | V | T | V | T | V | T | V | T | V | T | V | T | $\alpha$7 | d$\alpha$7 |
| E4[a] | 334 | A→G | 0 | 113 | 1 | 43 | 0 | 6 | 0 | 103 | 0 | 55 | 1 | 8 | X | |
| E5[b] | 370 | G→A | 0 | 112 | 0 | 42 | 1 | 7 | 0 | 100 | 0 | 53 | 2 | 8 | | X[l] |
| E6[c] | 497/8 | -TG | 68 | 86[c] | 15 | 50 | 5 | 7 | 48 | 71[c] | 12 | 54 | 4 | 4 | | X |
| E7[d] | 698 | A→G | 0 | 85 | 0 | 38 | 1 | 7 | 0 | 58 | 0 | 4 | 0 | 4 | | X[l] |
| E9[e] | 970 | G→A | 0 | 110 | 10 | 52 | 0 | 6 | 0 | 79 | 4 | 52 | 0 | 7 | | X |
| E10[f] | 1116 | C→G | 0 | 106 | 0 | 36 | 0 | 6 | 0 | 71 | 1 | 49 | 0 | 4 | | X |
| E10[g] | 1354 | G→A | 1 | 102 | 0 | 41 | 0 | 6 | 1 | 63 | 0 | 3 | 0 | 3 | X | |
| E10[h] | 1456 | A→G | 0 | 91 | 0 | 40 | 0 | 6 | 1 | 58 | 0 | 4 | 0 | 3 | | X |
| E10[i] | 1466 | C→T | 23 | 110 | 7 | 49 | 1 | 7 | 27 | 82 | 3 | 52 | 3 | 7 | | X |
| E10[j] | 1487 | C→A | 0 | 62 | 1 | 10 | 0 | 6 | 0 | 12 | 0 | 50 | 0 | 3 | X | |

TABLE 18

Synonomous Variants Identified in CHRNA7 and dupCHRNA7

| | | | Schizophrenics | | | | | | Controls | | | | | Map | |
| | | | Cauc. | | Afr. Am. | | Hisp. | | Cauc. | | Afr. Am. | | Hisp. | | | |
| Site | bp | change | V | T | V | T | V | T | V | T | V | T | V | T | α7 | dα7 |
|---|---|---|---|---|---|---|---|---|---|---|---|---|---|---|---|---|
| E1 | 45 | G→A | 1 | 99 | 0 | 41 | 0 | 6 | 0 | 64 | 0 | 3 | 0 | 3 | X | |
| E7 | 654 | C→T | 77 | 90 | 32 | 47 | 5 | 6 | 57 | 70 | 3 | 4 | 3 | 3 | | X |
| E7 | 690 | G→A | 82 | 83 | 36 | 36 | 6 | 6 | 59 | 59 | 4 | 4 | 3 | 3 | X | X |
| E8 | 861 | C→T | 4 | 98 | 1 | 40 | 1 | 7 | 1 | 59 | 0 | 4 | 0 | 3 | | X |
| E9 | 921 | G→A | 2 | 112 | 1 | 45 | 0 | 6 | 4 | 77 | 0 | 50 | 0 | 7 | | X |
| E9 | 933 | G→A | 56 | 127 | 28 | 53 | 6 | 8 | 39 | 79 | 18 | 50 | 6 | 7 | X | |
| | | A only | 2 | 127 | | | | | | | | | | | | |
| E9 | 966 | C→T | 1 | 110 | 6 | 46 | 0 | 6 | 0 | 79 | 2 | 52 | 0 | 7 | | X[1] |
| E10 | 1044 | C→T | 12 | 123 | 3 | 43 | 0 | 6 | 9 | 72 | 1 | 55 | 1 | 5 | | X |
| E10 | 1116 | C→T | 2 | 107 | 8 | 44 | 0 | 6 | 0 | 71 | 6 | 54 | 1 | 5 | — | — |
| E10 | 1269 | C→T | 75 | 95 | 29 | 40 | 5 | 6 | 47 | 57 | 2 | 3 | 3 | 3 | X | X |
| | | T only | 2 | 95 | 1 | 40 | | | 1 | 57 | | | | | | |
| E10 | 1335 | C→T | 32 | 74 | 3 | 11 | 2 | 7 | 30 | 65 | 2 | 4 | 1 | 3 | X | X |

TABLE 19

Non-coding Variants Identified in CHRNA7 and dupCHRNA7

| | | | Schizophrenics | | | | | | Controls | | | | | Map | |
| | | | Cauc. | | Afr. Am. | | Hisp. | | Cauc. | | Afr. Am. | | Hisp. | | | |
| Site | bp | change | V | T | V | T | V | T | V | T | V | T | V | T | α7 | dα7 |
|---|---|---|---|---|---|---|---|---|---|---|---|---|---|---|---|---|
| I2 | +75 | G→A | 0 | 87 | 1 | 38 | 0 | 6 | 1 | 50 | 0 | 3 | 0 | 1 | X | |
| I2 | +82 | A→C | 0 | 87 | 2 | 38 | 0 | 6 | 0 | 50 | 0 | 3 | 0 | 1 | X | |
| I3 | −9 | A→G | 0 | 113 | 3 | 45 | 0 | 6 | 0 | 103 | 1 | 55 | 0 | 8 | X | |
| I7 | +21 | C→T | 21 | 31 | 1 | 6 | 1 | 3 | 3 | 3 | 0 | 0 | 0 | 0 | — | — |
| I7 | −11 | +GTT | 10 | 38 | 2 | 4 | 0 | 4 | 5 | 10 | 0 | 1 | 0 | 1 | — | — |
| I7 | −20 | G→A | 15 | 37 | 1 | 4 | 2 | 4 | 5 | 10 | 1 | 1 | 1 | 1 | — | — |
| I7 | −29 | T→G | 1 | 37 | 0 | 4 | 0 | 4 | 0 | 10 | 0 | 1 | 0 | 1 | — | — |
| I9 | +19 | C→T | 0 | 43 | 0 | 5 | 0 | 7 | 1 | 78 | 4 | 54 | 0 | 7 | — | — |
| I9 | +27 | −TCGGAG | 0 | 110 | 1 | 44 | 0 | 6 | 0 | 78 | 2 | 54 | 0 | 7 | — | — |
| I9 | +37 | G→C | 56 | 126 | 36 | 58[k] | 6 | 8 | 38 | 79 | 17 | 53 | 6 | 7 | — | — |
| 3'UT | 1737 | C→A | 1 | 34 | 0 | 5 | 0 | 2 | 0 | 33 | 0 | 1 | 0 | 1 | — | — |
| 3'UT | 1837 | T→G | 0 | 34 | 1 | 6 | 0 | 2 | 0 | 33 | 0 | 1 | 0 | 1 | — | — |

TABLE 20

Allele Frequencies of Rare Variants

| Site | bp | change | Amino Acid | Ethnicity | Frequency Schizo. | Frequency Controls | Map α7 | Map dα7 |
|---|---|---|---|---|---|---|---|---|
| E1 | 45 | G→A | | Cauc. | 0.005 | 0 | X | |
| I2 | +75 | G→A | | Cauc. | 0 | 0.01 | X | |
| I2 | +82 | A→C | | Afr. Am. | 0.026 | 0 | X | |
| I3 | −9 | A→G | | Afr. Am. | 0.033 | 0.009 | X | |
| E4 | 334 | A→G | I112V | Afr. Am./Hisp. | 0.010 | 0.008* | X | |
| E8 | 861 | C→T | | Cauc. | 0.020 | 0.008 | | X |
| E9 | 921 | G→A | | Cauc. | 0.009 | 0.026 | | X |
| E9 | 921 | G→A | | Afr. Am. | 0.011 | 0 | | X |
| I9 | +19 | C→T | | Cauc. | 0 | 0.006 | — | — |
| I9 | +27 | −TCGGAG | | Afr. Am. | 0.011 | 0.019 | — | — |
| E10 | 1116 | C→G | S372R | Afr. Am. | 0 | 0.010 | — | X |
| E10 | 1354 | G→A | 452K | Cauc. | 0.005 | 0 | X | |
| E10 | 1456 | A→G | I486V | Cauc. | 0 | 0.009 | | X |
| 3'UT | 1737 | C→A | | Cauc. | 0.015 | 0 | — | — |

*Variant 334 was found in 1/43 African American and 0/6 Hispanic schizophrenics, and 0/55 African American and 1/8 Hispanic controls.

TABLE 21

Variants with Significantly Different Frequencies by Ethnicity

| Site | bp | change | Caucasian V | Caucasian T | African American V | African American T | P values | Map α7 | Map dα7 |
|---|---|---|---|---|---|---|---|---|---|
| I3 | −9 | A→G | 0 | 216 | 4 | 100 | 0.0104 | X | |
| E6 | 497/8 | −TG | 116 | 167 | 27 | 104 | <0.0001 | | X |
| E7 | 654 | C→T | 134 | 160 | 35 | 51 | <0.0001 | | X |
| E9 | 966 | C→T | 1 | 189 | 8 | 98 | 0.0010 | | X |
| E9 | 970 | G→A | 0 | 189 | 14 | 104 | <0.0001 | | X |
| I9 | +19 | C→T | 0 | 121 | 4 | 59 | 0.0475 | — | — |
| I9 | +27 | −TCGGAG | 0 | 188 | 3 | 98 | 0.0394 | — | — |
| E10 | 1116 | C→T | 2 | 178 | 14 | 98 | <0.0001 | — | — |
| E10 | 1466 | C→T | 50 | 192 | 10 | 101 | 0.0011 | | X |

Example 19

Mapping Variants to the CHRNA7 and dupCHRNA7 Genes

CHRNA7 exons 5-10 are duplicated and nearly homologous (>99%), complicating the mutation screen. However, the duplicated exons are transcribed with different 5' sequence and thus were isolated as unique mRNA species. The cDNA primer sets, used to specifically amplify full-length cDNA from either CHRNA7 or its duplication (dupCHRNA7), are listed as the last two entries in Table 16. These cDNA templates were then used to map the variants in exons 5-10, using RT-PCR and subsequent SSCP and sequence analysis of the RT-PCR products.

Eighty-four samples from the mutation screening study were used for cDNA mapping of the eight common variants. Immortalized cell lines were not available from the NIMH Schizophrenia Initiative samples and, thus, postmortem brain and immortalized lymphoblasts collected locally in the Denver Schizophrenia Center were utilized.

Immortalized lymphocytes were cultured 6 hours with 1 mg/ml cyclohexamide before RNA isolation. Total RNA was isolated from postmortem human hippocampus or cyclohexamide-treated immortalized lymphocytes, using TRIzol reagent (Life Technologies, Gibco-BRL). RNA was reverse transcribed (500 ng) using Superscript II reverse transcriptase components (Gibco-BRL) with 8 µM random hexamers (Pharmacia & Upjohn Diagnostics, Kalamazoo, Mich.) and 0.5 U placental RNase inhibitor (Boehringer-Mannheim, Indianapolis, Ind.). A primary PCR was performed using specific primers designed with Oligo software 4.1 (National Biosciences, Inc., Plymouth Minn.). Full-length CHRNA7 transcripts were amplified using 1 M GC-melt and 10× cDNA buffer (Clontech, K1905-1) from the Advantage cDNA PCR kit (CLONTECH, Laboratories Inc., Palo Alto, Calif.) and a two-step program with annealing temperatures from 72° C. to 68° C. Partially duplicated dupCHRNA7 transcripts were amplified using 1 M GC melt and 5× cDNA buffer from the Advantage-GC cDNA PCR kit (K1907-1). These primary reactions were then analyzed using SSCP and sequence analysis.

As shown herein, exons 5-10 of the α7 nicotinic receptor subunit gene are duplicated. Genomic variants in these exons, therefore, are contemplated to be present in either the full-length CHRNA7 gene or in dupCHRNA7. Polymorphisms were mapped, when possible, to one of the two duplicons, utilizing mRNA isolated from either immortalized lymphoblasts or postmortem brain by using gene specific PCR. In some cases a given variant was present in both duplicons. In others, only tissue from a schizophrenic subject was available for mapping. In this case, the map site is indicated as provisional, since gene rearrangements or conversions could have occurred.

Eight of the more common variants were mapped in 32 samples from individuals with schizophrenia and 52 samples from control individuals (total of 84). Four common variants: the 497/8 2 bp deletion, the neutral variant at 654 bp, the neutral variant at 1044 bp, and the amino acid changing variant at 1466 bp, all mapped only to dupCHRNA7 (See, Table 22). The 2 bp deletion in exon 6 was found in 15 out of the 32 Caucasians with schizophrenia, 29 out of the 49 Caucasian control samples, 1 out of the 4 African Americans with schizophrenia, and 2 out of the 3 African American controls.

Three common neutral variants, at 690 bp, 1269 bp, and 1335 bp mapped to both duplicons. The very common variant at 690 bp mapped primarily to the duplicated gene (69 out of 72 individuals). The 1269 bp variant mapped to both CHRNA7 genes in 14 out of 54 individuals, while the neutral variant at 1335 bp mapped primarily to the full-length CHRNA7 gene, and the variant at 933 bp mapped only to the full-length gene. Variant 933 bp G→A is in linkage disequilibrium with an intronic variant, and is contemplated to involve splicing.

TABLE 22

Mapping of common variants, identified in the CHRNA7 gene and its partial duplication

| Exon/Intron | bp | Δ | Schizophrenics Caucasian genomic V | Schizophrenics Caucasian genomic T | Schizophrenics Caucasian cDNA α7 | Schizophrenics Caucasian cDNA dα7 | Schizophrenics Caucasian cDNA T | Schizophrenics Af. Am. genomic V | Schizophrenics Af. Am. genomic T | Schizophrenics Af. Am. cDNA α7 | Schizophrenics Af. Am. cDNA dα7 | Schizophrenics Af. Am. cDNA T | Controls Caucasian genomic V | Controls Caucasian genomic T | Controls Caucasian cDNA α7 | Controls Caucasian cDNA dα7 | Controls Caucasian cDNA T | Controls Af. Am. genomic V | Controls Af. Am. genomic T | Controls Af. Am. cDNA α7 | Controls Af. Am. cDNA dα7 | Controls Af. Am. cDNA T | Map α7 | Map dα7 |
|---|---|---|---|---|---|---|---|---|---|---|---|---|---|---|---|---|---|---|---|---|---|---|---|---|
| E-6[a] | 497-8 | −TG | 68 | 96 | 0 | 15 | 15 | 15 | 50 | 0 | 1 | 1 | 48 | 71 | 0 | 29 | 29 | 12 | 54 | 0 | 2 | 2 | | X |
| E-7 | 654 | C→T | 77 | 90 | 0 | 20 | 20 | 32 | 47 | 0 | 1 | 1 | 57 | 70 | 0 | 33 | 33 | 3 | 4 | 0 | 1 | 1 | | X |

TABLE 22-continued

Mapping of common variants, identified in the CHRNA7 gene and its partial duplication

| Exon/Intron | bp | Δ | Schizophrenics | | | | | | | | | | Controls | | | | | | | | | | Map | |
|---|---|---|---|---|---|---|---|---|---|---|---|---|---|---|---|---|---|---|---|---|---|---|---|---|
| | | | Caucasian | | | | | Af. Am. | | | | | Caucasian | | | | | Af. Am. | | | | | | |
| | | | genomic | | cDNA | | | genomic | | cDNA | | | genomic | | cDNA | | | genomic | | cDNA | | | | |
| | | | V | T | α7 | dα7 | T | V | T | α7 | dα7 | T | V | T | α7 | dα7 | T | V | T | α7 | dα7 | T | α7 | dα7 |
| E-7 | 690 | G→A | 82 | 83 | 4 | 22 | 24 | 36 | 36 | 1 | 3 | 4 | 59 | 59 | 4 | 41 | 41 | 4 | 4 | 0 | 3 | 3 | X | X |
| E-9 | 933 | G→A | 56 | 127 | 12 | 0 | 12 | 28 | 53 | 3 | 0 | 3 | 39 | 79 | 15 | 0 | 15 | 18 | 50 | 1 | 0 | 1 | X | |
| | | A only | 2 | 127 | | | | | | | | | | | | | | | | | | | | |
| E-10 | 1044 | C→T | 12 | 123 | 0 | 3 | 3 | 3 | 43 | 0 | 1 | 1 | 9 | 72 | 0 | 3 | 3 | 1 | 55 | 0 | 0 | 0 | | X |
| E-10 | 1269 | C→T | 75 | 95 | 9 | 13 | 18 | 29 | 40 | 2 | 3 | 4 | 47 | 57 | 18 | 22 | 31 | 2 | 3 | 0 | 1 | 1 | X | X |
| | | T only | 2 | 95 | | | | 1 | 40 | | | | 1 | 57 | | | | | | | | | | |
| E-10 | 1335 | C→T | 32 | 74 | 6 | 2 | 7 | 3 | 11 | 0 | 0 | 0 | 30 | 65 | 17 | 3 | 19 | 2 | 4 | 2 | 0 | 2 | X | X |
| E-10[b] | 1466 | C→T | 23 | 110 | 0 | 4 | 4 | 7 | 49 | 0 | 0 | 0 | 27 | 82 | 0 | 12 | 12 | 3 | 52 | 0 | 0 | 0 | | X |

E, exon;
I, intron.
Numbering for exons and 3'UT is from the ATG start.
α7, full-length gene.
dα7, duplicated gene.
total, number of individuals with the variant that were mapped.
[a]exon 6, 2 bp deletion at leu a.a. 166;
[b]exon 10, ser to leu a.a. 489.

Ten of the thirty-three variants in Tables 17-19 were not mapped. Seven of the unmapped variants lie in introns and could not be mapped using the cDNA specific RT-PCR methodology. One unmapped variant in exon 10 was discovered late in the screen and was found to be synonymous.

A large number of variants (12) were found in a short proximal promoter region 5' of the translation start as shown in FIG. 16 panel A and as published (Leonard et al., Arch Gen Psychiatry, 59:1085-1096, 2002). As described herein, many of the variants were found to functionally reduce transcription in a reporter gene assay and to be associated with both the P50 auditory gating deficit and with schizophrenia. The relationships of these promoter polymorphisms to some of the variants in the coding and non-coding sequence are discussed below.

Non-Synonymous Variants

The coding region of the full-length CHRNA7 gene consists of 10 exons. Eleven variants mapping to the full-length gene are reported in Tables 17-19, three of which are non-synonymous. The A→G variant at 334 bp in exon 4, results in a conservative amino acid change of an isoleucine to a valine at amino acid 112. However, this residue lies in the putative agonist-binding site (Galzi et al., Annu Rev Pharmacol, 31:37-72, 1991), where a conformational alteration is contemplated to result in a change in agonist affinity. The rare variant at 334 bp was found in one African American schizophrenic but not in an affected sibling and in one Hispanic control subject. The control subject exhibited abnormal auditory evoked potential responses, having a P50 test to conditioning ratio of 1.91. Both subjects with this rare 334 bp variant also have a rare insertion in the α7 core promoter (−190+G), indicating that this represents a minor haplotype. The schizophrenic, however, also carries a core promoter mutation on the other chromosome (−178-G).

The G→A variant at 1354 bp in exon 10 changes a glutamic acid to a lysine in the large intracellular loop of the protein. A glutamic acid at this position is conserved across species. In the rat, a large deletion of sequence including this codon resulted in a two-fold increase of both α-bungarotoxin binding and current in transfected oocytes (Valor et al., Biochem, 41:7931-7938, 2002). However, the single non-conservative change from an acidic to a basic residue described herein is expected to effect a functional change in the receptor. The rare variant at 1354 bp was found in one Caucasian schizophrenic and in one Caucasian control subject. Both of these subjects have normal core promoter sequences. Although not having the 1354 bp variant, an affected brother of the schizophrenic has a mutation in the core α7 promoter (−86 bp), indicative of two α7 alleles for schizophrenia in this family.

The C→A variant at base pair 1487 in exon 10 changes an alanine to an aspartic acid in the extracellular carboxyl terminus. The 1487 bp variant was found in one African American schizophrenic but not in an affected child. A family member with an abnormal P50 test to conditioning ratio of 61.7 carried an α7 core promoter mutation (−191 G→A), again indicative of two alleles for schizophrenia.

Sixteen variants found in α7 exons 5-10 mapped to the duplicated gene dupCHRNA7, which is also in the region of chromosome 15q14 genetically linked to schizophrenia (Tables 17-19 and FIG. 16 panel A). The mRNA for dupCHRNA7 is expressed in multiple tissues, including brain (Drebing et al., Soc Neurosci Abst, 24:832, 1998). DupCHRNA7 is present in only one copy in approximately 30% of the general population, but is homozygotically deleted in 5% of schizophrenic subjects (Gault et al., Genomics 52: 173-185, 1998; and Leonard et al., Biol Psych 49:571, 2001). Recent evidence suggests that dupCHRNA7 transcripts are translated, but the function of this protein is not yet known (Lee et al., Soc Neurosci Abst, 27:144.10, 2001). Six single nucleotide polymorphisms (SNP) change amino acids in a putative open reading frame found in dupCHRNA7 (370 bp in exon 5, 698 bp in exon 7, 970 bp in exon 9, and 1116 bp, 1456 bp, and 1466 bp in exon 10).

A 2 bp deletion at bases 497/8 in exon 6 was found in one copy of the duplicated gene in 57.5% of schizophrenic subjects and in 49.6% of controls (not a significant difference). It was, however, found more frequently in Caucasian control subjects than in African American controls ($X^2=25.31$, $p<0.0001$). This deletion, found only in dupCHRNA7, shifts the reading frame, resulting in three stop codons within the next 53 codons. These stop codons, however, are the most frequently skipped during translation (MacBeath and Kast, BioTechniques, 24:789-794, 1998). Further, the site surrounding the deletion in exon 6 is a consensus exon splice enhancer site (ESE) for enhancer factor SC35 (Cartegni et al., Nat Rev Gen, 3:285-298, 2002). Deletion of the two base pairs (TG) is contemplated to disrupt this site, indicating that exon 6 is spliced out in these subjects, leaving an exon 5/exon 7 junction. This splice variant would leave the coding sequence in frame. Deletion of exon 6 removes the cysteine bridge and part of a putative ligand binding site, leaving the remainder of the α7 coding sequence intact. In the analysis of the CHRNA7 proximal promoter described herein, subjects with a promoter variant were much less likely to have a 2 bp deletion in exon 6 of the dupCHRNA7 gene ($X^2=16.46, 1$; $p<0.0001$). There was also a striking relationship with a three base pair insertion in intron 7. Every subject (50 out of 50) with a 2 bp deletion in exon 6 of the dupCHRNA7 gene, also had this insertion (+GTT) at the −11 bp position in intron 7. This intronic variant is contemplated to reside in the gene duplication rather than in the full-length gene.

Synonymous Variants

Eleven SNPs in the coding regions that do not result in an amino acid change were found. Four conservative exon variants at bp 690, 1269, and 1335 map to both the duplicated gene and the full-length CHRNA7 gene. The variant at 690 bp in exon 7 is the most common variant found in the α7 nicotinic receptor genes, and it is heterozygous in genomic DNA from 190 of 191 samples examined. The G primarily maps to CHRNA7 and the A primarily maps to dupCHRNA7. The 1269 bp and 1335 bp variants were found in 80% and 43% of all subjects, respectively.

Another common synonymous variant in exon 9, at bp 933, is of interest. It was found only in the full-length gene and is also inversely associated with the presence of a polymorphism in the proximal promoter in all subjects examined, $X^2=6.916, 1; p=0.0085$. The association was significant in the controls ($X^2=5.183, 1; p=0.0228$), but only suggestive in the schizophrenic subjects. The 933 G→C variant is found within the loop of a putative stem and loop structure formed by a tri-nucleotide repeat of $(GGT)_3$ and its complement repeat $(ACC)_3$ in exon 9 ($\Delta G=-16.2$ kcal/mol). The 933 bp variant is also in linkage disequilibrium with a common intronic variant in intron 9 as discussed below.

Intronic Variants

Ten intron changes were identified, none of which change the consensus sequences at RNA splice junctions. However, a number of these variants may affect splicing by introducing a favorable splice site or affecting the binding sites of splice enhancer proteins. In intron 3, a variant at −9 (G→A) changes the sequence near the 3' acceptor site to a sequence identical to nine bp in exon 4, thereby forming a cryptic splice site. Although found in only 3 of 45 African American schizophrenic families (3/90 alleles), this polymorphism was found in only 1 of 55 African American controls (1/110 alleles). The single control subject with this variant had a P50 (test to conditioning ratio) of 0.32, in the unstable range, and had been diagnosed with major depression.

The intron 7 variant at −11 (+GTT) was mentioned above in relation to the 2 bp deletion in exon 6. Insertion of these three base pairs introduces additional pyrimidines into the splice acceptor site for exon 7, possibly increasing site use. Another intron 7 variant at −20 (G→A), is inversely associated with the presence of proximal promoter variants. Only 1 of 29 subjects with the polymorphism had a promoter mutation, while 20 of 58 subjects with the wild-type sequence had a promoter polymorphism ($X^2=10.17, 1; p=0.0014$).

A variant in intron 9 (+37, counted from the splice donor site) was found more frequently in the African American schizophrenic sample than in the control sample ($X^2=9.986, 1; P=0.0016$). This same variant was not found at significantly different frequencies in the Caucasian schizophrenia sample. One unaffected family member was identified with a homozygous C at base pair +37. Interestingly, the exon 9 variant at 933 bp (G→A) is in linkage disequilibrium with the intron 9 variant at +37 (G→C). Since the exon 9 variant at 933 appears to be in the full-length gene, it is contemplated that the intron 9 variant is also located in the full-length gene. If the intron 9 variant at +37 is not associated with the exon 9 variant at 933, then there is contemplated to be another polymorphism present nearby (e.g., exon 9 variant at 966, C→T), which is also present in the full-length gene. However, the exon 9 variant at 966 is rare and was only mapped in one individual who was a schizophrenic, and thus its map location is provisional.

Example 20

Statistical Analysis of CHRNA7 and dupCHRNA7 Variants

Chi square statistics or Fisher's exact tests were used to determine whether a variant was found more frequently in the schizophrenic sample than the control sample. Allele frequencies were calculated for variants in exons 1-4, but could not be determined for polymorphisms in the duplicated exons. A case-control study was done. All schizophrenic subjects in each family were screened for polymorphisms to determine if variants cosegregate with affected family members and to ensure that no mutations were missed. Total counts from schizophrenic individuals include one schizophrenic individual from each family, unless other schizophrenic family members differed from the proband at that nucleotide position. When this occurred, the other family member was also counted. The sample size provided sufficient power to detect a 0.11 difference in allele frequency between the schizophrenic and control groups at a $p<0.05$ for an allele with a population frequency of 0.050.

Two population-specific loci, FY-null and RB2300, were used to estimate the degree of admixture in African American samples of schizophrenic individuals and controls (Parra et al., Am J Hum Gen, 63:1839-1851, 1998). The FY-NULL*1 allele is the normal allele with a C at −46 in the promoter of the DARC gene (Duffy antigen receptor of chemokines). The FY NULL*1 allele has an allele frequency of 1.0 in European populations, 0 in African populations and 0.06-0.2 in African American populations (Parra et al., supra, 1998). FY-NULL*1 allele frequencies did not vary significantly between the African American controls (0.2) and the schizophrenic individuals (0.18) studied herein. The RB2300*1 allele has an allele frequency of 0.900 to 0.944 in African populations, 0.776 to 0.888 in African American populations, and 0.287 to 0.588 in European populations (Parra et al., supra, 1998). The RB2300*1 allele does not have a BamHI polymorphism in intron 1 of the human retinoblastoma gene. The RB2300*1 allele was found at a frequency of 0.82 in our African American controls and 0.86 in the African American subjects with schizophrenia (not significantly different). These data suggest that there is a similar degree of admixture in our African American control and schizophrenic samples and that differences in variant frequencies between these samples should not reflect ethnic bias.

Example 21

Identification and Analysis of Distal Promoter Polymorphisms

Subjects

Characteristics of study participants are shown below. See, Table 28 and Table 29.

TABLE 28

Number of individuals for case-control and family-based association studies with the a priori outcome of schizophrenia

| Case-control | Denver SZ | NIMH SZ | COS | Total SZ | Total controls |
|---|---|---|---|---|---|
| African-American | 56 | 47 | 2 | 105 | 45 |
| Caucasian | 234 | 73 | 56 | 363 | 99 |

| NIMH Families | Schizophrenics | Family Members |
|---|---|---|
| African-American | 113 | 32 |
| Caucasian | 14242 | |

Denver SZ = schizophrenics collected locally in Denver.
NIMHSZ = schizophrenic individuals from the NIMH Schizophrenia Genetics Initiative included in case control association studies.
COS = Childhood onset schizophrenics collected in Denver.
Family Members = NIMH family members with a diagnosis of never mentally ill.

TABLE 29

Number of individuals for case-control and family-based association studies with the outcome of smoking status

| Case-control | Denver Sm | NIMH Sm | Total Sm | Denver NS | NIMH NS | Total NS |
|---|---|---|---|---|---|---|
| African-American | 54 | 5 | 59 | 49 | 15 | 64 |
| Caucasian | 160 | 10 | 170 | 112 | 13 | 125 |

| NIMH Families | Smokers (Sm) | Non-Smokers (NS) |
|---|---|---|
| African-American | 17 | 45 |
| Caucasian | 25 | 51 |

Sm = smokers,
NS = non-smokers.

DNA samples from both case-control subjects collected in Denver, and schizophrenic subjects from NIMH families were included in the association studies. For the family-based study, a total of 329 African-Americans (47 nuclear families) and Caucasian-Non Hispanic subjects (73 nuclear families) from the NIMH Schizophrenia Genetics Initiative were chosen based on a diagnosis of schizophrenia. This cohort has previously shown positive LOD scores and association to markers at the 15q14 locus in both African-American and Caucasian individuals. Kaufmann et al., "NIMH Genetics Initiative Millenium Schizophrenia Consortium: linkage analysis of African-American pedigrees" *Am. J. Med. Genet.* 81:282-289 (1998); Leonard et al., "Further investigation of a chromosome 15 locus in schizophrenia: analysis of affected sibpairs from the NIMH Genetics Initiative" *Am. J. Med. Genet.* 81:308-312 (1998); and Freedman et al., "Genetic linkage to schizophrenia at chromosome 15q14 "*Am. J. Med. Genet.* 105: 655-657 (2001). Detailed information on the NIMH family structure is available from the web site nimh-genetics.org.

Case-control association studies of 612 African-American and Caucasian-Non Hispanic schizophrenics and controls included individuals collected in our laboratory, and schizophrenic subjects from the NIMH families. Ethnicities of case-control subjects were recorded from self-report or family interview. The Caucasian-Non Hispanic case-control sample was comprised of 307 schizophrenic patients, 56 childhood onset schizophrenics, and 99 controls. The African-American case-control sample included 103 schizophrenics, 2 childhood onset schizophrenics, and 45 controls. P50 data were available for 89 Caucasian-Non Hispanic controls subjects and 43 African-American controls.

Adult case subjects were chosen based on a diagnosis of schizophrenia, utilizing a Structured Clinical Interview for DSM-IV Axis I Disorders. First et al., "Structured Clinical Interview for Axis I DSM-IV Disorders—Patient Edition (With Psychotic Screen)—(SCID-I/P, W/PSYCHOTIC SCREEN) (Version 2.0)" Biometrics Research Department, New York State Psychiatric Institute, New York (1996). Control subjects were interviewed and found to have no evidence for current or past psychosis, using a Structured Clinical Interview for DSM-IV Axis I Disorders for non-patients. First et al., "Structured Clinical Interview for Axis I DSM-IV Disorders—Non-patient Edition—(SCID-I/NP, Version 2.0)" Biometrics Research Department, New York State Psychiatric Institute, New York (1996). Childhood onset schizophrenia cases were diagnosed utilizing the K-SADS-PL. (Kaufman et al., "Schedule for affective disorders and schizophrenia for school-age children present and lifetime version (K-SADS-PL): initial reliability and validity data" *J. Am. Acad. Child Adolesc. Psych.* 36: 980-988 (1997). Smoking history was determined on local subjects utilizing a detailed questionnaire. Breese et al., "Effect of smoking history on [3H]nicotine binding in human postmortem brain" *J. Pharmacol. Exp. Ther.* 282:7-13 (1997); Breese et al., "Abnormal regulation of high affinity nicotinic 614 receptors in subjects with schizophrenia" *Neuropsychopharmacology* 23:615:351-364 (2000). NIMH Genetics Initiative subjects utilized the questionnaire from the NIMH web site (nimhgenetics.org). P50 auditory evoked potentials were recorded on controls. Freedman et al., "Elementary neuronal dysfunctions in schizophrenia" *Schizophr. Res.* 4:233-243 (1991).

DNA Isolation

Nucleated cells were obtained from anticoagulated blood (EDTA) via lysis with a high sucrose solution (0.3 M sucrose) were not associated with either schizophrenia or the P50 112340123456789 gating deficit. Gault et al., "Comparison of polymorphisms in the $\alpha$7 nicotinic receptor gene and its partial duplication in schizophrenic and control subjects" *Am. J. Med. Genet.* 123B:39-49 (2003).

Mutation screening of the core promoter in the CHRNA7 gene identified a large number of polymorphisms. Functional analysis of polymorphisms in the 231 base pairs upstream of the translation initiation site, the core promoter region, demonstrated that most decrease transcription. These polymorphisms were also found to be statistically more prevalent in schizophrenics than in control subjects (P=0.007). Further, the presence of a promoter polymorphism in non-schizophrenic controls was associated with a P50 gating deficit (P<0.0001). Leonard et al., "Association of promoter variants in the alpha 7 nicotinic acetylcholine receptor subunit gene with an inhibitory deficit found in schizophrenia" *Arch. Gen. Psychiatry* 59:1085-1096 (2002).

Reporter gene assays with fragments 1.0 kb and 2.6 kb proximal to the translation initiation site exhibit less activity than the core promoter, suggesting that repressor elements may lie upstream of the core promoter. Utilizing overlapping genomic fragments, 35 SNPs have been identified in the 2 kb upstream regulatory region of CHRNA7. SNPs were genotyped utilizing a combination of heteroduplexanalysis by denaturing high-performance liquid chromatography and sequencing, and were analyzed for association with schizophrenia in Caucasian-Non Hispanic and African-American subjects. Smoking history was considered as a secondary outcome. The results show significant association of a specific SNP, rs3087454 (−1831 bp), in the 5' upstream regulatory region of the CHRNA7 gene with schizophrenia.

Genotyping and Fragment Analysis

Eleven amplicons were designed to screen 2.0 kb of DNA in the 5'-upstream regulatory region of the CHRNA7 gene. The Polymerase Chain Reaction (PCR) with AmpliTaq Gold™ and GeneAmp® PCR System 9600 (Perkin-Elmer, Foster City, Calif.) was used for fragment amplification wherein thermal cycler conditions were unique to each amplicon. See, FIG. 20.

Fragments were characterized using temperature modulated heteroduplex analysis with Denaturing High-Performance Liquid Chromatography (DHPLC; Transgenomic WAVE™) (Transgenomic Inc., San Jose, Calif.) as previously described. Leonard et al., "Association of promoter variants in the alpha 7 nicotinic acetylcholine receptor subunit gene with an inhibitory deficit found in schizophrenia" *Arch. Gen. Psychiatry* 59:1085-1096 (2002); and Gault et al., "Comparison of polymorphisms in the α7 nicotinic receptor gene and its partial duplication in schizophrenic and control subjects" *Am. J. Med. Genet.* 123B:39-49 (2003). Samples were "spiked" with control DNA to ensure that a homozygous variant that might migrate as a single peak would be detected. When a sample resulted in an unusual WAVE™ pattern, automated DNA sequencing on an Applied Biosystems 3100 Avant DNA Sequencer (Applied Biosystems, Foster City, Calif.) was employed for genotyping. For most SNPs, a specific and recognizable WAVE™ pattern was generated.

Cell Culture

The human neuroblastoma cell lines SH-SY5Y (a gift from Dr. June Biedler); Biedler et al., "Multiple neurotransmitter synthesis by human neuroblastoma cell lines and clones" *Cancer Res.* 38:3751-3757. (1978), and SK-N-BE (ATCC number CRL-271; ATCC, Manassas, Va.) were grown in 1:1 Ham F12 Dulbecco Eagle medium supplemented with 15% fetal bovine serum, 100 µg/ml streptomycin, 100 units/ml penicillin, and 2 mM L-glutamine (Invitrogen, Carlsbad, Calif.) at 37° C. in a 5% $CO_2$ incubator.

Plasmid Constructs

Isolation and characterization of 2.6 kb of 5'-flanking sequence in the human CHRNA7 subunit gene was described previously. Gault et al., "Genomic organization and partial duplication of the human α7 neuronal nicotinic acetylcholine receptor gene" *Genomics* 52:173-185 (1998); Leonard et al., "Association of promoter variants in the alpha 7 nicotinic acetylcholine receptor subunit gene with an inhibitory deficit found in schizophrenia" *Arch. Gen. Psychiatry* 59:1085-1096 (2002).

The promoter-luciferase construct Pr2B contains a CHRNA7 5'-upstream regulatory region fragment from −2004 bp to the translation start site at +1 bp inserted upstream of the luciferase gene in the pGL3-Basic vector. Pr2B was generated by first TA cloning a 2004 bp PCR fragment from the previously cloned 2.6 kb promoter into pDrive, according to manufacturer's instructions (Promega, Madison, Wis.). Restriction enzymes (HindIII and KpnI) were then used to isolate the 2004 bp fragment and insert it into the pGL3 reporter plasmid. The promoter-luciferase fusions were confirmed by DNA sequencing. Pr2B contains the (C) allele at −1831 bp. The −1831 (A) polymorphism was introduced into Pr2B by PCR, utilizing the QuikChange II XL Site-Directed Mutagenesis Kit, according to the manufacturer's protocols (Stratagene). The mutagenesis primers were: α7Prom-1831A forward (5'-gccatacatactccagaaaaaat Aaataaattcccttggccc-3') (SEQ ID NO: 182) and α7Prom-1831A reverse (5'-gggccaagggaatttattTattttttct ggagtatg-tatggc-3') (SEQ ID NO: 183); the mutant construct was confirmed by DNA sequencing and named Pr2B-1831A.

Transient Transfection and Reporter Gene Assay

SH-SY5Y and SK-N-BE cells grown to subconfluency were transfected with the ProFection Mammalian Transfection Calcium Phosphate System (Promega). A pGL3-Control construct in which the luciferase gene is regulated by the SV40 promoter and enhancer was used as a positive control to measure the maximum reporter gene activity. A pRL-TK construct (Promega) with the *Renilla luciferase* gene, controlled by the HSV thymidine kinase promoter, served as an internal control for normalization of transfection efficiency.

$2\times10^5$ cells/35 mm plate were incubated with molar equivalents of Pr2B, Pr2B-1831A, pGL3-Control, or pGL3-Basic luciferase reporter constructs and 1 µg of pRL-TK vector as an internal control for the transfection efficiency. Cells were harvested after 48 h and luciferase activity was determined with the Dual-Luciferase Reporter Assay System according to the manufacturer's instructions (Promega). Each transfection was performed using eight separate plates in triplicate.

Statistical Analysis

1. Case-Control Data

The case group of schizophrenic individuals included one randomly chosen schizophrenic individual per family. For each marker, allele frequencies were estimated and conformance of genotype frequencies with Hardy-Weinberg Equilibrium (HWE) expected proportions was tested via a 1 df chi-squared goodness-of-fit test using Haploview. Barrett et al., "Haploview: analysis and visualization of LD and haplotype maps" *Bioinformatics* 21, 263-265 (2005).

Linkage disequilibrium parameters D' and $r2$ were calculated for each pair of markers and tests for differences in allele frequencies between cases and controls were computed using a chi-squared test (1 df) for each SNP in Haploview. Since several of the SNPs were rare, empirical P-values were utilized rather than relying on the large-sample approximation. Further, since several SNPs were tested for each outcome, empirical P-values were generated via permutation that were corrected for the number of SNPs tested. For each permutation, the minimum P-value over all SNPs was compared to the minimum P-value over all SNPs in the original data.

Chi-squared tests of association (2 df) between each SNP and schizophrenia under a genotypic model were calculated using the UNPHASED software version 3.0.13; a similar permutation procedure was applied. Dudbridge, F., "Pedigree disequilibrium tests for multilocus haplotypes" *Genet. Epidemiol* 25:115-121 (2003).

Corrected P-values are indicated with an (*). Odds ratio estimates (OR) and 95% confidence intervals (CI) for comparing relevant genotype or allele classes were computed with SPSS 16 301 software (SPSS Inc., Chicago Ill.).

Analysis of the P50 gating deficit in controls was conducted using simple linear regression models that tested the mean differences in P50 ratios under both additive and genotypic models of association separately for each SNP.

In the absence of evidence for ethnic-specific effects, ethnicities were combined for most SNPs in order to gain power to detect association, and ethnicity was included as a covariate.

All analyses were performed using SAS version 9.1 software (SAS Institute Inc.: Cary, N.C., 2004). Power estimates (at a significance level of 5%) for case-control analyses were obtained with the Quanto software. Gauderman, W. J., "Sample size requirements for association studies of gene-gene interaction" *Am. J. Epidemiol.* 155:478-484 (2002); and Gauderman, W. J., "Sample size requirements for matched case-control studies of gene-environment interaction" *Stat. Med.* 21:35-50 (2002).

Results indicated that the Caucasian schizophrenic/control sample size had power between 0.74 and 0.99 to detect a genotype relative risk $(GRR) \geqq 2.0$ over a range of marker allele frequencies between 0.10 and 0.40. At $(GRR) \geqq 2.0$, power was substantially lower (0.12-0.88) for most allele frequencies. The African-American schizophrenic/control sample size had less power to detect a $GRR \geqq 2.0$ (0.38-0.87) over a range of marker allele frequencies between 0.10 and 0.40. Similarly, at $(GRR) \geqq 2.0$, power was considerably lower (0.07-0.49) for all allele frequencies 2. Admixture Analysis For both ethnicities, case-control samples were evaluated for the presence of admixture by genotyping 176 ancestry-informative SNP markers. Hodgkinson et al., "Addictions biology:haplotype-based analysis for 130 candidate genes on a single array. *Alcohol.* 43:505-515 (2008). Within each ethnic group, relative frequencies of alleles between the cases and controls were compared using a chi-squared test. Pritchard et al., "Use of unlinked genetic markers to detect population stratification in association studies" *Am. J. Hum. Genet.* 65:220-228. (1999). There were no significant differences from what was expected, indicating a similar degree of admixture between cases and controls in both ethnic groups. These conclusions were corroborated by estimating individual admixture proportions within each ethnic group using structure. Pritchard et al., "Inference of population structure using multilocus genotype data" *Genetics* 155:945-959 (2000). These analyses indicated no significant differences in average admixture proportions between cases and controls within each ethnic group.

3. Family-Based Data

Prior to data analysis, PEDCHECK software was utilized to detect marker allele errors in Mendelian inheritance. O'Connell et al., "PedCheck: a program for identification of genotype incompatibilities in linkage analysis" *Am. J. Hum. Genet.* 63:259-266 (1998). Pedigree Disequilibrium Test(s) (PDTs) of association at SNP markers were determined using UNPHASED software version 3.0.13. Dudbridge, F., "Pedigree disequilibrium tests for multilocus haplotypes" *Genet. Epidemiol* 25:115-121 (2003). Similar to the case-controls, UNPHASED analysis generated an empirical P– value corrected for the number of SNPs.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention, which are obvious to those skilled in molecular biology or related fields, are intended to be within the scope of the following claims.

---

We claim:

1. A method, comprising:
   a) providing;
      i) an individual suspected of having a predisposition to schizophrenia;
      ii) a nucleic acid derived from said individual, wherein said nucleic acid comprises an α7 nicotinic acid receptor regulatory allele;
   b) detecting at least one polymorphism within said α7 regulatory allele, wherein said polymorphism comprises −1831 C/A of SEQ ID NO: 181; and
   c) correlating the presence of said at least one polymorphism with a predisposition to schizophrenia.

2. The method of claim 1, wherein said at least one polymorphism comprises one or more of those listed in Table 23.

3. The method of claim 2, wherein said at least one polymorphism comprises two or more polymorphisms.

4. The method of claim 1, wherein said at least one polymorphism contributes to reduced α7 regulatory protein transcription.

5. The method of claim 1, wherein said detecting comprises at least one technique selected from the group consisting of polymerase chain reaction, heteroduplex analysis, single stand conformational polymorphism analysis, denaturing high performance liquid chromatography, ligase chain reaction, comparative genome hybridisation, Southern blotting, and sequencing.

6. The method of claim 1, wherein said nucleic acid is derived from a biological sample selected from the group consisting of a biopsy material and blood.

7. The method of claim 1, further comprising step (d) providing a diagnosis to said individual based on the presence or absence of the at least one polymorphism.

8. The method of claim 1, wherein said diagnosis differentiates schizophrenia from other forms of mental illness.

* * * * *

SEQUENCE LISTING

```
<160> NUMBER OF SEQ ID NOS: 201

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
tcctgatgtc ggctcccaac t                                       21

<210> SEQ ID NO 2
<211> LENGTH: 21
<212> TYPE: DNA
<213> ORGANISM: Artificial Sequence
<220> FEATURE:
<223> OTHER INFORMATION: Synthetic

<400> SEQUENCE: 2
ggtacggatg tgccaaggat a                                       21

<210> SEQ ID NO 3
<211> LENGTH: 21
<212> TYPE: DNA
<213> ORGANISM: Artificial Sequence
<220> FEATURE:
<223> OTHER INFORMATION: Synthetic

<400> SEQUENCE: 3
tttgggggtg ctaatccagg a                                       21

<210> SEQ ID NO 4
```

```
<211> LENGTH: 21
<212> TYPE: DNA
<213> ORGANISM: Artificial Sequence
<220> FEATURE:
<223> OTHER INFORMATION: Synthetic

<400> SEQUENCE: 4
ttgttttcct tccaccagtc a                                              21

<210> SEQ ID NO 5
<211> LENGTH: 22
<212> TYPE: DNA
<213> ORGANISM: Artificial Sequence
<220> FEATURE:
<223> OTHER INFORMATION: Synthetic

<400> SEQUENCE: 5
ctcgctgcag ctccgggact ca                                             22

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
ggaggctcag ggagaagtag                                                20

<210> SEQ ID NO 7
<211> LENGTH: 21
<212> TYPE: DNA
<213> ORGANISM: Artificial Sequence
<220> FEATURE:
<223> OTHER INFORMATION: Synthetic

<400> SEQUENCE: 7
ctccaggatc ttggccaagt c                                              21

<210> SEQ ID NO 8
<211> LENGTH: 21
<212> TYPE: DNA
<213> ORGANISM: Artificial Sequence
<220> FEATURE:
<223> OTHER INFORMATION: Synthetic

<400> SEQUENCE: 8
agatgcccaa gtggaccaga g                                              21

<210> SEQ ID NO 9
<211> LENGTH: 337
<212> TYPE: DNA
<213> ORGANISM: Artificial Sequence
<220> FEATURE:
<223> OTHER INFORMATION: Synthetic

<400> SEQUENCE: 9
agatgcccaa gtggaccaga gtcatccttc tgaactggtg cgcgtggttc ctgcgaatga    60
agaggcccgg ggaggacaag gtgcgcccgg cctgccagca caagcagcgg cgctgcagcc   120
tggccagtgt ggagatgagc gccgtgggcc cgccgcccgc cagcaacggg aacctgctgt   180
acatcggctt ccgcggcctg acggcgtgc actgtgtccc gacccccgac tctggggtag   240
tgtgtggccg catggcctgc tcccccacgc acgatgagca cctcctgcac ggcgggcaac   300
cccccgaggg ggacccggac ttggccaaga tcctgga                            337
```

```
<210> SEQ ID NO 10
<211> LENGTH: 32
<212> TYPE: DNA
<213> ORGANISM: Artificial Sequence
<220> FEATURE:
<223> OTHER INFORMATION: Synthetic

<400> SEQUENCE: 10
cacacacaca cacacacaca cacacacaca ca                                    32

<210> SEQ ID NO 11
<211> LENGTH: 54
<212> TYPE: DNA
<213> ORGANISM: Artificial Sequence
<220> FEATURE:
<223> OTHER INFORMATION: Synthetic

<400> SEQUENCE: 11
cacacacaca tcacacacac acacacacac acacatacac acacacacca caca            54

<210> SEQ ID NO 12
<211> LENGTH: 16
<212> TYPE: DNA
<213> ORGANISM: Artificial Sequence
<220> FEATURE:
<223> OTHER INFORMATION: Synthetic

<400> SEQUENCE: 12
gatctttggt agaagc                                                      16

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
accaccacta ccatacagac                                                  20

<210> SEQ ID NO 14
<211> LENGTH: 21
<212> TYPE: DNA
<213> ORGANISM: Artificial Sequence
<220> FEATURE:
<223> OTHER INFORMATION: Synthetic

<400> SEQUENCE: 14
caaagaacgc aagggagagg t                                                21

<210> SEQ ID NO 15
<211> LENGTH: 21
<212> TYPE: DNA
<213> ORGANISM: Artificial Sequence
<220> FEATURE:
<223> OTHER INFORMATION: Synthetic

<400> SEQUENCE: 15
cggctcgcgc gcctttaagg a                                                21

<210> SEQ ID NO 16
<211> LENGTH: 21
<212> TYPE: DNA
<213> ORGANISM: Artificial Sequence
<220> FEATURE:
<223> OTHER INFORMATION: Synthetic
```

```
<400> SEQUENCE: 16
gggctcgtca cgtggaaaag c                                              21

<210> SEQ ID NO 17
<211> LENGTH: 21
<212> TYPE: DNA
<213> ORGANISM: Artificial Sequence
<220> FEATURE:
<223> OTHER INFORMATION: Synthetic

<400> SEQUENCE: 17
ggatcccacg gaggagtgga g                                              21

<210> SEQ ID NO 18
<211> LENGTH: 21
<212> TYPE: DNA
<213> ORGANISM: Artificial Sequence
<220> FEATURE:
<223> OTHER INFORMATION: Synthetic

<400> SEQUENCE: 18
cctgcccggg tcttctctcc t                                              21

<210> SEQ ID NO 19
<211> LENGTH: 23
<212> TYPE: DNA
<213> ORGANISM: Artificial Sequence
<220> FEATURE:
<223> OTHER INFORMATION: Synthetic

<400> SEQUENCE: 19
aactagagtg ccccagccga gct                                            23

<210> SEQ ID NO 20
<211> LENGTH: 24
<212> TYPE: DNA
<213> ORGANISM: Artificial Sequence
<220> FEATURE:
<223> OTHER INFORMATION: Synthetic

<400> SEQUENCE: 20
aacaacgctc tcgacagtca gatc                                           24

<210> SEQ ID NO 21
<211> LENGTH: 22
<212> TYPE: DNA
<213> ORGANISM: Artificial Sequence
<220> FEATURE:
<223> OTHER INFORMATION: Synthetic

<400> SEQUENCE: 21
aagatcttgc agcccatggg ag                                             22

<210> SEQ ID NO 22
<211> LENGTH: 22
<212> TYPE: DNA
<213> ORGANISM: Artificial Sequence
<220> FEATURE:
<223> OTHER INFORMATION: Synthetic

<400> SEQUENCE: 22
ggaattctct ttggttttgc ac                                             22

<210> SEQ ID NO 23
<211> LENGTH: 21
<212> TYPE: DNA
```

<213> ORGANISM: Artificial Sequence
<220> FEATURE:
<223> OTHER INFORMATION: Synthetic

<400> SEQUENCE: 23
acatatccag catctctgtg a                                                 21

<210> SEQ ID NO 24
<211> LENGTH: 23
<212> TYPE: DNA
<213> ORGANISM: Artificial Sequence
<220> FEATURE:
<223> OTHER INFORMATION: Synthetic

<400> SEQUENCE: 24
tcatgcagtc cttttcctgt ttc                                               23

<210> SEQ ID NO 25
<211> LENGTH: 23
<212> TYPE: DNA
<213> ORGANISM: Artificial Sequence
<220> FEATURE:
<223> OTHER INFORMATION: Synthetic

<400> SEQUENCE: 25
ctcgcttcag ttttctaaca tgg                                               23

<210> SEQ ID NO 26
<211> LENGTH: 22
<212> TYPE: DNA
<213> ORGANISM: Artificial Sequence
<220> FEATURE:
<223> OTHER INFORMATION: Synthetic

<400> SEQUENCE: 26
ggaactgctg tgtattttca gc                                                22

<210> SEQ ID NO 27
<211> LENGTH: 22
<212> TYPE: DNA
<213> ORGANISM: Artificial Sequence
<220> FEATURE:
<223> OTHER INFORMATION: Synthetic

<400> SEQUENCE: 27
ttaaagcttg cccaggaata gg                                                22

<210> SEQ ID NO 28
<211> LENGTH: 23
<212> TYPE: DNA
<213> ORGANISM: Artificial Sequence
<220> FEATURE:
<223> OTHER INFORMATION: Synthetic

<400> SEQUENCE: 28
gcttgtgtgt ggtatacaca ttg                                               23

<210> SEQ ID NO 29
<211> LENGTH: 23
<212> TYPE: DNA
<213> ORGANISM: Artificial Sequence
<220> FEATURE:
<223> OTHER INFORMATION: Synthetic

<400> SEQUENCE: 29
tccagagctg atctcagcag aag                                               23

```
<210> SEQ ID NO 30
<211> LENGTH: 23
<212> TYPE: DNA
<213> ORGANISM: Artificial Sequence
<220> FEATURE:
<223> OTHER INFORMATION: Synthetic

<400> SEQUENCE: 30
gcccctcgtt agacagaatt gag                                              23

<210> SEQ ID NO 31
<211> LENGTH: 23
<212> TYPE: DNA
<213> ORGANISM: Artificial Sequence
<220> FEATURE:
<223> OTHER INFORMATION: Synthetic

<400> SEQUENCE: 31
ctgggcacac tctaacccta acc                                              23

<210> SEQ ID NO 32
<211> LENGTH: 22
<212> TYPE: DNA
<213> ORGANISM: Artificial Sequence
<220> FEATURE:
<223> OTHER INFORMATION: Synthetic

<400> SEQUENCE: 32
tgtgacgtgc agtgccacag ga                                               22

<210> SEQ ID NO 33
<211> LENGTH: 23
<212> TYPE: DNA
<213> ORGANISM: Artificial Sequence
<220> FEATURE:
<223> OTHER INFORMATION: Synthetic

<400> SEQUENCE: 33
aaaaccctag gaggagcctc ctt                                              23

<210> SEQ ID NO 34
<211> LENGTH: 21
<212> TYPE: DNA
<213> ORGANISM: Artificial Sequence
<220> FEATURE:
<223> OTHER INFORMATION: Synthetic

<400> SEQUENCE: 34
gatcagcccg tttccgcctc a                                                21

<210> SEQ ID NO 35
<211> LENGTH: 21
<212> TYPE: DNA
<213> ORGANISM: Artificial Sequence
<220> FEATURE:
<223> OTHER INFORMATION: Synthetic

<400> SEQUENCE: 35
ggtacggatg tgccaaggat a                                                21

<210> SEQ ID NO 36
<211> LENGTH: 27
<212> TYPE: DNA
<213> ORGANISM: Artificial Sequence
<220> FEATURE:
<223> OTHER INFORMATION: Synthetic
```

-continued

```
<400> SEQUENCE: 36
ggactctgct tttgataaat atgtatg                                         27

<210> SEQ ID NO 37
<211> LENGTH: 24
<212> TYPE: DNA
<213> ORGANISM: Artificial Sequence
<220> FEATURE:
<223> OTHER INFORMATION: Synthetic

<400> SEQUENCE: 37
ttgctgtcac tttctgtgtt tcat                                            24

<210> SEQ ID NO 38
<211> LENGTH: 23
<212> TYPE: DNA
<213> ORGANISM: Artificial Sequence
<220> FEATURE:
<223> OTHER INFORMATION: Synthetic

<400> SEQUENCE: 38
gacaatccaa aggtgcagaa agc                                             23

<210> SEQ ID NO 39
<211> LENGTH: 23
<212> TYPE: DNA
<213> ORGANISM: Artificial Sequence
<220> FEATURE:
<223> OTHER INFORMATION: Synthetic

<400> SEQUENCE: 39
ttcgtatctg tatacagaca gtc                                             23

<210> SEQ ID NO 40
<211> LENGTH: 24
<212> TYPE: DNA
<213> ORGANISM: Artificial Sequence
<220> FEATURE:
<223> OTHER INFORMATION: Synthetic

<400> SEQUENCE: 40
cctcagcatc atattagttc agtg                                            24

<210> SEQ ID NO 41
<211> LENGTH: 22
<212> TYPE: DNA
<213> ORGANISM: Artificial Sequence
<220> FEATURE:
<223> OTHER INFORMATION: Synthetic

<400> SEQUENCE: 41
gcggacaaga gaaacaggaa ag                                              22

<210> SEQ ID NO 42
<211> LENGTH: 21
<212> TYPE: DNA
<213> ORGANISM: Artificial Sequence
<220> FEATURE:
<223> OTHER INFORMATION: Synthetic

<400> SEQUENCE: 42
ggcagtggtg ctgttgccct t                                               21

<210> SEQ ID NO 43
<211> LENGTH: 22
<212> TYPE: DNA
```

```
<213> ORGANISM: Artificial Sequence
<220> FEATURE:
<223> OTHER INFORMATION: Synthetic

<400> SEQUENCE: 43
tttctcctgg gactctgggc ac                                            22

<210> SEQ ID NO 44
<211> LENGTH: 21
<212> TYPE: DNA
<213> ORGANISM: Artificial Sequence
<220> FEATURE:
<223> OTHER INFORMATION: Synthetic

<400> SEQUENCE: 44
tgacgccaca ttccacacta a                                             21

<210> SEQ ID NO 45
<211> LENGTH: 21
<212> TYPE: DNA
<213> ORGANISM: Artificial Sequence
<220> FEATURE:
<223> OTHER INFORMATION: Synthetic

<400> SEQUENCE: 45
ttgttttcct tccaccagtc a                                             21

<210> SEQ ID NO 46
<211> LENGTH: 25
<212> TYPE: DNA
<213> ORGANISM: Artificial Sequence
<220> FEATURE:
<223> OTHER INFORMATION: Synthetic

<400> SEQUENCE: 46
ccaagtttta accaccaaca tttgg                                         25

<210> SEQ ID NO 47
<211> LENGTH: 33
<212> TYPE: DNA
<213> ORGANISM: Artificial Sequence
<220> FEATURE:
<223> OTHER INFORMATION: Synthetic

<400> SEQUENCE: 47
tccccgcgga agaatgtctg gtttccaaat ctg                                33

<210> SEQ ID NO 48
<211> LENGTH: 16
<212> TYPE: DNA
<213> ORGANISM: Artificial Sequence
<220> FEATURE:
<223> OTHER INFORMATION: Synthetic

<400> SEQUENCE: 48
aggacccaaa cttcag                                                   16

<210> SEQ ID NO 49
<211> LENGTH: 48
<212> TYPE: DNA
<213> ORGANISM: Artificial Sequence
<220> FEATURE:
<223> OTHER INFORMATION: Synthetic

<400> SEQUENCE: 49
caucaucauc auccagcgta catcgatgta gcaggaactc ttgaatat                48
```

```
<210> SEQ ID NO 50
<211> LENGTH: 47
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (36)..(37)
<223> OTHER INFORMATION: n is a, c, g, t or u
<220> FEATURE:
<221> NAME/KEY: misc_feature
<222> LOCATION: (40)..(41)
<223> OTHER INFORMATION: n is a, c, g, t or u
<220> FEATURE:
<221> NAME/KEY: misc_feature
<222> LOCATION: (45)..(46)
<223> OTHER INFORMATION: n is a, c, g, t or u

<400> SEQUENCE: 50
cuacuacuac uaggccacgc gtcgactagt acgggnnggn ngggnng        47

<210> SEQ ID NO 51
<211> LENGTH: 25
<212> TYPE: DNA
<213> ORGANISM: Artificial Sequence
<220> FEATURE:
<223> OTHER INFORMATION: Synthetic

<400> SEQUENCE: 51
cgctgcagct ccgggactca acatg        25

<210> SEQ ID NO 52
<211> LENGTH: 25
<212> TYPE: DNA
<213> ORGANISM: Artificial Sequence
<220> FEATURE:
<223> OTHER INFORMATION: Synthetic

<400> SEQUENCE: 52
tgcccatctg tgagttttcc acatg        25

<210> SEQ ID NO 53
<211> LENGTH: 21
<212> TYPE: DNA
<213> ORGANISM: Artificial Sequence
<220> FEATURE:
<223> OTHER INFORMATION: Synthetic

<400> SEQUENCE: 53
tgacgccaca ttccacacta a        21

<210> SEQ ID NO 54
<211> LENGTH: 18
<212> TYPE: DNA
<213> ORGANISM: Artificial Sequence
<220> FEATURE:
<223> OTHER INFORMATION: Synthetic

<400> SEQUENCE: 54
ccccaaatct cgccaagc        18

<210> SEQ ID NO 55
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 55
ctcggtgccc cttgccattt                                              20

<210> SEQ ID NO 56
<211> LENGTH: 25
<212> TYPE: DNA
<213> ORGANISM: Artificial Sequence
<220> FEATURE:
<223> OTHER INFORMATION: Synthetic

<400> SEQUENCE: 56
ccttgcccat ctgtgagttt tccac                                        25

<210> SEQ ID NO 57
<211> LENGTH: 25
<212> TYPE: DNA
<213> ORGANISM: Artificial Sequence
<220> FEATURE:
<223> OTHER INFORMATION: Synthetic

<400> SEQUENCE: 57
cccagtactt cgccagcacc atgat                                        25

<210> SEQ ID NO 58
<211> LENGTH: 25
<212> TYPE: DNA
<213> ORGANISM: Artificial Sequence
<220> FEATURE:
<223> OTHER INFORMATION: Synthetic

<400> SEQUENCE: 58
ccccgtcggg gtcgtggtgg tggta                                        25

<210> SEQ ID NO 59
<211> LENGTH: 25
<212> TYPE: DNA
<213> ORGANISM: Artificial Sequence
<220> FEATURE:
<223> OTHER INFORMATION: Synthetic

<400> SEQUENCE: 59
tccccggcaa gaggagtgaa aggtt                                        25

<210> SEQ ID NO 60
<211> LENGTH: 25
<212> TYPE: DNA
<213> ORGANISM: Artificial Sequence
<220> FEATURE:
<223> OTHER INFORMATION: Synthetic

<400> SEQUENCE: 60
acaccagcag ggcgagggcg gagat                                        25

<210> SEQ ID NO 61
<211> LENGTH: 25
<212> TYPE: DNA
<213> ORGANISM: Artificial Sequence
<220> FEATURE:
<223> OTHER INFORMATION: Synthetic

<400> SEQUENCE: 61
gaccagagtc atccttctga actgg                                        25

<210> SEQ ID NO 62
<211> LENGTH: 25
<212> TYPE: DNA
```

```
<213> ORGANISM: Artificial Sequence
<220> FEATURE:
<223> OTHER INFORMATION: Synthetic

<400> SEQUENCE: 62
tttcaggtag accttcatgc agaca                                              25

<210> SEQ ID NO 63
<211> LENGTH: 25
<212> TYPE: DNA
<213> ORGANISM: Artificial Sequence
<220> FEATURE:
<223> OTHER INFORMATION: Synthetic

<400> SEQUENCE: 63
cgatgtacgc tggtttccct ttgat                                              25

<210> SEQ ID NO 64
<211> LENGTH: 25
<212> TYPE: DNA
<213> ORGANISM: Artificial Sequence
<220> FEATURE:
<223> OTHER INFORMATION: Synthetic

<400> SEQUENCE: 64
ttcccactag gtcccattct ccatt                                              25

<210> SEQ ID NO 65
<211> LENGTH: 25
<212> TYPE: DNA
<213> ORGANISM: Artificial Sequence
<220> FEATURE:
<223> OTHER INFORMATION: Synthetic

<400> SEQUENCE: 65
cgctgcagct ccgggactca acatg                                              25

<210> SEQ ID NO 66
<211> LENGTH: 25
<212> TYPE: DNA
<213> ORGANISM: Artificial Sequence
<220> FEATURE:
<223> OTHER INFORMATION: Synthetic

<400> SEQUENCE: 66
tgcccatctg tgagttttcc acatg                                              25

<210> SEQ ID NO 67
<211> LENGTH: 21
<212> TYPE: DNA
<213> ORGANISM: Artificial Sequence
<220> FEATURE:
<223> OTHER INFORMATION: Synthetic

<400> SEQUENCE: 67
tgacgccaca ttccacacta a                                                  21

<210> SEQ ID NO 68
<211> LENGTH: 18
<212> TYPE: DNA
<213> ORGANISM: Artificial Sequence
<220> FEATURE:
<223> OTHER INFORMATION: Synthetic

<400> SEQUENCE: 68
ccccaaatct cgccaagc                                                      18
```

<210> SEQ ID NO 69
<211> LENGTH: 20
<212> TYPE: DNA
<213> ORGANISM: Artificial Sequence
<220> FEATURE:
<223> OTHER INFORMATION: Synthetic

<400> SEQUENCE: 69
ctcggtgccc cttgccattt                                              20

<210> SEQ ID NO 70
<211> LENGTH: 25
<212> TYPE: DNA
<213> ORGANISM: Artificial Sequence
<220> FEATURE:
<223> OTHER INFORMATION: Synthetic

<400> SEQUENCE: 70
ccttgcccat ctgtgagttt tccac                                        25

<210> SEQ ID NO 71
<211> LENGTH: 18
<212> TYPE: DNA
<213> ORGANISM: Artificial Sequence
<220> FEATURE:
<223> OTHER INFORMATION: Synthetic

<400> SEQUENCE: 71
tgtaaaacga cggccagt                                                18

<210> SEQ ID NO 72
<211> LENGTH: 18
<212> TYPE: DNA
<213> ORGANISM: Artificial Sequence
<220> FEATURE:
<223> OTHER INFORMATION: Synthetic

<400> SEQUENCE: 72
caggaaacag ctatgacc                                                18

<210> SEQ ID NO 73
<211> LENGTH: 25
<212> TYPE: DNA
<213> ORGANISM: Artificial Sequence
<220> FEATURE:
<223> OTHER INFORMATION: Synthetic

<400> SEQUENCE: 73
aaggagctgg tcaagaacta caatc                                        25

<210> SEQ ID NO 74
<211> LENGTH: 25
<212> TYPE: DNA
<213> ORGANISM: Artificial Sequence
<220> FEATURE:
<223> OTHER INFORMATION: Synthetic

<400> SEQUENCE: 74
ccggaatctg caggaagcag gaaca                                        25

<210> SEQ ID NO 75
<211> LENGTH: 26
<212> TYPE: DNA
<213> ORGANISM: Artificial Sequence
<220> FEATURE:
<223> OTHER INFORMATION: Synthetic

```
<400> SEQUENCE: 75
ccaggcgtgg ttacgcaaag tctttg                                          26

<210> SEQ ID NO 76
<211> LENGTH: 21
<212> TYPE: DNA
<213> ORGANISM: Artificial Sequence
<220> FEATURE:
<223> OTHER INFORMATION: Synthetic

<400> SEQUENCE: 76
gatgtgcagc actgcaaaca a                                               21

<210> SEQ ID NO 77
<211> LENGTH: 22
<212> TYPE: DNA
<213> ORGANISM: Artificial Sequence
<220> FEATURE:
<223> OTHER INFORMATION: Synthetic

<400> SEQUENCE: 77
ttaaagcttg cccaggaata gg                                              22

<210> SEQ ID NO 78
<211> LENGTH: 22
<212> TYPE: DNA
<213> ORGANISM: Artificial Sequence
<220> FEATURE:
<223> OTHER INFORMATION: Synthetic

<400> SEQUENCE: 78
ggaactgctg tgtattttca gc                                              22

<210> SEQ ID NO 79
<211> LENGTH: 21
<212> TYPE: DNA
<213> ORGANISM: Artificial Sequence
<220> FEATURE:
<223> OTHER INFORMATION: Synthetic

<400> SEQUENCE: 79
aagaccagga cccaaacttg t                                               21

<210> SEQ ID NO 80
<211> LENGTH: 23
<212> TYPE: DNA
<213> ORGANISM: Artificial Sequence
<220> FEATURE:
<223> OTHER INFORMATION: Synthetic

<400> SEQUENCE: 80
gcttgtgtgt ggtatacaca ttg                                             23

<210> SEQ ID NO 81
<211> LENGTH: 17
<212> TYPE: DNA
<213> ORGANISM: Artificial Sequence
<220> FEATURE:
<223> OTHER INFORMATION: Synthetic

<400> SEQUENCE: 81
gtagagtgtc ctgcggc                                                    17

<210> SEQ ID NO 82
<211> LENGTH: 18
<212> TYPE: DNA
```

<213> ORGANISM: Artificial Sequence
<220> FEATURE:
<223> OTHER INFORMATION: Synthetic

<400> SEQUENCE: 82
ggtccgctac attgccaa                                                    18

<210> SEQ ID NO 83
<211> LENGTH: 21
<212> TYPE: DNA
<213> ORGANISM: Artificial Sequence
<220> FEATURE:
<223> OTHER INFORMATION: Synthetic

<400> SEQUENCE: 83
tgatggtgaa gaccgagaag g                                                21

<210> SEQ ID NO 84
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(48)
<223> OTHER INFORMATION: n is a, c, g, or t

<400> SEQUENCE: 84
nnnnnnnnnn nnnnnnnnnn nnnnnnnnnn nnnnnnnnnn nnnnnnnnct gcacg           55

<210> SEQ ID NO 85
<211> LENGTH: 10
<212> TYPE: DNA
<213> ORGANISM: Artificial Sequence
<220> FEATURE:
<223> OTHER INFORMATION: Synthetic

<400> SEQUENCE: 85
tctccttaag                                                             10

<210> SEQ ID NO 86
<211> LENGTH: 10
<212> TYPE: DNA
<213> ORGANISM: Artificial Sequence
<220> FEATURE:
<223> OTHER INFORMATION: Synthetic

<400> SEQUENCE: 86 tttttttgaag                                                            10

<210> SEQ ID NO 87
<211> LENGTH: 10
<212> TYPE: DNA
<213> ORGANISM: Artificial Sequence
<220> FEATURE:
<223> OTHER INFORMATION: Synthetic

<400> SEQUENCE: 87
tgtgtgtcag                                                             10

<210> SEQ ID NO 88
<211> LENGTH: 11
<212> TYPE: DNA
<213> ORGANISM: Artificial Sequence
<220> FEATURE:
<223> OTHER INFORMATION: Synthetic

<400> SEQUENCE: 88
ctgtttctag t                                                    11

<210> SEQ ID NO 89
<211> LENGTH: 10
<212> TYPE: DNA
<213> ORGANISM: Artificial Sequence
<220> FEATURE:
<223> OTHER INFORMATION: Synthetic

<400> SEQUENCE: 89
acccacacag                                                      10

<210> SEQ ID NO 90
<211> LENGTH: 10
<212> TYPE: DNA
<213> ORGANISM: Artificial Sequence
<220> FEATURE:
<223> OTHER INFORMATION: Synthetic

<400> SEQUENCE: 90
ccctatggag                                                      10

<210> SEQ ID NO 91
<211> LENGTH: 10
<212> TYPE: DNA
<213> ORGANISM: Artificial Sequence
<220> FEATURE:
<223> OTHER INFORMATION: Synthetic

<400> SEQUENCE: 91
tatgttttag                                                      10

<210> SEQ ID NO 92
<211> LENGTH: 10
<212> TYPE: DNA
<213> ORGANISM: Artificial Sequence
<220> FEATURE:
<223> OTHER INFORMATION: Synthetic

<400> SEQUENCE: 92
ctctccacag                                                      10

<210> SEQ ID NO 93
<211> LENGTH: 10
<212> TYPE: DNA
<213> ORGANISM: Artificial Sequence
<220> FEATURE:
<223> OTHER INFORMATION: Synthetic

<400> SEQUENCE: 93
gtctccccag                                                      10

<210> SEQ ID NO 94
<211> LENGTH: 457
<212> TYPE: DNA
<213> ORGANISM: Artificial Sequence
<220> FEATURE:
<223> OTHER INFORMATION: Synthetic

<400> SEQUENCE: 94
agaacgcaag ggagaggtag agcctggcct tgggcagccc ctggcctggc cagaggcgcg      60
aggccgagag cccgctcggt ggagactggg ggtggaggtg cccggagcgt acccagcgcc     120
gggagtacct cccgctcaca cctcgggctg cagttccctg ggtggccgcc gagacgctgg     180

```
cccgggctgg agggatggcg gggcggggac gggggcgggg gcgggctcg tcacgtggag      240 aggcgcgcgg gggcggcgg ggcggggcg cgcgcccggc tccttaaagg cgcgcgagcc      300
gagcggcgag gtgcctctgt ggccgcaggc gcaggcccgg gcgacagccg agacgtggag    360
cgcgccggct cgctgcagct ccgggactca acatgcgctg ctcgccggga ggcgtctggc    420
tggcgctggc cgcgtcgctc ctgcacggta aagccac                             457

<210> SEQ ID NO 95
<211> LENGTH: 307
<212> TYPE: DNA
<213> ORGANISM: Artificial Sequence
<220> FEATURE:
<223> OTHER INFORMATION: Synthetic

<400> SEQUENCE: 95
caggccgcca catagctccc gccaagtcct cggtgcccct tgccattttc cagccgcgtc     60
ccacgagggt cacggcggcg gggagaggtg gagccgcgag agctcggccg ggggccccgc   120
ctggtggccg cggccatgac agcggctcgg gactggctcc ttttccgcgc ccctcccgcc   180
ggaggtgagg ggaagatgtc catgtcaggg ttcaaggcca aaccgaagtt actggcctct    240
atcttccagg agaaccagga gccacagccg cggctcacgc cccaccgcaa cattaaggtg   300
agtcgcc                                                             307

<210> SEQ ID NO 96
<211> LENGTH: 145
<212> TYPE: DNA
<213> ORGANISM: Artificial Sequence
<220> FEATURE:
<223> OTHER INFORMATION: Synthetic

<400> SEQUENCE: 96
ctcatttcag attacaagtg gacacctgag tcagcaggac ctggaatccc agatgagaga    60
gcttatctac acgactcaga tcttgttgtc accccccatta ttgacaatcc aaaggtgcag   120
aaagcactct gacaagtgag ttgta                                         145

<210> SEQ ID NO 97
<211> LENGTH: 84
<212> TYPE: DNA
<213> ORGANISM: Artificial Sequence
<220> FEATURE:
<223> OTHER INFORMATION: Synthetic

<400> SEQUENCE: 97
ttaaccacag ataatgaaac aaccaccatc ggttaaattt gatgcaaaaa tattgcatct     60
accagcattt tcaggtagga tcat                                           84

<210> SEQ ID NO 98
<211> LENGTH: 67
<212> TYPE: DNA
<213> ORGANISM: Artificial Sequence
<220> FEATURE:
<223> OTHER INFORMATION: Synthetic

<400> SEQUENCE: 98
tttattctag ttccaattgc taatccagca tttgtggata gctgcaaact gcgatatgta     60
agtaaca                                                              67

<210> SEQ ID NO 99
<211> LENGTH: 100
<212> TYPE: DNA
```

```
<213> ORGANISM: Artificial Sequence
<220> FEATURE:
<223> OTHER INFORMATION: Synthetic

<400> SEQUENCE: 99
ctgtttctag tgctgatgag cgctttgacg ccacattcca cactaacgtg ttggtgaatt    60
cttctgggca ttgccagtac ctgcctccag gtaagctgca                         100

<210> SEQ ID NO 100
<211> LENGTH: 37
<212> TYPE: DNA
<213> ORGANISM: Artificial Sequence
<220> FEATURE:
<223> OTHER INFORMATION: Synthetic

<400> SEQUENCE: 100
acccacacag gcatattcaa gagttcctgc tacatcg                              37

<210> SEQ ID NO 101
<211> LENGTH: 392
<212> TYPE: DNA
<213> ORGANISM: Artificial Sequence
<220> FEATURE:
<223> OTHER INFORMATION: Synthetic

<400> SEQUENCE: 101
agaacgcaag ggagaggtag agcctggcct tgggcagccc ctggcctggc cagaggcgcg    60
aggccgagag cccgctcggt ggagactggg ggtggaggtg cccggagcgt acccagcgcc   120
gggagtacct cccgctcaca cctcgggctg cagttccctg ggtggccgcc gagacgctgg   180
cccgggctgg agggatggcg gggcggggac ggggcgggg gcggggctcg tcacgtggag    240
aggcgcgcgg gggcgggcgg ggcgggggcg cgcgcccggc tccttaaagg cgcgcgagcc   300
gagcggcgag gtgcctctgt ggccgcaggc gcaggcccgg gcgacagccg agacgtggag   360
cgcgccggct cgctgcagct ccgggactca ac                                 392

<210> SEQ ID NO 102
<211> LENGTH: 689
<212> TYPE: DNA
<213> ORGANISM: Artificial Sequence
<220> FEATURE:
<223> OTHER INFORMATION: Synthetic

<400> SEQUENCE: 102 agcccttttcc caggcggtag cgggggcagt ggtgctgttg ccctttttaaa ctgcggcttg    60 acgggagccg cgcctcctgt cggtggagtc ggttataaag ggagcagccc cgcaggccgc   120
cacatagctc ccgccaagtc ctcggtgccc cttgccattt tccagccgcg ctcccacgag   180
ggtcacggcg gcggggagag gtggagccgc gagagctcgg ccggggcccc cgcctggtgg   240
ccgcggccat gacagcggct cgggactggc tccttttccg cgcccctccc gccggaggtg   300
aggggaagat gtccatgtca gggttcaagg ccaaaccgaa gttactggcc tctatcttcc   360
aggagaacca ggagccacag ccgcggctca cgcccaccg caacattaag attacaagtg    420
gacacctgag tcagcaggac ctggaatccc agatgagaga gcttatctac acgactcaga   480
tcttgttgtc accccatta ttgacaatcc aaaggtgcag aaagcactct gacaattcca    540
attgctaatc cagcatttgt ggatagctgc aaactgcgat attgctgatg agcgctttga   600
cgccacattc cacactaacg tgttggtgaa ttcttctggg cattgccagt acctgcctcc   660
aggcatattc aagagttcct gctacatcg                                      689
```

<210> SEQ ID NO 103
<211> LENGTH: 641
<212> TYPE: DNA
<213> ORGANISM: Artificial Sequence
<220> FEATURE:
<223> OTHER INFORMATION: Synthetic

<400> SEQUENCE: 103

```
caggccgcca catagctccc gccaagtcct cggtgcccct tgccattttc cagccgcgct      60
cccacgaggg tcacggcggc ggggagaggt ggagccgcga gagctcggcc gggggccccg     120
cctggtggcc gcggccatga cagcggctcg ggactggctc cttttccgcg ccctcccgc      180
cggaggtgag gggaagatgt ccatgtcagg gttcaaggcc aaaccgaagt tactggcctc     240
tatcttccag gagaaccagg agccacagcc gcggctcacg ccccaccgca acattaagat     300
tacaagtgga cacctgagtc agcaggacct ggaatcccag atgagagagc ttatctacac     360
gactcagatc ttgttgtcac cccattatt gacaatccaa aggtgcagaa agcactctga      420
caaataatga acaaccacc atcggttaaa tttgatgcaa aaatattgca tctaccagca      480
ttttcagttc caattgctaa tccagcattt gtggatagct gcaaactgcg atattgctga     540
tgagcgcttt gacgccacat tccacactaa cgtgttggtg aattcttctg ggcattgcca     600
gtacctgcct ccaggcatat tcaagagttc ctgctacatc g                        641
```

<210> SEQ ID NO 104
<211> LENGTH: 10
<212> TYPE: DNA
<213> ORGANISM: Artificial Sequence
<220> FEATURE:
<223> OTHER INFORMATION: Synthetic

<400> SEQUENCE: 104

```
gtaaagccac                                                            10
```

<210> SEQ ID NO 105
<211> LENGTH: 140
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(134)
<223> OTHER INFORMATION: n is a, c, g, or t

<400> SEQUENCE: 105

```
tgtccnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnngacgtg                                                 140
```

<210> SEQ ID NO 106
<211> LENGTH: 10
<212> TYPE: DNA
<213> ORGANISM: Artificial Sequence
<220> FEATURE:
<223> OTHER INFORMATION: Synthetic

<400> SEQUENCE: 106

```
gtgagtcccg                                                            10
```

<210> SEQ ID NO 107
<211> LENGTH: 44
<212> TYPE: DNA

-continued

<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(38)
<223> OTHER INFORMATION: n is a, c, g, or t

<400> SEQUENCE: 107
gatgagnnnn nnnnnnnnnn nnnnnnnnnn nnnnnnnnca aatg          44

<210> SEQ ID NO 108
<211> LENGTH: 10
<212> TYPE: DNA
<213> ORGANISM: Artificial Sequence
<220> FEATURE:
<223> OTHER INFORMATION: Synthetic

<400> SEQUENCE: 108
gtaagttaag          10

<210> SEQ ID NO 109
<211> LENGTH: 110
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(105)
<223> OTHER INFORMATION: n is a, c, g, or t

<400> SEQUENCE: 109
tcttggnnnn nnnnnnnnnn nnnnnnnnnn nnnnnnnnnn nnnnnnnnnn nnnnnnnnnn          60
nnnnnnnnnn nnnnnnnnnn nnnnnnnnnn nnnnnnnnnn nnnnnaacag          110

<210> SEQ ID NO 110
<211> LENGTH: 10
<212> TYPE: DNA
<213> ORGANISM: Artificial Sequence
<220> FEATURE:
<223> OTHER INFORMATION: Synthetic

<400> SEQUENCE: 110
gtaagcatat          10

<210> SEQ ID NO 111
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(73)
<223> OTHER INFORMATION: n is a, c, g, or t

<400> SEQUENCE: 111
gctgatnnnn nnnnnnnnnn nnnnnnnnnn nnnnnnnnnn nnnnnnnnnn nnnnnnnnnn          60
nnnnnnnnnn nnncctccag          80

<210> SEQ ID NO 112
<211> LENGTH: 10
<212> TYPE: DNA
<213> ORGANISM: Artificial Sequence
<220> FEATURE:
<223> OTHER INFORMATION: Synthetic

```
<400> SEQUENCE: 112
gtaagctgca                                                          10

<210> SEQ ID NO 113
<211> LENGTH: 168
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(161)
<223> OTHER INFORMATION: n is a, c, g, or t

<400> SEQUENCE: 113
gcatannnnn nnnnnnnnnn nnnnnnnnnn nnnnnnnnnn nnnnnnnnnn nnnnnnnnnn     60
nnnnnnnnnn nnnnnnnnnn nnnnnnnnnn nnnnnnnnnn nnnnnnnnnn nnnnnnnnnn    120
nnnnnnnnnn nnnnnnnnnn nnnnnnnnnn nnnnnnnnnn nctagtgg                 168

<210> SEQ ID NO 114
<211> LENGTH: 10
<212> TYPE: DNA
<213> ORGANISM: Artificial Sequence
<220> FEATURE:
<223> OTHER INFORMATION: Synthetic

<400> SEQUENCE: 114
gtaagccatg                                                          10

<210> SEQ ID NO 115
<211> LENGTH: 195
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(188)
<223> OTHER INFORMATION: n is a, c, g, or t

<400> SEQUENCE: 115
gaatcnnnnn nnnnnnnnnn nnnnnnnnnn nnnnnnnnnn nnnnnnnnnn nnnnnnnnnn     60
nnnnnnnnnn nnnnnnnnnn nnnnnnnnnn nnnnnnnnnn nnnnnnnnnn nnnnnnnnnn    120
nnnnnnnnnn nnnnnnnnnn nnnnnnnnnn nnnnnnnnnn nnnnnnnnnn nnnnnnnnnn    180
nnnnnnnntc cctgg                                                    195

<210> SEQ ID NO 116
<211> LENGTH: 10
<212> TYPE: DNA
<213> ORGANISM: Artificial Sequence
<220> FEATURE:
<223> OTHER INFORMATION: Synthetic

<400> SEQUENCE: 116
gtaagcgccc                                                          10

<210> SEQ ID NO 117
<211> LENGTH: 87
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(80)
```

<223> OTHER INFORMATION: n is a, c, g, or t

<400> SEQUENCE: 117
ggatannnnn nnnnnnnnnn nnnnnnnnnn nnnnnnnnnn nnnnnnnnnn nnnnnnnnnn    60
nnnnnnnnnn nnnnnnnnnn ttgatag    87

<210> SEQ ID NO 118
<211> LENGTH: 10
<212> TYPE: DNA
<213> ORGANISM: Artificial Sequence
<220> FEATURE:
<223> OTHER INFORMATION: Synthetic

<400> SEQUENCE: 118
gtaaggcaag    10

<210> SEQ ID NO 119
<211> LENGTH: 110
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(104)
<223> OTHER INFORMATION: n is a, c, g, or t

<400> SEQUENCE: 119
cccagnnnnn nnnnnnnnnn nnnnnnnnnn nnnnnnnnnn nnnnnnnnnn nnnnnnnnnn    60
nnnnnnnnnn nnnnnnnnnn nnnnnnnnnn nnnnnnnnnn nnnnaagtgg    110

<210> SEQ ID NO 120
<211> LENGTH: 10
<212> TYPE: DNA
<213> ORGANISM: Artificial Sequence
<220> FEATURE:
<223> OTHER INFORMATION: Synthetic

<400> SEQUENCE: 120
gtacgttcct    10

<210> SEQ ID NO 121
<211> LENGTH: 519
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(519)
<223> OTHER INFORMATION: n is a, c, g, or t

<400> SEQUENCE: 121
accagannnn nnnnnnnnnn nnnnnnnnnn nnnnnnnnnn nnnnnnnnnn nnnnnnnnnn    60
nnnnnnnnnn nnnnnnnnnn nnnnnnnnnn nnnnnnnnnn nnnnnnnnnn nnnnnnnnnn    120
nnnnnnnnnn nnnnnnnnnn nnnnnnnnnn nnnnnnnnnn nnnnnnnnnn nnnnnnnnnn    180
nnnnnnnnnn nnnnnnnnnn nnnnnnnnnn nnnnnnnnnn nnnnnnnnnn nnnnnnnnnn    240
nnnnnnnnnn nnnnnnnnnn nnnnnnnnnn nnnnnnnnnn nnnnnnnnnn nnnnnnnnnn    300
nnnnnnnnnn nnnnnnnnnn nnnnnnnnnn nnnnnnnnnn nnnnnnnnnn nnnnnnnnnn    360
nnnnnnnnnn nnnnnnnnnn nnnnnnnnnn nnnnnnnnnn nnnnnnnnnn nnnnnnnnnn    420
nnnnnnnnnn nnnnnnnnnn nnnnnnnnnn nnnnnnnnnn nnnnnnnnnn nnnnnnnnnn    480
nnnnnnnnnn nnnnnnnnnn nnnnnnnnnn nnnnnnnnn      519

<210> SEQ ID NO 122
<211> LENGTH: 2619
<212> TYPE: DNA
<213> ORGANISM: Homo sapiens

<400> SEQUENCE: 122

| | | | | |
|---|---|---|---|---|
| gaattctaaa | ccatataata | cacatttgga | ctccacacct | aagcctaatg | cacttttgg | 60 |
| ttttaaatg | tgtaattatc | ttttccccc | tatccggagc | ccaagcagaa | aacatgcttc | 120 |
| cttccacttc | cctggctaat | ggttgaggtt | tcctggtctt | tttacactg | gaaaggagat | 180 |
| tacaccaatt | tctggattta | tgtgaatatc | tcagttccag | ttccccacct | ctcataggcc | 240 |
| ccaagcccaa | ggtcacctta | cctcctgaga | gtgtgttaaa | atttccctct | tacccataga | 300 |
| atctatattt | ttggtatgcc | caggcatgta | ttcacatcct | gctatgtttt | atttgctgtt | 360 |
| tttttttgt | ttttttttgt | tttttttttt | tttgctttgg | gaacgggagt | gagtgtagaa | 420 |
| cctatacagt | cccgtcagct | ctattccaag | aatgttctgc | tcttttcttc | gtttcacaaa | 480 |
| tgaaaaacct | gagtcccata | gatgggagtc | aatacagcca | aactcacaga | cctacctatg | 540 |
| gcacagggga | gactgaagtt | tatttccaa | cttccagcag | tcctacattg | taagctgagt | 600 |
| gagtggactg | cgcttgcagg | tcctccaggt | gcctagcgag | aacagaggac | aaataaatat | 660 |
| ttacgaattg | cttgtctcac | ctgaaaatgg | tttatttcta | ggtttctgat | attatggggt | 720 |
| gcaatggcgg | taagaagca | gttctggttt | caggaatgtg | atcctgatag | ccatactcca | 780 |
| gaaaaaatca | ataaattccc | ttggccccat | gggctcatgc | tcttctagaa | gggaagacag | 840 |
| ggctcttagg | tactttcagc | gctcgtagaa | gagtgttgtt | acagtcccat | gaccagtgca | 900 |
| ggggatgtgc | cactgagaat | cttttcactg | atgcttcatg | ggctttctct | attctgctac | 960 |
| tgggttttat | ttccttctt | ctaattctcc | ctttaccaac | aactaatccc | ctgtagataa | 1020 |
| ttaattcatc | aagtgcctgc | tctgtgatgt | ccggactgct | agaagtggta | gggggactca | 1080 |
| agagccagat | gaagctaagg | gcacgcctgt | ctgctctcca | gggacccctg | gcgtcccttt | 1140 |
| ctcctggcag | aatgactgct | atcctttgag | gtgaatccag | ttcagctgtc | acctcttcta | 1200 |
| ttaaccactc | tccaaaaaca | gctaatcctt | cttctaggct | cttaccgcag | ttatgaaagc | 1260 |
| ctatgctgac | cctttgttta | aacatgtgta | cattaacagt | aatacattta | agacacttca | 1320 |
| tggcaagggc | aatatactgc | gttattcttc | caaatcaaat | agttgggctc | agtcccccat | 1380 |
| tcctgctact | ggggtacagt | caagctcagt | cacccttttgg | tgagcctttc | cctagttctt | 1440 |
| ggagtcttaa | aagaatcccg | tggttttcgg | cagttcagaa | acccaggcat | gccgctgcg | 1500 |
| tggtccacgg | gagttgctct | ggtggagctc | ggatgcccgg | gggctgcagg | aaagaaggtg | 1560 |
| gcagcgcccc | ctacgcggac | gcagggcgct | gctgtgctca | gcagaaggga | gcaaatggga | 1620 |
| tggagcttca | gccaccctgg | aagccgcccc | ttggcgcctt | cctccctccc | ttcctctttc | 1680 |
| caaaatcaag | cccctcttc | aacatcaaga | actctccgca | ctccctggac | ctctcagagc | 1740 |
| ctctcctcat | ttactctttc | caatgcgctg | gctcaaaaga | gcctagataa | gaacaccaag | 1800 |
| ttctggctgt | ccttccagca | aagagttagg | agttaacttt | tcaatctttt | ttaatctcct | 1860 |
| ttaaaaaaga | atgagccata | cattaggta | accactggga | atcccatcac | acacattggc | 1920 |
| ggcatctctc | ctccccgaca | gggtgcctcc | agcacttcag | atcccagccg | agagtctggc | 1980 |
| tgctggcgcc | cagcaaacgg | tgcggaaagc | aaaccggggc | tcgcgaaag | cgggaggagg | 2040 |
| ggggcttcct | cgggtctgtt | ttgtctggtt | ggcaagactt | ccgaagcctg | gttccctata | 2100 |

```
gctgccaccc ggtcgctggc gtggaggagg gagtccggga agactggacc ccagaattgt    2160
cccggctttc tcccgagtgc ccagcgcagc ttctggctga gagcgggagc gggctgagtg    2220
gggacaaaga acgcaaggga gaggtagagc ctggccttgg gcagcccctg gcctggccag    2280
aggcgcgagg ccgagagccc gctcggtgga gactgggggt ggaggtgccc ggagcgtacc    2340
cagcgccggg agtacctccc gctcacacct cgggctgcag ttccctgggt ggccgccgag    2400
acgctggccc gggctggagg gatgggggg cggga cggg ggcggggg cg gggctcgtca    2460 cgtggagagg cgcgcggggg cgggcggggc ggggcgcgc gcccggctcc ttaaaggcgc    2520
gcgagccgag cggcgaggtg cctctgtggc cgcaggcgca ggcccgggcg acagccgaga    2580
cgtggagcgc gccggctcgc tgcagctccg ggactcaac                           2619
```

<210> SEQ ID NO 123
<211> LENGTH: 2087
<212> TYPE: DNA
<213> ORGANISM: Homo sapiens

<400> SEQUENCE: 123

```
ggcacgagga gccgagcggc gaggtgcctc tgtggccgca cggcaggccc gggcgacacg      60
gagacgtgga gcgcgccggc tcgctgcagc tccgggactc aacatgcgct gctcgccggg     120
aggcgtctgg ctgggcctgg ccgcgtcgct cctgcacgtg tccctgcaag gcagttcca     180 gaggaagctt tacaaggagc tggtcaagaa ctacaatccc ttggagaggc ccgtggccaa     240
tgactcgcaa ccactcaccg tctacttctc cctgagcctc ctgcagatca tggacgtgga     300
tgagaagaac caagttttaa ccaccaacat ttggctgcaa atgtcttgga cagatcacta     360
tttacagtgg aatgtgtcag aatatccagg ggtgaagact gttcgtttcc cagatggcca     420
gatttggaaa ccagacattc ttctctataa cagtgctgat gagcgctttg acgccacatt     480
ccacactaac gtgttggtga attcttctgg gcattgccag tacctgcctc caggcatatt     540
caagagttcc tgctacatcg atgtacgctg gtttcccttt gatgtgcagc actgcaaact     600
gaagtttggg tcctggtctt acggaggctg gtccttggat ctgcagatgc aggaggcaga     660
tatcagtggc tatatcccca tggagaatg ggacctagtg ggaatccccg gcaagaggag     720
tgaaaggttc tatgagtgct gcaaagagcc ctaccccgat gtcaccttca cagtgaccat     780
gcgccgcagg acactctact atggcctcaa cctgctgatc ccctgtgtgc tcatctccgc     840
cctcgccctg ctggtgttcc tgcttcctgc agattccggg gagaagattt ccctgtgggat    900 aacagtctta ctctctctta ccgtcttcat gctgctcgtg gctgagatca tgcccgcaac    960
atccgattcg gtaccattga tagcccagta cttcgccagc accatgatca tcgtgggcct   1020
ctcggtggtg gtgacagtga tcgtgctgca gtaccaccac cacgaccccg acggggcaa    1080 gatgcccaag tggaccagag tcatccttct gaactggtgc gcgtggttcc tgcgaatgaa    1140
gaggcccggg gaggacaagg tgcgcccggc ctgccagcac aagcagcggc gctgcagcct    1200
ggccagtgtg gagatgagcg ccgtgggccc gccgcccgcc agcaacggga acctgctgta    1260
catcggcttc cgcggcctgg acggcgtgca ctgtgtcccg accccgact ctgggtagt     1320 gtgtggccgc atggcctgct cccccacgca cgatgagcac ctcctgcacg gcgggcaacc    1380
ccccgagggg gacccggact tggccaagat cctggaggag gtccgctaca ttgccaaccg    1440
cttccgctgc caggacgaaa gcgaggcggt ctgcagcgag tggaagttcg ccgcctgtgt    1500 ggtgaccgc ctgtgcctca tggccttctc ggtcttcacc atcatctgca ccatcggcat    1560
cctgatgtcg gctcccaact tcgtggaggc cgtgtccaaa gactttgcgt aaccacactg    1620
```

```
gttctgtaca tgtggaaaac tcacagatgg gcaaggcctt tggcttggcg agatttgggg   1680
gtgctaatcc aggacagcat tacacgccac aactccagtg ttcccttctg gctgtcagtc   1740
gtgttgctta cggtttcttt gttactttag gtagtagaat ctcagcactt tgtttcatat   1800
tctcagatgg gctgatagat actccttggc acatccgtac catcggtcag cagggccact   1860
gagtagtcat tttgccatta gccctcagcc tggaaagccc ttcggagagc tccccatggc   1920
tcctcaccac cgagacagtt ggttttgcat gtctgcatga aggtctacct gaaaattcaa   1980
catttgcttt ttgcttgtgt acaaacccag attgaagcta aaataaacca gactcactaa   2040
atcctttcca ataattgact ggtggaagga aacaaaaaa  aaaaaaa              2087
```

```
<210> SEQ ID NO 124
<211> LENGTH: 502
<212> TYPE: PRT
<213> ORGANISM: Homo sapiens

<400> SEQUENCE: 124

Met Arg Cys Ser Pro Gly Gly Val Trp Leu Gly Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Ser Leu Leu Gln Ile Met Asp
    50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
        115                 120                 125

Asn Val Leu Val Asn Ser Ser Gly His Cys Gln Tyr Leu Pro Pro Gly
    130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
        195                 200                 205

Phe Tyr Glu Cys Cys Lys Glu Pro Tyr Pro Asp Val Thr Phe Thr Val
    210                 215                 220

Thr Met Arg Arg Arg Thr Leu Tyr Tyr Gly Leu Asn Leu Leu Ile Pro
225                 230                 235                 240

Cys Val Leu Ile Ser Ala Leu Ala Leu Leu Val Phe Leu Leu Pro Ala
                245                 250                 255

Asp Ser Gly Glu Lys Ile Ser Leu Gly Ile Thr Val Leu Leu Ser Leu
            260                 265                 270

Thr Val Phe Met Leu Leu Val Ala Glu Ile Met Pro Ala Thr Ser Asp
        275                 280                 285

Ser Val Pro Leu Ile Ala Gln Tyr Phe Ala Ser Thr Met Ile Ile Val
    290                 295                 300
```

```
Gly Leu Ser Val Val Thr Val Ile Val Leu Gln Tyr His His His
305                 310                 315                 320

Asp Pro Asp Gly Gly Lys Met Pro Lys Trp Thr Arg Val Ile Leu Leu
            325                 330                 335

Asn Trp Cys Ala Trp Phe Leu Arg Met Lys Arg Pro Gly Glu Asp Lys
            340                 345                 350

Val Arg Pro Ala Cys Gln His Lys Gln Arg Arg Cys Ser Leu Ala Ser
            355                 360                 365

Val Glu Met Ser Ala Val Gly Pro Pro Ala Ser Asn Gly Asn Leu
    370                 375                 380

Leu Tyr Ile Gly Phe Arg Gly Leu Asp Gly Val His Cys Val Pro Thr
385                 390                 395                 400

Pro Asp Ser Gly Val Val Cys Gly Arg Met Ala Cys Ser Pro Thr His
                405                 410                 415

Asp Glu His Leu Leu His Gly Gly Gln Pro Pro Glu Gly Asp Pro Asp
                420                 425                 430

Leu Ala Lys Ile Leu Glu Glu Val Arg Tyr Ile Ala Asn Arg Phe Arg
            435                 440                 445

Cys Gln Asp Glu Ser Glu Ala Val Cys Ser Glu Trp Lys Phe Ala Ala
            450                 455                 460

Cys Val Val Asp Arg Leu Cys Leu Met Ala Phe Ser Val Phe Thr Ile
465                 470                 475                 480

Ile Cys Thr Ile Gly Ile Leu Met Ser Ala Pro Asn Phe Val Glu Ala
                485                 490                 495

Val Ser Lys Asp Phe Ala
            500

<210> SEQ ID NO 125
<211> LENGTH: 276
<212> TYPE: DNA
<213> ORGANISM: Homo sapiens

<400> SEQUENCE: 125
gggagtacct cccgctcaca cctcgggctg cagttccctg ggtggccgcc gagacgctgg      60
cccgggctgg agggatgggg gggcggggac ggggggcgggg gcgggggctcc gtcacgtgga    120 gaggcgcgcg ggggcgggcg gggcggggggc gcgcgcccgg ctccttaaag gcgcgcgagc    180
cgagcggcga ggtgcctctg tggccgcagg cgcaggcccg ggcgacagcc gagacgtgga    240
gcgcgccggc tcgctgcagc tccgggactc aacatg                              276

<210> SEQ ID NO 126
<211> LENGTH: 22
<212> TYPE: DNA
<213> ORGANISM: Artificial Sequence
<220> FEATURE:
<223> OTHER INFORMATION: Synthetic

<400> SEQUENCE: 126
ggttggcaag acttccgaag cc                                              22

<210> SEQ ID NO 127
<211> LENGTH: 22
<212> TYPE: DNA
<213> ORGANISM: Artificial Sequence
<220> FEATURE:
<223> OTHER INFORMATION: Synthetic

<400> SEQUENCE: 127
```
gtggctttac cgtgcaggag cg                                    22

<210> SEQ ID NO 128
<211> LENGTH: 22
<212> TYPE: DNA
<213> ORGANISM: Artificial Sequence
<220> FEATURE:
<223> OTHER INFORMATION: Synthetic

<400> SEQUENCE: 128
agtacctccc gctcacacct cg                                    22

<210> SEQ ID NO 129
<211> LENGTH: 22
<212> TYPE: DNA
<213> ORGANISM: Artificial Sequence
<220> FEATURE:
<223> OTHER INFORMATION: Synthetic

<400> SEQUENCE: 129
atgttgagtc ccggagctgc ag                                    22

<210> SEQ ID NO 130
<211> LENGTH: 21
<212> TYPE: DNA
<213> ORGANISM: Artificial Sequence
<220> FEATURE:
<223> OTHER INFORMATION: Synthetic

<400> SEQUENCE: 130
ctggccagag gcgcgaggcc g                                     21

<210> SEQ ID NO 131
<211> LENGTH: 22
<212> TYPE: DNA
<213> ORGANISM: Artificial Sequence
<220> FEATURE:
<223> OTHER INFORMATION: Synthetic

<400> SEQUENCE: 131
ggggctcgtc acgtggagag gc                                    22

<210> SEQ ID NO 132
<211> LENGTH: 25
<212> TYPE: DNA
<213> ORGANISM: Artificial Sequence
<220> FEATURE:
<223> OTHER INFORMATION: Synthetic

<400> SEQUENCE: 132
agcagcgcat gttgagtccc ggagc                                 25

<210> SEQ ID NO 133
<211> LENGTH: 20
<212> TYPE: DNA
<213> ORGANISM: Artificial Sequence
<220> FEATURE:
<223> OTHER INFORMATION: Synthetic

<400> SEQUENCE: 133
gtacctcccg ctcacacctc                                       20

<210> SEQ ID NO 134
<211> LENGTH: 21
<212> TYPE: DNA
<213> ORGANISM: Artificial Sequence
<220> FEATURE:

<223> OTHER INFORMATION: Synthetic

<400> SEQUENCE: 134
cggctcgcgc gcctttaagg a                                              21

<210> SEQ ID NO 135
<211> LENGTH: 22
<212> TYPE: DNA
<213> ORGANISM: Artificial Sequence
<220> FEATURE:
<223> OTHER INFORMATION: Synthetic

<400> SEQUENCE: 135
agtacctccc gctcacacct cg                                             22

<210> SEQ ID NO 136
<211> LENGTH: 20
<212> TYPE: DNA
<213> ORGANISM: Artificial Sequence
<220> FEATURE:
<223> OTHER INFORMATION: Synthetic

<400> SEQUENCE: 136
ggaggctcag ggagaagtag                                                20

<210> SEQ ID NO 137
<211> LENGTH: 18
<212> TYPE: DNA
<213> ORGANISM: Artificial Sequence
<220> FEATURE:
<223> OTHER INFORMATION: Synthetic

<400> SEQUENCE: 137
gcggcgaggt gcctctgt                                                  18

<210> SEQ ID NO 138
<211> LENGTH: 21
<212> TYPE: DNA
<213> ORGANISM: Artificial Sequence
<220> FEATURE:
<223> OTHER INFORMATION: Synthetic

<400> SEQUENCE: 138
ggatcccacg gaggagtgga g                                              21

<210> SEQ ID NO 139
<211> LENGTH: 21
<212> TYPE: DNA
<213> ORGANISM: Artificial Sequence
<220> FEATURE:
<223> OTHER INFORMATION: Synthetic

<400> SEQUENCE: 139
cctgcccggg tcttctctcc t                                              21

<210> SEQ ID NO 140
<211> LENGTH: 23
<212> TYPE: DNA
<213> ORGANISM: Artificial Sequence
<220> FEATURE:
<223> OTHER INFORMATION: Synthetic

<400> SEQUENCE: 140
aactagagtg ccccagccga gct                                            23

<210> SEQ ID NO 141

```
<211> LENGTH: 24
<212> TYPE: DNA
<213> ORGANISM: Artificial Sequence
<220> FEATURE:
<223> OTHER INFORMATION: Synthetic

<400> SEQUENCE: 141
aacaacgctc tcgacagtca gatc                                              24

<210> SEQ ID NO 142
<211> LENGTH: 22
<212> TYPE: DNA
<213> ORGANISM: Artificial Sequence
<220> FEATURE:
<223> OTHER INFORMATION: Synthetic

<400> SEQUENCE: 142
aagatcttgc agcccatggg ag                                                22

<210> SEQ ID NO 143
<211> LENGTH: 22
<212> TYPE: DNA
<213> ORGANISM: Artificial Sequence
<220> FEATURE:
<223> OTHER INFORMATION: Synthetic

<400> SEQUENCE: 143
ggaattctct ttggttttgc ac                                                22

<210> SEQ ID NO 144
<211> LENGTH: 21
<212> TYPE: DNA
<213> ORGANISM: Artificial Sequence
<220> FEATURE:
<223> OTHER INFORMATION: Synthetic

<400> SEQUENCE: 144
acatatccag catctctgtg a                                                 21

<210> SEQ ID NO 145
<211> LENGTH: 23
<212> TYPE: DNA
<213> ORGANISM: Artificial Sequence
<220> FEATURE:
<223> OTHER INFORMATION: Synthetic

<400> SEQUENCE: 145
tcatgcagtc cttttcctgt ttc                                               23

<210> SEQ ID NO 146
<211> LENGTH: 23
<212> TYPE: DNA
<213> ORGANISM: Artificial Sequence
<220> FEATURE:
<223> OTHER INFORMATION: Synthetic

<400> SEQUENCE: 146
ctcgcttcag ttttctaaca tgg                                               23

<210> SEQ ID NO 147
<211> LENGTH: 22
<212> TYPE: DNA
<213> ORGANISM: Artificial Sequence
<220> FEATURE:
<223> OTHER INFORMATION: Synthetic

<400> SEQUENCE: 147
```

```
ggaactgctg tgtattttca gc                                          22
```

<210> SEQ ID NO 148
<211> LENGTH: 22
<212> TYPE: DNA
<213> ORGANISM: Artificial Sequence
<220> FEATURE:
<223> OTHER INFORMATION: Synthetic

<400> SEQUENCE: 148

```
ttaaagcttg cccaggaata gg                                          22
```

<210> SEQ ID NO 149
<211> LENGTH: 23
<212> TYPE: DNA
<213> ORGANISM: Artificial Sequence
<220> FEATURE:
<223> OTHER INFORMATION: Synthetic

<400> SEQUENCE: 149

```
gcttgtgtgt ggtatacaca ttg                                         23
```

<210> SEQ ID NO 150
<211> LENGTH: 23
<212> TYPE: DNA
<213> ORGANISM: Artificial Sequence
<220> FEATURE:
<223> OTHER INFORMATION: Synthetic

<400> SEQUENCE: 150

```
tccagagctg atctcagcag aag                                         23
```

<210> SEQ ID NO 151
<211> LENGTH: 21
<212> TYPE: DNA
<213> ORGANISM: Artificial Sequence
<220> FEATURE:
<223> OTHER INFORMATION: Synthetic

<400> SEQUENCE: 151

```
gaggaaccgc tgtgtgttta t                                           21
```

<210> SEQ ID NO 152
<211> LENGTH: 23
<212> TYPE: DNA
<213> ORGANISM: Artificial Sequence
<220> FEATURE:
<223> OTHER INFORMATION: Synthetic

<400> SEQUENCE: 152

```
ctgggcacac tctaacccta acc                                         23
```

<210> SEQ ID NO 153
<211> LENGTH: 22
<212> TYPE: DNA
<213> ORGANISM: Artificial Sequence
<220> FEATURE:
<223> OTHER INFORMATION: Synthetic

<400> SEQUENCE: 153

```
tgtgacgtgc agtgccacag ga                                          22
```

<210> SEQ ID NO 154
<211> LENGTH: 22
<212> TYPE: DNA
<213> ORGANISM: Artificial Sequence
<220> FEATURE:

```
<223> OTHER INFORMATION: Synthetic

<400> SEQUENCE: 154
aaaccctagg aggagcctcc tt                                            22

<210> SEQ ID NO 155
<211> LENGTH: 22
<212> TYPE: DNA
<213> ORGANISM: Artificial Sequence
<220> FEATURE:
<223> OTHER INFORMATION: Synthetic

<400> SEQUENCE: 155
gatcagcccg tttccgcctc ag                                            22

<210> SEQ ID NO 156
<211> LENGTH: 25
<212> TYPE: DNA
<213> ORGANISM: Artificial Sequence
<220> FEATURE:
<223> OTHER INFORMATION: Synthetic

<400> SEQUENCE: 156
ccgatgtaca gcaggttccc gttgc                                         25

<210> SEQ ID NO 157
<211> LENGTH: 17
<212> TYPE: DNA
<213> ORGANISM: Artificial Sequence
<220> FEATURE:
<223> OTHER INFORMATION: Synthetic

<400> SEQUENCE: 157
cagtacctgc ctccagg                                                  17

<210> SEQ ID NO 158
<211> LENGTH: 23
<212> TYPE: DNA
<213> ORGANISM: Artificial Sequence
<220> FEATURE:
<223> OTHER INFORMATION: Synthetic

<400> SEQUENCE: 158
tccaaggacc agcctccgta aga                                           23

<210> SEQ ID NO 159
<211> LENGTH: 18
<212> TYPE: DNA
<213> ORGANISM: Artificial Sequence
<220> FEATURE:
<223> OTHER INFORMATION: Synthetic

<400> SEQUENCE: 159
ctatgagtgc tgcaaaga                                                 18

<210> SEQ ID NO 160
<211> LENGTH: 17
<212> TYPE: DNA
<213> ORGANISM: Artificial Sequence
<220> FEATURE:
<223> OTHER INFORMATION: Synthetic

<400> SEQUENCE: 160
caggggatca gcaggtt                                                  17

<210> SEQ ID NO 161
```

```
<211> LENGTH: 17
<212> TYPE: DNA
<213> ORGANISM: Artificial Sequence
<220> FEATURE:
<223> OTHER INFORMATION: Synthetic

<400> SEQUENCE: 161
gccgcaggac actctac                                                     17

<210> SEQ ID NO 162
<211> LENGTH: 23
<212> TYPE: DNA
<213> ORGANISM: Artificial Sequence
<220> FEATURE:
<223> OTHER INFORMATION: Synthetic

<400> SEQUENCE: 162
tccagagctg atctcagcag aag                                              23

<210> SEQ ID NO 163
<211> LENGTH: 23
<212> TYPE: DNA
<213> ORGANISM: Artificial Sequence
<220> FEATURE:
<223> OTHER INFORMATION: Synthetic

<400> SEQUENCE: 163
gcccctcgtt agacagaatt gag                                              23

<210> SEQ ID NO 164
<211> LENGTH: 23
<212> TYPE: DNA
<213> ORGANISM: Artificial Sequence
<220> FEATURE:
<223> OTHER INFORMATION: Synthetic

<400> SEQUENCE: 164
ctgggcacac tctaaccta acc                                               23

<210> SEQ ID NO 165
<211> LENGTH: 22
<212> TYPE: DNA
<213> ORGANISM: Artificial Sequence
<220> FEATURE:
<223> OTHER INFORMATION: Synthetic

<400> SEQUENCE: 165
gatcagcccg tttccgcctc ag                                               22

<210> SEQ ID NO 166
<211> LENGTH: 25
<212> TYPE: DNA
<213> ORGANISM: Artificial Sequence
<220> FEATURE:
<223> OTHER INFORMATION: Synthetic

<400> SEQUENCE: 166
ccgatgtaca gcaggttccc gttgc                                            25

<210> SEQ ID NO 167
<211> LENGTH: 17
<212> TYPE: DNA
<213> ORGANISM: Artificial Sequence
<220> FEATURE:
<223> OTHER INFORMATION: Synthetic

<400> SEQUENCE: 167
```
tcccgacccc cgactct            17

<210> SEQ ID NO 168
<211> LENGTH: 21
<212> TYPE: DNA
<213> ORGANISM: Artificial Sequence
<220> FEATURE:
<223> OTHER INFORMATION: Synthetic

<400> SEQUENCE: 168
tgatggtgaa gaccgagaag g        21

<210> SEQ ID NO 169
<211> LENGTH: 17
<212> TYPE: DNA
<213> ORGANISM: Artificial Sequence
<220> FEATURE:
<223> OTHER INFORMATION: Synthetic

<400> SEQUENCE: 169
tcccgacccc cgactct            17

<210> SEQ ID NO 170
<211> LENGTH: 21
<212> TYPE: DNA
<213> ORGANISM: Artificial Sequence
<220> FEATURE:
<223> OTHER INFORMATION: Synthetic

<400> SEQUENCE: 170
tgatggtgaa gaccgagaag g        21

<210> SEQ ID NO 171
<211> LENGTH: 20
<212> TYPE: DNA
<213> ORGANISM: Artificial Sequence
<220> FEATURE:
<223> OTHER INFORMATION: Synthetic

<400> SEQUENCE: 171
ccttctcggt cttcaccatc         20

<210> SEQ ID NO 172
<211> LENGTH: 20
<212> TYPE: DNA
<213> ORGANISM: Artificial Sequence
<220> FEATURE:
<223> OTHER INFORMATION: Synthetic

<400> SEQUENCE: 172
gcctccacga agttgggagc         20

<210> SEQ ID NO 173
<211> LENGTH: 18
<212> TYPE: DNA
<213> ORGANISM: Artificial Sequence
<220> FEATURE:
<223> OTHER INFORMATION: Synthetic

<400> SEQUENCE: 173
ggtccgctac attgccaa           18

<210> SEQ ID NO 174
<211> LENGTH: 19
<212> TYPE: DNA
<213> ORGANISM: Artificial Sequence
<220> FEATURE:

<223> OTHER INFORMATION: Synthetic

<400> SEQUENCE: 174
ccttgcccat ctgtgagtt                                               19

<210> SEQ ID NO 175
<211> LENGTH: 19
<212> TYPE: DNA
<213> ORGANISM: Artificial Sequence
<220> FEATURE:
<223> OTHER INFORMATION: Synthetic

<400> SEQUENCE: 175
gtgttgctta cggtttctt                                               19

<210> SEQ ID NO 176
<211> LENGTH: 25
<212> TYPE: DNA
<213> ORGANISM: Artificial Sequence
<220> FEATURE:
<223> OTHER INFORMATION: Synthetic

<400> SEQUENCE: 176
tttcaggtag accttcatgc agaca                                        25

<210> SEQ ID NO 177
<211> LENGTH: 25
<212> TYPE: DNA
<213> ORGANISM: Artificial Sequence
<220> FEATURE:
<223> OTHER INFORMATION: Synthetic

<400> SEQUENCE: 177
tgcccatctg tgagttttcc acatg                                        25

<210> SEQ ID NO 178
<211> LENGTH: 25
<212> TYPE: DNA
<213> ORGANISM: Artificial Sequence
<220> FEATURE:
<223> OTHER INFORMATION: Synthetic

<400> SEQUENCE: 178
cgctgcagct ccgggactca acatg                                        25

<210> SEQ ID NO 179
<211> LENGTH: 20
<212> TYPE: DNA
<213> ORGANISM: Artificial Sequence
<220> FEATURE:
<223> OTHER INFORMATION: Synthetic

<400> SEQUENCE: 179
ctcggtgccc cttgccattt                                              20

<210> SEQ ID NO 180
<211> LENGTH: 25
<212> TYPE: DNA
<213> ORGANISM: Artificial Sequence
<220> FEATURE:
<223> OTHER INFORMATION: Synthetic

<400> SEQUENCE: 180
ccttgcccat ctgtgagttt tccac                                        25

<210> SEQ ID NO 181

<211> LENGTH: 2043
<212> TYPE: DNA
<213> ORGANISM: Homo sapiens

<400> SEQUENCE: 181

```
gtcctacatt gtaagctgag tgagtggact gcgcttgcag gtcctccagg tgcctagcga      60
gaacagagga caaataaata tttacgaatt gcttgtctca cctgaaaatg gtttatttct     120
aggtttctga tattatgggg tgcaatggcg gtaaagaagc agttctggtt tcaggaatgt     180
gatcctgata gccataccc agaaaaaatc aataaattcc cttggcccca tgggctcatg      240
ctcttctaga agggaagaca gggctcttag gtactttcag cgctcgtaga agagtgttgt     300
tacagtccca tgaccagtgc aggggatgtg ccactgagaa tcttttcact gatgcttcat     360
gggctttctc tattctgcta ctgggtttta tttcccttct tctaattctc cctttaccaa     420
caactaatcc cctgtagata attaattcat caagtgcctg ctctgtgatg tccggactgc     480
tagaagtggt aggggactc aagagccaga tgaagctaag gcacgcctg tctgctctcc       540
agggacccct ggcgtccctt tctcctggca gaatgactgc tatcctttga ggtgaatcca     600
gttcagctgt cacctcttct attaaccact ctccaaaaac agctaatcct tcttctaggc     660
tcttaccgca gttatgaaag cctatgctga ccctttgttt aaacatgtgt acattaacag     720
taatacattt aagacacttc atggcaaggg caatatactg cgttattctt ccaaatcaaa     780
tagttgggct cagtccccca ttcctgctac tggggtacag tcaagctcag tcaccttttg     840
gtgagccttt ccctagttct tggagtctta aaagaatccc gtggttttcg gcagttcaga     900
aacccaggca ttgccgctgc gtggtccacg ggagttgctc tggtggagct cggatgcccg     960
ggggctgcag gaaagaaggt ggcagcgccc cctacgcgga cgcagggcgc tgctgtgctc    1020
agcagaaggg agcaaatggg atggagcttc agccaccctg gaagccgccc cttggcgcct    1080
tcctccctcc cttcctcttt ccaaaatcaa gccccctctt caacatcaag aactctccgc    1140
actccctgga cctctcagag cctctcctca tttactcttt ccaatgcgct ggctcaaaag    1200
agcctagata gaacaccaa gttctggctg tccttccagc aaagagttag gagttaactt     1260
ttcaatcttt tttaatctcc tttaaaaaag aatgagccat acattagggt aaccactggg    1320
aatcccatca cacacattgg cggcatctct cctccccgac agggtgcctc cagcacttca    1380
gatcccagcc gagagtctgg ctgctggcgc ccagcaaacg gtgcggaaag caaccgggg     1440
ctcgcggaaa gcgggaggag gggggcttcc tcgggtctgt tttgtctggt tggcaagact    1500
tccgaagcct ggttccctat agctgccacc cggtcgctgg cgtggaggag ggagtccggg    1560
aagactggac cccagaattg tcccggcttt ctcccgagtg cccagcgcag cttctggctg    1620
agagcgggag cgggctgagt ggggacaaag aacgcaaggg agaggtagag cctggccttg    1680
ggcagcccct ggcctggcca gaggcgcgag gccgagagcc cgctcggtgg agactggggg    1740
tggaggtgcc cggagcgtac ccagcgccgg gagtacctcc cgctcacacc tcgggctgca    1800
gttccctggg tggccgccga dacgctggcc cgggctggag ggatggggg gcggggacgg     1860
gggcggggc ggggctcgtc acgtggagag gcgcgcgggg gcgggcgggg cggggcgcg      1920
cgcccggctc cttaaaggcg cgcgagccga gcggcgaggt gcctctgtgg ccgcaggcgc    1980
aggcccgggc gacagccgag acgtggagcg cgccggctcg ctgcagctcc gggactcaac    2040
atg                                                                  2043
```

<210> SEQ ID NO 182
<211> LENGTH: 42
<212> TYPE: DNA

<213> ORGANISM: Artificial Sequence
<220> FEATURE:
<223> OTHER INFORMATION: synthetic

<400> SEQUENCE: 182
gccatacata ctccagaaaa aataaataaa ttcccttggc cc    42

<210> SEQ ID NO 183
<211> LENGTH: 42
<212> TYPE: DNA
<213> ORGANISM: Artificial sequence
<220> FEATURE:
<223> OTHER INFORMATION: synthetic

<400> SEQUENCE: 183
gggccaaggg aatttattta tttttctgg agtatgtatg gc    42

<210> SEQ ID NO 184
<211> LENGTH: 22
<212> TYPE: DNA
<213> ORGANISM: Artificial Sequence
<220> FEATURE:
<223> OTHER INFORMATION: synthetic

<400> SEQUENCE: 184
agtacctccc gctcacacct cg    22

<210> SEQ ID NO 185
<211> LENGTH: 23
<212> TYPE: DNA
<213> ORGANISM: Artificial sequence
<220> FEATURE:
<223> OTHER INFORMATION: synthetic

<400> SEQUENCE: 185
gacgtctgag gccctgagtt gta    23

<210> SEQ ID NO 186
<211> LENGTH: 26
<212> TYPE: DNA
<213> ORGANISM: Artificial Sequence
<220> FEATURE:
<223> OTHER INFORMATION: synthetic

<400> SEQUENCE: 186
cgggagcggg ctggagtggg gacaaa    26

<210> SEQ ID NO 187
<211> LENGTH: 22
<212> TYPE: DNA
<213> ORGANISM: Artificial sequence
<220> FEATURE:
<223> OTHER INFORMATION: synthetic

<400> SEQUENCE: 187
cggcggccac ccagggaact gc    22

<210> SEQ ID NO 188
<211> LENGTH: 25
<212> TYPE: DNA
<213> ORGANISM: Artificial Sequence
<220> FEATURE:
<223> OTHER INFORMATION: synthetic

<400> SEQUENCE: 188
cagcacttca gatcccagcc gagag    25

<210> SEQ ID NO 189
<211> LENGTH: 20
<212> TYPE: DNA
<213> ORGANISM: Artificial sequence
<220> FEATURE:
<223> OTHER INFORMATION: synthetic

<400> SEQUENCE: 189 ccaccccag tctccaccga                                         20

<210> SEQ ID NO 190
<211> LENGTH: 25
<212> TYPE: DNA
<213> ORGANISM: Artificial Sequence
<220> FEATURE:
<223> OTHER INFORMATION: synthetic

<400> SEQUENCE: 190
gaatgagcca tacattaggg taacc                                  25

<210> SEQ ID NO 191
<211> LENGTH: 23
<212> TYPE: DNA
<213> ORGANISM: Artificial sequence
<220> FEATURE:
<223> OTHER INFORMATION: synthetic

<400> SEQUENCE: 191
cggaagtctt gccaaccaga caa                                    23

<210> SEQ ID NO 192
<211> LENGTH: 25
<212> TYPE: DNA
<213> ORGANISM: Artificial Sequence
<220> FEATURE:
<223> OTHER INFORMATION: synthetic

<400> SEQUENCE: 192
tctttccaat gcgctggctc aaaag                                  25

<210> SEQ ID NO 193
<211> LENGTH: 23
<212> TYPE: DNA
<213> ORGANISM: Artificial sequence
<220> FEATURE:
<223> OTHER INFORMATION: synthetic

<400> SEQUENCE: 193
aggagagatg ccgccaatgt gtg                                    23

<210> SEQ ID NO 194
<211> LENGTH: 22
<212> TYPE: DNA
<213> ORGANISM: Artificial Sequence
<220> FEATURE:
<223> OTHER INFORMATION: synthetic

<400> SEQUENCE: 194
ggagcaatgg gatggagctt ca                                     22

<210> SEQ ID NO 195
<211> LENGTH: 25
<212> TYPE: DNA
<213> ORGANISM: Artificial sequence
<220> FEATURE:
<223> OTHER INFORMATION: synthetic

```
<400> SEQUENCE: 195
ggaaggacag ccagaacttg gtgtt                                        25

<210> SEQ ID NO 196
<211> LENGTH: 20
<212> TYPE: DNA
<213> ORGANISM: Artificial Sequence
<220> FEATURE:
<223> OTHER INFORMATION: synthetic

<400> SEQUENCE: 196
ctgtctgctc tccagggacc                                              20

<210> SEQ ID NO 197
<211> LENGTH: 23
<212> TYPE: DNA
<213> ORGANISM: Artificial sequence
<220> FEATURE:
<223> OTHER INFORMATION: synthetic

<400> SEQUENCE: 197
cggaaacgga tcaagaacct cag                                          23

<210> SEQ ID NO 198
<211> LENGTH: 24
<212> TYPE: DNA
<213> ORGANISM: Artificial Sequence
<220> FEATURE:
<223> OTHER INFORMATION: synthetic

<400> SEQUENCE: 198
ctccctttac cacacactaa tccc                                         24

<210> SEQ ID NO 199
<211> LENGTH: 23
<212> TYPE: DNA
<213> ORGANISM: Artificial sequence
<220> FEATURE:
<223> OTHER INFORMATION: synthetic

<400> SEQUENCE: 199
agatccgaga atggcgtcaa tac                                          23

<210> SEQ ID NO 200
<211> LENGTH: 25
<212> TYPE: DNA
<213> ORGANISM: Artificial Sequence
<220> FEATURE:
<223> OTHER INFORMATION: synthetic

<400> SEQUENCE: 200
aagcagttct ggtttcagga atctg                                        25

<210> SEQ ID NO 201
<211> LENGTH: 25
<212> TYPE: DNA
<213> ORGANISM: Artificial sequence
<220> FEATURE:
<223> OTHER INFORMATION: synthetic

<400> SEQUENCE: 201
cacaacaatg tcagggtact ggtca                                        25
```